US012575941B2

(12) United States Patent
Cryder et al.

(10) Patent No.: US 12,575,941 B2
(45) Date of Patent: *Mar. 17, 2026

(54) EXPANDABLE FUSION DEVICE AND METHOD OF INSTALLATION THEREOF

(71) Applicant: GLOBUS MEDICAL, INC., Audubon, PA (US)

(72) Inventors: Joel Cryder, Warrington, PA (US); James Himmelberger, Souderton, PA (US); Mark Weiman, Downingtown, PA (US); Jason Zappacosta, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 188 days.

This patent is subject to a terminal disclaimer.

(21) Appl. No.: 18/493,131

(22) Filed: Oct. 24, 2023

(65) Prior Publication Data

US 2024/0058138 A1 Feb. 22, 2024

Related U.S. Application Data

(63) Continuation of application No. 16/597,211, filed on Oct. 9, 2019, now Pat. No. 11,793,654, which is a
(Continued)

(51) Int. Cl.
*A61F 2/44* (2006.01)
*A61F 2/30* (2006.01)
*A61F 2/46* (2006.01)
(52) U.S. Cl.
CPC ................ *A61F 2/447* (2013.01); *A61F 2/44* (2013.01); *A61F 2/442* (2013.01); *A61F 2/4455* (2013.01); *A61F 2002/30266*

(2013.01); *A61F 2002/30387* (2013.01); *A61F 2002/30405* (2013.01); *A61F 2002/30411* (2013.01); *A61F 2002/30471* (2013.01); *A61F 2002/30482* (2013.01); *A61F 2002/30484* (2013.01); *A61F 2002/30517* (2013.01); *A61F 2002/30522* (2013.01); *A61F 2002/30523* (2013.01); *A61F 2002/30538* (2013.01); *A61F 2002/30556* (2013.01); *A61F 2002/30558* (2013.01);
(Continued)

(58) Field of Classification Search
None
See application file for complete search history.

(56) References Cited

U.S. PATENT DOCUMENTS 4,349,921 A 9/1982 Kuntz
4,599,086 A 7/1986 Doty
(Continued)

FOREIGN PATENT DOCUMENTS

CA 2088066 A1 1/1992
DE 4012622 C1 7/1991
(Continued)

*Primary Examiner* — Jan Christopher L Merene

(57) ABSTRACT

The present disclosure relates to an anti-rotation locking system for an expandable implant. The anti-rotation locking system may include a screw comprising a screw head comprising a plurality of notches. The anti-rotation locking system further comprises a housing and a locking member comprising a ring, a partial ring, and a strut coupling the ring to the partial ring.

19 Claims, 105 Drawing Sheets

1474
1490
1480
1482
1456
1458
1484
1456a

Related U.S. Application Data continuation-in-part of application No. 15/805,176, filed on Nov. 7, 2017, now Pat. No. 10,758,367, which is a continuation-in-part of application No. 15/635,267, filed on Jun. 28, 2017, now Pat. No. 10,842,644, which is a continuation-in-part of application No. 15/189,188, filed on Jun. 22, 2016, now Pat. No. 10,085,849, which is a continuation-in-part of application No. 15/014,189, filed on Feb. 3, 2016, now Pat. No. 9,907,673.

(60) Provisional application No. 62/743,833, filed on Oct. 10, 2018.

(52) U.S. Cl.
CPC .............. *A61F 2002/30579* (2013.01); *A61F 2002/30593* (2013.01); *A61F 2002/30601* (2013.01); *A61F 2002/30622* (2013.01); *A61F 2002/30841* (2013.01); *A61F 2002/30843* (2013.01); *A61F 2002/30904* (2013.01); *A61F 2/4611* (2013.01); *A61F 2220/0016* (2013.01); *A61F 2310/00011* (2013.01); *A61F 2310/00017* (2013.01); *A61F 2310/00023* (2013.01); *A61F 2310/00179* (2013.01)

(56) References Cited

U.S. PATENT DOCUMENTS

| | | | |
|---|---|---|---|
| 4,812,094 A * | 3/1989 | Grube ..................... | F16C 25/06 |
| | | | 301/124.1 |
| 4,863,476 A | 9/1989 | Shepperd | |
| 4,863,477 A | 9/1989 | Monson | |
| 5,123,926 A | 6/1992 | Pisharodi | |
| 5,251,995 A * | 10/1993 | Chi ......................... | B62K 19/32 |
| | | | 403/373 |
| 5,290,312 A | 3/1994 | Kojimoto et al. | |
| 5,306,310 A | 4/1994 | Siebels | |
| 5,375,823 A | 12/1994 | Navas | |
| 5,390,683 A | 2/1995 | Pisharodi | |
| 5,522,899 A | 6/1996 | Michelson | |
| 5,534,030 A | 7/1996 | Navarro et al. | |
| 5,554,191 A | 9/1996 | Lahille et al. | |
| 5,571,192 A | 11/1996 | Schonhoffer | |
| 5,645,596 A | 7/1997 | Kim | |
| 5,653,763 A | 8/1997 | Errico et al. | |
| 5,665,122 A | 9/1997 | Kambin | |
| 5,676,701 A | 10/1997 | Yuan et al. | |
| 6,039,761 A | 3/2000 | Li et al. | |
| 6,045,579 A | 4/2000 | Hochschuler et al. | |
| 6,080,193 A | 6/2000 | Hochschuler et al. | |
| 6,099,531 A | 8/2000 | Bonutti | |
| 6,126,689 A | 10/2000 | Brett | |
| 6,176,682 B1 | 1/2001 | Mills | |
| 6,176,882 B1 | 1/2001 | Biedermann et al. | |
| 6,258,125 B1 | 7/2001 | Paul et al. | |
| 6,554,863 B2 | 4/2003 | Paul et al. | |
| 6,558,423 B1 | 5/2003 | Michelson | |
| 6,562,074 B2 | 5/2003 | Gerbec et al. | |
| 6,576,016 B1 | 6/2003 | Hochschuler et al. | |
| 6,641,614 B1 | 11/2003 | Wagner et al. | |
| 6,648,917 B2 | 11/2003 | Gerbec et al. | |
| 6,666,891 B2 | 12/2003 | Boehm, Jr. et al. | |
| 6,692,495 B1 | 2/2004 | Zacouto | |
| 6,706,070 B1 | 3/2004 | Wagner et al. | |
| 6,752,832 B2 | 6/2004 | Ulrich | |
| 6,814,756 B1 | 11/2004 | Michelson | |
| 6,830,589 B2 | 12/2004 | Erickson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,881,228 B2 | 4/2005 | Zdeblick et al. | |
| 7,018,415 B1 | 3/2006 | McKay | |

| | | |
|---|---|---|
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | JImenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | JImenez et al. |
| 9,532,883 B2 | 1/2017 | McLuen et al. |
| 9,622,878 B2 | 4/2017 | Grotz |
| 2002/0045945 A1 | 4/2002 | Liu |
| 2002/0068976 A1 | 6/2002 | Jackson |
| 2002/0068977 A1 | 6/2002 | Jackson |
| 2003/0176926 A1 | 9/2003 | Boehm et al. |
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |

(56)　　　　　References Cited

U.S. PATENT DOCUMENTS

| | | |
|---|---|---|
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0182383 A1* | 7/2009 | Prybyla .............. A61B 17/8047 |
| | | 606/280 |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0059473 A1* | 3/2012 | Weiman .................... A61F 2/44 |
| | | 623/17.16 |
| 2012/0059475 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158664 A1 | 6/2013 | Palmatier et al. |
| 2013/0158669 A1 | 6/2013 | Sungarian et al. |
| 2013/0172939 A1* | 7/2013 | Ziolo ................. A61B 17/8605 |
| | | 606/301 |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2014/0277471 A1 | 9/2014 | Gray et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0223945 A1 | 8/2015 | Weiman et al. |
| 2015/0289988 A1 | 10/2015 | Ashley et al. |
| 2015/0374508 A1 | 12/2015 | Sandul |
| 2015/0374512 A1 | 12/2015 | Glerum et al. |
| 2016/0166396 A1 | 6/2016 | McClintock |
| 2016/0324654 A1 | 11/2016 | Loebl et al. |
| 2016/0361176 A1 | 12/2016 | Weiman et al. |
| 2017/0100258 A1 | 4/2017 | Jimenez et al. |
| 2017/0119543 A1 | 5/2017 | Dietzel et al. |
| 2017/0268561 A1* | 9/2017 | Hess ....................... F16B 39/24 |
| 2018/0177604 A1* | 6/2018 | Weiman ................ A61F 2/4611 |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2009124269 A1 | 10/2009 |
| WO | 2010103344 A1 | 9/2010 |
| WO | 2012031267 A1 | 3/2012 |
| WO | 2014165319 A1 | 10/2014 |
| WO | 2015009793 A1 | 1/2015 |
| WO | 2015187569 A1 | 12/2015 |
| WO | 2016069796 A1 | 5/2016 |
| WO | 2017015244 A2 | 1/2017 |
| WO | 2017015244 W | 1/2017 |
| WO | 2017117513 A1 | 7/2017 |
| WO | 2017136620 A1 | 8/2017 |

* cited by examiner

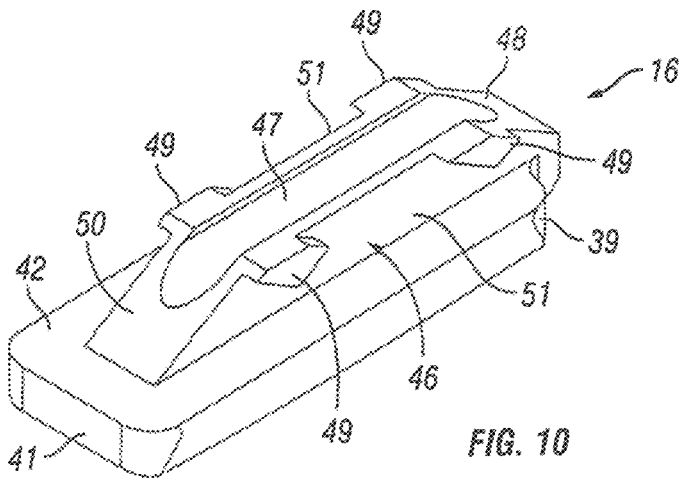
*FIG. 10*
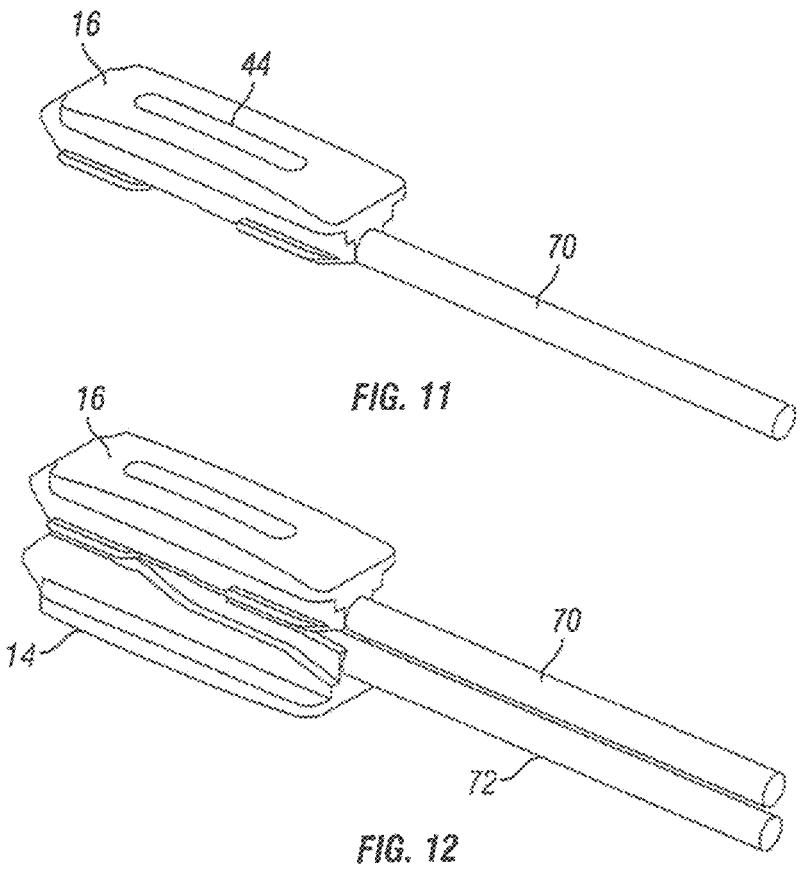
*FIG. 11*
*FIG. 12*

Flat	Convex	Lordotic	Lordotic/Convex

Straight Rise	Straight and Toggle	Phase Off Straight Rise

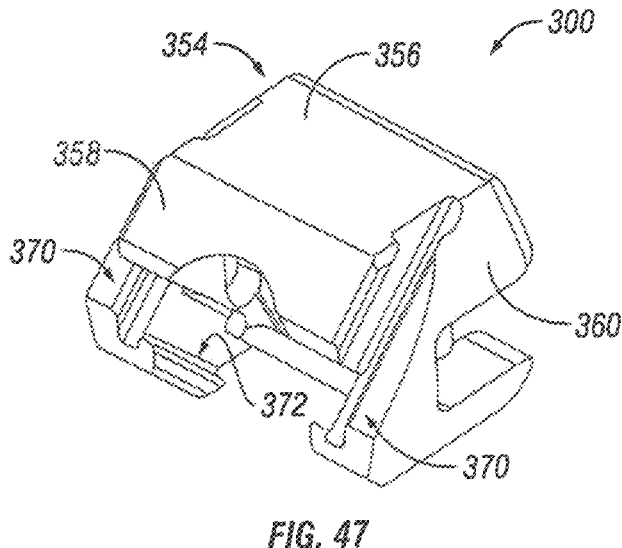
FIG. 47
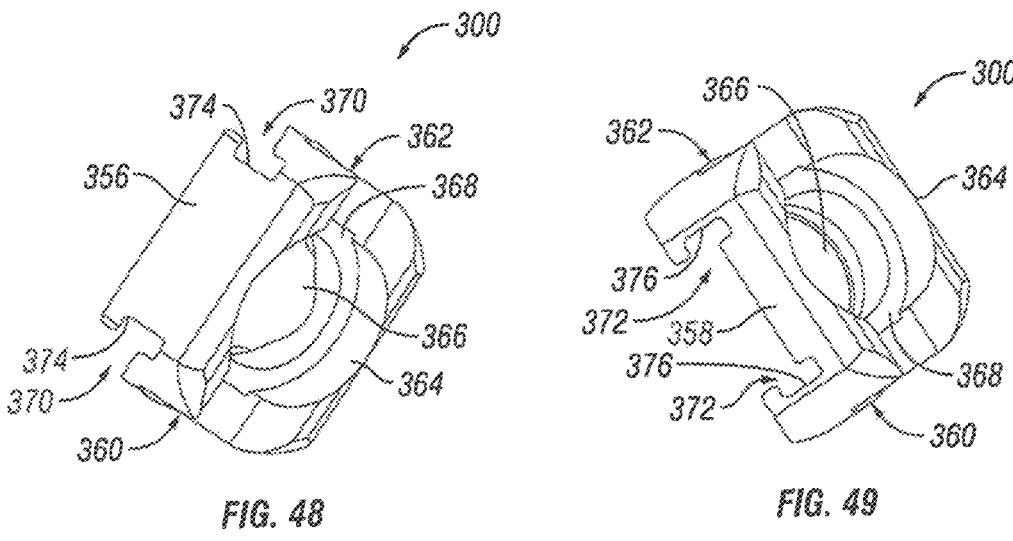
FIG. 48                    FIG. 49

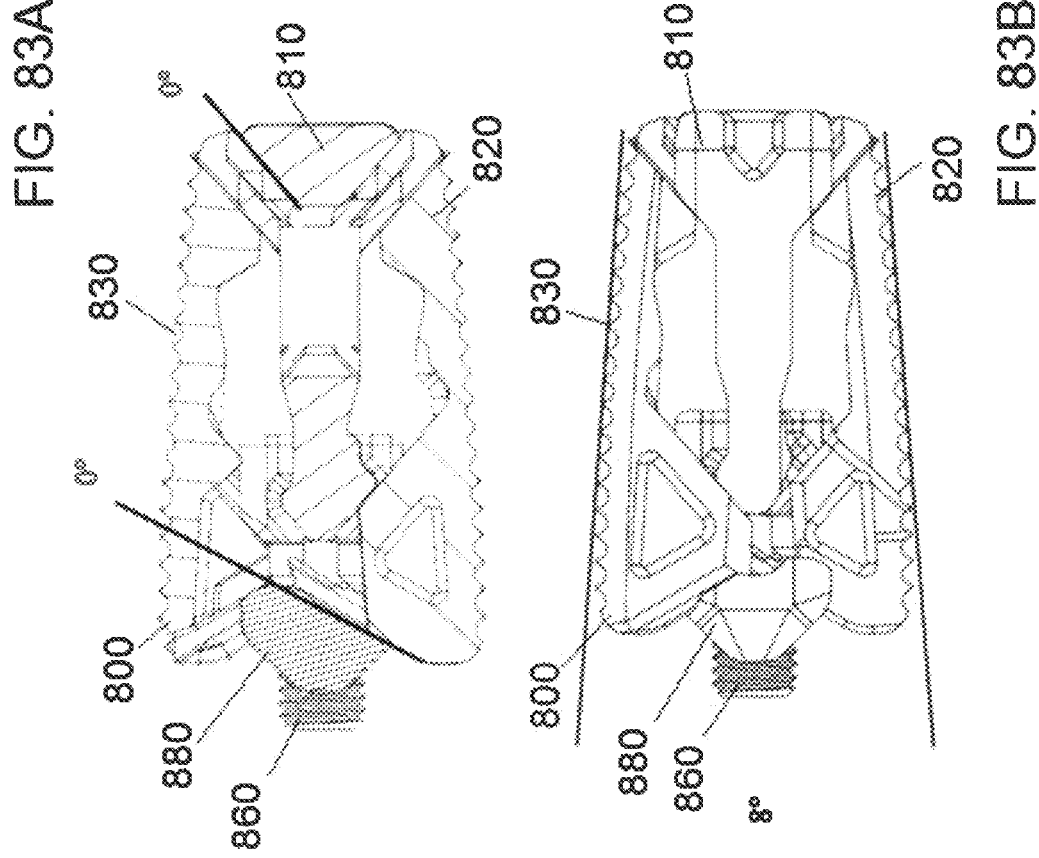

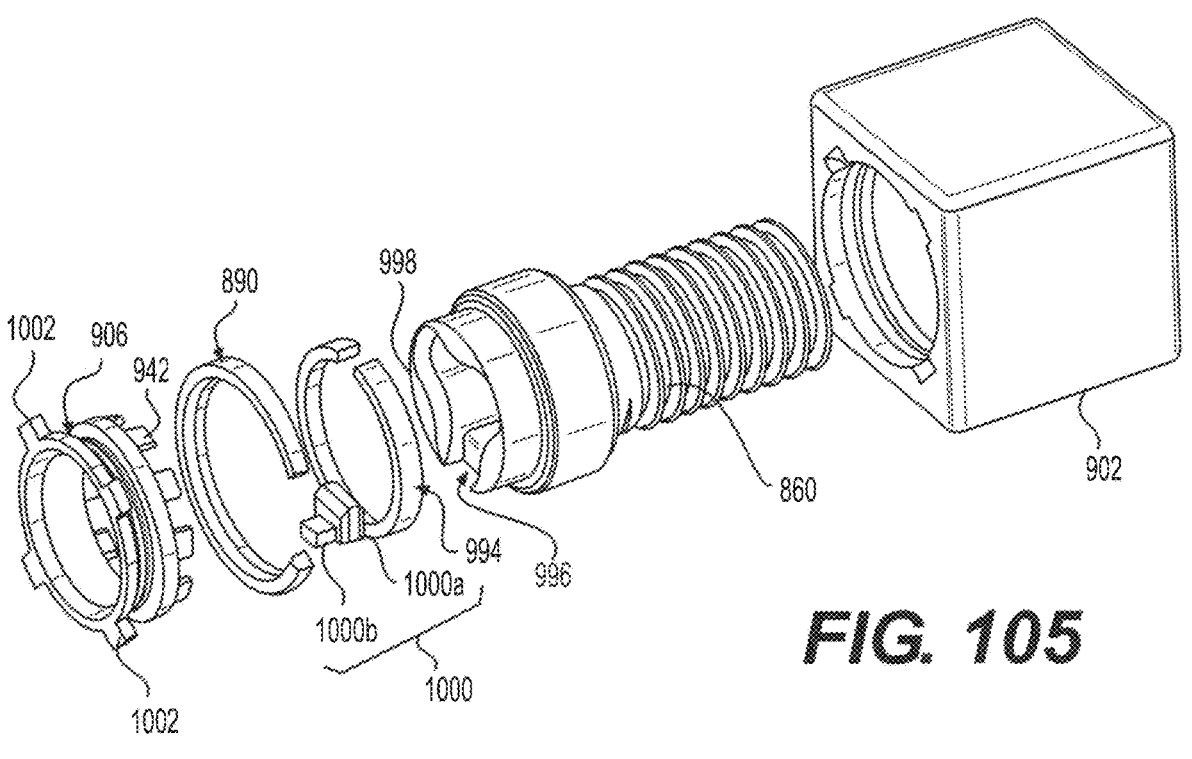
FIG. 105
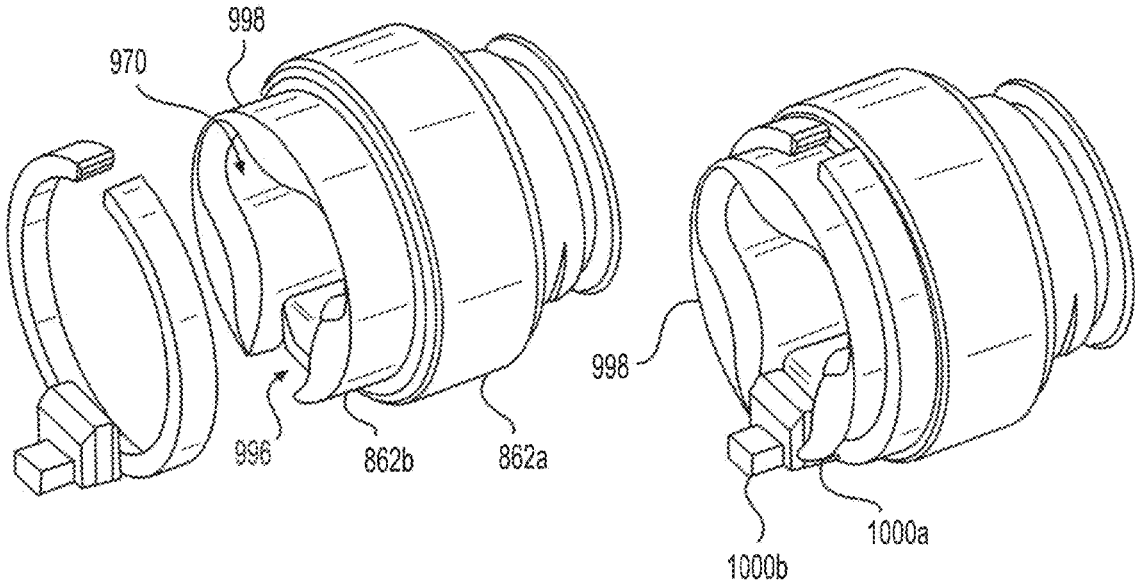
FIG. 106
FIG. 107

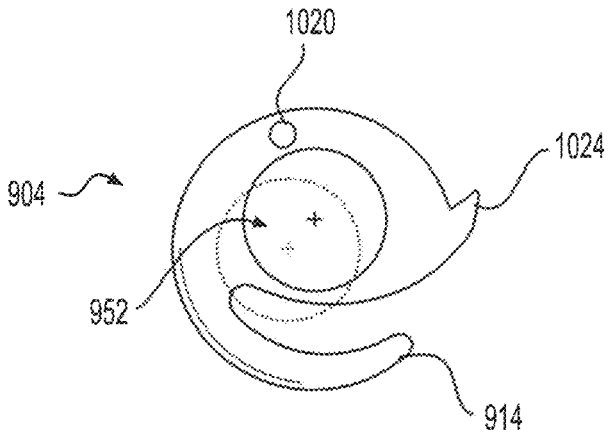
FIG. 123
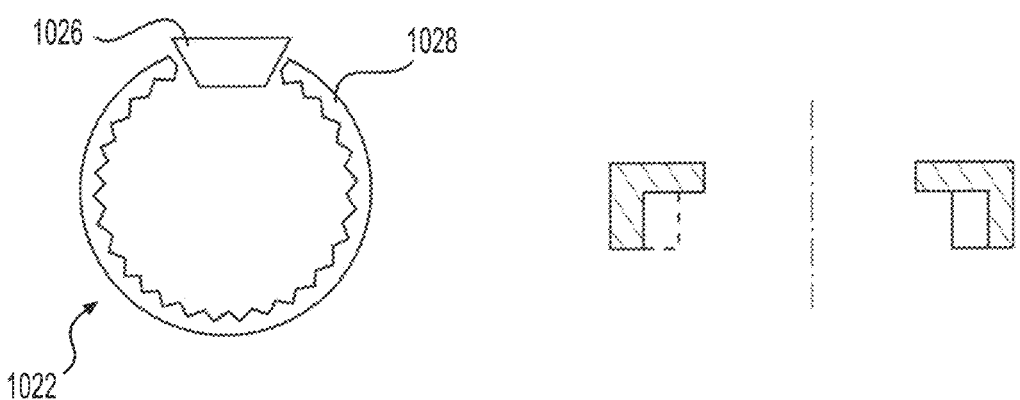
FIG. 124                    FIG. 125

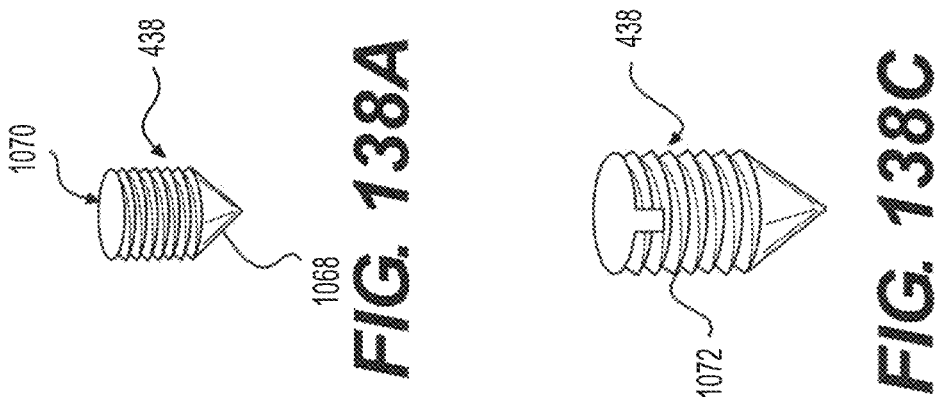
*FIG. 138A*
*FIG. 138C*
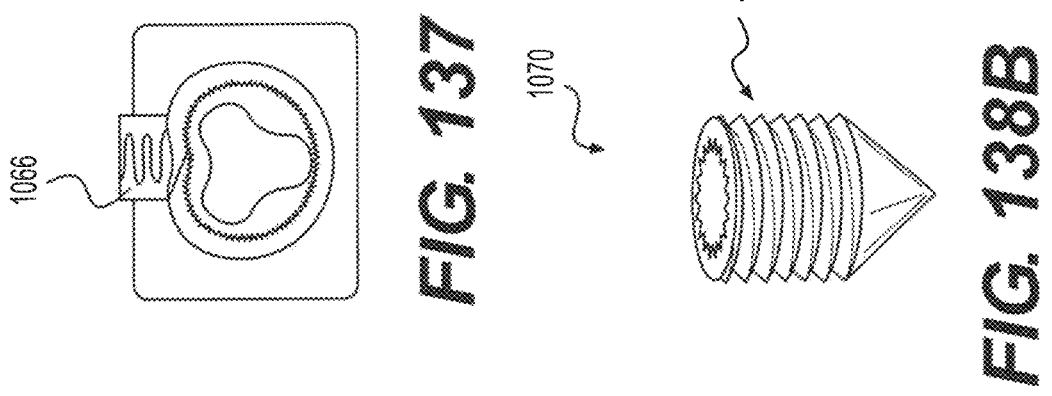
*FIG. 137*
*FIG. 138B*

1464a

1472

1470

1468

1454

1452

1472a

1450

1470

1474

1476

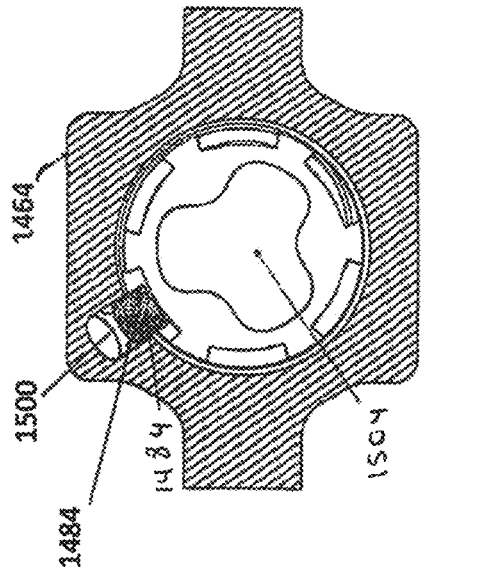
FIG. 149B
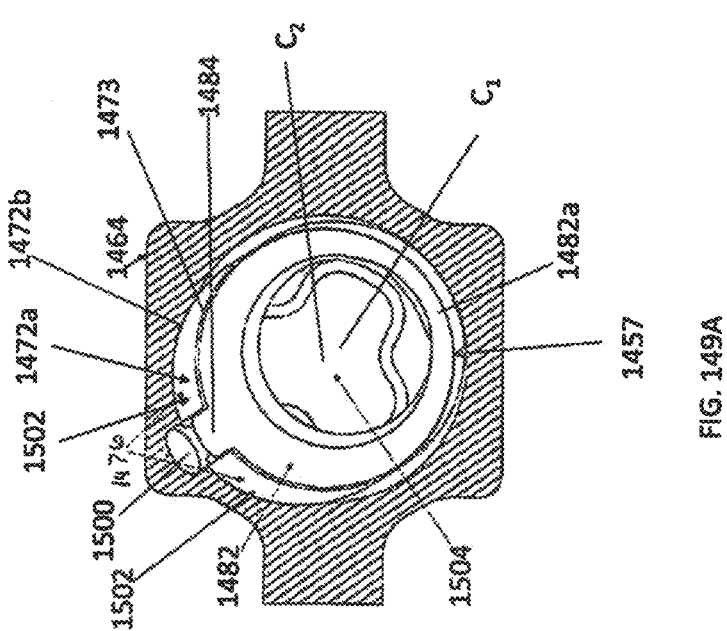
FIG. 149A

EXPANDABLE FUSION DEVICE AND METHOD OF INSTALLATION THEREOF

CROSS-REFERENCE TO RELATED APPLICATIONS

This patent application is a continuation of U.S. patent application Ser. No. 16/597,211, filed Oct. 9, 2019, which (i) claims priority to U.S. Provisional Patent Application No. 62/743,833, filed Oct. 10, 2018 and (ii) is also a continuation in part of U.S. patent application Ser. No. 15/805,176, filed Nov. 7, 2017, which is a continuation-in-part of U.S. Ser. No. 15/635,267 filed Jun. 28, 2017, which is a continuation-in-part of U.S. Ser. No. 15/189,188, filed Jun. 22, 2016, which is a continuation-in-part of U.S. Ser. No. 15/014,189, filed Feb. 3, 2016, the entire disclosures of which are incorporated by reference herein.

BACKGROUND

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY

In an exemplary embodiment, the present invention provides an expandable fusion device capable of being installed inside an intervertebral disc space to maintain normal disc spacing and restore spinal stability, thereby facilitating an intervertebral fusion. In one embodiment, the fusion device includes a central ramp, a first endplate, and a second endplate. The central ramp may be capable of moving in a first direction to push the first and second endplates outwardly and into an unexpanded configuration. The expandable fusion device may be capable of being placed into the disc space down an endoscopic tube and then expanded into an expanded configuration. In an exemplary embodiment, an apparatus may be provided comprising: a first endplate for an intervertebral implant, wherein the first endplate may comprise a first plate portion having a first upper surface and a first lower surface, wherein the first endplate further comprises first front ramped portions extending away from the first lower surface and first rear ramped portions extending away from first lower surface. The apparatus may further comprise a second endplate for an intervertebral implant, wherein the second endplate may comprise a second plate portion having a second upper surface and a second lower surface, wherein the second endplate further comprises second front ramped portions extending away from the second lower surface and second rear ramped portions extending away from second lower surface. The apparatus may further comprise a body positioned between the first endplate and the second endplate, wherein the body may comprise rear endplate engaging ramps. The apparatus may further comprise a driving ramp positioned at a front end of the apparatus, wherein the driving ramp comprises front endplate engaging ramps. When the apparatus is in an unexpanded configuration, the rear endplate engaging ramps and the front endplate engaging ramps may have ramp angles with respect to a longitudinal axis of the apparatus that differ from ramp angles of the first rear ramped portions and first front ramped portions of the first endplate with respect to the longitudinal axis. The apparatus may be configured such that movement of the driving ramp in one direction causes the first and second endplates to move apart and a movement of the driving ramp in a second direction causes the first and second endplates to move towards one another.

In an exemplary embodiment, an apparatus may include a fastening device including a head, wherein the head includes an opening and a portion of the opening extends to an outer diameter of the head, a first ring including a protuberance extending from a first side, wherein the protuberance comprises a first portion and a second portion, and wherein the first ring is operatively connected to the head by positioning the first portion within the portion of the opening of the head that extends to the outer diameter of the head; and a second ring comprising a plurality of recesses, wherein the second portion of the protuberance is selectively engageable with at least one of the plurality of recesses.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 10 is a perspective of an endplate of the expandable fusion device of FIG. 1 in accordance with one embodiment of the present invention;

FIG. 11 a perspective view showing placement of the first endplate of an embodiment of an expandable fusion device down an endoscopic tube and into the disc space in accordance with one embodiment of the present invention;

FIG. 12 is a perspective view showing placement of the second endplate of the expandable fusion device down an endoscopic tube and into the disc space in accordance with one embodiment of the present invention;

FIGS. 47-49 are perspective views of the driving ramp of the expandable fusion device of FIG. 40 in accordance with one embodiment of the present invention;

FIGS. 83A-83B are different views of the expandable fusion device of FIG. 79 in a fully expanded state in accordance with some embodiments.

FIG. 105 is a diagram showing one embodiment of a locking mechanism according to the present invention.

FIG. 106 is a diagram showing a close up view of one embodiment of the spring and drive screw head.

FIG. 107 is a diagram showing a close up view the spring operatively connected to the drive screw head in accordance with one embodiment of the present invention.

FIG. 122 is a diagram showing exemplary tapered notches according to one embodiment of a drive screw head.

FIG. 123 is a diagram showing an exemplary locking mechanism according to one embodiment of the present invention.

FIG. 124 is a diagram showing an exemplary snap-ring according to one embodiment of the present invention.

FIG. 125 is a diagram showing exemplary teeth according to one embodiment of the present invention.

FIG. 126 is a diagram showing another exemplary locking mechanism according to one embodiment of the present invention.

FIGS. 127A, 127B and 127C are diagrams showing an exemplary locking mechanism according to one embodiment of the present invention.

FIG. 128 is a diagram showing a close up view of one embodiment of a housing.

FIG. 129A is a diagram showing one embodiment of a screw lock ring in a closed position.

FIG. 129B is a diagram showing one embodiment of the screw lock ring of 129A in an opened position.

FIG. 130 is a diagram showing another embodiment of a screw lock ring.

FIG. 131 is a diagram showing an exemplary embodiment of a screw lock ring.

FIG. 132 is a diagram showing an exemplary locking mechanism according to one embodiment of the present invention.

Figures 132, 133, 134:
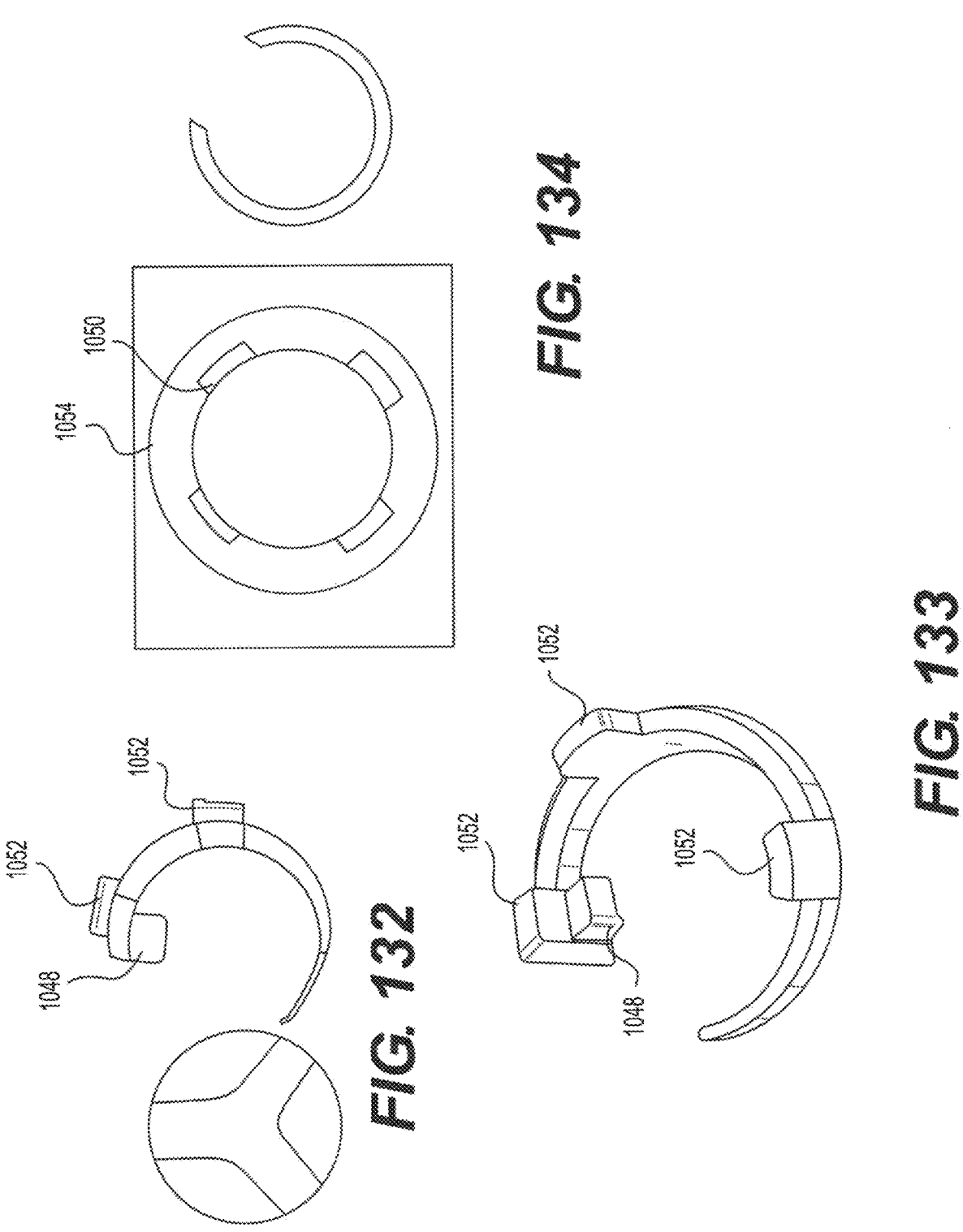

FIG. 133 is a diagram showing a close up view of one embodiment of a screw lock ring shown in FIG. 132.

FIG. 134 is a diagram showing a close up view of one embodiment of a housing.

Figure 135:
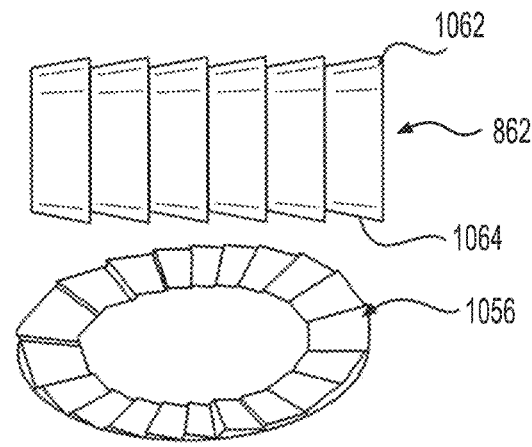

FIG. 135 is a diagram showing a close up view of an exemplary locking mechanism according to one embodiment of the present invention.

Figure 136:
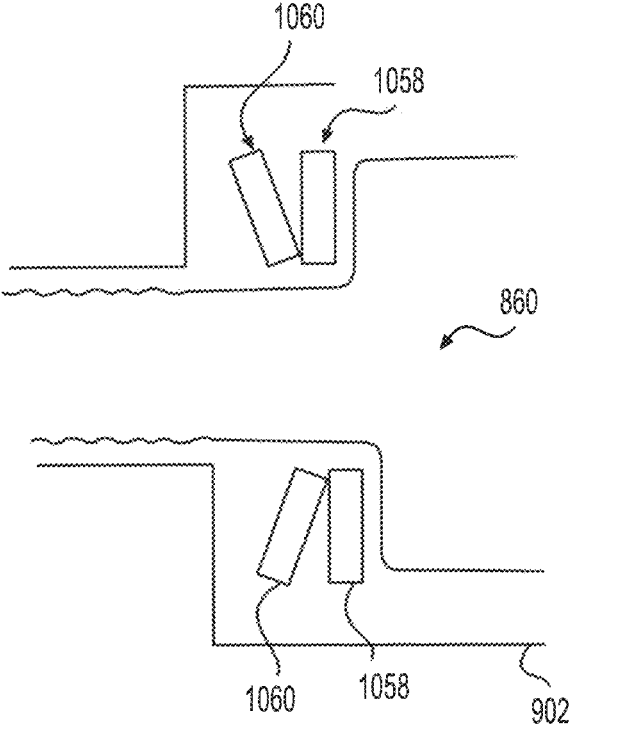

FIG. 136 is a diagram showing a side view of an exemplary locking mechanism according to one embodiment of the present invention.

FIG. 137 is a diagram showing an exemplary locking mechanism according to one embodiment of the present invention.

FIGS. 138A, 138B, and 138C are diagrams showing different aspects of a screw according to one embodiment of the present invention.

Figure 139:
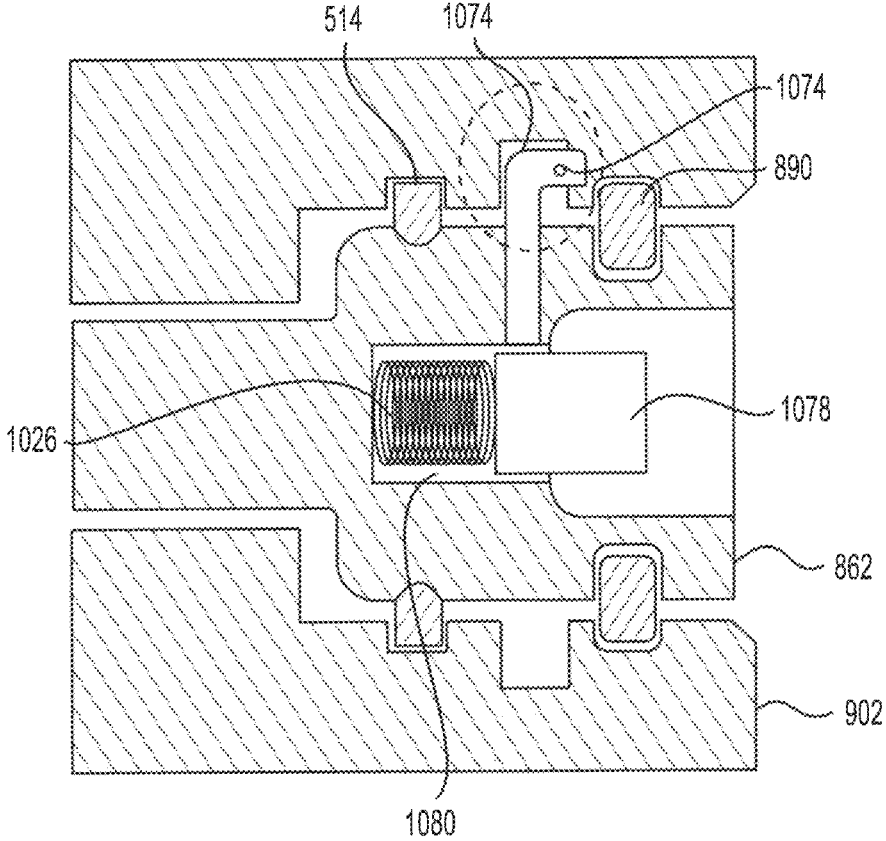

FIG. 139 is a diagram showing an exemplary locking mechanism according to one embodiment of the present invention.

Figures 140, 141:
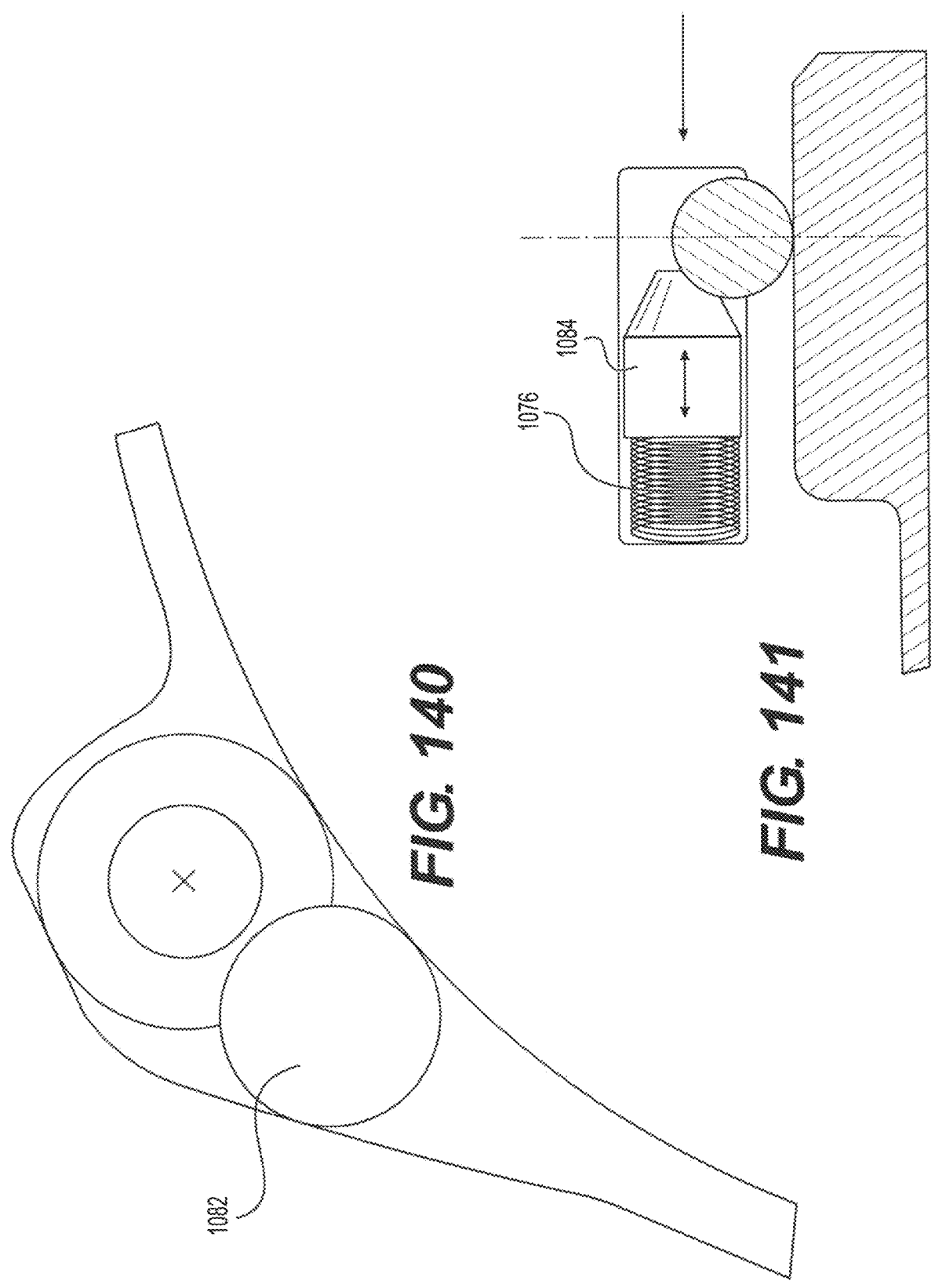

FIG. 140 is a diagram showing an exemplary locking mechanism according to one embodiment of the present invention.

FIG. 141 is a close up view of the exemplary locking mechanism shown in FIG. 140.

Figure 142:
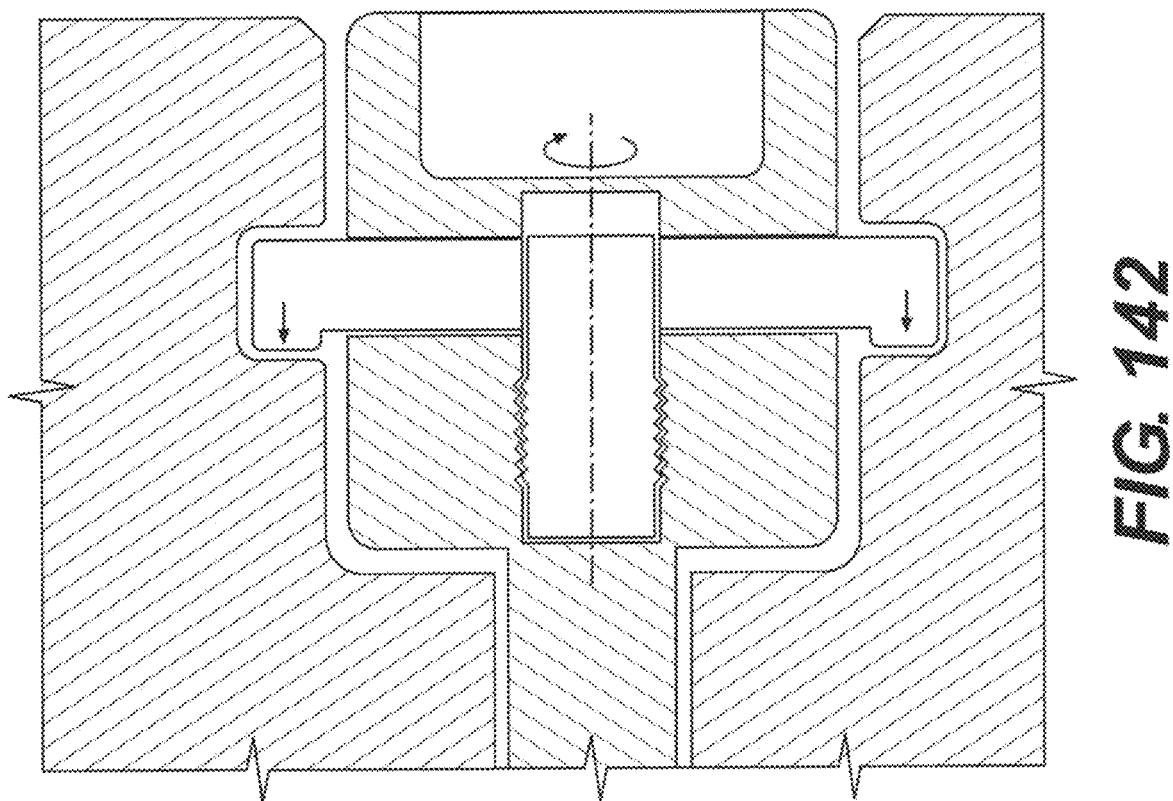

FIG. 142 is a diagram showing an exemplary locking mechanism according to one embodiment of the present invention.

Figure 143:
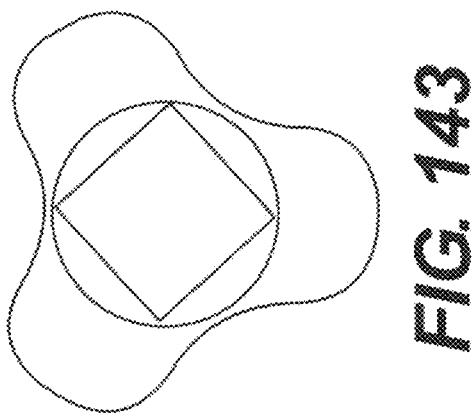

FIG. 143 is a diagram showing a top view of the exemplary locking mechanism shown in FIG. 142.

Figure 144:
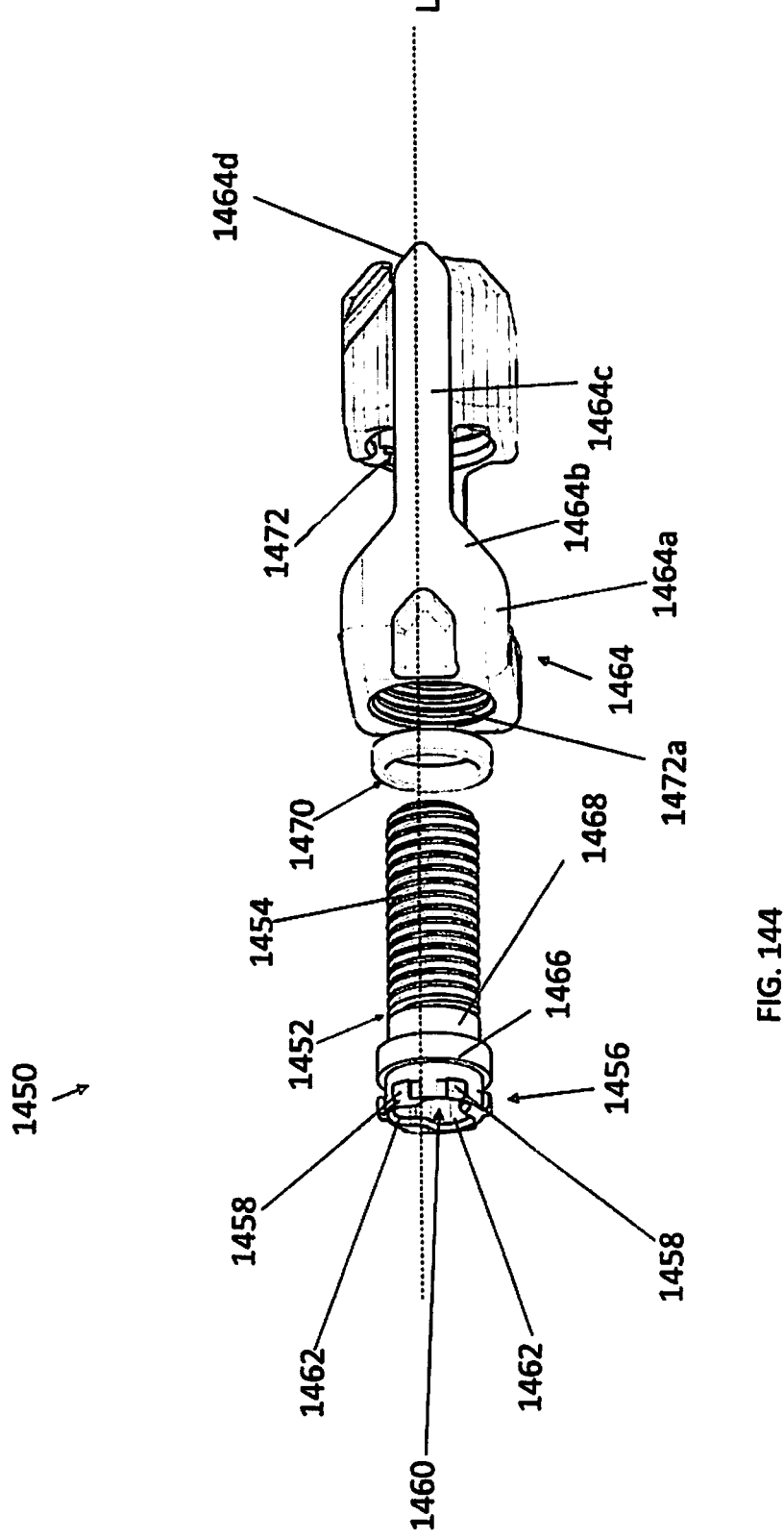

FIG. 144 illustrates an anti-rotation locking mechanism ("ARLM") in accordance with embodiments of the present disclosure.

Figure 145:
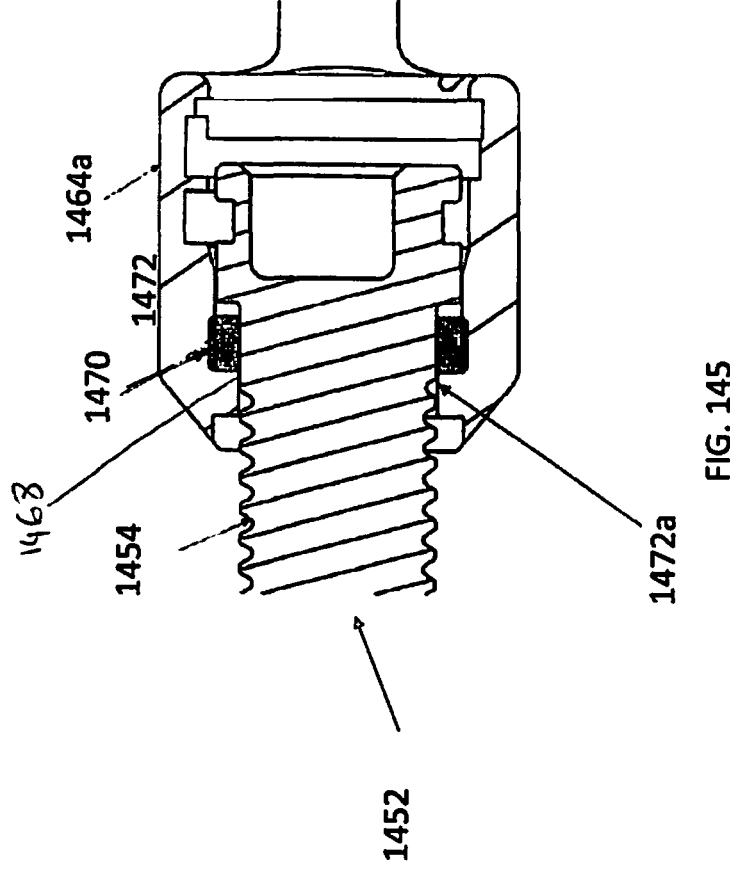

FIG. 145 is a cross-section of the ARLM of FIG. 144 in accordance with particular embodiments of the present disclosure.

Figure 146:
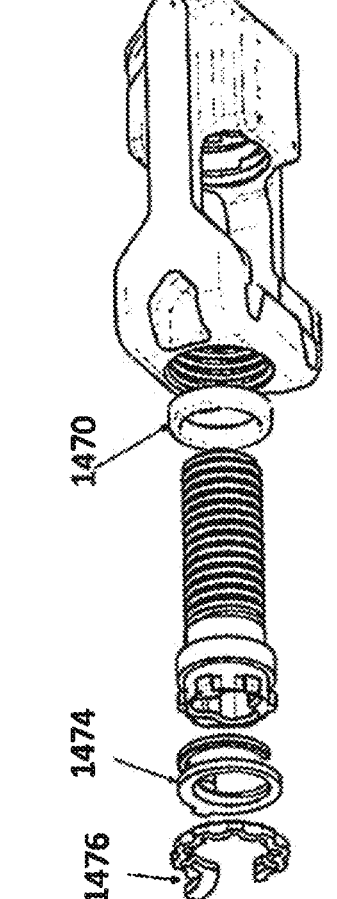

FIG. 146 illustrates the ARLM of FIG. 144 further including a locking member and a retaining member in accordance with embodiments of the present disclosure.

Figure 147:
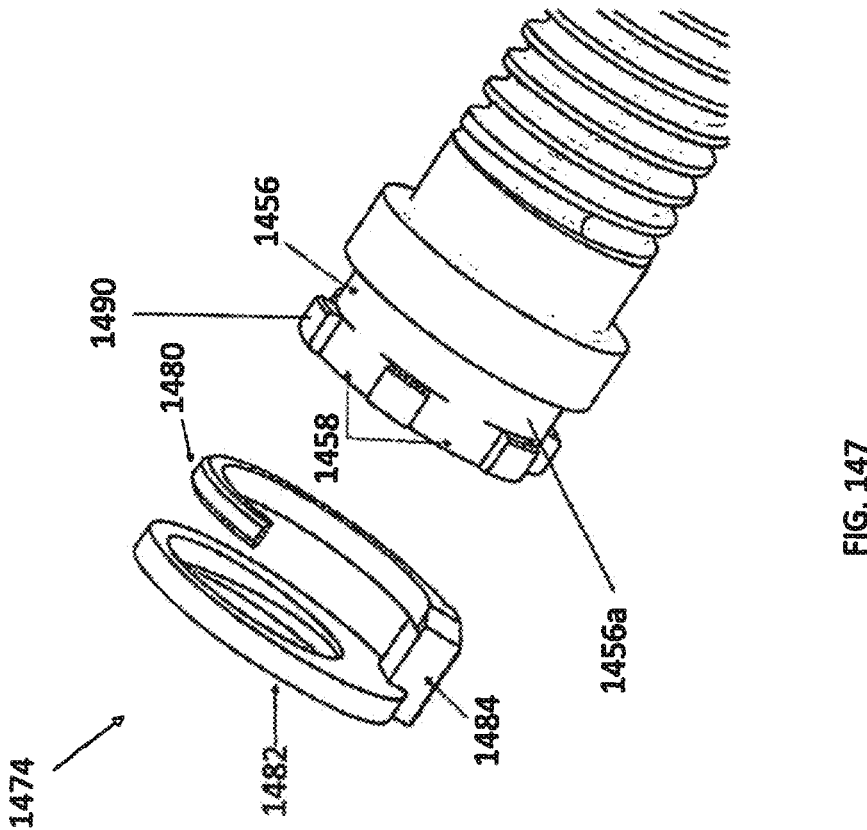

FIG. 147 is a close-up view of the locking member of FIG. 146 and a screw head in accordance with embodiments of the present disclosure.

Figure 148:
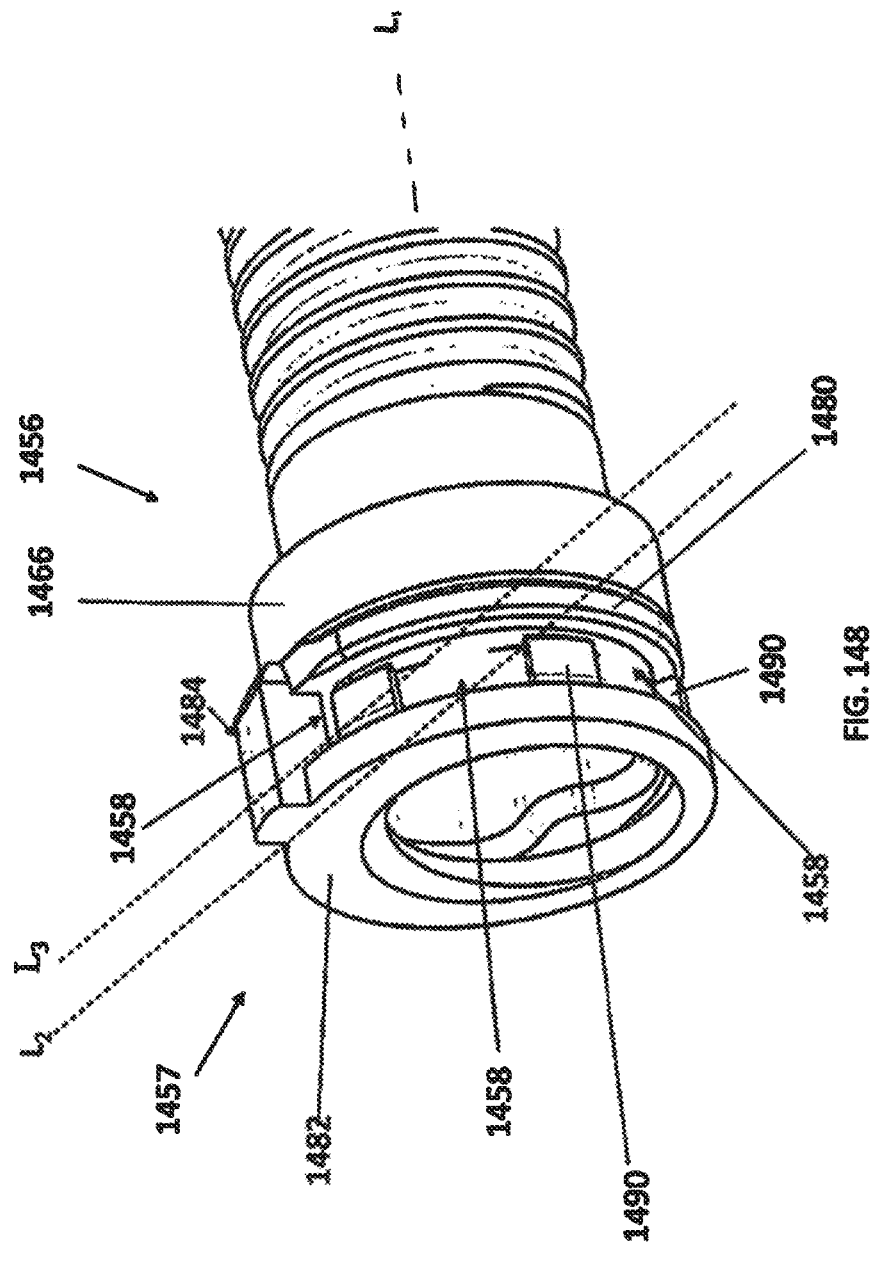

FIG. 148 illustrates a screw assembly in accordance with embodiments of the present disclosure.

FIG. 149A is a cross-section of the screw assembly of FIG. 148 inserted into the housing in accordance with embodiments of the present disclosure.

FIG. 149B is a cross-section of the screw head of FIG. 148 positioned in the housing in accordance with embodiments of the present disclosure.

Figure 150B:
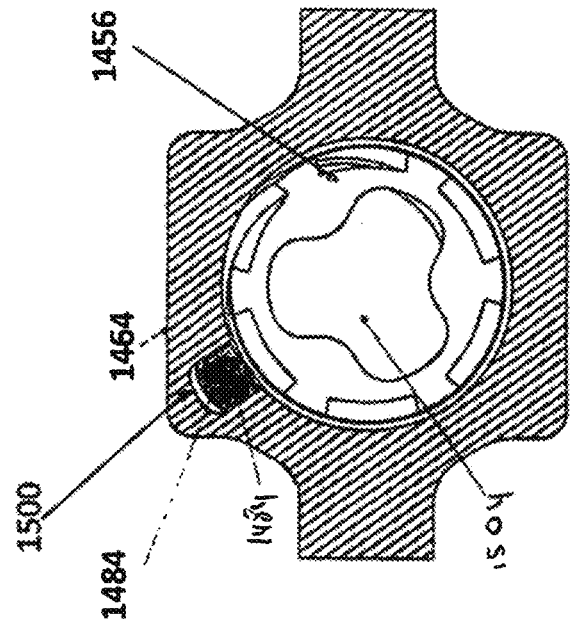
Figure 150A:
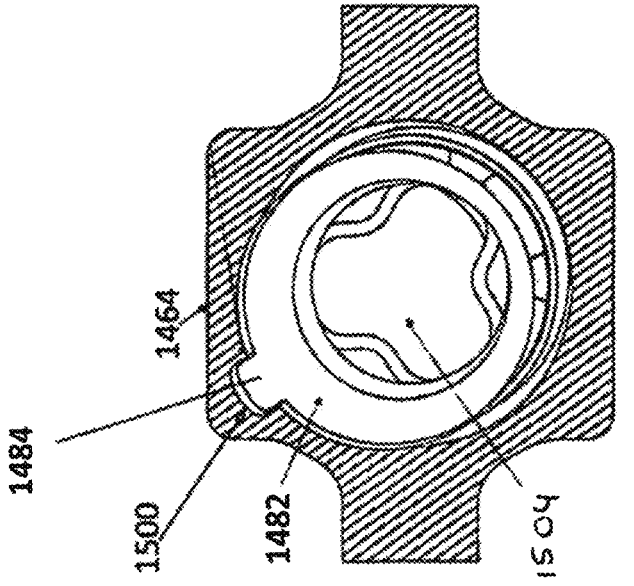

FIG. 150A is a cross-section of the screw assembly of FIG. 148 locked into the housing in accordance with embodiments of the present disclosure.

FIG. 150B is a cross-section of the screw head of FIG. 148 positioned in the housing in accordance with embodiments of the present disclosure.

Figure 151:
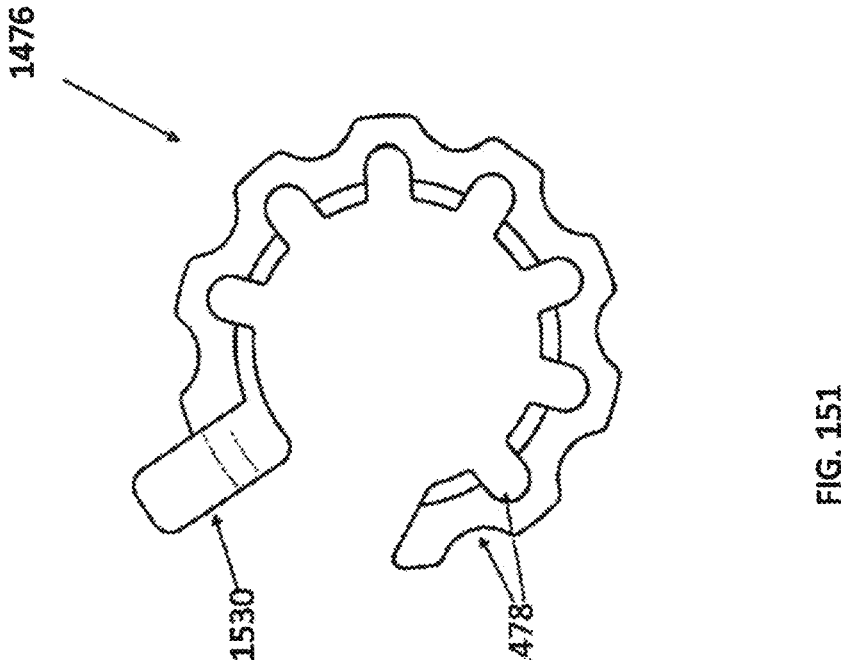

FIG. 151 illustrates a retaining member in accordance with embodiments of the present disclosure.

DETAILED DESCRIPTION

The following description of the preferred embodiment(s) is merely exemplary in nature and is in no way intended to limit the invention, its application, or uses.

A spinal fusion is typically employed to eliminate pain caused by the motion of degenerated disk material. Upon successful fusion, a fusion device becomes permanently fixed within the intervertebral disc space. Looking at FIG. 1, an exemplary embodiment of an expandable fusion device 10 is shown between adjacent vertebral bodies 2 and 3. The fusion device 10 engages the endplates 4 and 5 of the adjacent vertebral bodies 2 and 3 and, in the installed position, maintains normal intervertebral disc spacing and restores spinal stability, thereby facilitating an intervertebral fusion. The expandable fusion device 10 can be manufactured from a number of materials including titanium, stainless steel, titanium alloys, non-titanium metallic alloys, polymeric materials, plastics, plastic composites, PEEK, ceramic, and elastic materials. In an embodiment, the expandable fusion device 10 can be configured to be placed down an endoscopic tube and into the disc space between the adjacent vertebral bodies 2 and 3.

In an exemplary embodiment, bone graft or similar bone growth inducing material can be introduced around and within the fusion device 10 to further promote and facilitate the intervertebral fusion. The fusion device 10, in one embodiment, is preferably packed with bone graft or similar bone growth inducing material to promote the growth of bone through and around the fusion device. Such bone graft may be packed between the endplates of the adjacent vertebral bodies prior to, subsequent to, or during implantation of the fusion device.

With reference to FIGS. 2-7, an embodiment of the fusion device 10 is shown. In an exemplary embodiment, the fusion device 10 includes a first endplate 14, a second endplate 16, a central ramp 18, and a driving ramp 260. In an embodiment, the expandable fusion device 10 can be configured to be placed down an endoscopic tube and into the disc space between the adjacent vertebral bodies 2 and 3. One or more components of the fusion device 10 may contain features, such as through bores, that facilitate placement down an endoscopic tube. In an embodiment, components of the fusion device 10 are placed down the endoscopic tube with assembly of the fusion device 10 in the disc space.

Although the following discussion relates to the second endplate 16, it should be understood that it also equally applies to the first endplate 14 as the second endplate 16 is substantially identical to the first endplate 14 in embodiments of the present invention. Turning now to FIGS. 2-7 and 10, in an exemplary embodiment, the second endplate 16 has a first end 39 and a second end 41. In the illustrated embodiment, the second endplate 16 further comprise an upper surface 40 connecting the first end 39 and the second end 41, and a lower surface 42 connecting the first end 39 and the second end 41. In an embodiment, the second endplate 16 further comprises a through opening 44, as seen on FIG. 11. The through opening 44, in an exemplary embodiment, is sized to receive bone graft or similar bone growth inducing material and further allow the bone graft or similar bone growth inducing material to be packed in the central opening in the central ramp 18.

Figure 7:
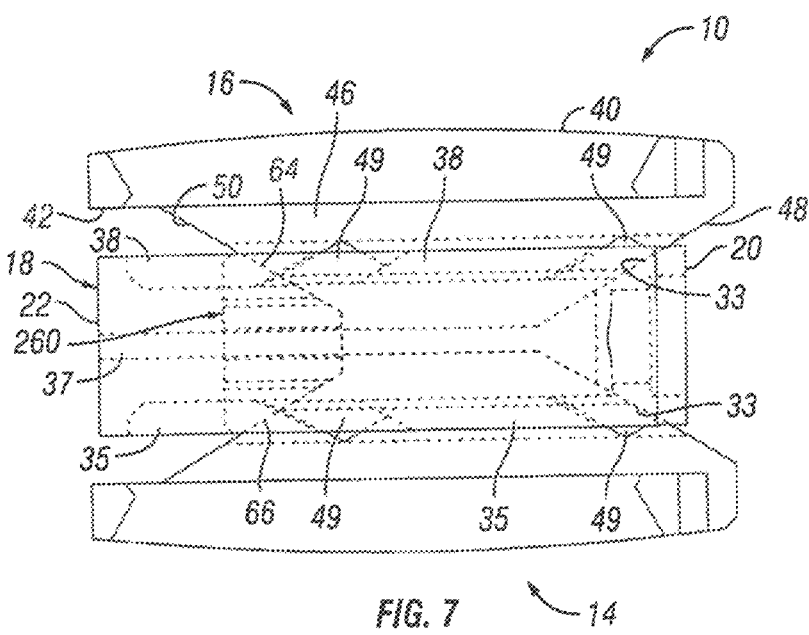
FIG. 7 is a side view of the expandable fusion device of FIG. 1 shown in an expanded position in accordance with one embodiment of the present invention.

As best seen in FIGS. 7 and 10, the lower surface 42 includes at least one extension 46 extending along at least a portion of the lower surface 42, in an embodiment. In an exemplary embodiment, the extension 46 can extend along a substantial portion of the lower surface 42, including, along the center of the lower surface 42. In the illustrated embodiment, the extension 46 includes a generally concave surface 47. The concave surface 47 can form a through bore with the corresponding concave surface 47 (not illustrated) of the first endplate 14, for example, when the device 10 is in an unexpanded configuration. In another exemplary embodiment, the extension 46 includes at least one ramped surface 48. In another exemplary embodiment, there are two ramped surfaces 48, 50 with the first ramped surface 48 facing the first end 39 and the second ramped surface facing the second end 41. In an embodiment, the first ramped surface 48 can be proximate the first end 39, and the second ramped surface 50 can be proximate the second end 41. It is contemplated that the slope of the ramped surfaces 48, 50 can be equal or can differ from each other. The effect of varying the slopes of the ramped surfaces 48, 50 is discussed below.

In one embodiment, the extension 46 can include features for securing the endplate 16 when the expandable fusion device 10 is in an expanded position. In an embodiment, the extension 46 includes one or more protuberances 49 extending from the lateral sides 51 of the extension. In the illustrated embodiment, there are two protuberances 49 extending from each of the lateral sides 51 with each of the sides 53 having one of the protuberances 49 extending from a lower portion of either end. As will be discussed in more detail below, the protuberances 49 can be figured to engage the central ramp 18 preventing and/or restricting longitudinal movement of the endplate 16 when the device 10 is in an expanded position.

Figure 15:
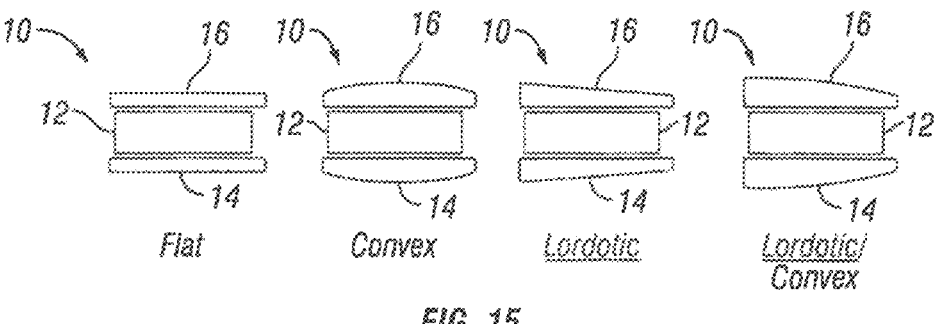
FIG. 15 is a side schematic view of the expandable fusion device of FIG. 1 having different endplates.

As illustrated in FIGS. 2-5, in one embodiment, the upper surface 40 of the second endplate 16 is flat and generally planar to allow the upper surface 40 of the endplate 16 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. While not illustrated, in an exemplary embodiment, the upper surface 40 includes texturing to aid in gripping the adjacent vertebral bodies. Although not limited to the following, the texturing can include teeth, ridges, friction increasing elements, keels, or gripping or purchasing projections.

Referring now to FIGS. 2-8, in an exemplary embodiment, the central ramp 18 has a first end 20, a second end 22, a first side portion 24 connecting the first end 20 and the second end 22, and a second side portion 26 (best seen on FIG. 5) on the opposing side of the central ramp 12 connecting the first end 20 and the second end 22. The first side portion 24 and the second side portion 26 may be curved, in an exemplary embodiment. The central ramp 18 further includes a lower end 28, which is sized to receive at least a portion of the first endplate 14, and an upper end 30, which is sized to receive at least a portion of the second endplate 16.

The first end 20 of the central ramp 18, in an exemplary embodiment, includes an opening 32. The opening 32 can be configured to receive an endoscopic tube in accordance with one or more embodiments. The first end 20 of the central ramp 18, in an exemplary embodiment, includes at least one angled surface 33, but can include multiple angled surfaces. The angled surface 33 can serve to distract the adjacent vertebral bodies when the fusion device 10 is inserted into an intervertebral space.

The second end 22 of the central ramp 18, in an exemplary embodiment, includes an opening 36. The opening 36 extends from the second end 22 of the central ramp 18 into a central guide 37 in the central ramp 18.

Figure 8:
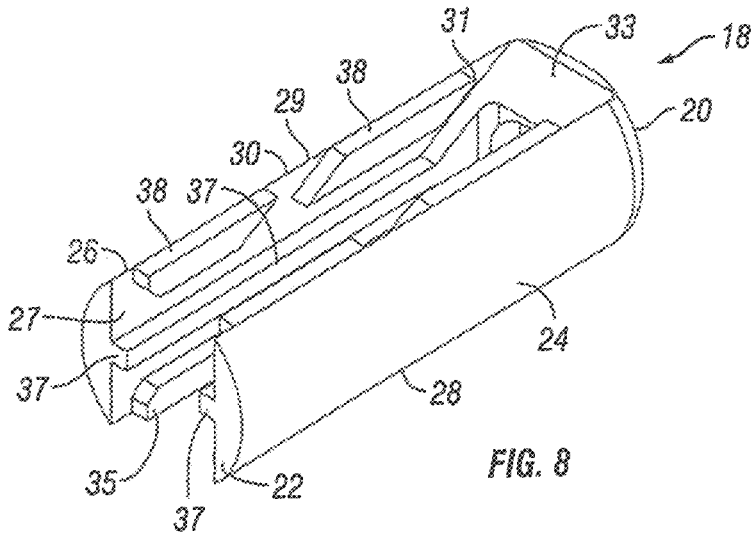
FIG. 8 is a perspective view of the central ramp of the expandable fusion device of FIG. 1 in accordance with one embodiment of the present invention.
Figure 9:
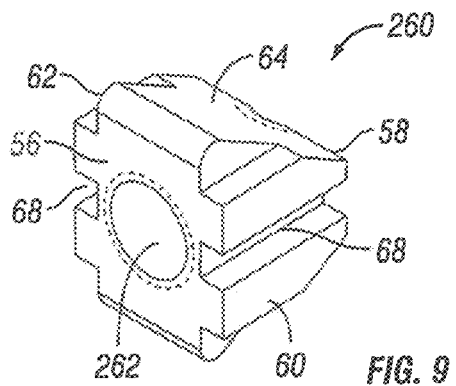
FIG. 9 is a perspective view of the driving ramp of the expandable fusion device of FIG. 1 in accordance with one embodiment of the present invention.
Figure 13:
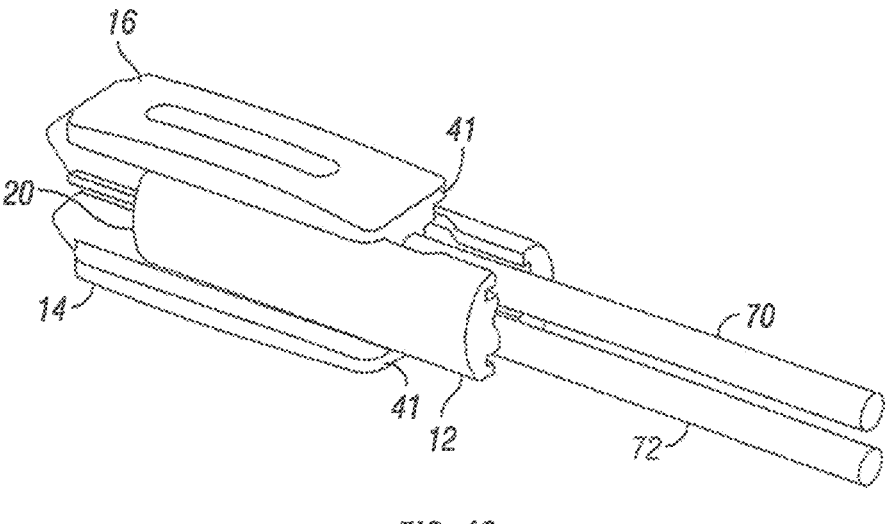
FIG. 13 is a perspective view showing placement of the central ramp of the expandable fusion device down an endoscopic tube and into the disc space in accordance with one embodiment of the present invention.
Figure 14:
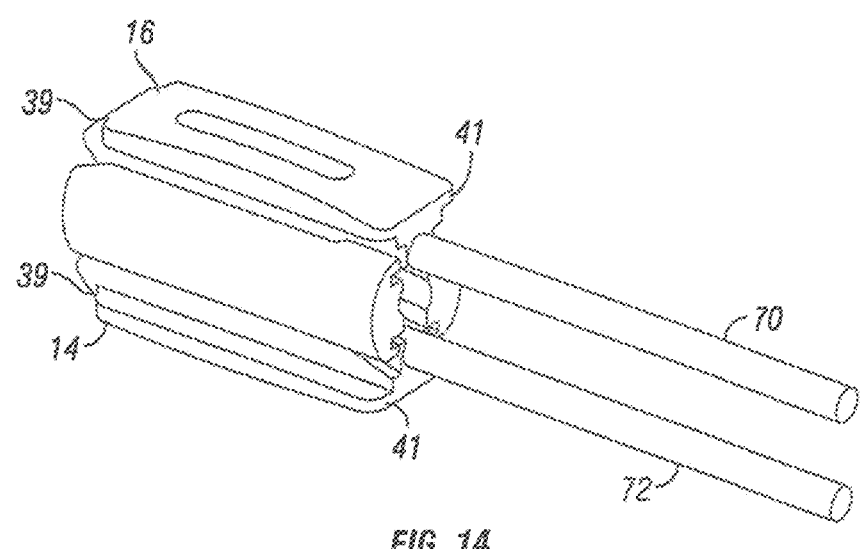
FIG. 14 is a perspective view showing expansion of the expandable fusion device in accordance with one embodiment of the present invention.

In an embodiment, the central ramp 18 further includes one or more ramped surfaces 33. As best seen in FIG. 8, the one or more ramped surfaces 33 positioned between the first side portion 24 and the second side portion 26 and between the central guide 37 and the second end 22. In an embodiment, the one or more ramped surfaces 33 face the second end 22 of the central ramp 18. In one embodiment, the central ramp 18 includes two ramped surfaces 33 with one of the ramped surfaces 33 being sloped upwardly and the other of the ramped surfaces 33 being sloped downwardly. The ramped surfaces 33 of the central ramp can be configured and dimensioned to engage the ramped surface 48 in each of the first and second endplates 14, 16.

Although the following discussion relates to the second side portion 26 of the central ramp 18, it should be understood that it also equally applies to the first side portion 24 in embodiments of the present invention. In the illustrated embodiment, the second side portion 26 includes an inner surface 27. In an embodiment, the second side portion 26 further includes a lower guide 35, a central guide 37, and an upper guide 38. In the illustrated embodiment, the lower guide 35, central guide 37, and the upper guide 38 extend out from the inner surface 27 from the second end 22 to the one or more ramped surfaces 31. In the illustrated embodiment, the second end 22 of the central ramp 18 further includes one or more guides 38. The guides 38 can serve to guide the translational movement of the first and second endplates 14, 16 with respect to the central ramp 18. For example, protuberances 49 on the second endplate 16 may be sized to be received between the central guide 37 and the upper guide 38. Protuberances 49 of the first endplate 16 may be sized to be received between the central guide 37 and the lower guide 35. A first slot 29 may be formed proximate the middle of the upper guide 38. A second slot 31 may be formed between end of the upper guide 38 and the one or more ramped surfaces 33. The protuberances 49 may be sized to be received within the first slot 29 and/or the second slot 31 when the device 10 is in the expanded position.

Referring now to FIGS. 4-7 and 9, the driving ramp 260 has a through bore 262. In an embodiment, the driving ramp 260 is generally wedge-shaped. As illustrated, the driving ramp 260 may comprise a wide end 56, a narrow end 58, a first side portion 60 connecting the wide end 56 and the narrow end 58, and a second side portion 62 connecting the wide end 56 and the narrow end 58. The driving ramp 260 further may comprise ramped surfaces, including an upper ramped surface 64 and an opposing lower ramped surface 66. The upper ramped surface 64 and the lower ramped surface 66 may be configured and dimensioned to engage the ramped surface 50 proximate the second end 41 in of the first and the second endplates 14, 16. The first and second side portions 60, 62 may each include grooves 68 that extend, for example, in a direction parallel to the longitudinal axis of the through bore 262. The grooves 68 may be sized to receive the central guide 37 on the interior surface 27 of each of the side portions 24, 26 of the central ramp 18. In this manner, the grooves 68 together with the central guide 37 can surface to guide the translational movement of the driving ramp 260 in the central ramp 18.

Figure 1:
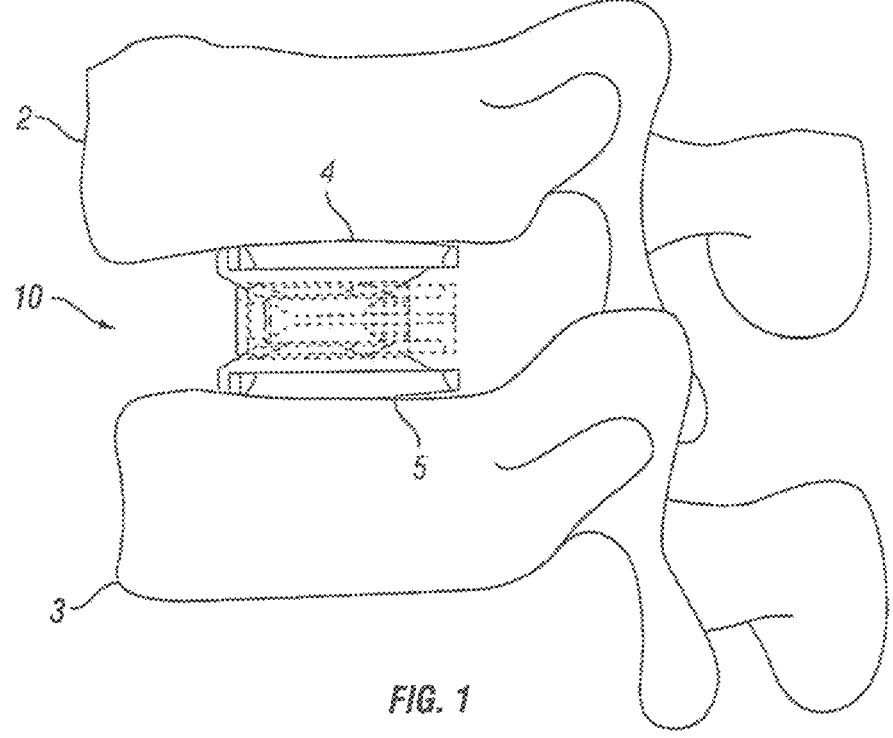
FIG. 1 is a side view of an embodiment of an expandable fusion device shown between adjacent vertebrae according to the present invention.
Figure 2:
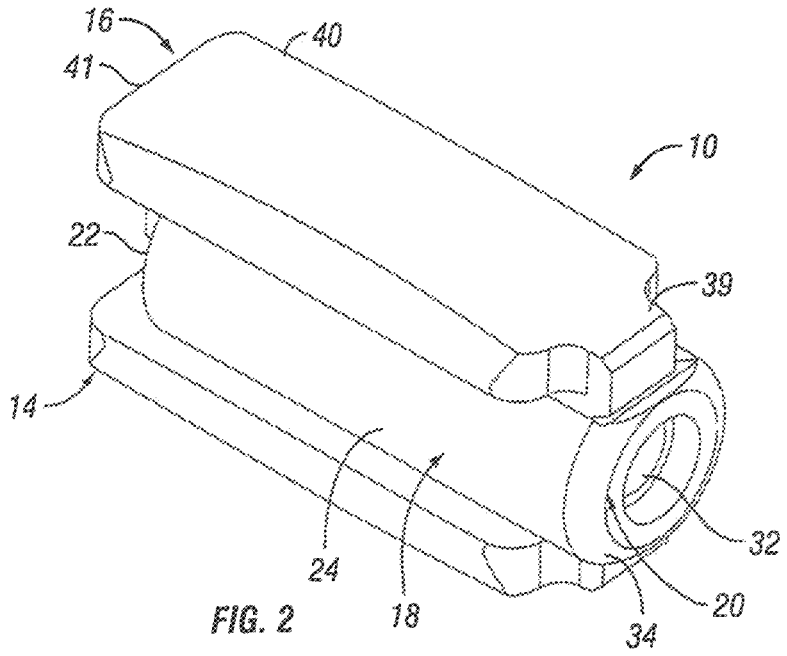
FIG. 2 is a front perspective view of the expandable fusion device of FIG. 1 shown in an unexpanded position in accordance with one embodiment of the present invention.
Figure 3:
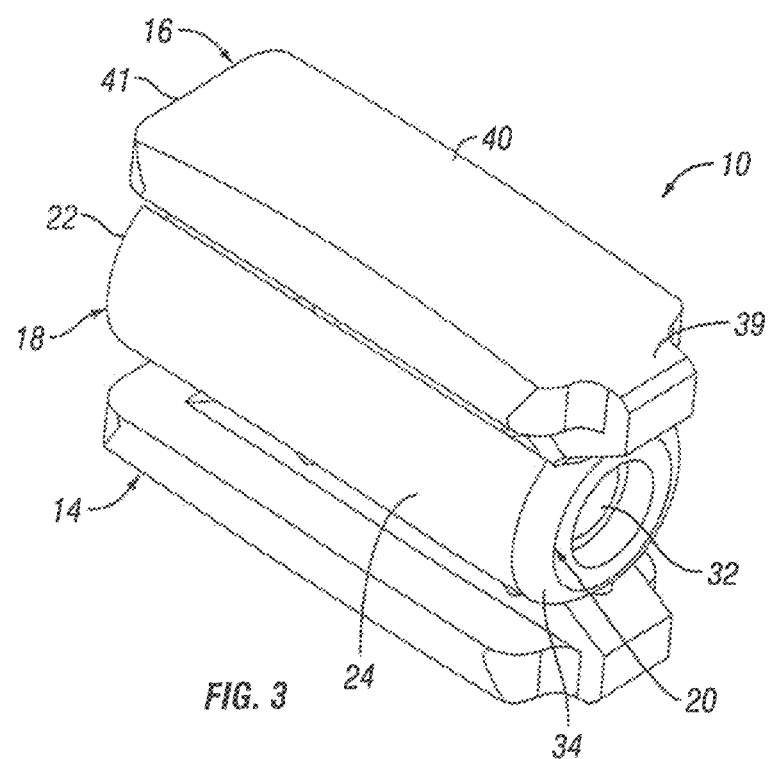
FIG. 3 is a front perspective view of the expandable fusion device of FIG. 1 shown in an expanded position in accordance with one embodiment of the present invention.
Figures 4, 5:
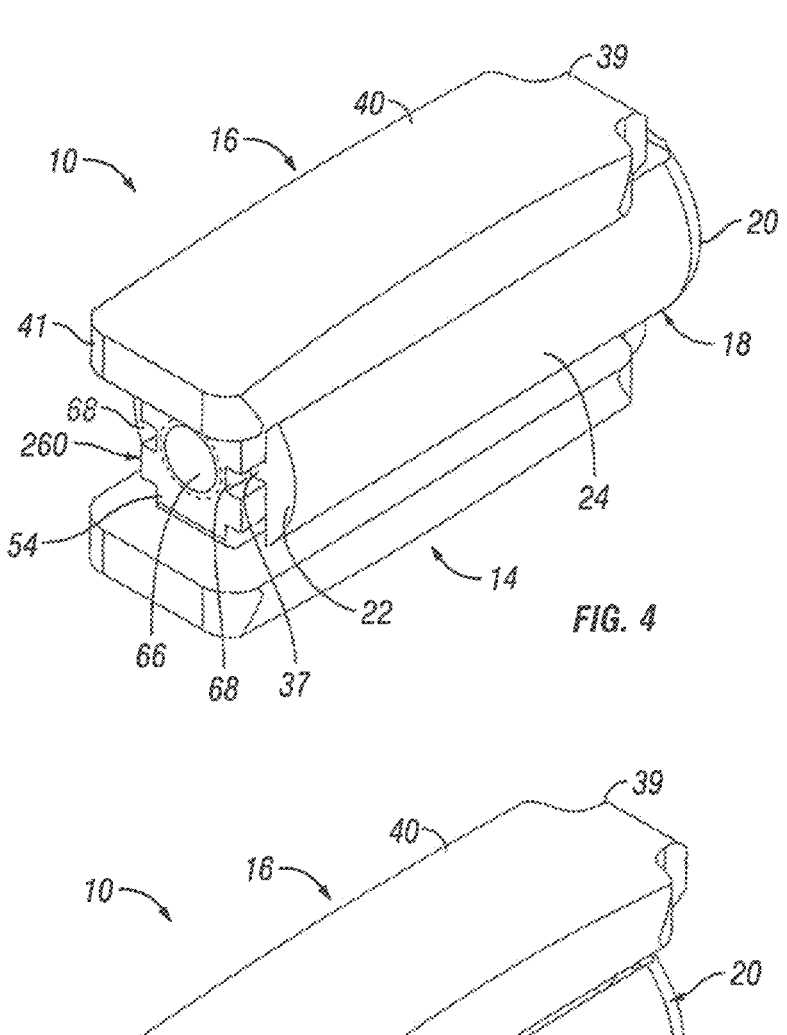
FIG. 4 is a rear perspective view of the expandable fusion device of FIG. 1 shown in an unexpanded position in accordance with one embodiment of the present invention.
FIG. 5 is a rear perspective view of the expandable fusion device of FIG. 1 shown in an expanded position in accordance with one embodiment of the present invention.
Figure 6:
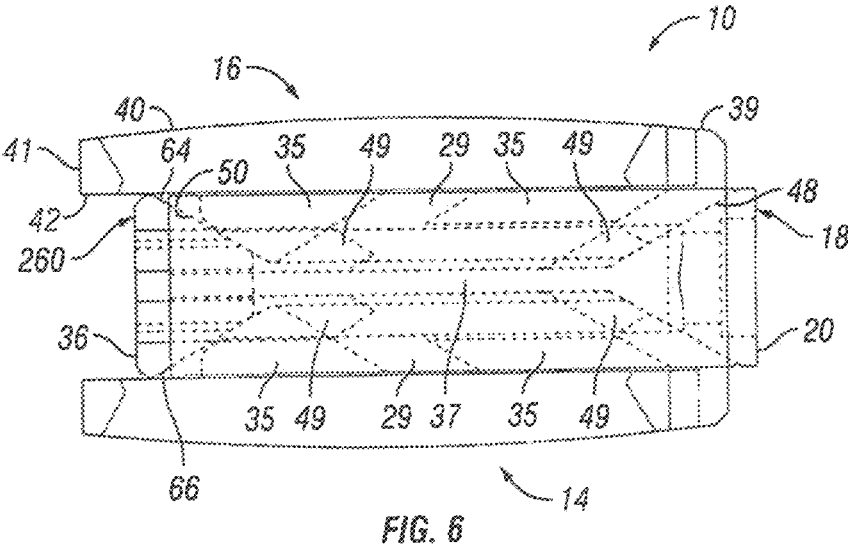
FIG. 6 is a side view of the expandable fusion device of FIG. 1 shown in an unexpanded position in accordance with one embodiment of the present invention.

A method of installing the expandable fusion device 10 of FIG. 1 is now discussed in accordance with one embodiment of the present invention. Prior to insertion of the fusion device 10, the intervertebral space is prepared. In one method of installation, a discectomy is performed where the intervertebral disc, in its entirety, is removed. Alternatively, only a portion of the intervertebral disc can be removed. The endplates of the adjacent vertebral bodies 2, 3 are then scraped to create an exposed end surface for facilitating bone growth across the intervertebral space. One or more endoscopic tubes can then be inserted into the disc space. The expandable fusion device 10 can then be introduced into the intervertebral space down an endoscopic tube and seated in an appropriate position in the intervertebral disc space.

After the fusion device 10 has been inserted into the appropriate position in the intervertebral disc space, the fusion device 10 can then be expanded into the expanded position. To expand the fusion device 10, the driving ramp 260 may be moved in a first direction with respect to the central ramp 18. Translational movement of the driving ramp 260 through the central ramp 18 may be guided by the central guide 37 on each of the first and second side portions 24, 26 of the central ramp 18. As the driving ramp 260 moves, the upper ramped surface 64 pushes against the ramped surface 50 proximate the second end 41 of the second endplate 16, and the lower ramped surface 66 pushes against the ramped surface 50 proximate the second end 41 of the first endplate 14. In addition, the ramped surfaces 33 in the central ramp 18 push against the ramped surface 48 proximate the first end 41 of the first and second endplates 14, 16. In this manner, the first and second endplates 14, 16 are pushed outwardly into an expanded configuration. As discussed above, the central ramp 16 includes locking features for securing the endplates 14, 16.

Figure 16:
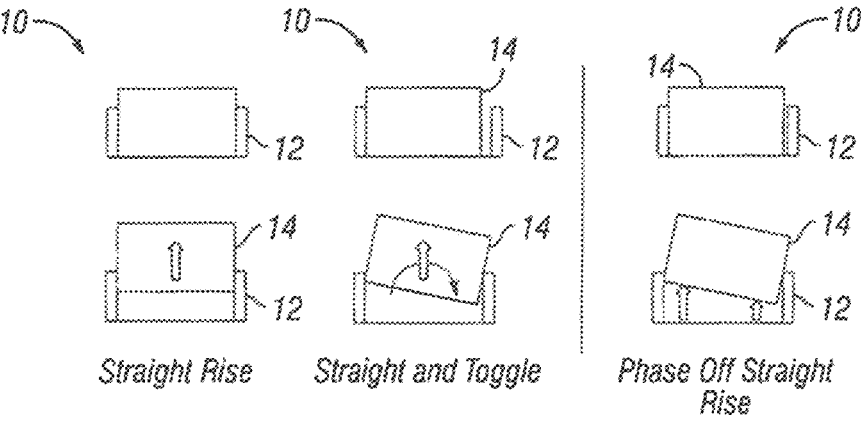
FIG. 16 is a partial side schematic view of the expandable fusion device of FIG. 1 showing different modes of endplate expansion.

It should also be noted that the expansion of the endplates 14, 16 can be varied based on the differences in the dimensions of the ramped surfaces 48, 50 and the angled surfaces 62, 64. As best seen in FIG. 16, the endplates 14, 16 can be expanded in any of the following ways: straight rise expansion, straight rise expansion followed by a toggle into a lordotic expanded configuration, or a phase off straight rise into a lordotic expanded configuration.

Turning back to FIGS. 2-7, in the event the fusion device 10 needs to be repositioned or revised after being installed and expanded, the fusion device 10 can be contracted back to the unexpanded configuration, repositioned, and expanded again once the desired positioning is achieved. To contract the fusion device 10, the central ramp 18 is moved with respect to the central ramp 260 away from the central ramp 260. As the central ramp 18 moves, the ramped surfaces 33 in the central ramp 18 ride along the ramped surfaces 48 of the first and second endplates 14, 16 with the endplates 14, 16 moving inwardly into the unexpanded position.

Figure 17:
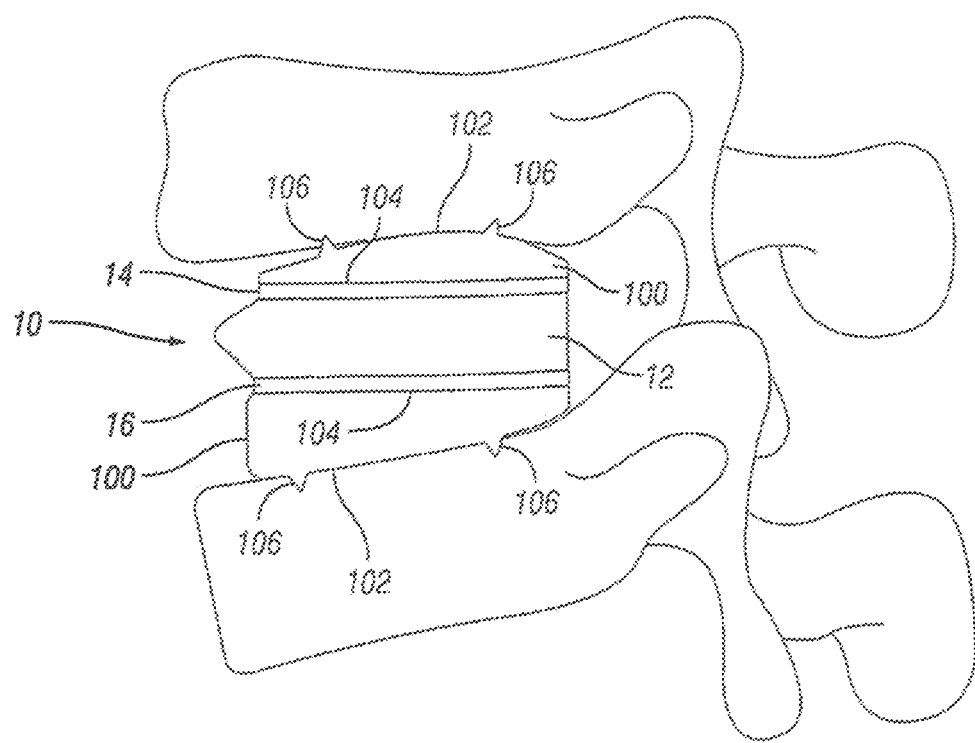
FIG. 17 is a side schematic view of the expandable fusion device of FIG. 1 with artificial endplates shown between adjacent vertebrae.
Figure 18:
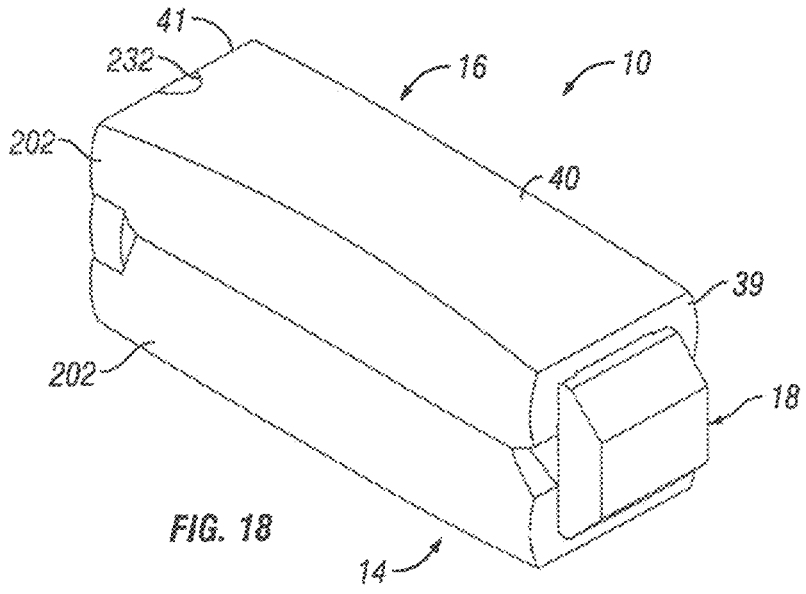
FIG. 18 is a front perspective view of an alternative embodiment of an expandable fusion device shown in an unexpanded position in accordance with one embodiment of the present invention.

With reference now to FIG. 17, fusion device 10 is shown with an exemplary embodiment of artificial endplates 100. Artificial endplates 100 allows the introduction of lordosis even when the endplates 14 and 16 of the fusion device 10 are generally planar. In one embodiment, the artificial endplates 100 have an upper surface 102 and a lower surface 104. The upper surfaces 102 of the artificial endplates 100 have at least one spike 106 to engage the adjacent vertebral bodies. The lower surfaces 104 have complementary texturing or engagement features on their surfaces to engage with the texturing or engagement features on the upper endplate 14 and the lower endplate 16 of the fusion device 10. In an exemplary embodiment, the upper surface 102 of the artificial endplates 100 have a generally convex profile and the lower surfaces 104 have a generally parallel profile to achieve lordosis. In another exemplary embodiment, fusion device 10 can be used with only one artificial endplate 100 to introduce lordosis even when the endplates 14 and 16 of the fusion device 10 are generally planar. The artificial endplate 100 can either engage endplate 14 or engage endplate 16 and function in the same manner as described above with respect to two artificial endplates 100.

With reference to FIGS. 11-14, an embodiment for placing an expandable fusion device 10 into an intervertebral disc space is illustrated. The expandable fusion device 10 can be introduced into the intervertebral space down an endoscopic tube utilizing a tool 70 that is attached to endplate 16, with the second endplate 16 being first placed down the tube with tool 70 and into the disc space, as seen in FIG. 11. After insertion of the second endplate 16, the first endplate 14 can be placed down the same endoscopic tube with tool 72 and into the disc space, as shown on FIG. 12. Following the first endplate 14, the central ramp 12 can be placed down the same endoscopic tube and into the disc space guided by tools 70 and 72, as shown on FIGS. 13 and 14.

Referring now to FIGS. 18-23, an alternative embodiment of the expandable fusion device 10 is shown. In an exemplary embodiment, the fusion device 10 includes a first endplate 14, a second endplate 16, a central ramp 18, and an actuator assembly 200. As will be discussed in more detail below, the actuator assembly 200 drives the central ramp 18 which forces apart the first and second endplates 14, 16 to place the expandable fusion device in an expanded position. One or more components of the fusion device 10 may contain features, such as through bores, that facilitate placement down an endoscopic tube. In an embodiment, components of the fusion device 10 are placed down the endoscopic tube with assembly of the fusion device 10 in the disc space.

Although the following discussion relates to the second endplate 16, it should be understood that it also equally applies to the first endplate 14 as the second endplate 16 is substantially identical to the first endplate 14 in embodiments of the present invention. With additional reference to FIG. 24, in an exemplary embodiment, the second endplate 16 has a first end 39 and a second end 41. In the illustrated embodiment, the second endplate 16 further comprise an upper surface 40 connecting the first end 39 and the second end 41, and a lower surface 42 connecting the first end 39 and the second end 41. While not illustrated, in an embodiment, the second endplate 16 further comprises a through opening. The through opening, in an exemplary embodiment, is sized to receive bone graft or similar bone growth inducing material.

In one embodiment, the upper surface 40 of the second endplate 16 is flat and generally planar to allow the upper surface 40 of the endplate 16 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. While not illustrated, in an exemplary embodiment, the upper surface 40 includes texturing to aid in gripping the adjacent vertebral bodies. Although not limited to the following, the texturing can include teeth, ridges, friction increasing elements, keels, or gripping or purchasing projections.

In one embodiment, the second endplate 16 further comprises a first side portion 202 connecting the first end 39 and the second end 41, and a second side portion 204 connecting the first end 39 and the second end 41. In the illustrated embodiment, the first and second side portions 202, 204 are extensions from the lower surface 42. In an exemplary embodiment, the first and second side portions 202, 204 each include ramped surfaces 206, 208. In the illustrated embodiment, the ramped surfaces 206, 208 extend from the first end 39 of the second endplate 16 to bottom surfaces 210, 212 of each of the side portions 202, 204. In one embodiment, the ramped surfaces 206, 208 are forward facing in that the ramped surfaces 206, 208 face the first end 39 of the second endplate. As previously discussed, the slope of the ramped surfaces 206, 208 may be varied as desired for a particular application.

Figure 24:
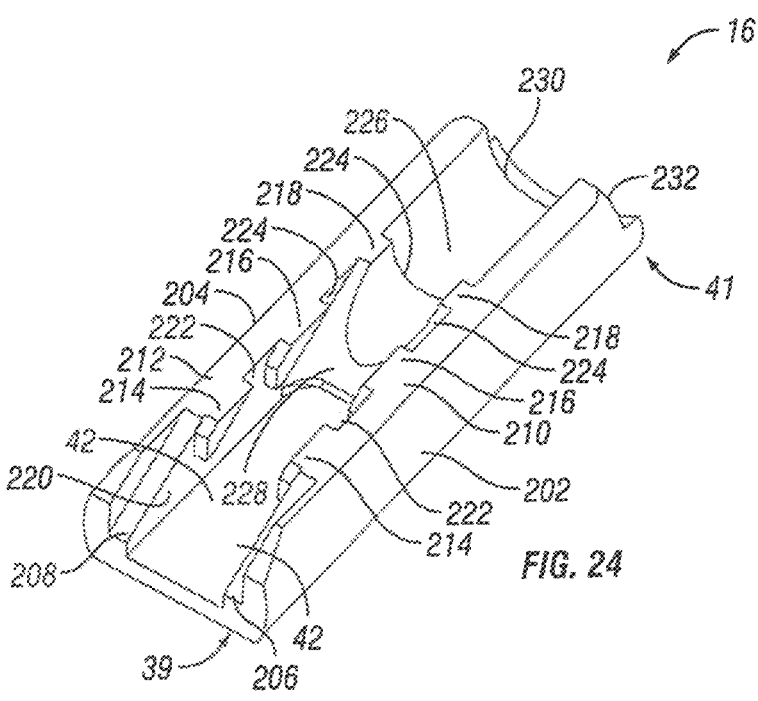
FIG. 24 is a perspective of an endplate of the expandable fusion device of FIG. 18 in accordance with one embodiment of the present invention.

In an embodiment, the first and second side portions 202, 204 each comprise at least one protuberance 214. In an exemplary embodiment, the first and second side portions 202, 204 each comprise a first protuberance 214, a second protuberance 216, and a third protuberance 218. In one embodiment, the protuberances 214, 216, 218 extend from the interior surface 220 of the first and second side portions 202, 204. In an exemplary embodiment, the protuberances 214, 216, 218 extend at the lower side of the interior surface 220. As best seen in FIG. 24, the first and the second protuberances 214, 216 form a first slot 222, and the second and third protuberances 216, 218 form a second slot 224.

As best seen in FIG. 24, the lower surface 42 of the second endplate 16, in an embodiment, includes a central extension 224 extending along at least a portion of the lower surface. In the illustrated embodiment, the central extension 224 extends between the first and second side portions 202 and 204. In an exemplary embodiment, the central extension 224 can extend from the second end 41 of the endplate 16 to the central portion of the endplate. In one embodiment, the central extension 224 includes a generally concave surface 226 configured and dimensioned to form a through bore with the corresponding concave surface 226 (not illustrated) of the first endplate 14. The central extension 224 can further include, in an exemplary embodiment, a ramped surface 228. In the illustrated embodiment, the ramped surface 228 faces the first end 39 of the endplate 16. The ramped surface 228 can be at one end of the central extension 224. In an embodiment, the other end of the central extension 224 forms a stop 230. In the illustrated embodiment, the stop 230 is recessed from the second end 41 of the second endplate 16.

Figure 25:
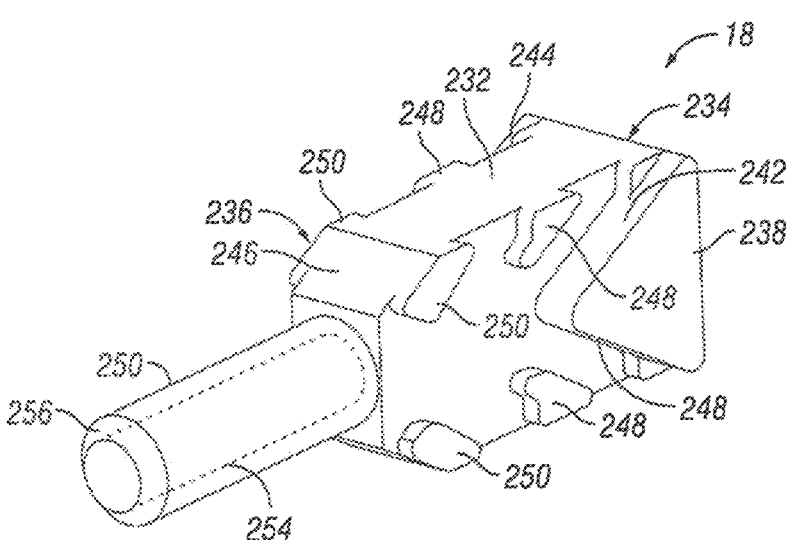
FIG. 25 is a perspective view of the central ramp of the expandable fusion device of FIG. 18 in accordance with one embodiment of the present invention.
Figure 26:
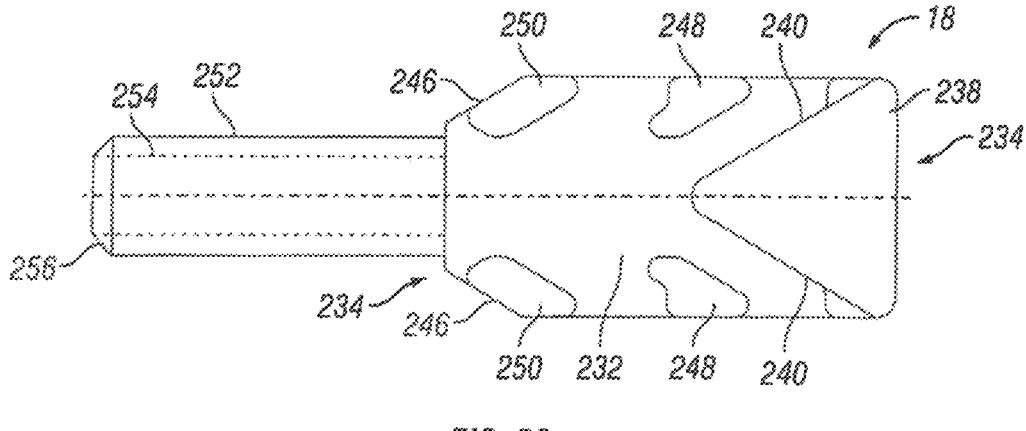
FIG. 26 is a side view of the central ramp of the expandable fusion device of FIG. 18 in accordance with one embodiment of the present invention.
Figure 27:
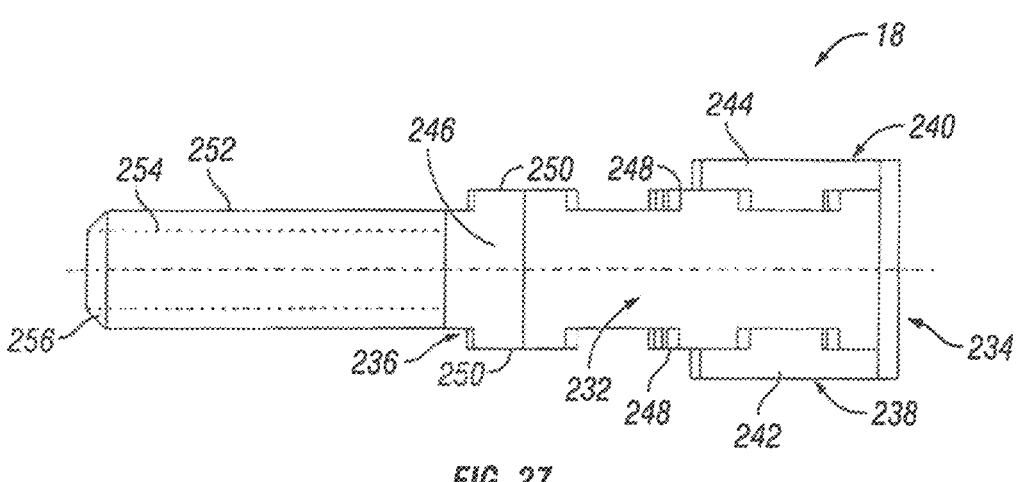
FIG. 27 is a top view of the central ramp of the expandable fusion device of FIG. 18 in accordance with one embodiment of the present invention.

Referring to FIGS. 25-27, in an exemplary embodiment, the central ramp 18 includes a body portion 232 having a first end 234 and a second end 236. In an embodiment, the body portion 232 includes at least a first expansion portion 238. In an exemplary embodiment, the body portion 232 includes a first expansion portion 238 and a second expansion portion 240 extending from opposing sides of the body portion with each of the first and second expansion portions 238, 240 having a generally triangular cross-section. In one embodiment, the expansion portions 238, 240 each have angled surfaces 242, 244 configured and dimensioned to engage the ramped surfaces 206, 208 of the first and second endplates 14, 16 and force apart the first and second endplates 14, 16. In an embodiment, the engagement between the angled surfaces 242, 244 of the expansion portions 238, 240 with the ramped surfaces 206, 208 of the first and second endplates 14, 16 may be described as a dovetail connection.

The second end 236 of the central ramp 18, in an exemplary embodiment, includes opposing angled surfaces 246. The angled surfaces 246 can be configured and dimensioned to engage the ramped surface 228 in the central extension 224 in each of the first and second endplates 14, 16. In other words, one of the angled surfaces 246 can be upwardly facing and configured, in one embodiment, to engage the ramped surface 228 in the central extension 224 in the second endplate 16. In an embodiment, the engagement between the angled surfaces 246 of the second end 236 of the central ramp 18 with the ramped surface 228 in the first and second endplates 14, 16 may be described as a dovetail connection.

The second end 236, in an exemplary embodiment, can further include an extension 252. In the illustrated embodiment, the extension 252 is generally cylindrical in shape with a through bore 254 extending longitudinally therethrough. In one embodiment, the extension 252 can include a beveled end 256. While not illustrated, at least a portion of the extension 252 can be threaded.

Figure 19:
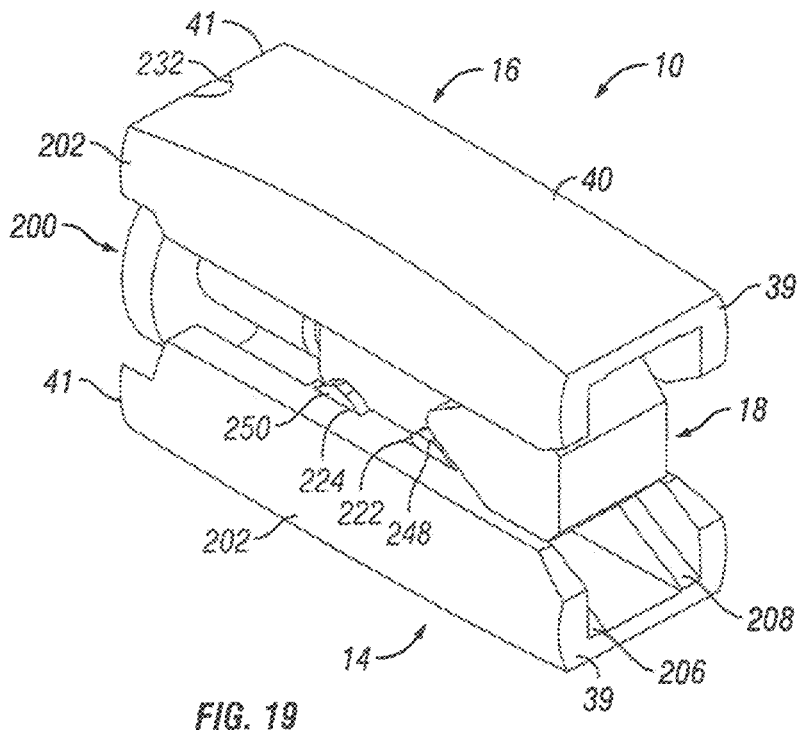
FIG. 19 is a front perspective view of the expandable fusion device of FIG. 18 shown in an expanded position in accordance with one embodiment of the present invention.
Figure 20:
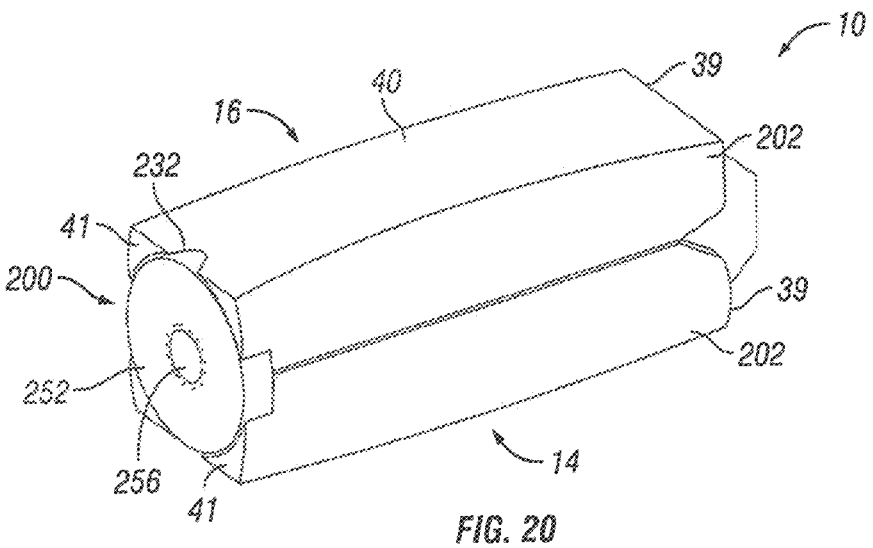
FIG. 20 is a rear perspective view of the expandable fusion device of FIG. 18 shown in an unexpanded position in accordance with one embodiment of the present invention.
Figure 21:
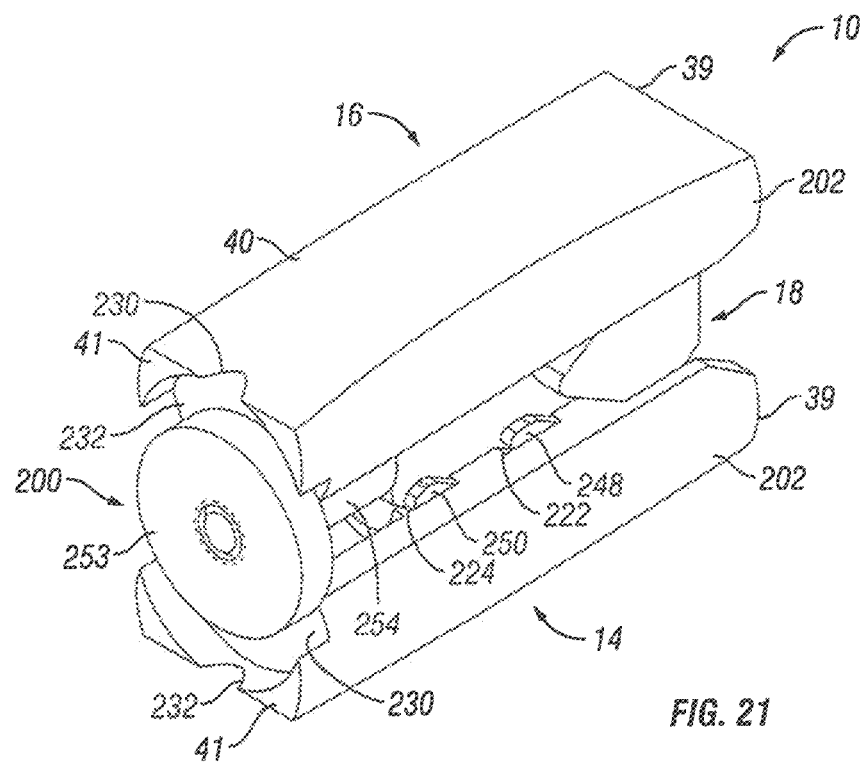
FIG. 21 is a rear perspective view of the expandable fusion device of FIG. 18 shown in an expanded position in accordance with one embodiment of the present invention.

Referring still to FIGS. 25-27, the central ramp 18 can further include features for securing the first and second endplates 14, 16 when the expandable fusion device 10 is in an expanded position. In an embodiment, the body portion 232 of the central ramp 18 includes one or more protuberances 248, 250 extending from opposing sides of the body portion 232. As illustrated, the protuberances 248, 250, in one embodiment, can be spaced along the body portion 232. In an exemplary embodiment, the protuberances 248, 250 can be configured and dimensioned for insertion into the corresponding slots 222, 224 in the first and second endplates 14, 16 when the device 10 is in an expanded position, as best seen in FIGS. 19 and 21. The protuberances 248, 250 can engage the endplates 14, 16 preventing and/or restricting movement of the endplates 14, 16 with respect to the central ramp 18 after expansion of the device 10.

With reference to FIGS. 20-23, in an exemplary embodiment, the actuator assembly 200 has a flanged end 253 configured and dimensioned to engage the stop 232 in the central extension 224 of the first and the second endplates 14, 16. In an embodiment, the actuator assembly 200 further includes an extension 254 that extends from the flanged end 253. In a further embodiment, the actuator assembly 200 includes a threaded hole 256 that extends through the actuator assembly 200. It should be understood that, while the threaded hole 256 in the actuator assembly 200 is referred to as threaded, the threaded hole 256 may only be partially threaded in accordance with one embodiment. In an exemplary embodiment, the threaded hole 256 is configured and dimensioned to threadingly receive the extension 252 of the central ramp 18.

Figure 28:
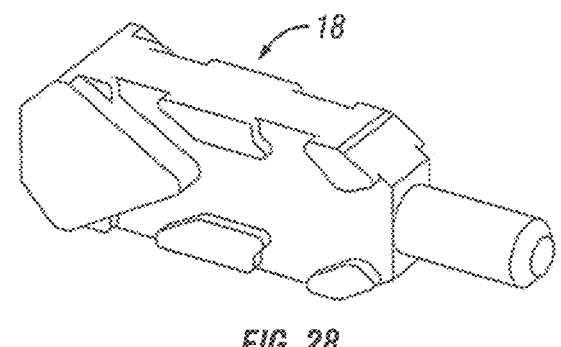
FIG. 28 a perspective view showing placement of the central ramp of the expandable fusion device of FIG. 18 in accordance with one embodiment of the present invention.
Figure 29:
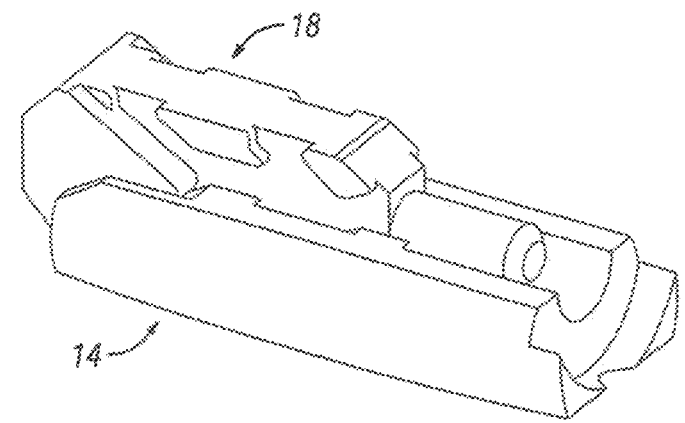
FIG. 29 is a perspective view showing placement of the first endplate of the expandable fusion device of FIG. 18 in accordance with one embodiment of the present invention.
Figure 30:
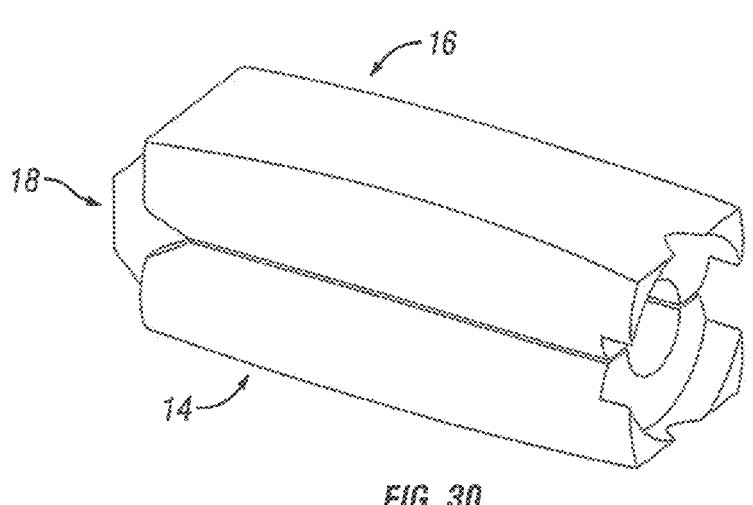
FIG. 30 is a perspective view showing placement of the second endplate of the expandable fusion device of FIG. 18 in accordance with one embodiment of the present invention.
Figure 31:
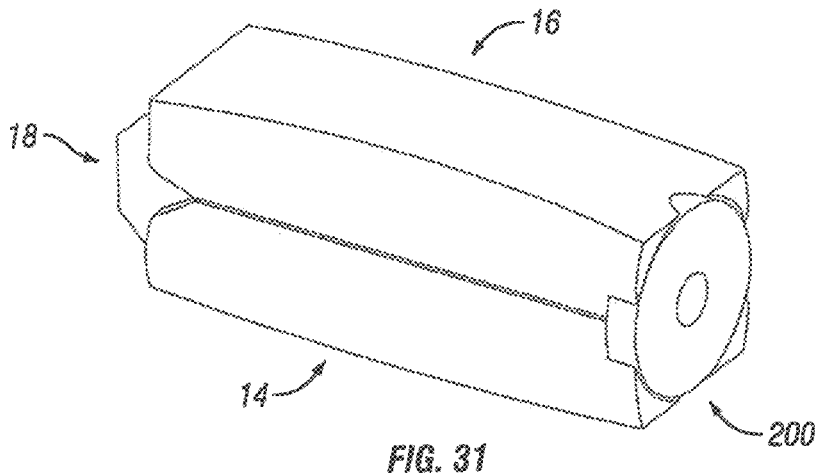
FIG. 31 is a perspective view showing placement of the actuation member of the expandable fusion device of FIG. 18 in accordance with one embodiment of the present invention.
Figure 32:
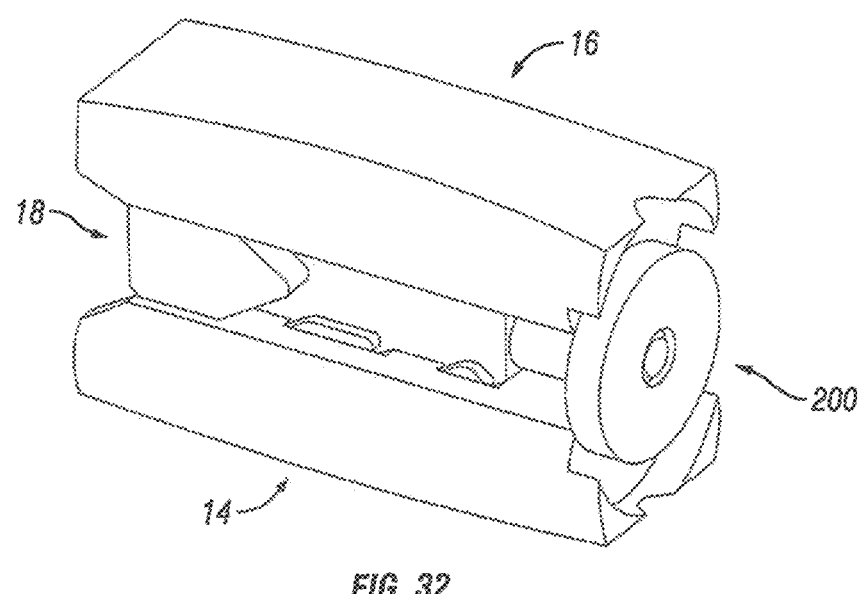
FIG. 32 is a perspective view showing expansion of the expandable fusion device of FIG. 18 in accordance with one embodiment of the present invention.
Figure 33:
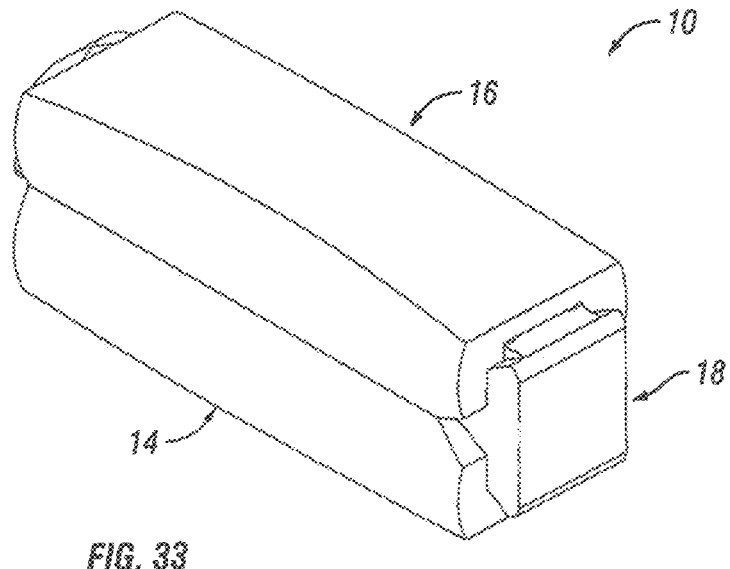
FIG. 33 is a front perspective view of an alternative embodiment of an expandable fusion device shown in an unexpanded position in accordance with one embodiment of the present invention.
Figure 34:
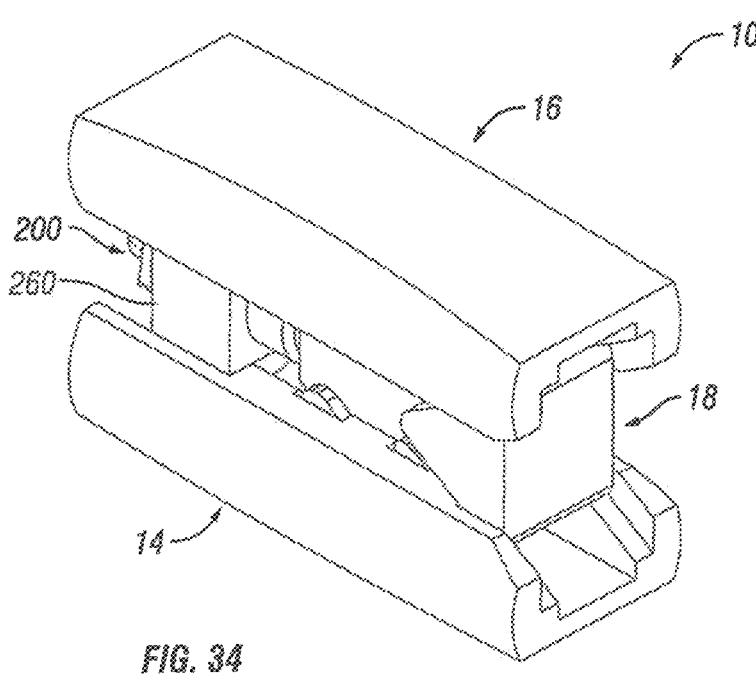
FIG. 34 is a front perspective view of the expandable fusion device of FIG. 33 shown in an expanded position in accordance with one embodiment of the present invention.
Figures 35, 36:
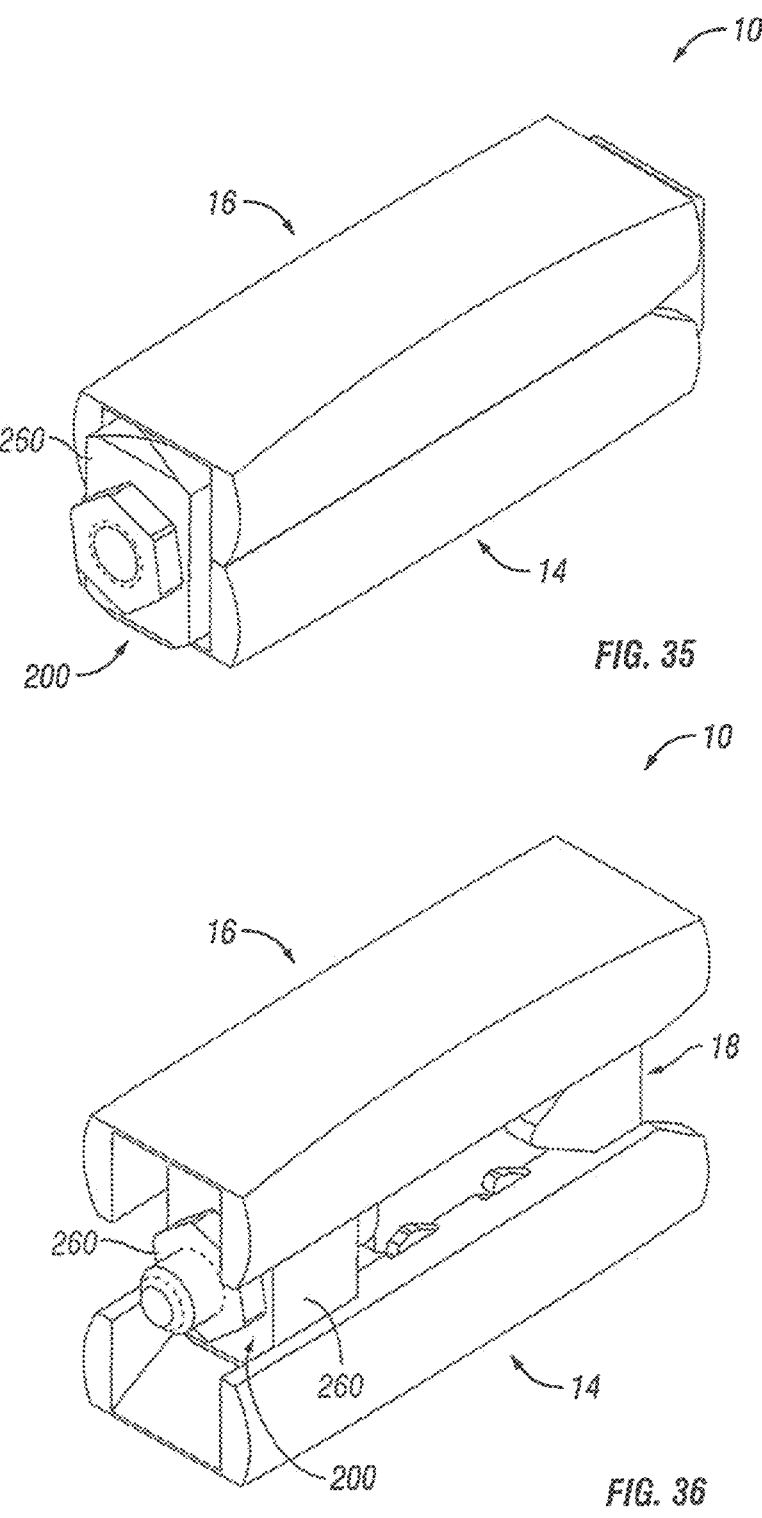
FIG. 35 is a rear perspective view of the expandable fusion device of FIG. 33 shown in an unexpanded position in accordance with one embodiment of the present invention.
FIG. 36 is a rear perspective view of the expandable fusion device of FIG. 33 shown in an expanded position in accordance with one embodiment of the present invention.
Figure 37:
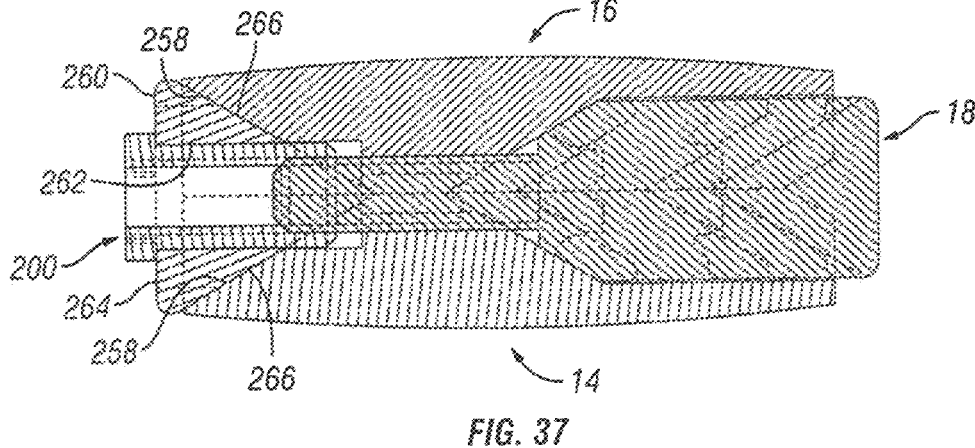
FIG. 37 is a side cross-sectional view of the expandable fusion device of FIG. 33 shown in an unexpanded position in accordance with one embodiment of the present invention.
Figure 38:
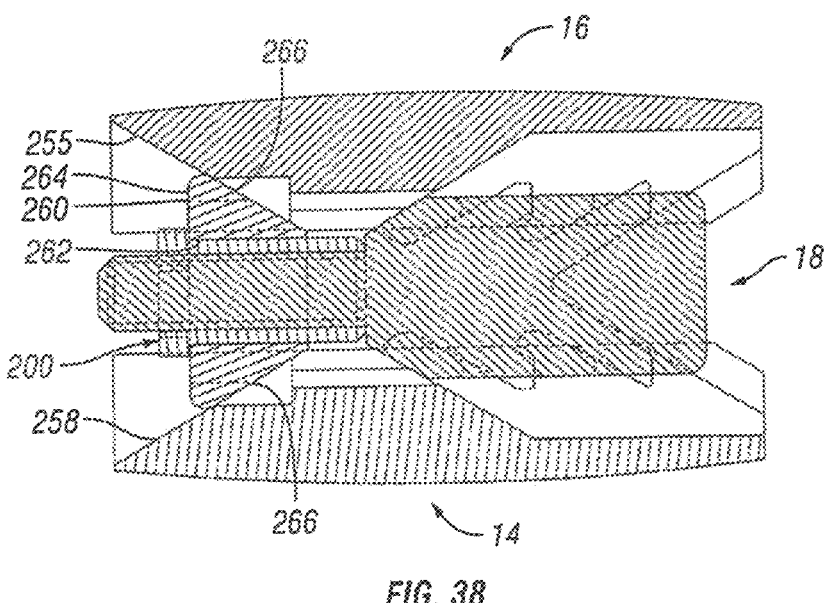
FIG. 38 is a side cross-sectional view of the expandable fusion device of FIG. 33 shown in an expanded position in accordance with one embodiment of the present invention.

With additional reference to FIGS. 28-32, a method of installing the expandable fusion device 10 of FIGS. 18-27 is now discussed in accordance with one embodiment of the present invention. Prior to insertion of the fusion device, the disc space may be prepared as described above and then one or more endoscopic tubes may then inserted into the disc space. The expandable fusion device 10 can then be inserted into and seated in the appropriate position in the intervertebral disc space, as best seen in FIGS. 28-32. The expandable fusion device 10 can be introduced into the intervertebral space down an endoscopic tube (not illustrated), with the central ramp 18 being first placed down the tube and into the disc space, as seen in FIG. 28. After insertion of the central ramp, the first endplate 14 can be placed down an endoscopic tube, as shown on FIG. 29, followed by insertion of the second endplate 16, as shown on FIG. 30. After the second endplate 16, the actuator assembly 200 can then be inserted to complete assembly of the device 10, as best seen in FIG. 31.

Figure 22:
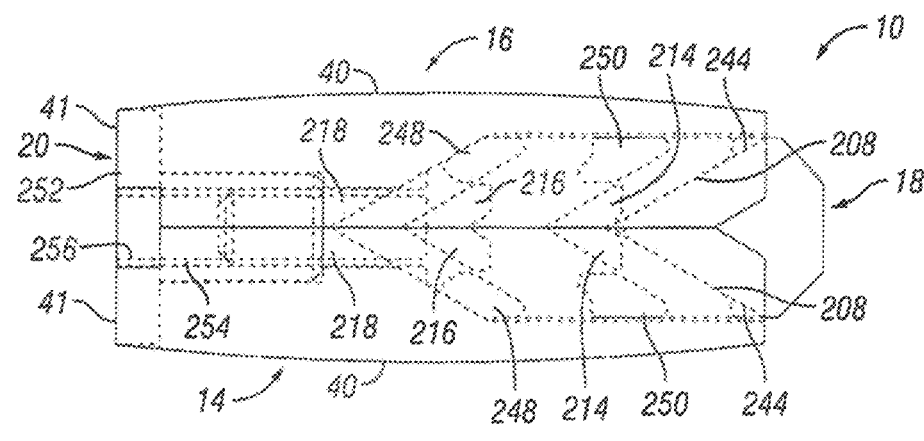
FIG. 22 is a side view of the expandable fusion device of FIG. 18 shown in an unexpanded position in accordance with one embodiment of the present invention.
Figure 23:
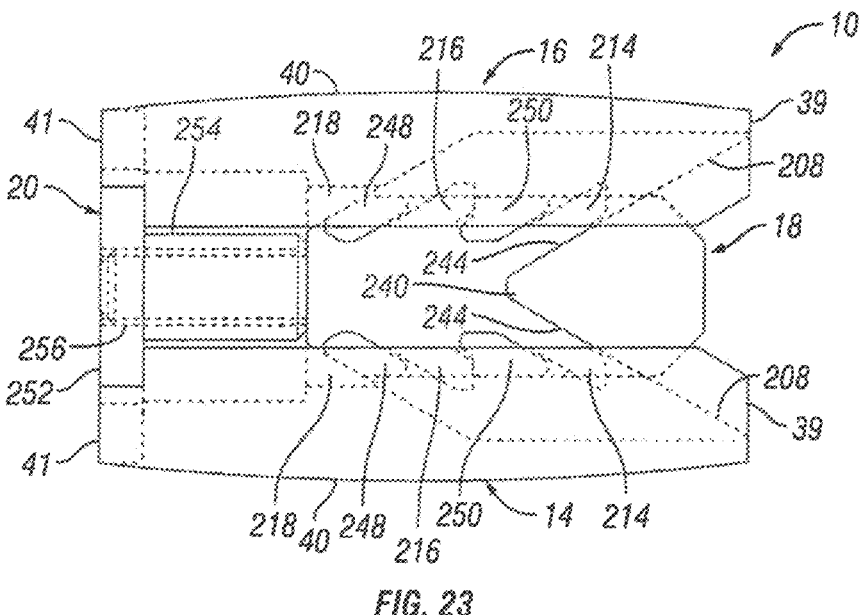
FIG. 23 is a side view of the expandable fusion device of FIG. 18 shown in an expanded position in accordance with one embodiment of the present invention.

After the fusion device 10 has been inserted into and assembled in the appropriate position in the intervertebral disc space, the fusion device 10 can then be expanded into the expanded position. To expand the fusion device 10, the actuator assembly 200 can be rotated. As discussed above, the actuator assembly 200 is in threaded engagement with the extension 250 of the central ramp 18. Thus, as the actuator assembly 200 is rotated in a first direction, the central ramp 18 moves toward the flanged end 253 of the actuator assembly 200. In another exemplary embodiment, the actuator assembly 200 can be moved in a linear direction with the ratchet teeth as means for controlling the movement of the central ramp 18. As the central ramp 18 moves, the angled surfaces 242, 244 in the expansion portions 238, 240 of the central ramp 18 push against the ramped surfaces 206, 208 in the first and second side portions 202, 204 of the first and second endplates 14, 16. In addition, the angled surfaces 246 in the second end 236 of the central ramp 18 also push against the ramped surfaces 228 in the central extension 224 of each of the endplates 14, 16. This is best seen in FIGS. 22-23.

Since the expansion of the fusion device 10 is actuated by a rotational input, the expansion of the fusion device 10 is infinite. In other words, the endplates 14, 16 can be expanded to an infinite number of heights dependent on the rotational advancement of the actuator assembly 200. As discussed above, the central ramp 16 includes locking features for securing the endplates 14, 16.

In the event the fusion device 10 needs to be repositioned or revised after being installed and expanded, the fusion device 10 can be contracted back to the unexpanded configuration, repositioned, and expanded again once the desired positioning is achieved. To contract the fusion device 10, the actuator assembly 200 can be rotated in a second direction. As discussed above, actuator assembly 200 is in threaded engagement with the extension 250 of the central ramp 18; thus, as the actuator assembly 200 is rotated in a second direction, opposite the first direction, the central ramp 18 moves with respect to the actuator assembly 200 and the first and second endplates 14, 16 away from the flanged end 253. As the central ramp 18 moves, the first and second endplates are pulled inwardly into the unexpanded position.

Referring now to FIGS. 33-38, an alternative embodiment of the expandable fusion device 10 is shown. In the illustrated embodiment, the fusion device includes a first endplate 14, a second endplate 16, a central ramp 18, and an actuator assembly 200. The fusion device 10 of FIGS. 33-38 and its individual components are similar to the device 10 illustrated on FIGS. 18-23 with several modifications. The modifications to the device 10 will be described in turn below.

Although the following discussion relates to the second endplate 16, it should be understood that it also equally applies to the first endplate 14 as the second endplate 16 is substantially identical to the first endplate 14 in embodiments of the present invention. With additional reference to FIG. 39, in an exemplary embodiment, the lower surface 42 of the second endplate 16 has been modified. In one embodiment, the central extension 224 extending from the lower surface 42 has been modified to include a second ramped surface 258 rather than a stop. In an exemplary embodiment, the second ramped surface 258 faces the second end 41 of the second endplate 16. In contrast, ramped surface 228 on the central extension 228 faces the first end 39 of the second endplate. The concave surface 228 connects the ramped surface 228 and the second ramped surface 258.

With reference to FIGS. 35-38, in an exemplary embodiment, the actuator assembly 200 has been modified to further include a driving ramp 260. In the illustrated embodiment, the driving ramp 260 has a through bore 262 through which the extension 254 extends. In an embodiment, the driving ramp 260 is generally wedge-shaped. As illustrated, the driving ramp 260 may comprise a blunt end 264 in engagement with the flanged end 253. In an exemplary embodiment, the driving ramp 260 further comprises angled surfaces 266 configured and dimensioned to engage the second ramped surface 258 of each of the endplates 14, 16 and force apart the first and second endplates 14, 16.

Referring now to FIGS. 40-44, an alternative embodiment of the expandable fusion device 10 is shown. In the illustrated embodiment, the fusion device 10 includes a first endplate 14, a second endplate 16, a central ramp 18, an actuator assembly 200, and a driving ramp 300. As will be discussed in more detail below, the actuator assembly 200 functions, in an embodiment, to pull the central ramp 18 and the driving ramp 300 together, which forces apart the first and second endplates 14, 16.

Although the following discussion relates to the first endplate 14, it should be understood that it also equally applies to the second endplate 16 as the second endplate 16 is substantially identical to the first endplate 14 in embodiments of the present invention. With reference to FIGS. 40-45, in an exemplary embodiment, the first endplate 14 has a first end 39 and a second end 41. In the illustrated embodiment, the first endplate 14 further comprises an upper surface 40 connecting the first end 39 and the second end 41, and a lower surface 42 connecting the first end 39 and the second end 41. While not illustrated, in an embodiment, the first endplate 14 may comprise further comprises a through opening. The through opening, in an exemplary embodiment, is sized to receive bone graft or similar bone growth inducing material.

In one embodiment, the upper surface 40 of the first endplate 14 is flat and generally planar to allow the upper surface 40 of the endplate 14 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. While not illustrated, in an exemplary embodiment, the upper surface 40 includes texturing to aid in gripping the adjacent vertebral bodies. Although not limited to the following, the texturing can include teeth, ridges, friction increasing elements, keels, or gripping or purchasing projections.

In one embodiment, the first endplate 14 further comprises a first side portion 202 connecting the first end 39 and the second end 41, and a second side portion 204 connecting the first end 39 and the second end 41. In the illustrated embodiment, the first and second side portions 202, 204 are extensions from the lower surface 42. In an embodiment, the first and second side portions each have an interior surface 302 and an exterior surface 304. In an exemplary embodiment, the first and second side portions 202, 204 each include one or more ramped portions. In the illustrated embodiment, the first and second side portions 202, 204 include first ramped portions 306, 308 at the first end 39 of the endplate 14 and second ramped portions 310, 312 at the second end 41 of the endplate. The first and second side portions 202, 204 each can include a bridge portion 314 connecting the first ramped portions 306, 308 and the second ramped portions 310, 312. In an embodiment, the first ramped portions 306, 308 abut the exterior surface 304 of the respective side portions 202, 204, and the second ramped portions 310, 312 abut the interior surface 302 of the respective side portions 202, 204. As illustrated, the first ramped portions 306, 308 may include tongue portions 316, 318 with the tongue portions 316, 318 extending in an oblique direction with respect to the upper surface 40 of the endplate 14. As further illustrated, the second ramped portions 310, 312 may include tongue portions 320, 322 that extend in an oblique direction with respect to the upper surface 40 of the endplate 14.

Figure 45:
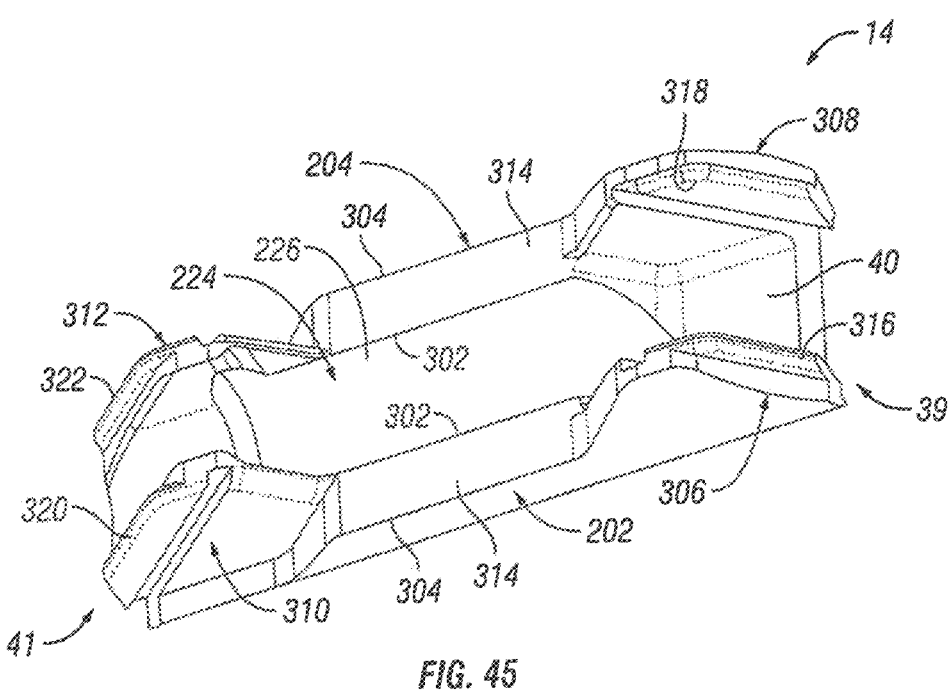
FIG. 45 is a perspective view of an endplate of the expandable fusion device of FIG. 40 in accordance with one embodiment of the present invention.

As best seen in FIG. 45, the lower surface 42 of the second endplate 16, in an embodiment, includes a central extension 224 extending along at least a portion of the lower surface. In the illustrated embodiment, the central extension 224 extends between the first and second side portions 202 and 204. In an exemplary embodiment, the central extension 224 can extend generally between the first ramped portions 306, 308 and the second ramped portions 310, 312. In one embodiment, the central extension 224 includes a generally concave surface 226 configured and dimensioned to form a through bore with the corresponding concave surface 226 (not illustrated) of the second endplate 16.

Figure 43:
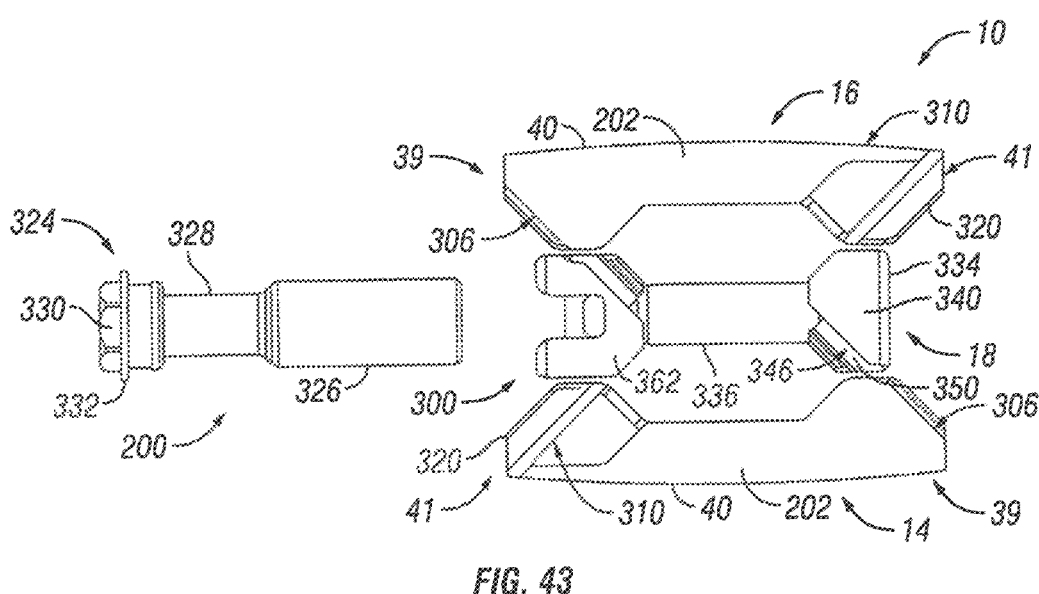
FIG. 43 is a side exploded view of the expandable fusion device of FIG. 40 in accordance with one embodiment of the present invention.
Figure 44:
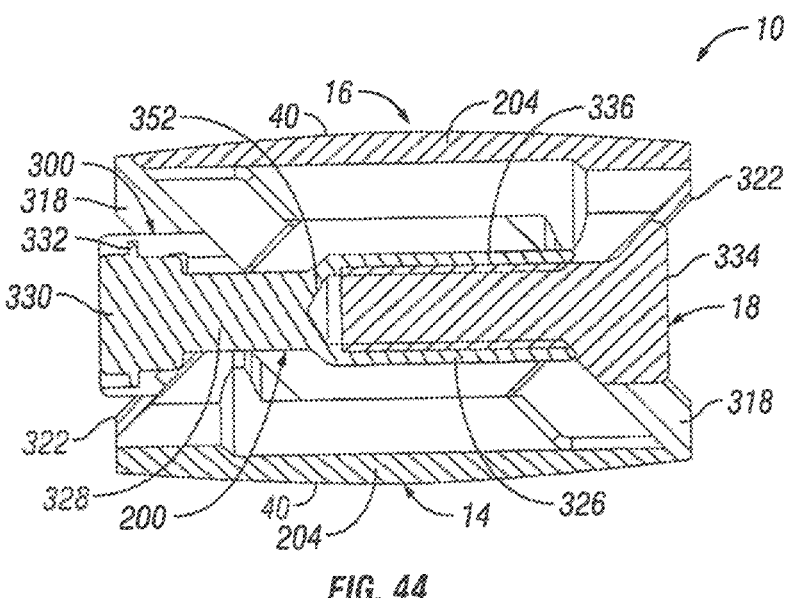
FIG. 44 is a side cross-sectional view of the expandable fusion device of FIG. 40 shown in an unexpanded position in accordance with one embodiment of the present invention.

With reference to FIGS. 43 and 44, the actuator assembly 200 includes a head portion 324, a rod receiving extension 326, and a connecting portion 328 that connecting portions that connects the head portion 324 and the rod receiving extension 326. As illustrated, the head portion 324 may include one or more instrument gripping features 330 that can allow it to be turned by a suitable instrument. In addition, the head portion 324 has a larger diameter than the other components of the actuator assembly 200 to provide a contact surface with the driving ramp 300. In the illustrated embodiment, the head portion 324 includes a rim 332 that provides a surface for contacting the driving ramp 300. As can be seen in FIG. 44, in an exemplary embodiment, the rod receiving extension 326 includes an opening sized and dimensioned to receive the extension 336 of the central ramp 18. In an embodiment, the rod receiving extension 326 includes threading for threadingly engaging the extension 336. In another embodiment, the rod receiving extension 326 includes ratchet teeth for engaging the extension 336. In the illustrated embodiment, the head portion 324 and the rod receiving extension 326 are connected by connecting portion 328 which can be generally cylindrical in shape.

Figure 46:
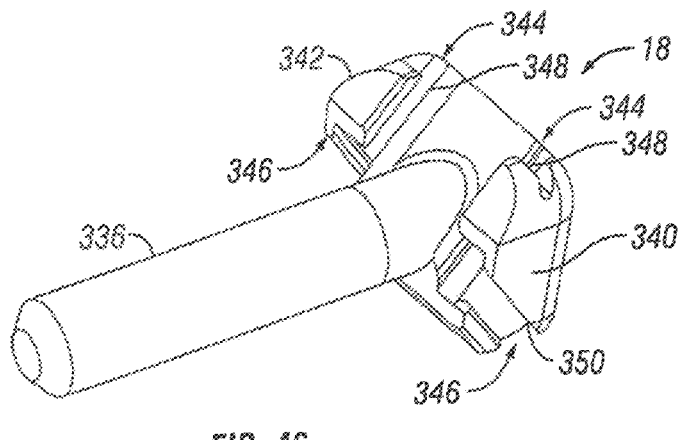
FIG. 46 is a perspective view of the central ramp of the expandable fusion device of FIG. 40 in accordance with one embodiment of the present invention.
Figure 50:
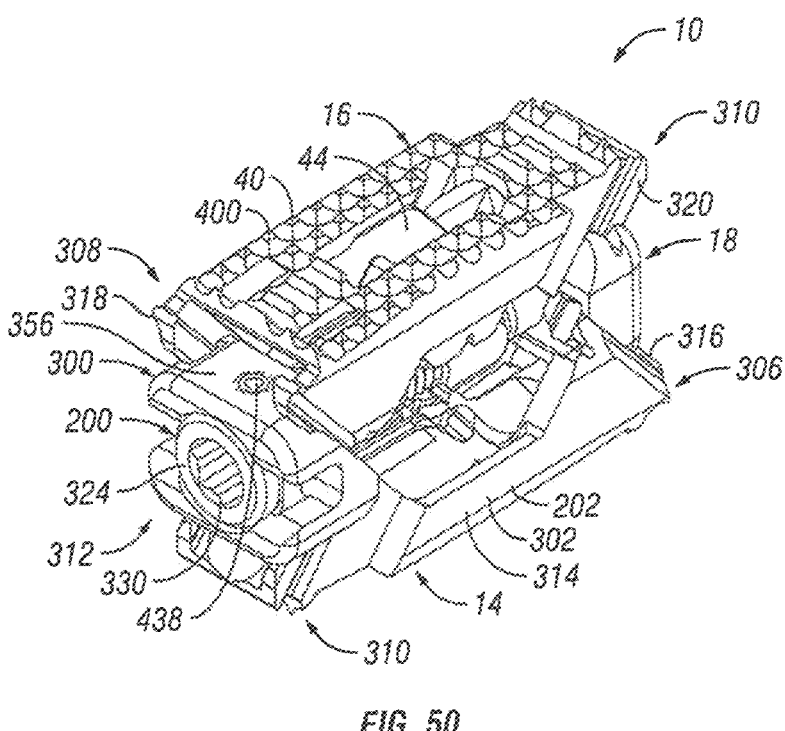
FIG. 50 is a rear perspective view of an alternative embodiment of an expandable fusion device shown in an expanded position in accordance with one embodiment of the present invention.

With reference to FIGS. 43, 44, and 46, the central ramp 18 includes expansion portion 334 and extension 336. As best seen in FIG. 46, the expansion portion 334 may include an upper portion 338 and side portions 340, 342 that extend down from the upper portion 338. In an embodiment, each of the side portions 340, 342 include dual, overlapping ramped portions. For example, side portions 340, 342 each include a first ramped portion 344 that overlaps a second ramped portion 346. In the illustrated embodiment, the first ramped portion 344 faces the extension 336 while the second ramped portion 344 faces away from the extension 336. In one embodiment, angled grooves 348, 350 are formed in each of the first and second ramped portions 344, 346. In another embodiment, the angled grooves 348, 350 are sized to receive the corresponding tongues 316, 318, 320, 322 in the first and second endplates with angled grooves 348 receiving tongues 320, 322 in the second endplate 16 and angled grooves 350 receiving tongues 316, 318 in the first endplate 14. Although the device 10 is described with tongues 316, 318, 320, 322 on the endplates 14, 16 and angled grooves 348, 350 on the central ramp 18, it should be understood that that device 10 can also be configured with grooves on the endplates 14, 16 and tongues on the central ramp 18, in accordance with one embodiment of the present invention.

In an exemplary embodiment, the extension 336 is sized to be received within the rod receiving extension 326 of the actuator assembly 200. In one embodiment, the extension 336 has threading with the extension 336 being threadingly received within the rod receiving extension 326. In another embodiment, the extension 336 has ratchet teeth with the extension 336 being ratcheted into the rod receiving extension 336. In an embodiment, the extension 336 include nose 352 at the end of the extension 336.

With reference to FIGS. 47-49, in an exemplary embodiment, the driving ramp 300 includes an upper portion 354 having an upper surface 356 and an oblique surface 358. In an embodiment, the driving ramp 300 further includes side portions 360, 362 that extend from the upper portion 354 connecting the upper portion 354 with the lower portion 364 of the driving ramp 300. As best seen in FIGS. 48-49, the driving ramp 300 further includes a bore 366, in an exemplary embodiment, sized to receive the connection portion 328 of the actuator assembly 200. In one embodiment, the driving ramp 300 moves along the connection portion 328 when the actuator assembly 200 is pushing the driving ramp 300. In an exemplary embodiment, the driving ramp 300 further includes contact surface 368 that engages the rim 332 of the head portion 324 of the actuator assembly 200. In the illustrated embodiment, the contact surface 368 has a generally annular shape.

In an exemplary embodiment, the side portions 360, 362 of the driving ramp 300 each include overlapping ramped portions. For example, the side portions 360, 362 each include first ramped portions 370 that overlap second ramped portions 372. In the illustrated embodiment, the first ramped portions 370 face central ramp 18 while the second ramped portions 372 face the opposite direction. In one embodiment, angled grooves 374, 376 are formed in each of the first and second ramped portions 370, 372. FIG. 48 is a perspective view of the driving ramp 300 that shows the top ends of the angled grooves 374 in ramped portions 370. FIG. 49 is a perspective view of the driving ramp 300 that shows the top ends of the angled grooves 376 in ramped portions 372. In an exemplary embodiment, the angled grooves 374, 376 are sized to receive corresponding tongues 316, 318, 320, 322 in the first and second endplates 14, 16 with angled grooves 370 receiving tongues 316, 318 in the second endplate 16 and angled grooves 372 receiving tongues 320, 322 in the first endplate 14. Although the device 10 is described with tongues 316, 318, 320, 322 in the first and second endplates 14, 16 and angled grooves 370, 372, 374, 376 on the driving ramp 300, it should be understood that that device 10 can also be configured with grooves on the second endplate 16 and tongues on the driving ramp 300, in accordance with one embodiment of the present invention.

Figures 39, 40:
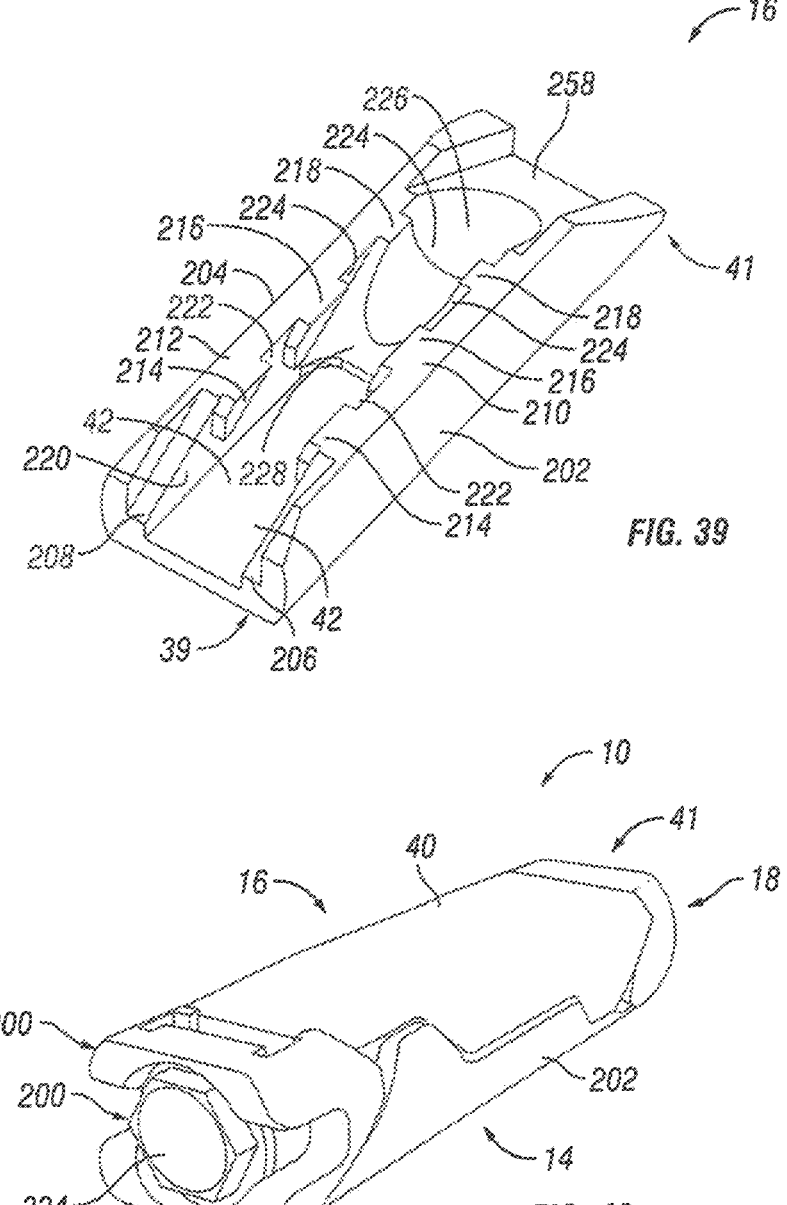
FIG. 39 is a perspective of an endplate of the expandable fusion device of FIG. 33 in accordance with one embodiment of the present invention.
FIG. 40 is a rear perspective view of an alternative embodiment of an expandable fusion device shown in an unexpanded position in accordance with one embodiment of the present invention.
Figure 41:
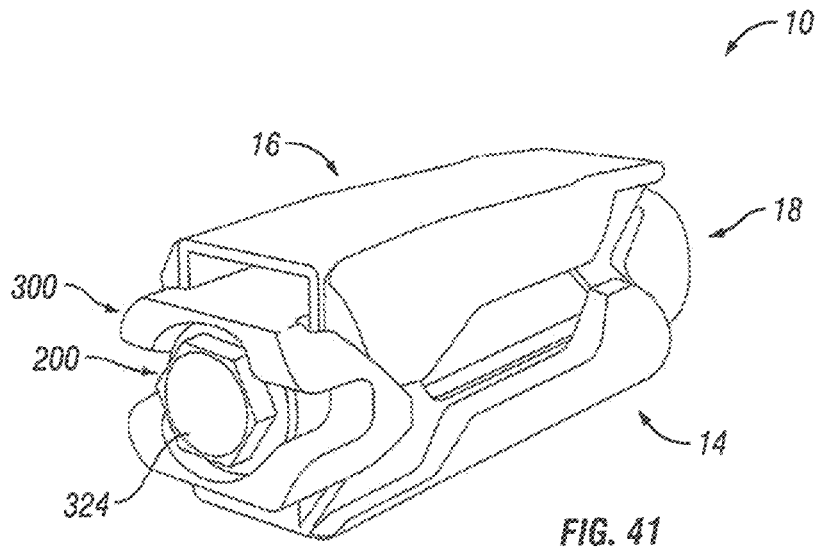
FIG. 41 is a rear perspective view of the expandable fusion device of FIG. 40 shown in a partially expanded position in accordance with one embodiment of the present invention.
Figure 42:
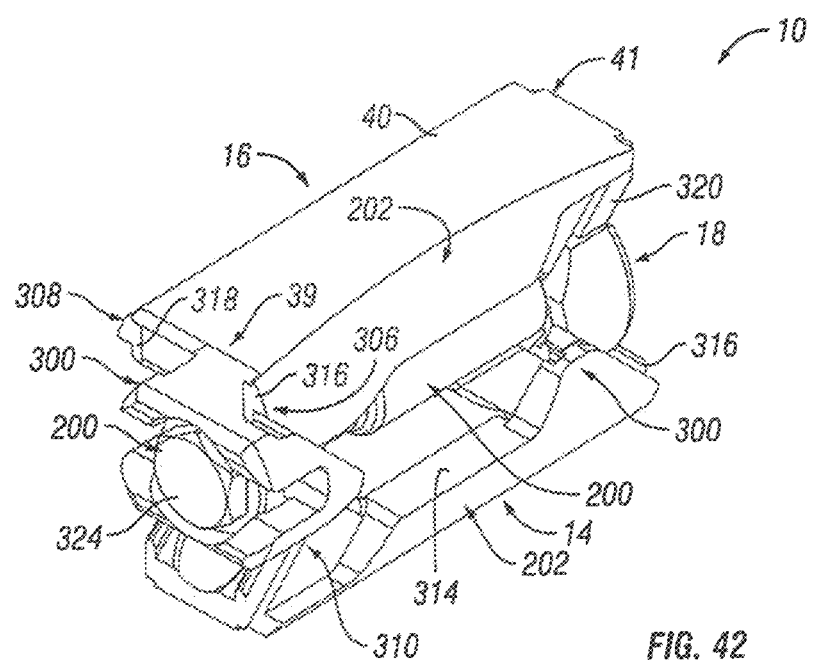
FIG. 42 is a rear perspective view of the expandable fusion device of FIG. 40 shown in an expanded position in accordance with one embodiment of the present invention.

Turning now to FIGS. 40-42, a method of installing the expandable fusion device 10 of FIGS. 40-49 is now discussed in accordance with one embodiment of the present invention. Prior to insertion of the fusion device, the disc space may be prepared as described above. The expandable fusion device 10 can then be inserted into and seated in the appropriate position in the intervertebral disc space. The expandable fusion device 10 is then introduced into the intervertebral space, with the end having the expansion portion 334 of the central ramp 18 being inserted. In an exemplary method, the fusion device 10 is in the unexpanded position when introduced into the intervertebral space. In an exemplary method, the intervertebral space may be distracted prior to insertion of the fusion device 10. The distraction provides some benefits by providing greater access to the surgical site making removal of the intervertebral disc easier and making scraping of the endplates of the vertebral bodies 2, 3 easier.

With the fusion device 10 inserted into and seated in the appropriate position in the intervertebral disc space, the fusion device can then be expanded into the expanded position, as best seen in FIG. 42. To expand the fusion device 10, an instrument is engaged with the head portion 324 of the actuator assembly 200. The instrument is used to rotate actuator assembly 200. As discussed above, actuator assembly 200 is threadingly engaged with the extension 336 of the central ramp 18; thus, as the actuator assembly 200 is rotated in a first direction, the central ramp 18 is pulled toward the actuator assembly 200. In an exemplary embodiment, the actuator assembly 200 is moved in a linear direction with the ratchet teeth engaging as means for controlling the movement of the actuator assembly 200 and the central ramp 18. As the central ramp 18 is pulled towards the actuator assembly 200, the first ramped portions 344 of the central ramp 18 push against the second ramped portions 310, 312 of the second endplate 16 and the second ramped portions 346 of the central ramp 18 push against first ramped portions 306, 308 of the first endplate 14. In this manner, the central ramp 18 acts to push the endplates 14, 16 outwardly into the expanded position. This can best be seen in FIGS. 40-42. As the endplates 14, 16 move outwardly the tongues 316, 318, 320, 322 in the endplates 14, 16 ride in the angled grooves 348, 350 with the tongues 320, 322 in the second endplate 16 riding in angled grooves 348 and the tongues 316, 318 in the first endplate 14 riding in angled grooves 350.

As discussed above, the actuator assembly 200 also engages driving ramp 300; thus, as the actuator assembly 200 is rotated in a first direction, the actuator assembly 200 pushes the driving ramp 300 towards the central ramp 18 in a linear direction. As the driving ramp 300 is pushed towards the central ramp 18, the first ramped portions 370 of the driving ramp 300 push against the first ramped portions 306, 308 of the second endplate 16 and the second ramped portions 372 of the driving ramp 300 push against the second ramped portions 310, 312 of the first endplate 14. In this manner, the driving ramp 300 also acts to push the endplates 14, 16 outwardly into the expanded position. This can best be seen in FIGS. 40-42. As the endplates 14, 16 move outwardly the tongues 316, 318, 320, 322 in the endplates 14, 16 ride in the angled grooves 370, 372 with the tongues 316, 318 in the second endplate 16 riding in angled grooves 370 and the tongues 320, 322 in the first endplate 14 riding in angled grooves 372.

Since the expansion of the fusion device 10 is actuated by a rotational input, the expansion of the fusion device 10 is infinite. In other words, the endplates 14, 16 can be expanded to an infinite number of heights dependent on the rotational advancement of the actuator assembly 200.

Referring now to FIGS. 50-54, an alternative embodiment of the expandable fusion device 10 is shown. In the illustrated embodiment, the fusion device 10 includes a first endplate 14, a second endplate 16, a central ramp 18, an actuator assembly 200, and a driving ramp 300. As will be discussed in more detail below, the actuator assembly 200 functions, in an embodiment, to pull the central ramp 18 and the driving ramp 300 together, which forces apart the first and second endplates 14, 16. In an embodiment, the expandable fusion device may contain features, such as a through bore, that facilitate placement down an endoscopic tube. In an embodiment, the assembled fusion device 10 may be placed down the endoscopic tube and then expanded.

Figure 54:
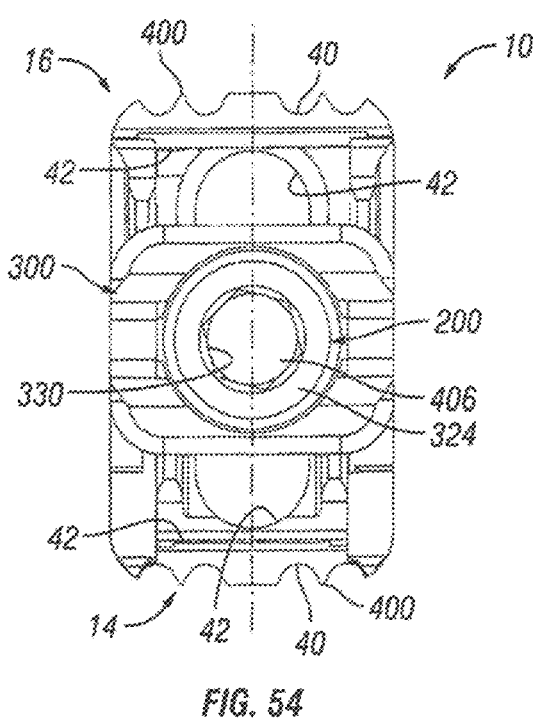
FIG. 54 is a read end view of the expandable fusion device of FIG. 50 shown in an expanded position in accordance with one embodiment of the present invention.
Figure 55:
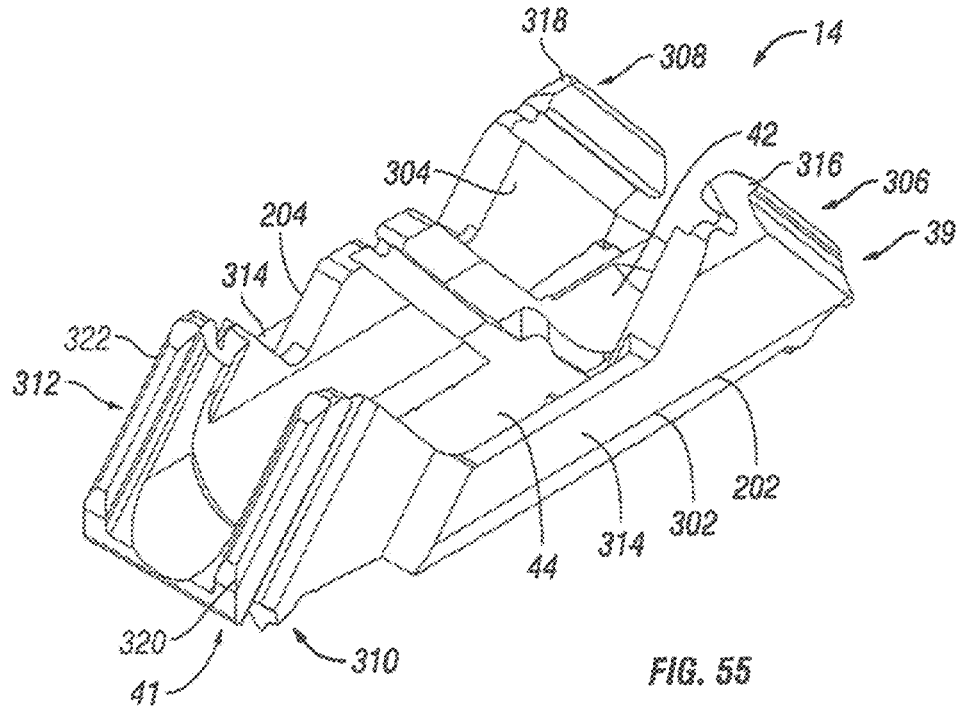
FIG. 55 is a perspective view of an endplate of the expandable fusion device of FIG. 50 in accordance with one embodiment of the present invention.

Although the following discussion relates to the first endplate 14, it should be understood that it also equally applies to the second endplate 16 as the second endplate 16 is substantially identical to the first endplate 14 in embodiments of the present invention. It should be understood that, in an embodiment, the first endplate 14 is configured to interlock with the second endplate 16. With additional reference to FIG. 55, in an exemplary embodiment, the first endplate 14 has a first end 39 and a second end 41. As illustrated, the first end 39 may be wider than the second end 41. In the illustrated embodiment, the first endplate 14 further comprises an upper surface 40 connecting the first end 39 and the second end 41, and a lower surface 42 connecting the first end 39 and the second end 41. As best seen in FIG. 54, the lower surface 42 can be curved concavely such that the first and second endplates 14, 16 form a through bore when the device 10 is in a closed position. In an embodiment, the first endplate 14 may comprise a through opening 44. The through opening 44, in an exemplary embodiment, is sized to receive bone graft or similar bone growth inducing material.

In one embodiment, the upper surface 40 of the first endplate 14 is flat and generally planar to allow the upper surface 40 of the endplate 14 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. As illustrated, in an exemplary embodiment, the upper surface 40 includes texturing to aid in gripping the adjacent vertebral bodies. For example, the upper surface 40 may further comprise texturing 400 to engage the adjacent vertebral bodies. Although not limited to the following, the texturing can include teeth, ridges, friction increasing elements, keels, or gripping or purchasing projections.

In one embodiment, the first endplate 14 further comprises a first side portion 202 connecting the first end 39 and the second end 41, and a second side portion 204 connecting the first end 39 and the second end 41. In the illustrated embodiment, the first and second side portions 202, 204 are extensions from the lower surface 42. In an embodiment, the first and second side portions 202, 204 each include an interior surface 302 and an exterior surface 304. In an embodiment, the first end 39 of the first endplate 14 is generally designed and configured to fit over the second end 41 of the second endplate 16 when the device 10 is in a closed position. As illustrated, the first and second side portions 202, 204 each may include first ramped portions 306, 308, second ramped portions 310, 312, and/or central ramped portion 402.

In an embodiment, the first ramped portions 306, 308 are proximate the first end 39 of the endplate 14. In accordance with embodiment of the present invention, the first ramped portions 306, 308 of the first endplate 14 are generally designed and configured to fit over the second ramped portions 310, 312 of the second endplate 16 when the device 10 is in a closed position. In an exemplary embodiment, the first ramped portions 306, 308 generally face the first end 39 and can extend in an oblique direction with respect to the upper surface 40, for example. As illustrated, the first ramped portions 306, 308 may include tongue portions 316, 318 extending in an oblique direction with respect to the upper surface 40 of the endplate 14.

In an embodiment, the second ramped portions 310, 312 are proximate the second end 41 of the endplate 14. In an exemplary embodiment, the second ramped portions 310, 312 can extend in an oblique direction with respect to the upper surface 40 and generally face the second end 41. The first and second side portions 202, 204, in an embodiment, each can include a bridge portion 314 connecting the first ramped portions 306, 308 and the second ramped portions 310, 312. As further illustrated, the second ramped portions 310, 312 may include tongue portions 320, 322 that extend in an oblique direction with respect to the upper surface 40 of the endplate 14.

In an embodiment, the endplate 14 further may include a central ramped portion 402 proximate the bridge portion 314. In the illustrated embodiment, the endplate 14 includes a central ramped portion 402 proximate the bridge portion 314 of the second side portion 204. In an exemplary embodiment, the central ramped portion 402 can extend in an oblique direction with respect to the upper surface 40 and face the first end 39 of the endplate 14. As illustrated, the first ramped portions 306, 308 may include tongue portions 316, 318 with the tongue portions 316, 318 extending in an oblique direction with respect to the upper surface 40 of the endplate 14.

With reference to FIGS. 50-52 and 54, in an embodiment, the actuator assembly 200 includes a head portion 324, an extension 404, and a through bore 406 that extends longitudinally through the actuator assembly 200. As illustrated, the head portion 324 may include one or more instrument gripping features 330 that can allow it to be turned by a suitable instrument. In addition, the head portion 324 has a larger diameter than the other components of the actuator assembly 200 to provide a contact surface with the driving ramp 300. In the illustrated embodiment, the head portion 324 includes a rim 332 that provides a surface for contacting the driving ramp 300. In an embodiment, the extension 404 is a generally rod-like extension. In another embodiment, the extension 404 includes ratchet teeth for engaging the extension 336.

Figure 51:
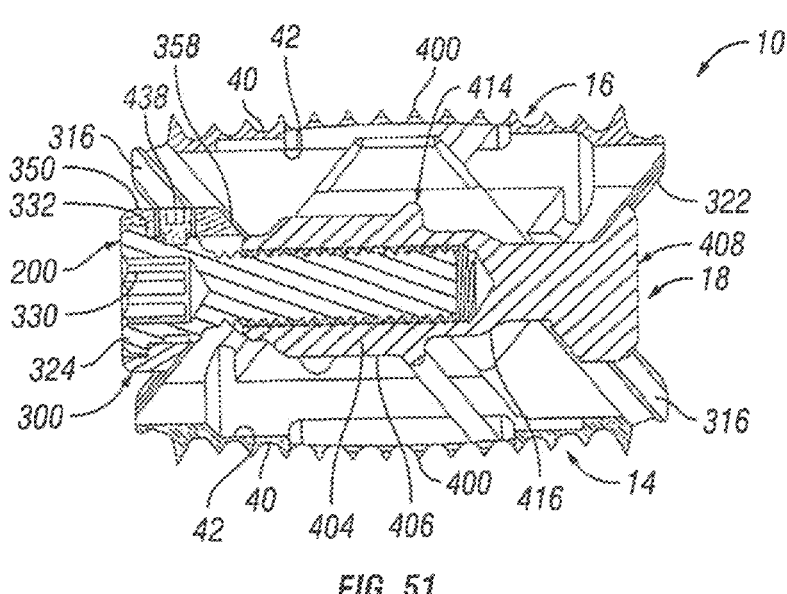
FIG. 51 is a side cross-sectional view of the expandable fusion device of FIG. 50 shown in an expanded position in accordance with one embodiment of the present invention.
Figure 52:
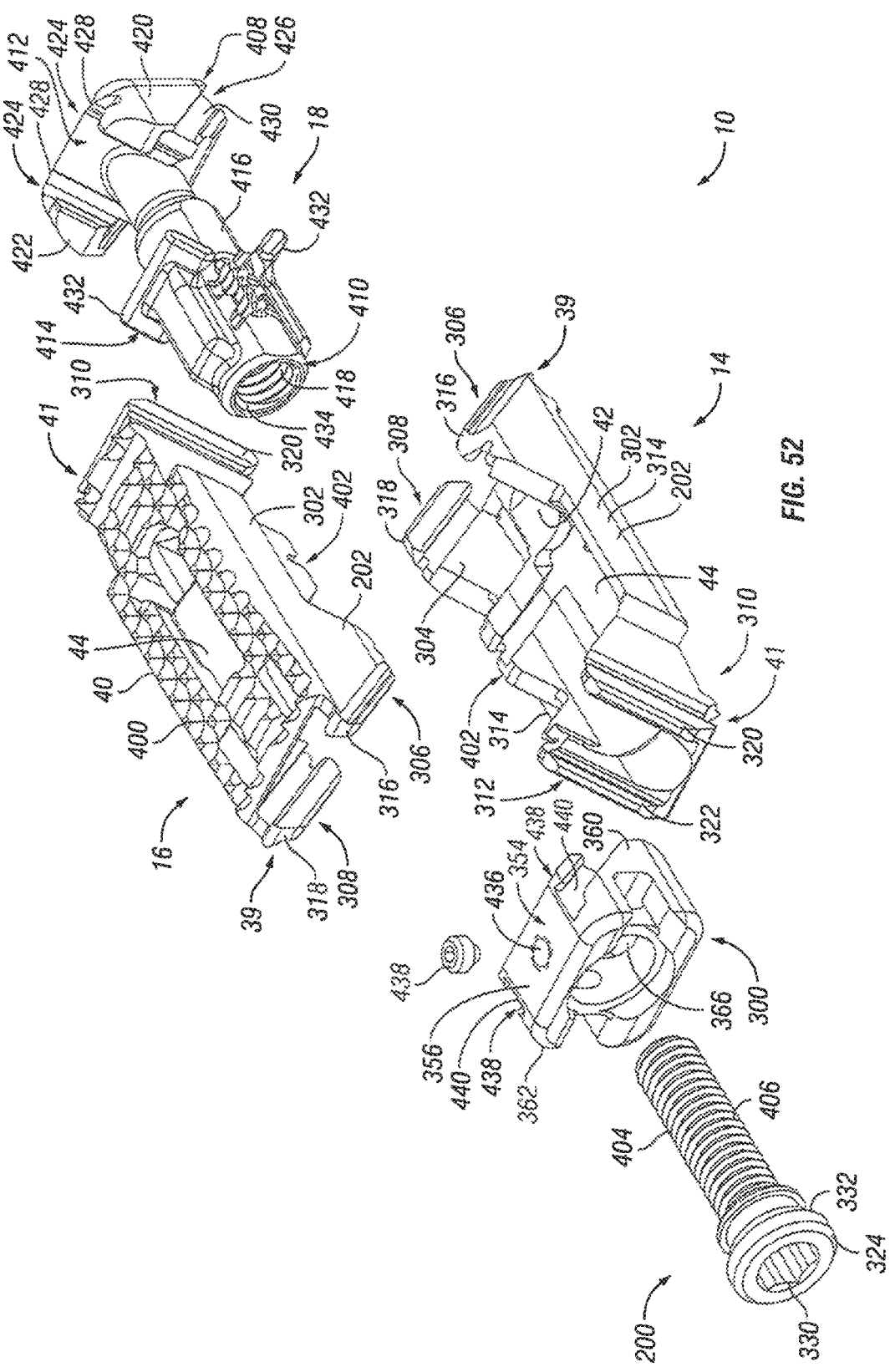
FIG. 52 is an exploded view of the expandable fusion device of FIG. 50 in accordance with one embodiment of the present invention.
Figure 53:
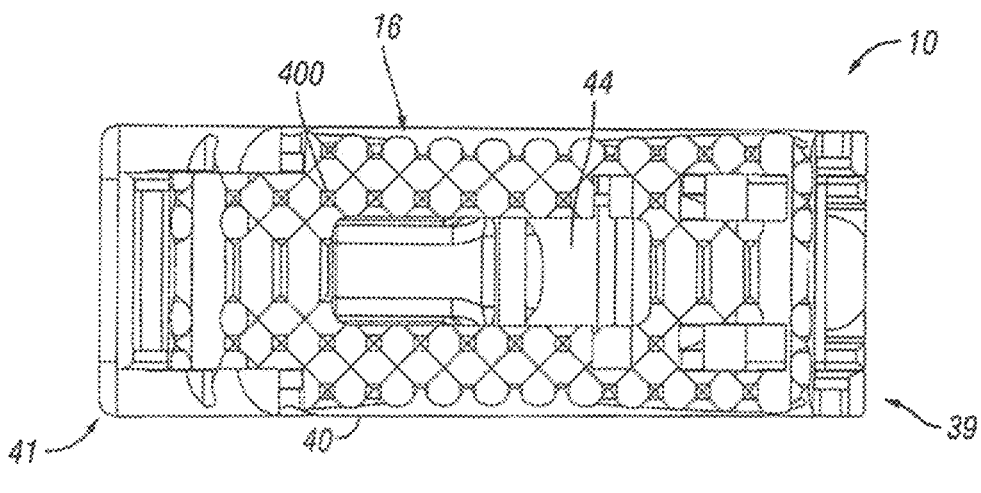
FIG. 53 is a top view of the expandable fusion device of FIG. 50 shown in an unexpanded position in accordance with one embodiment of the present invention.
Figure 56:
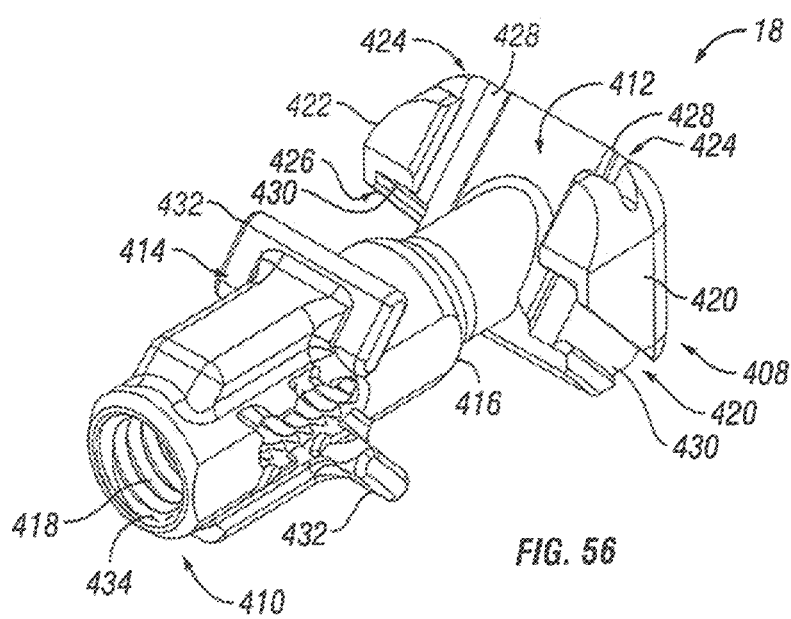
FIG. 56 is a perspective of a central ramp of the expandable fusion device of FIG. 50 in accordance with one embodiment of the present invention.
Figure 57:
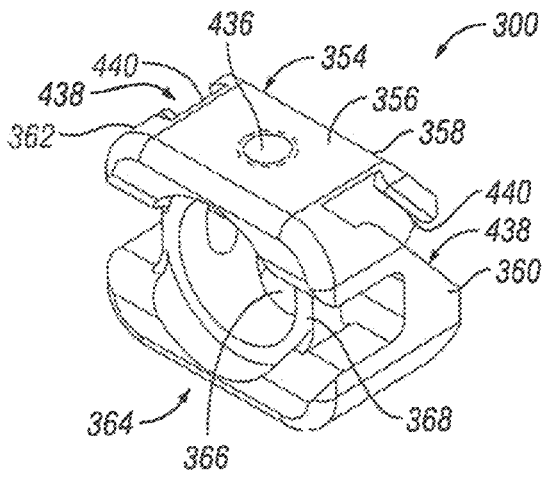
FIG. 57 is a perspective view of a driving ramp of the expandable fusion device of FIG. 50 in accordance with one embodiment of the present invention.

With reference to FIGS. 51, 52, and 56, the central ramp 18 has a first end 408 and a second end 410. In an embodiment, the central ramp 18 includes a first expansion portion 412, a second expansion portion 414, a rod-receiving extension 416, and a through bore 418 that extends longitudinally through the central ramp 18. In an exemplary embodiment, first expansion portion 412 can be proximate the first end 408 of the central ramp 18. As best seen in FIG. 56, the first expansion portion 412 may include side portions 420, 422. In an embodiment, each of the side portions 420, 422 includes dual, overlapping ramped portions that extend in oblique directions with respect to the through bore 418. For example, side portions 420, 422 each include a first ramped portion 424 that overlaps a second ramped portion 426. In the illustrated embodiment, the first ramped portion 424 faces the rod-receiving extension 416 while the second ramped portion 426 faces the opposite direction. In one embodiment, angled grooves 428, 430 are formed in each of the first and second ramped portions 424, 426. In an exemplary embodiment, the angled grooves 428, 430 are sized to receive the corresponding tongues 316, 318, 320, 322 in the first and second endplates 14, 16 with angled grooves 428 receiving tongues 320, 322 in the second endplate 16 and angled grooves 430 receiving tongues 316, 318 in the first endplate 14. Although the device 10 is described with tongues 316, 318, 320, 322 on the endplates 14, 16 and angled grooves 428, 430 on the central ramp 18, it should be understood that that device 10 can also be configured with grooves on the endplates 14, 16 and tongues on the central ramp 18, in accordance with one embodiment of the present invention.

In an embodiment, the second expansion portion 414 is located on the rod-receiving extension 416 between the first end 408 and the second end 410 of the central ramp 18. In an exemplary embodiment, the second expansion portion 414 includes central ramped portions 432. In one embodiment, the second expansion portion 414 includes two central ramped portions 432 on opposite sides of the rod-receiving extension 416. In an exemplary embodiment, the central ramped portions 424 extend in an oblique direction with respect to the through bore 418 and face the second end 410 of the central ramp 18.

The rod-receiving extension 416 extends from the first expansion portion 412 and has an opening 434 at the second end of the central ramp 18. In an embodiment, the rod-receiving extension 416 is sized and configured to receive the extension 404 of the actuator assembly 200. In an embodiment, the rod-receiving extension 416 has threading with the rod-receiving extension 416 threadingly receiving extension 404 of the actuator assembly 200. In another embodiment, the rod-receiving extension 416 has ratchet teeth with the extension 404 being ratcheted into the rod-receiving extension 416.

With reference to FIGS. 50-52 and 57, in an exemplary embodiment, the driving ramp 300 includes an upper portion 354 having an upper surface 356 and an oblique surface 358. In an embodiment, the driving ramp 300 further includes a bore 366, in an exemplary embodiment, sized to receive the extension 404 of the actuator assembly 200. In the illustrated, embodiment, the upper portion 354 has a hole 436 that extends through the upper surface 356 to the bore 366. Set screw 438 may be inserted through the hole 436 to secure the driving ramp 300 to the actuator assembly 200. In one embodiment, the driving ramp 300 further includes contact surface 368 that engages the rim 332 of the head portion 324 of the actuator assembly 200. In the illustrated embodiment, the contact surface 368 has a generally annular shape.

In an embodiment, the driving ramp 300 further includes side portions 360, 362 that extend from the upper portion 354 connecting the upper portion 354 with the lower portion 364 of the driving ramp 300. In an exemplary embodiment, the side portions 360, 362 of the driving ramp 300 each include a ramped portion 438. In the illustrated embodiment, the ramped portion 438 faces central ramp 300. In an embodiment, the ramped portion 438 is configured and dimensioned to engage the ramped portions 306, 308 at the first end 39 of the second endplate 16. In one embodiment, angled grooves 440 are formed in the ramped portions 316, 318. In an exemplary embodiment, the angled grooves 440 are sized to receive the corresponding tongues 316, 318 in the second endplate 16. Although the device 10 is described with tongues 316, 318 on the second endplate 16 and angled grooves 440 on the driving ramp 300, it should be understood that that device 10 can also be configured with grooves on the second endplate 16 and tongues on the driving ramp 300, in accordance with one embodiment of the present invention.

A method of installing the expandable fusion device 10 of FIGS. 50-57 is now discussed in accordance with one embodiment of the present invention. Prior to insertion of the fusion device, the disc space may be prepared as described above. The expandable fusion device 10 can then be inserted into and seated in the appropriate position in the intervertebral disc space. In an embodiment, the device 10 is assembled prior to insertion. The expandable fusion device 10 can be introduced into the intervertebral space, with the end having the first end 408 of the central ramp 18 being inserted. In an exemplary method, the fusion device 10 is in the unexpanded position when introduced into the intervertebral space. In an exemplary method, the intervertebral space may be distracted prior to insertion of the fusion device 10. The distraction provides some benefits by providing greater access to the surgical site making removal of the intervertebral disc easier and making scraping of the endplates of the vertebral bodies 2, 3 easier.

With the fusion device 10 inserted into and seated in the appropriate position in the intervertebral disc space, the fusion device can then expand into the expanded position. To expand the fusion device 10, an instrument is engaged with the head portion 324 of the actuator assembly 200. The instrument is used to rotate actuator assembly 200. As discussed above, actuator assembly 200 is threadingly engaged with the rod receiving extension 416 of the central ramp 18; thus, as the actuator assembly 200 is rotated in a first direction, the central ramp 18 is pulled toward the actuator assembly 200. In an exemplary embodiment, the actuator assembly 200 is moved in a linear direction with the ratchet teeth engaging as means for controlling the movement of the actuator assembly 200 and the central ramp 18.

As the central ramp space 18 is pulled towards the actuator assembly 200, the central ramp 18 acts to push endplates 14, 16 outwardly into the expanded position. By way of example, the first ramped portions 424, second ramped portions 426, and central ramped portions 432 push against the corresponding ramped portions in the first and second endplates 14, 16. The first ramped portions 424 in the first expansion portion 412 of the central ramp 18 push against the second ramped portions 310, 312 of the second endplate 16 with the corresponding tongues 320, 322 in the second ramped portions 310, 312 of the second endplate 16 riding in angled grooves 428 in the first ramped portions 424 in the first expansion portion 412. The second ramped portions 426 in the first expansion portion 412 push against the first ramped portions 316, 318 of the first endplate 14 with the corresponding tongues 316, 318 in first ramped portions 316, 318 of the first endplate 14 riding in angled grooves 430 in the second ramped portions 426 in the first expansion portion 412. The central ramped portions 432 in the second expansion portion 414 push against the central ramped portion 402 in the first and second endplates 14, 16.

As discussed above, the actuator assembly 200 also engages driving ramp 300; thus, as the actuator assembly 200 is rotated in a first direction, the actuator assembly 200 pushes the driving ramp 300 towards the central ramp 18 in a linear direction. As the driving ramp 300 is pushed towards the central ramp 18, the driving ramp 300 also acts to push the endplates 14, 16 outwardly into the expanded position. By way of example, the ramped portions 438 of the driving ramp 300 push against ramped portions 306, 308 at the first end 39 of the second endplate 16. As the endplates 14, 16 move outwardly, the tongues 316, 318 in the ramped portions 306, 308 of the second endplate 16 ride in the angled grooves 440 in the ramped portions 438 of the driving ramp 300.

It should also be noted that the expansion of the endplates 14, 16 can be varied based on the differences in the dimensions of the various ramped portions in the central ramp 18, the driving ramp 300, and the first and second endplates 14, 16. As best seen in FIG. 16, the endplates 14, 16 can be expanded in any of the following ways: straight rise expansion, straight rise expansion followed by a toggle into a lordotic expanded configuration, or a phase off straight rise into a lordotic expanded configuration.

Figure 58:
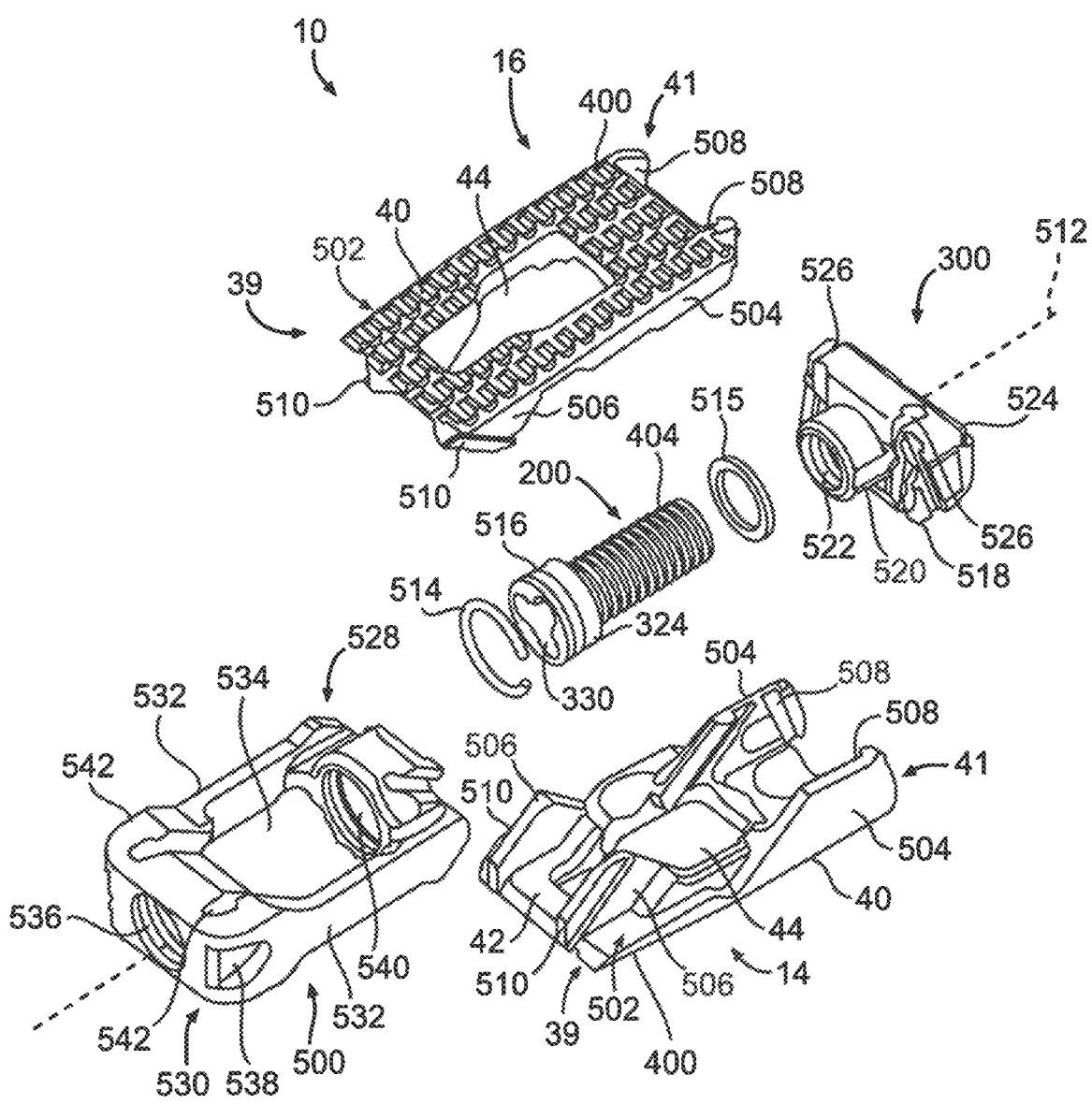
FIG. 58 is an exploded view of an alternative embodiment of an expandable fusion device in accordance with one embodiment of the present invention.
Figure 65:
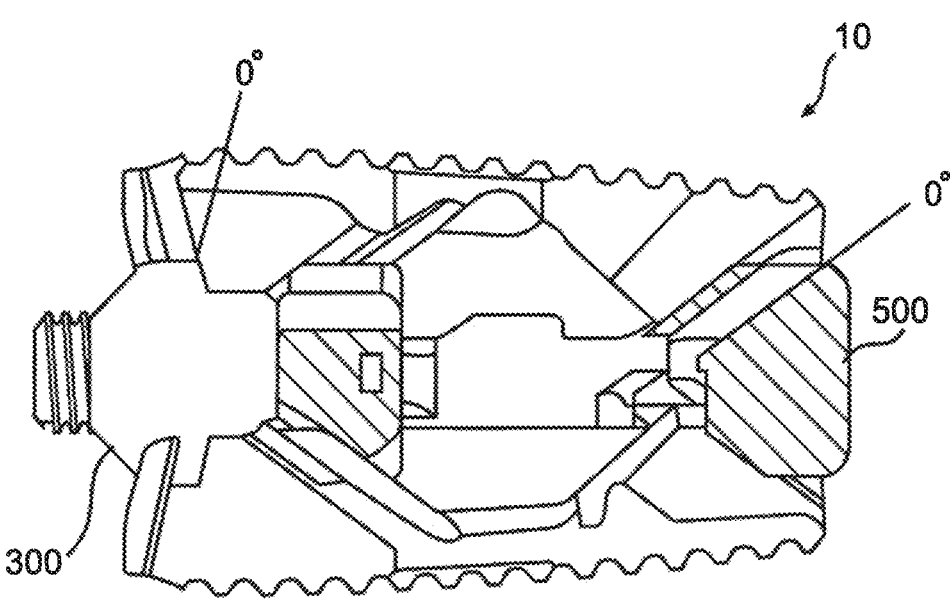
FIG. 65 is a side view of the expandable fusion device of FIG. 58 shown in partial cross-section in a fully expanded configuration in accordance with one embodiment of the present invention.
Figure 66:
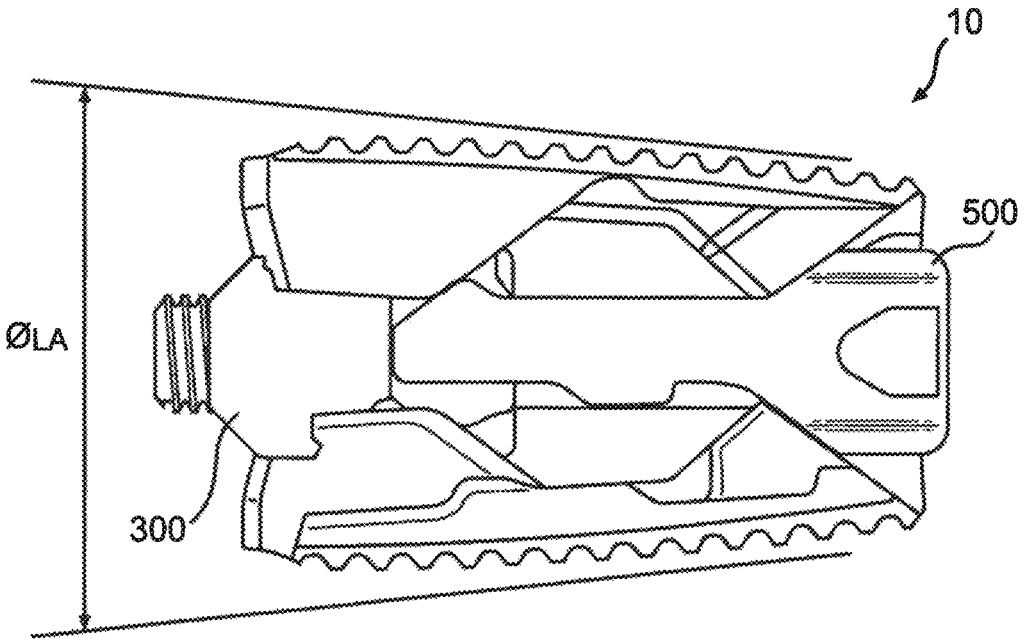
FIG. 66 is a side view of the expandable fusion device of FIG. 58 shown in a fully expanded configuration in accordance with one embodiment of the present invention.
Figure 67:
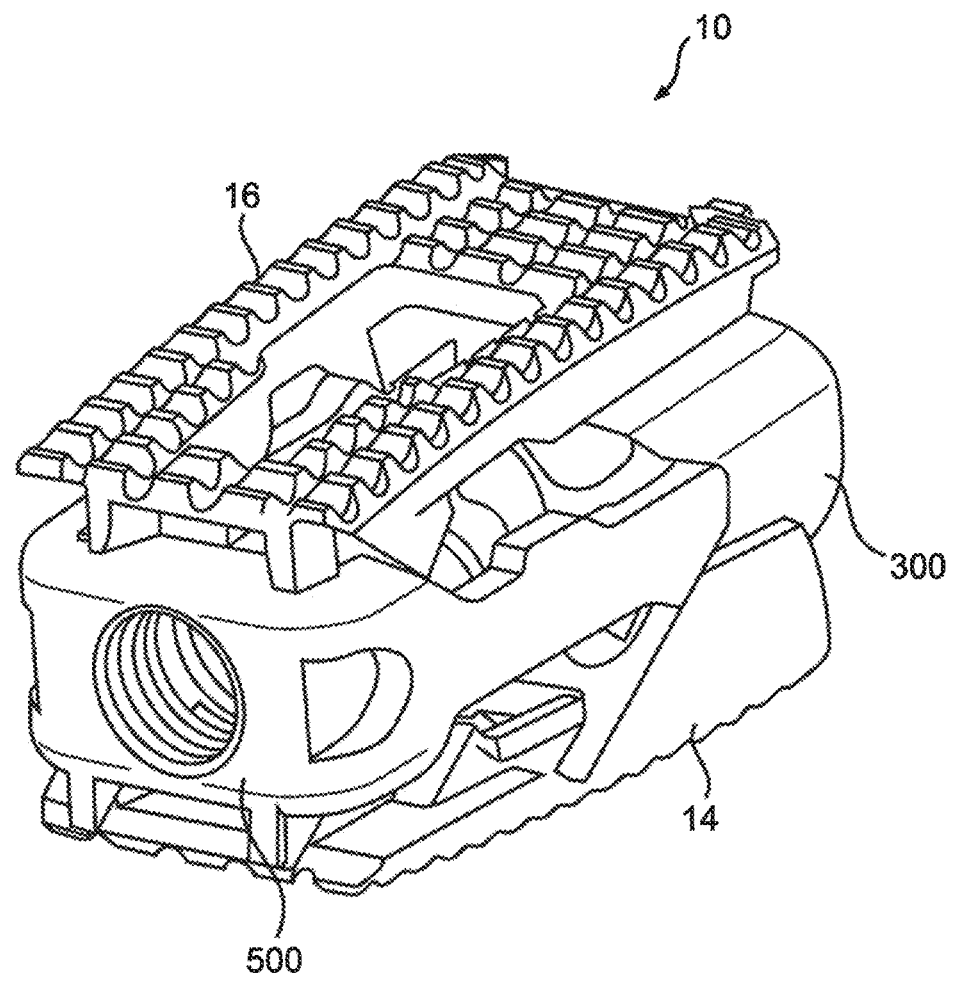
FIG. 67 is a perspective view of the expandable fusion device of FIG. 58 shown in a fully expanded configuration in accordance with one embodiment of the present invention.

Referring now to FIG. 58, an alternative embodiment of the expandable fusion device 10 is shown in which the expandable fusion device 10 expands into a lordotic expanded configuration. In the illustrated embodiment, the expandable fusion device 10 includes a first endplate 14, a second endplate 16, an actuator assembly 200, a driving ramp 300, and a body 500. As will be discussed in more detail below, the actuator assembly 200 functions, in an embodiment, to pull the driving ramp 300 and the body 500 together, which forces apart the first and second endplates 14, 16. For example, the actuator assembly 200 may be rotated to pull the driving ramp 300 toward the body 500. When this occurs, the expandable fusion device 10 first expands into a lordotic expanded configuration (FIGS. 62-64) and then expands in height until it is fully expanded (FIGS. 65-67). In embodiments, expandable fusion device 10 may have two stages of expansion, generally referred to as lordotic stage and parallel stage. In lordotic stage, the expandable fusion device 10 may expand at one end to achieve a lordotic angle. The expandable fusion device 10 may hen expand in parallel sage wherein the lordotic expansion may be maintained at both ends of the expandable fusion device 10 may expand at generally constant rates. In an embodiment, the expandable fusion device 10 may contain features, such as a through bore, that facilitate placement down an endoscopic tube. In an embodiment, the assembled fusion device 10 may be placed down the endoscopic tube and then expanded.

Although the following discussion relates to the first endplate 14, it should be understood that it also equally applies to the second endplate 16 as the second endplate 16 is substantially identical to the first endplate 14 in embodiments of the present invention. It should be understood that, in an embodiment, the first endplate 14 is configured to interlock with the second endplate 16. In an exemplary embodiment, the first endplate 14 has a first end 39 and a second end 41. In the illustrated embodiment, the first endplate 14 further comprises a plate portion 502 that may extend between first end 39 and the second end 41. Plate portion 502 may comprise an upper surface 40 and a lower surface 42. In an embodiment, the first endplate 14 may comprise a through opening 44. The through opening 44, in an exemplary embodiment, may be sized to receive bone graft or similar bone growth inducing material.

In one embodiment, the upper surface 40 of the plate portion 502 is flat and generally planar to allow the upper surface 40 of the plate portion 502 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. As illustrated, in an exemplary embodiment, the upper surface 40 includes texturing to aid in gripping the adjacent vertebral bodies. For example, the upper surface 40 may further comprise texturing 400 to engage the adjacent vertebral bodies. Although not limited to the following, the texturing can include teeth, ridges, friction increasing elements, keels, or gripping or purchasing projections.

In one embodiment, the first endplate 14 further comprises front side extensions 504 that extend from plate portion 502. As illustrated, the front side extensions 504 may extend from either side of plate portion 502 proximate to second end 41 of first endplate 14. The front side extensions 504 may extend opposite from the upper surface 40 of plate portion 502. In one embodiment, the first endplate 14 may further comprise rear side extensions 506 that extend from plate portion 502. As illustrated, the rear side extensions 506 may extend from either side of plate portion 502 proximate to first end 39 of first endplate 14. The rear side extensions 506 may extend opposite from the upper surface 40 of plate portion 502. As illustrated, the front side extensions 504 and the rear side extensions 506 may each include ramped portions. For example, the front side extension 504 may include front ramped portions 508 and the rear side extensions 506 may include rear ramped portions 510. The front ramped portions 508 and the rear ramped portions 510 may be considered ramped as they may be at an oblique angle with respect to longitudinal axis 512 of expandable fusion device 10. In an exemplary embodiment, the front ramped portions 508 may generally face the second end 41, and the rear ramped portions 510 may generally face the first end 39.

Embodiments of actuator assembly 200 will now be described in more detail with reference to FIG. 58. In the illustrated embodiment, the actuator assembly 200 is in the form of a drive screw. As illustrated, the actuator assembly 200 may include a head portion 324 and an extension 404. As illustrated, the head portion 324 may include one or more instrument gripping features 330 that can allow it to be turned by a suitable instrument. In addition, the head portion 324 may have a larger diameter than the other components of the actuator assembly 200 to provide a contact surface with the body 500. In the illustrated embodiment, ring 514 may ride in groove 516 on head portion 324. In some embodiments, ring 514 may be a compressible ring, such as a c-ring as shown on FIG. 58, that is configured to retain head portion 324 in rear throughbore 536 of body 500. In an embodiment, the extension 404 is a generally rod-like extension that may be threaded for engaging a corresponding opening 522 in driving ramp 300. In another embodiment, the extension 404 may include ratchet teeth (not shown) for engaging opening 522 in driving ramp 300.

Embodiments of driving ramp 300 will now be described in more detail with respect to FIG. 58. As illustrated, the driving ramp 300 may include a ramped body portion 518 and an extension 520. In the illustrated embodiment, extension 520 may extend from ramped body portion 518 toward first end 39 of expandable fusion device 10. Extension 520 may include an opening 522 that may engage extension 404 of actuator assembly 200. In embodiments, extension 520 may threadingly engage the extension 404 of actuator assembly 200. Rotation of driving ramp 300 may be limited so that when actuator assembly 200 may be rotated, driving ramp 300 may be pulled toward body 500. Driving ramp 300 may be secured to actuator assembly 200 at a front end of expandable fusion device 10. In embodiments, the front end of expandable fusion device 10 may be the front of the expandable fusion device 10 so that the driving ramp 300 may be considered the nose of the expandable fusion device 10. In embodiments, the front end 524 of driving ramp 300 may be angled, rounded, or otherwise tapered so that the driving ramp may serve to distract the adjacent vertebral bodies when the expandable fusion device 10 is inserted into an intervertebral space.

As illustrated, driving ramp 300 may include front endplate engaging ramps 526. Front endplate engaging ramps 526 may be at an oblique angle with respect to longitudinal axis 512 of the expandable fusion device 10. As illustrated, a pair of front endplate engaging ramps 526 that engage second endplate 16 may be on one side of driving ramp while another pair of front endplate engaging ramps 526 that engage first endplate 14 may be on an opposite side of driving ramp 300. In operation, front endplate engaging ramps 526 may engage front ramped portions 508 of the first and second endplates 14, 16. The first and second endplates 14, 16 may ride up the front endplate engaging ramps 526 as the driving ramp 300 may be pulled towards the body 300 causing the first and second endplates 14, 16 to be pushed relatively apart such that a height of expandable fusion device 10 may be increased.

Embodiments of body 500 will now be described in more detail with respect to FIG. 58. As illustrated, the body 500 may have a first body end 528 and a second body end 530. Lateral sides 532 may connect the first body end 528 and the second body end 530. In the illustrated embodiment, the body 500 may have a central opening 534 that may extend through the body 500 transverse to longitudinal axis 512 of expandable fusion device. As illustrated, first body end 528, second body end 530, and lateral sides 532 may define central opening 534. Rear throughbore 536 may be formed through second body end 530. Rear throughbore 536 may be centrally positioned and generally aligned with longitudinal axis 512 of expandable fusion device 10. As previously described, head portion 324 of actuator assembly 200 may be retained in rear throughbore 536, for example, using ring 514. Washer 515 may also be retained on corresponding grooves of head portion 324. Rear throughbore 506 may also be threaded, for example, to facilitate engagement with an insertion device. Second body end 530 may also include tool engaging features, such as side recesses 538, which may facilitate use of a device for insertion of expandable fusion device 10 into a desired position in a patient. First body end 528 may include a corresponding front throughbore 540. As illustrated, front throughbore 540 may be centrally positioned and generally aligned with longitudinal axis 512 of expandable fusion device. Extension 404 of actuator assembly 200 may extend through front throughbore 540 to engage driving ramp 300.

As illustrated, second body end 530 may include rear endplate engaging ramps 542. Rear endplate engaging ramps 542 may be at an oblique angle with respect to longitudinal axis 512 of the expandable fusion device 10. In operation, rear endplate engaging ramps 542 may engage rear ramped portions 510 of the first and second endplates 14, 16. As illustrated, a pair of rear endplate engaging ramps 542 that engage second endplate 16 may be on one side of second body end 530 while another pair of rear endplate engaging ramps 542 (not seen on FIG. 58) that engage first endplate 14 may be on an opposite side of second body 530. The first and second endplates 14, 16 may ride up the rear endplate engaging ramps 542 as the driving ramp 300 may be pulled towards the body 300 causing the first and second endplates 14, 16 to be pushed relatively apart such that a height of expandable fusion device 10 may be increased.

As previously described, the expandable fusion device 10 shown on FIG. 58 may first expand lordotically and then expand in parallel until full expansion of the expandable fusion device 10 may be reached. To achieve this lordotic expansion, the front ramped portions 508 and rear ramped potions 510 of the first and second endplates 14, 16 may be at a different angle with respect to longitudinal axis 512 than the front endplate engaging ramps 526 of the driving ramp 300 and the rear endplate engaging ramps 542 of the body 500. This difference in angles may be present when the expandable fusion device 10 is in the unexpanded configuration. As the driving ramp 300 may be pulled back towards the body 500, the position of the first and second endplates 14, 16 and/or the driving ramp 300 and the body 500 with respect to body 500 may change so that the difference in angles may be reduced and potentially approach zero as the first and second endplates 14, 16 are pushed outward. As this angle is being reduced, the rear portion of the expandable fusion device may be expanding causing a lordotic angle. When this angle is reduced (or reaches approximately zero), the first and second endplates 14, 16 may then expand in parallel with the first end 39 and second end 41 expanding at approximately the same height until the expandable fusion device 10 may reach its full height. The lordotic angle may be maintained while the first and second endplates 14, 16 expand in parallel.

Figure 59:
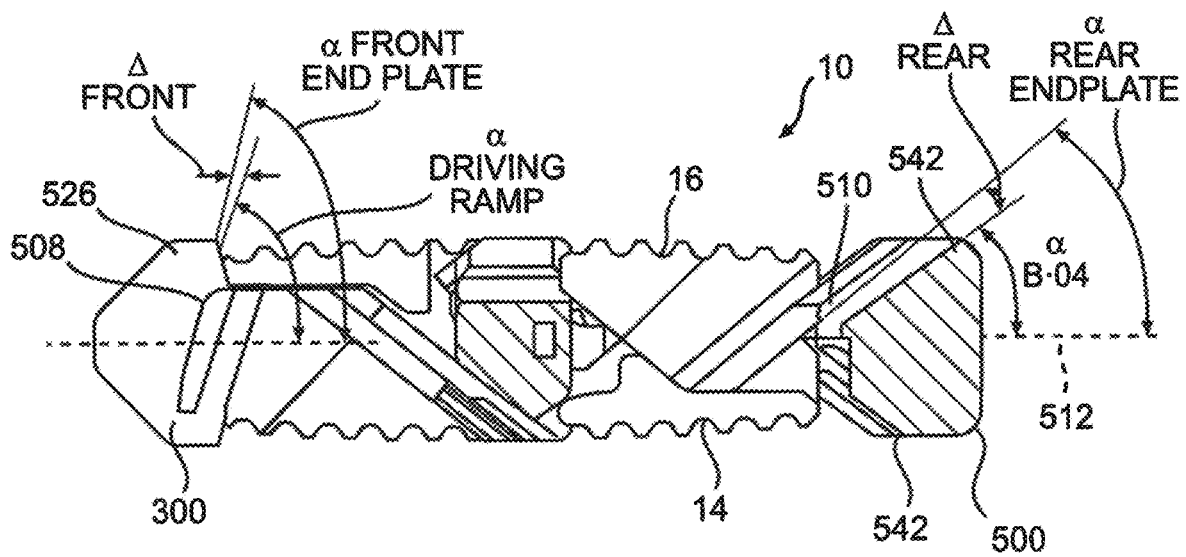
FIG. 59 is a side view of the expandable fusion device of FIG. 58 shown in partial cross-section in an unexpanded configuration in accordance with one embodiment of the present invention.
Figure 60:
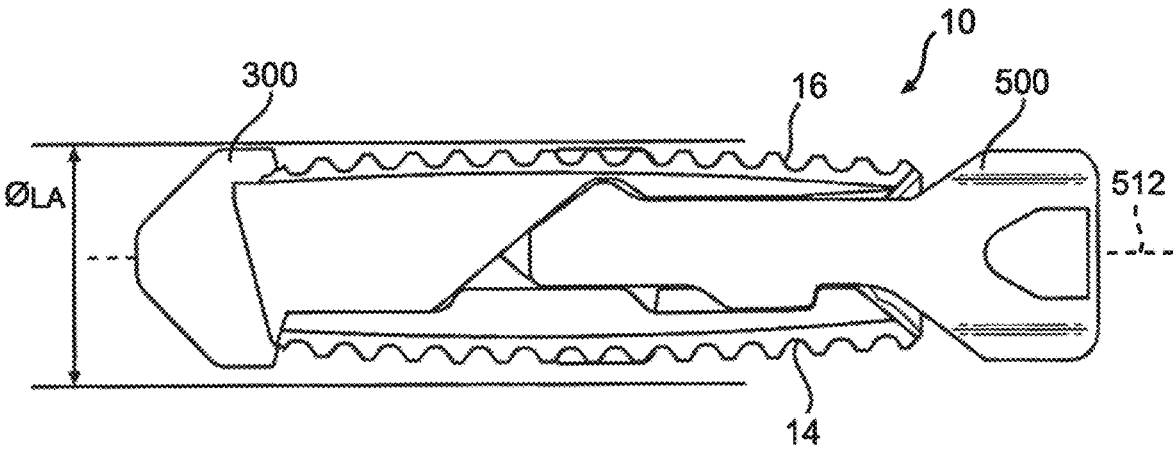
FIG. 60 is a side view of the expandable fusion device of FIG. 58 shown in an unexpanded configuration in accordance with one embodiment of the present invention.
Figure 61:
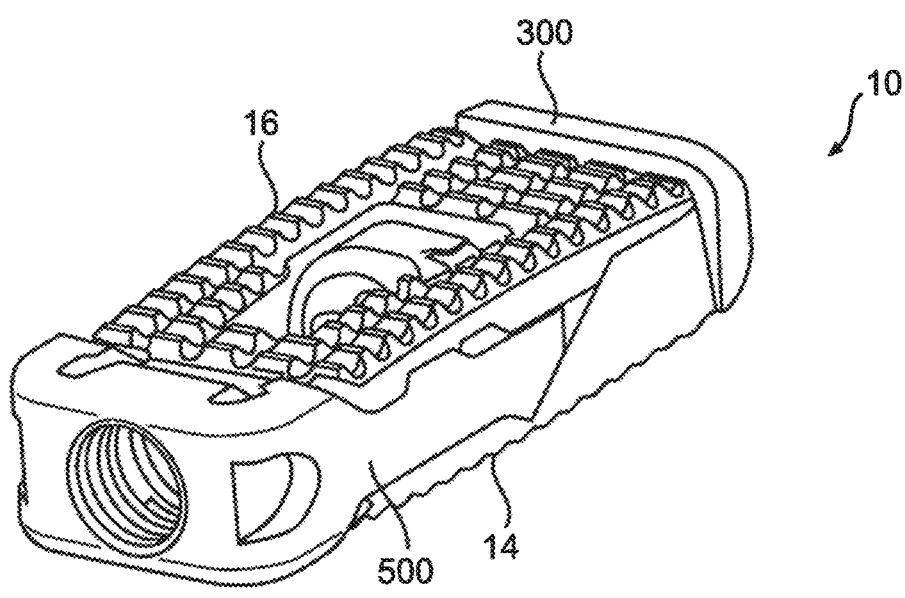
FIG. 61 is a perspective view of the expandable fusion device of FIG. 58 shown in an unexpanded configuration in accordance with one embodiment of the present invention.

FIGS. 59 to 61 illustrate the expandable fusion device 10 in the unexpanded configuration in accordance with present embodiments. As seen on FIG. 60, the expandable fusion device 10 may have a lordotic angle $\theta_{LA}$ of approximately 0° when unexpanded. By way of example, the first and second endplates 14, 16 may be generally aligned with longitudinal axis 512 of expandable fusion device 10. In accordance with present embodiments, lordotic expansion of expandable fusion device 10 may be achieved by use of different in ramp angles with respect to longitudinal axis 512. As best seen on FIG. 59, rear endplate engaging ramps 542 of the body 500 may have an angle $\alpha_{body}$ and rear ramped portions 510 of first and second endplates 14, 16 may have an angle $\alpha_{rearendplate}$. The front endplate engaging ramps 526 of the driving ramp 300 may have an angle $\alpha_{driving}$ ramp and the front ramped portions 508 of the first and second endplates 14, 16 may have an angle $\alpha_{frontendplate}$. These angles may be selected, for example, to provide a desired rate of height increase during expansion of expandable fusion device 10. By way of example, the angles may each individually by selected, for example, from about 5° to about 85° and alternatively from about 35° to about 65°. However, as described above, embodiments may provide differences in these angles, for example, to drive the lordotic expansion. As best seen on FIG. 59, the difference between the angles $\alpha_{rearendplate}$ and $\alpha_{body}$ may be provided by $\Delta_{rear}$, and the difference between the angles $\alpha_{frontendplate}$ and $\alpha_{driving}$ ramped may be provided by $\Delta_{front}$. $\Delta_{rear}$ and $\Delta_{front}$ may be the same or different. By way of example, $\Delta_{rear}$ and $\Delta_{front}$ may each range from 1° to about 20° and, alternatively, from about 2° to about 5°.

Figure 62:
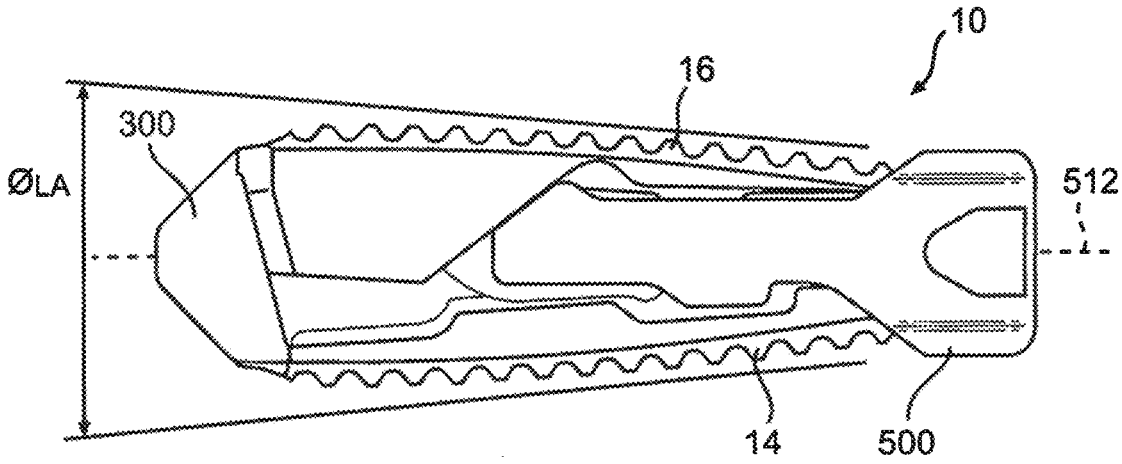
FIG. 62 is a side view of the expandable fusion device of FIG. 58 shown in partial cross-section in a lordoctic expanded configuration in accordance with one embodiment of the present invention.
Figure 63:
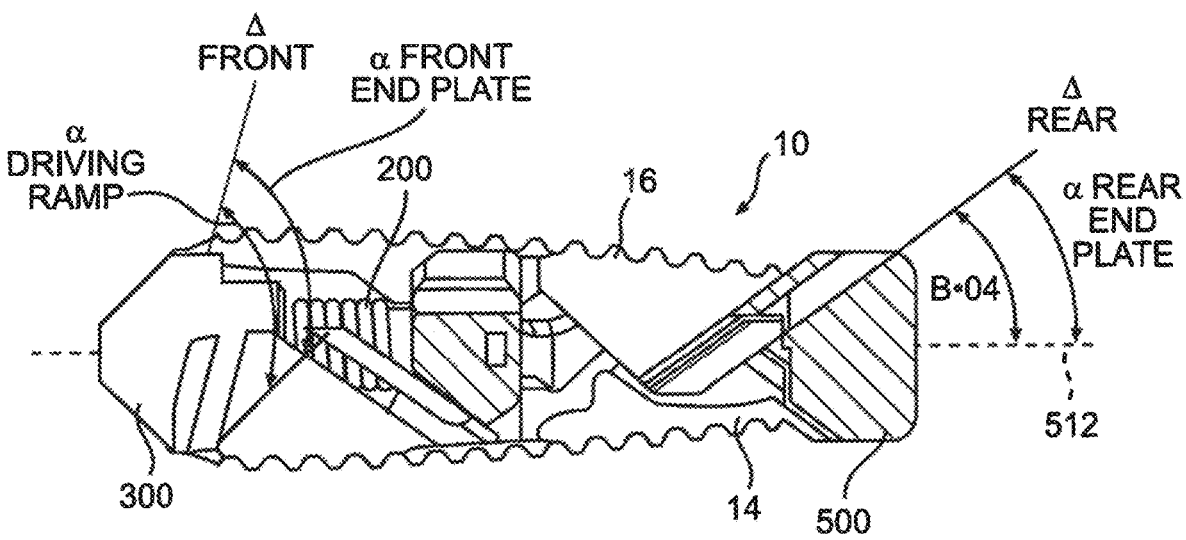
FIG. 63 is a side view of the expandable fusion device of FIG. 58 shown in a lordoctic expanded configuration in accordance with one embodiment of the present invention.
Figure 64:
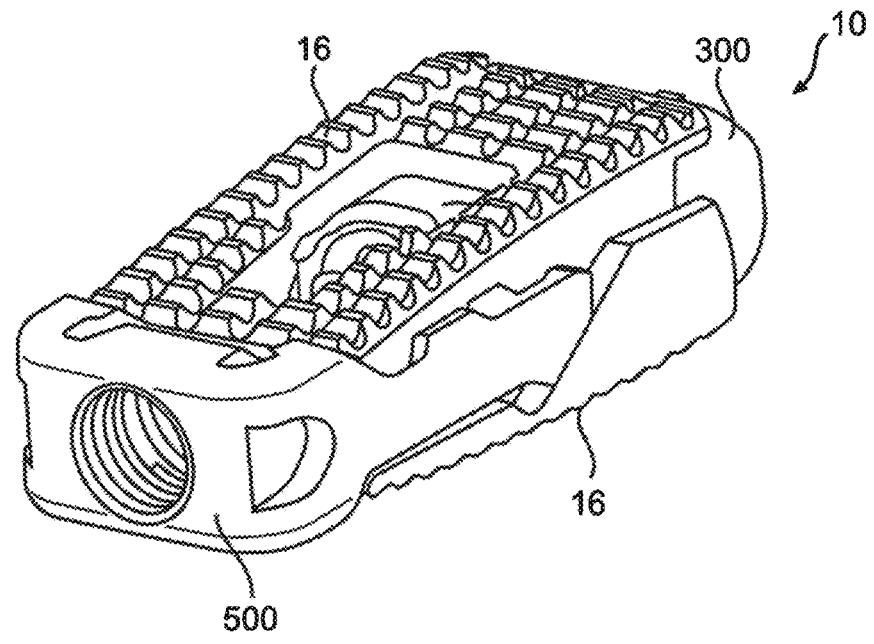
FIG. 64 is a perspective view of the expandable fusion device of FIG. 58 shown in a lordoctic expanded configuration in accordance with one embodiment of the present invention.

FIGS. 62 to 64 illustrate the expandable fusion device 10 in a lordotic expanded configuration in accordance present embodiments. The expandable fusion device 10 may be expanded to provide a lordotic angle $\theta_{LA}$ of up to about 15° and, more particularly, of about 4° to about 10°. Lordotic angles $\theta_{LA}$ of up to 12° may be desired in certain applications, such as cervical, but other lordotic angles $\theta_{LA}$ may be desired in alternative applications.

To expand the expandable fusion device 10, driving ramp 300 may be moved in a first direction with respect to body 500. By way of example, driving ramp 300 may be pulled towards body 500. In some embodiments, actuator assembly 200 (best seen on FIG. 58) may be rotated to pull driving ramp 300 towards body 500. As driving ramp 300 may be pulled towards body 500, the driving ramp 300 and body 500 may engage the first and second endplates 14, 16. By way of example, the front ramped portions 508 of the first and second endplates 14, 16 may engage the front endplate engaging ramps 526 of the driving ramp 300 and the rear ramped portions 510 of the first and second endplates 14, 16 may engage the rear endplate engaging ramps 542 of the body 500. However, because of the difference in ramp angles (shown as $\Delta_{rear}$ and $\Delta_{front}$ on FIG. 59), the first and second endplates 14, 16 may not ride up the front endplate engaging ramps 526 and the rear endplate engaging ramps 542 to increase the height of the expandable fusion device. Instead, in some embodiments, the first and second endplates 14, 16 may pivot at the contact point between the first and second endplates 14, 16 and the body 500 causing expansion of the endplates 14, 16 at the opposite end. As seen in FIGS. 62-64, this pivoting may result in expansion of the first and second endplates 14, 16 into an expanded lordotic configuration. As will be appreciated, pivoting of the first and second endplates 14, 16 may cause the angles $\alpha_{rearendplate}$ and $\alpha_{frontendplate}$ with respect to longitudinal axis 512 to change, thus reducing the difference in ramp angles $\Delta_{rear}$, Δfront. When the difference in ramp angles $\Delta_{rear}$, $\Delta_{front}$ approaches 0° (e.g., within 0.5°, 0.1°, or less), lordotic expansion may stop, and expandable fusion device 10 may be in its lordotic expanded configuration.

FIGS. 65 to 67 illustrate expandable fusion device 10 in a fully expanded configuration, in accordance with present embodiments. In some embodiments, it may be desired to further expand the expandable fusion device 10 from the lordotic expanded configuration of FIGS. 62-64. By way of example, continued movement of driving ramp 300, for example, translational movement towards body 500, may cause further expansion of expandable fusion device 10. This further expansion may be considered parallel expansion as both ends of the expandable fusion device 10 may expand at the same rate. Expansion may be continued, for example, until the expandable fusion device 10 has reached its fully expanded configuration or until a desired height of expandable fusion device 10 has been achieved. Expansion of expandable fusion device 10 may be limited by engagement of driving ramp 300 with body 500.

In the event the fusion device 10 needs to be repositioned or revised after being installed and expanded, the fusion device 10 can be contracted back to the unexpanded configuration, repositioned, and expanded again once the desired positioning is achieved. To contract the fusion device 10, an instrument can be used to rotate the actuator assembly 200 in a second direction that is opposite the first direction. Rotation of the actuator assembly 200 in the opposite direction may result in movement of the body 500 and the driving ramp 300 away from one another. As the body 500 and driving ramp 300 move away from one another, the endplates 14, 16 move inwardly into the unexpanded position.

Expanded heights of expandable fusion device 10 may typically range from 7 mm to 12 mm, but may be larger or smaller, including as small as 5 mm, and as large as 16 mm, although the size is dependent on the patient, and the joint into which the expandable fusion device 10 may be implanted. Expandable fusion device 10 may be implanted within any level of the spine, and may also be implanted in other joints of the body, including joints of the hand, wrist, elbow, shoulder, hip, knee, ankle, or foot.

Although the preceding discussion only discussed having a single fusion device 10 in the intervertebral space, it is contemplated that more than one fusion device 10 can be inserted in the intervertebral space. It is further contemplated that each fusion device 10 does not have to be finally installed in the fully expanded state. Rather, depending on the location of the fusion device 10 in the intervertebral disc space, the height of the fusion device 10 may vary from unexpanded to fully expanded. It should be noted that, as well as the height being varied from an unexpanded state to an expanded state, the fusion 10 may be positioned permanently anywhere between the expanded state and the unexpanded state.

In some embodiments, an expandable fusion device can be provided whereby expansion is performed via a ratcheting mechanism. By providing a ratcheting mechanism, this advantageously provides for rapid, convenient, non-continuous expansion of the fusion device.

Figure 68:
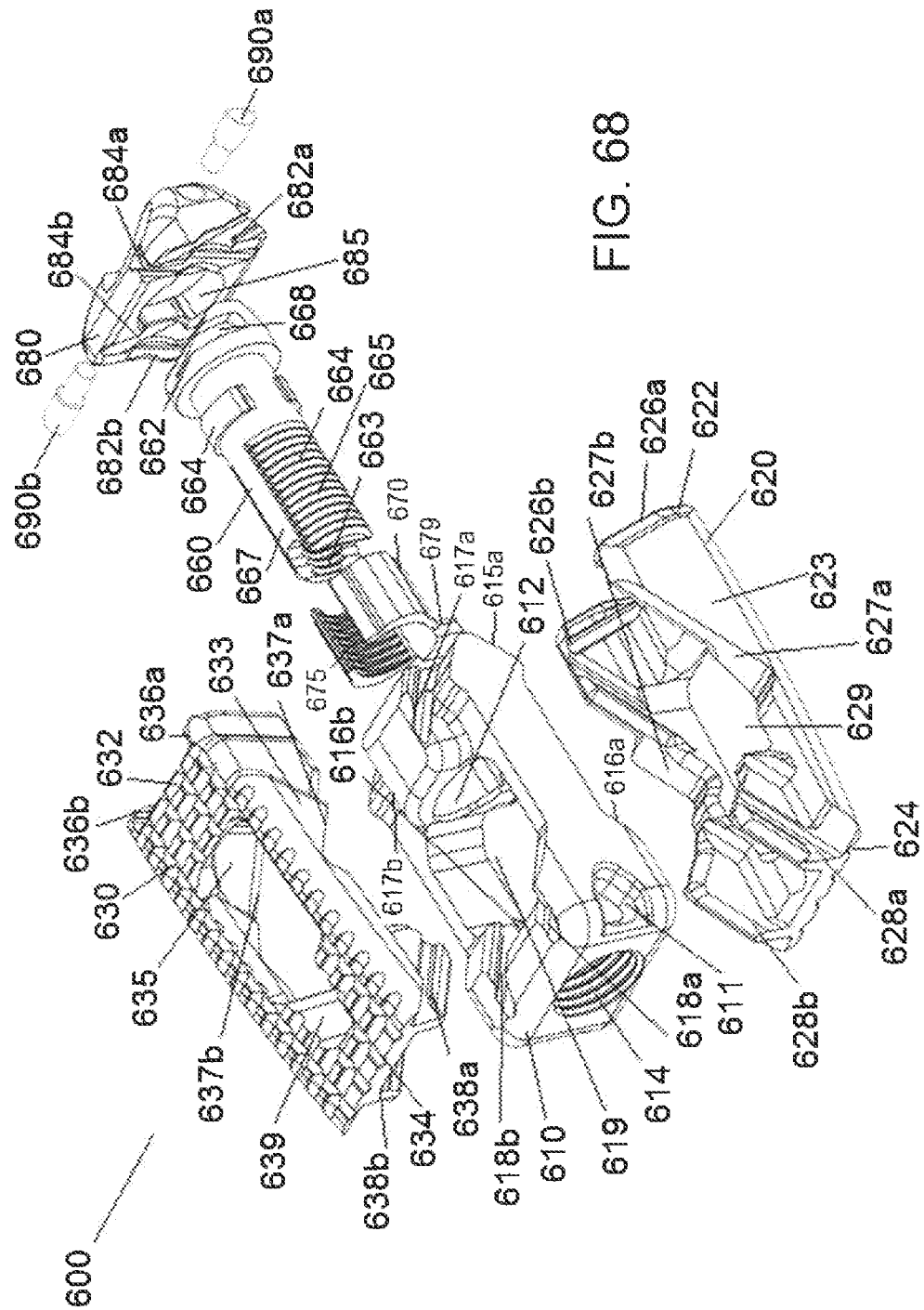
FIG. 68 is an exploded view of an expandable fusion device having a ratcheting mechanism in accordance with some embodiments.

FIG. 68 is an exploded view of an expandable fusion device having a ratcheting mechanism in accordance with some embodiments. The expandable fusion device 600 comprises a first endplate 620, a second endplate 630, a body 610 positioned between the first endplate 620 and the second endplate 630, a stem 660 and associated collar 670, and a nose 680. The stem 660 and associated collar 670 advantageously provide a non-continuous ratcheting mechanism to the expandable fusion device, whereby the expandable fusion device can alternatingly incrementally increase and then stop, until a desired expansion occurs.

The first endplate 620 comprises a lower endplate having a first end 622 and a second end 624. The first end 622 comprises a pair of first end ramped portions 626a, 626b. Each of these ramped portions 626a, 626b is configured to engage corresponding lower nose ramps 682a, 682b on the nose 680 to aid with expansion of the expandable fusion device. The second end 624 comprises a pair of second end ramped portions 628a, 628b. Each of these ramped portions 628a, 628b is configured to engage corresponding rear lower ramps 616a, 616b on the body 610 to aid with expansion of the expandable fusion device. A first side portion 623 having a central ramp 627a and a second side portion 625 having a central ramp 627b are positioned between the first end 622 and the second end 624 of the first endplate 620. Each of the central ramps 627a, 627b is configured to engage corresponding front lower ramps 615a, 615b (not visible) of the base 610 to aid with expansion of the expandable fusion device. The ramps of the first endplate 620 are formed along a perimeter that surrounds a central opening 629.

The second endplate 630 comprises an upper endplate having a first end 632 and a second end 634. The first end 632 comprises a pair of first end ramped portions 636a, 636b. Each of these ramped portions 636a, 636b is configured to engage corresponding upper nose ramps 684a, 684b on the nose 680 to aid with expansion of the expandable fusion device. The second end 634 comprises a pair of second end ramped portions 638a, 638b. Each of these ramped portions 638a, 638b is configured to engage corresponding rear upper ramps 618a, 618b on the body 610 to aid with expansion of the expandable fusion device. A first side portion 633 having a central ramp 637a and a second side portion 635 having a central ramp 637b are positioned between the first end 632 and the second end 634 of the second endplate 630. Each of the central ramps 637a, 637b is configured to engage corresponding front upper ramps 617a, 617b of the base 610 to aid with expansion of the expandable fusion device. The ramps of the second endplate 630 are formed along a perimeter that surrounds a central opening 639.

The body 610 comprises a front throughbore 612 and a rear throughbore 614. The front throughbore 614 comprises an opening for receiving the collar 670, and hence the stem 660, therethrough. The rear throughbore 614 comprises an opening through which one or more tools (e.g., an expansion tool and a disengagement tool) can pass through, as shown in FIGS. 78B and 78D. In some embodiments, the rear throughbore 614 is threaded to allow engagement by an insertion tool. In addition, the body 610 comprises one or more tool recesses 611 that can be engaged by an insertion tool to provide easy delivery of the implant into a surgical site. As shown in FIG. 68 and discussed above, the body 610 comprises a number of angled surfaces or ramps that are configured to engage corresponding ramps on the first endplate 620 or second endplate 630. As the ramps slide against one another, this causes expansion of the expandable fusion device.

The stem 660 and associated collar 670 form a ratcheting mechanism for causing expansion of the expandable fusion device. The stem 660 comprises a head 662 and a shaft 664. The stem 660 (via its head 662) is receivable within the nose 680 of the implant, whereby it is capable of rotation. In some embodiments, rotation of the stem 660 causes the implant to be changed from a "locked" ratcheting configuration into a "disengaged" non-ratcheting configuration, as will be discussed further below. The head 662 of the stem 660 comprises one or more grooves or slots 668 for receiving one or more nose pins 690a, 690b that extend through the nose 680. The shaft 664 of the stem 660 comprises an elongate body having an opening 663 for receiving an expansion tool 710 (shown in FIG. 78C) therethrough. The stem 660 further comprises ratchet teeth 665 that extend along a length of the shaft 664. In addition, the stem 660 comprises one or more flat areas 667 that are positioned adjacent to the ratchet teeth 665. In some embodiments, the stem 660 comprises a pair of flat areas 667 that are positioned 180 degrees apart from one another. In some embodiments, the stem 660 comprises a half ring portion 664 that is advantageously designed to hit against the body 610 at full expansion in order to prevent over expansion of the device.

The stem 660 is capable of two configurations. In a first "locked" configuration (shown in FIG. 78D), the ratchet teeth 665 of the stem 660 are engaged with corresponding ratchet recesses 675 of the collar 670, thereby creating a ratcheting mechanism that provides for expansion of the implant 600. In a second "disengaged" configuration (shown in FIG. 78E), the stem 660 is rotated such that the one or more flat areas 667 are positioned adjacent the ratchet recesses 675, such that the ratcheting mechanism is not operable. In this second disengaged configuration, the stem 660 is capable of being pulled back, thereby causing contraction of the implant 600.

The stem 660 is insertable through the collar 670, whereby it is placed in either the "locked" ratcheting configuration or the "disengaged" non-ratcheting configuration. In some embodiments, the collar 670 comprises a C-shaped ring having inner ratchet recesses 675 formed along an inner wall. In some embodiments, the collar 670 is housed within the front throughbore 616 of the body 610. In some embodiments, the collar 670 comprises a compressible C-ring type body that is capable of compression within the front throughbore 616. In some embodiments, the collar 670 is not rotatable, and can be keyed into place to prevent rotation. Advantageously, the collar 670 can comprise a tab 679 that prevents rotation of the collar 670 within the body 610. With the stem 660 attached to the collar 670, a ratcheting mechanism is formed whereby an expansion tool 710 (shown in FIG. 78C) can extend through the collar 670 and into the stem 660 via the shaft opening 663. The expansion tool 710 is capable of pulling or ratcheting the stem 660 in a direction towards the second ends of the first endplate 620 and second endplate 630. As the stem 660 is operably connected to the nose 680, the nose 680 is also drawn, thereby causing ramps of the first endplate 620 and second endplate 630 to slide up corresponding ramps of the body 610 and nose 680.

The nose 680 comprises a throughhole 685 through which the head 662 of the stem 660 can extend therethrough. A pair of nose pins 682a, 682b can then extend through the nose 680 and into the head 662, thereby retaining the stem 660 in the nose 680. As noted above, the nose 680 comprises one or more upper nose ramps 684a, 684b, which are configured to mate and engage corresponding ramps on the second endplate 630. In addition, the nose 680 comprises one or more lower nose ramps 682a, 682b, which are configured to mate and engage corresponding ramps on the first endplate 620.

Figures 69A, 69B, 69C:
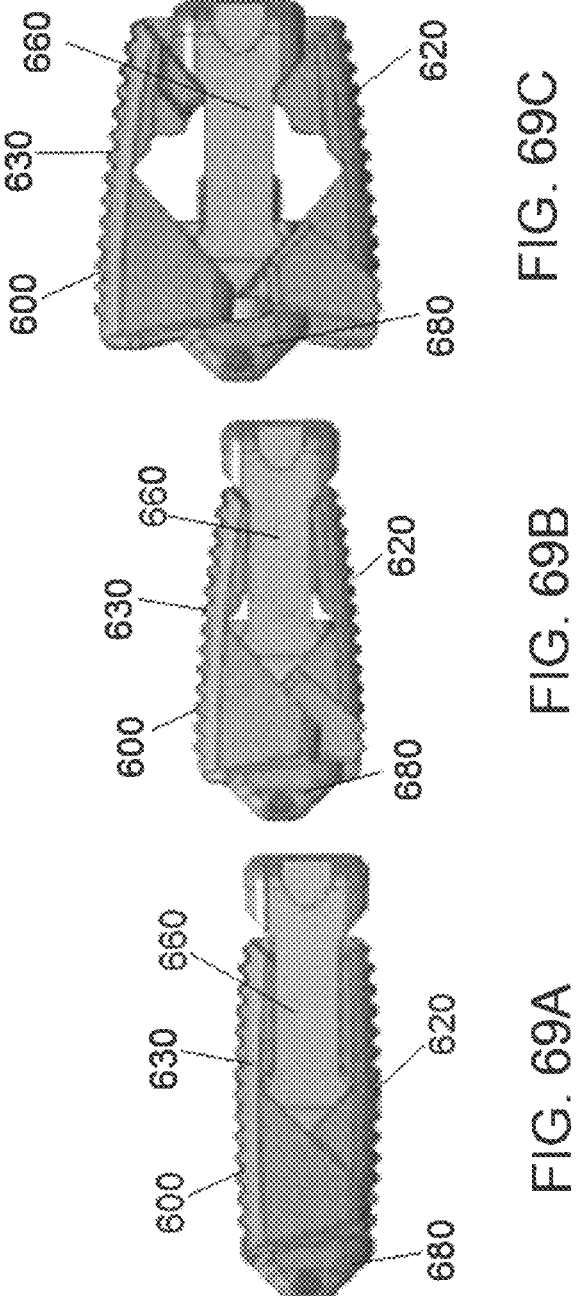
FIGS. 69A, 69B, and 69C are side views of the expandable fusion device of FIG. 68 in the process of expansion in accordance with some embodiments.

FIGS. 69A-69C are side views of the expandable fusion device of FIG. 68 in the process of expansion in accordance with some embodiments. In some embodiments, the expandable fusion device 600 is advantageously capable of expansion, and in particular, lordotic expansion. In some embodiments, the device 600 can begin in a contracted state, as shown in FIG. 69A. Afterwards, by pulling the nose 680 via a ratcheting mechanism, the device 600 can expand and tip into lordosis, as shown in FIG. 69B. Once the device 600 has achieved maximum lordosis, the device 600 can continue to expand in height in a parallel fashion, whereby both the anterior and posterior aspects expand at the same rate, until the implant 600 reaches a maximum expansion, as shown in FIG. 69C. In other words, once the device 600 reaches a particular lordotic angle (as shown in FIG. 69B), the device 600 will maintain the lordotic angle throughout the expansion range until maximum expansion has been achieved, as shown in FIG. 69C. More details on the expansion of the device 600 are provided with respect to FIGS. 70A-72C.

Figure 70A:
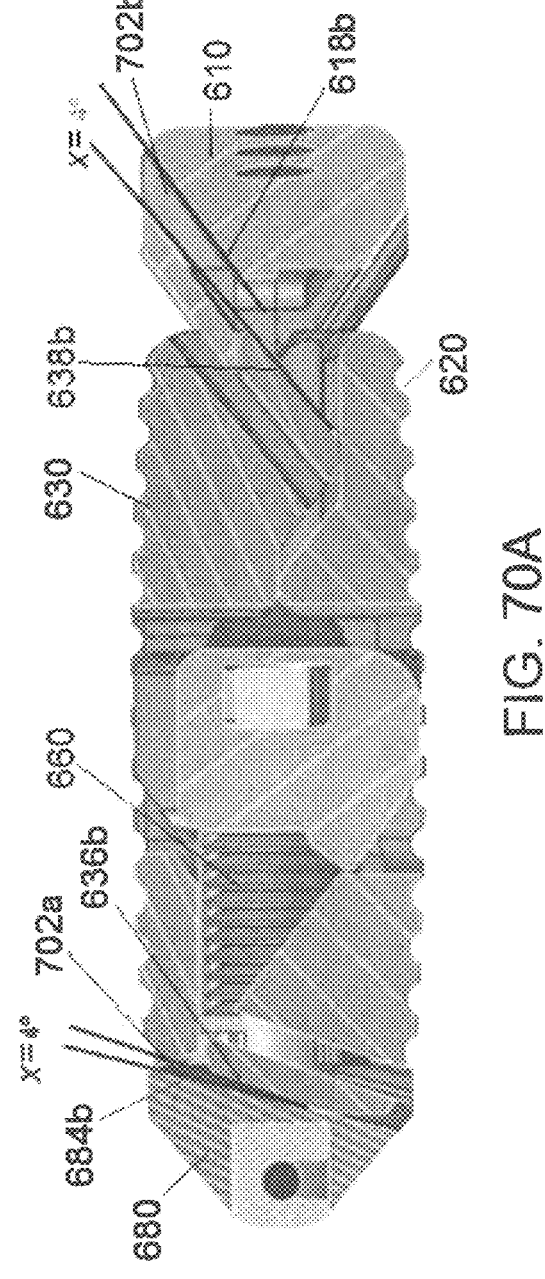
FIGS. 70A, 70B, and 70C are different views of the expandable fusion device of FIG. 68 in a contracted state in accordance with some embodiments.
Figures 70B, 70C:
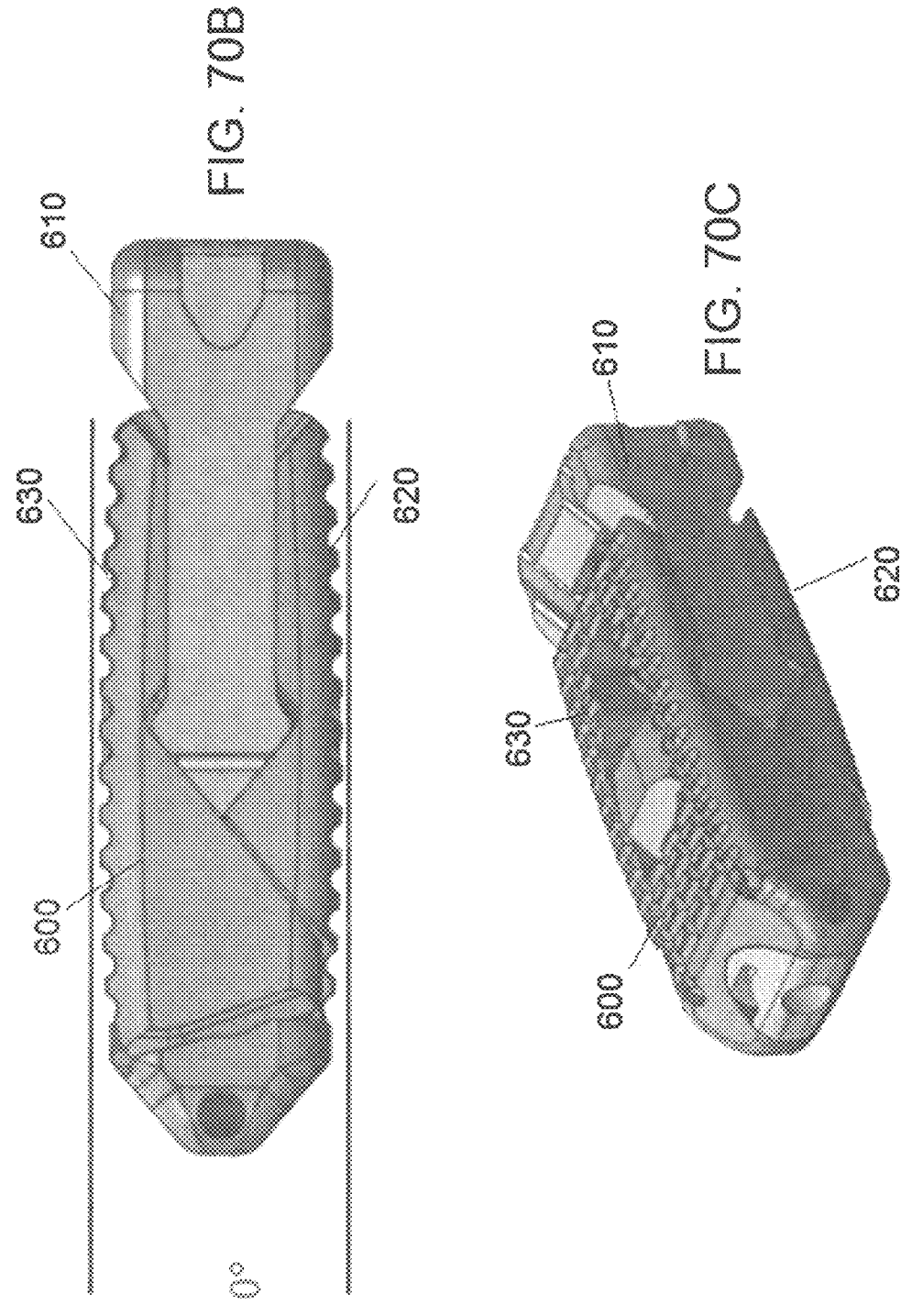

FIGS. 70A-70C are different views of the expandable fusion device of FIG. 68 in a contracted state in accordance with some embodiments. From the contracted state, the device 600 is capable of first expanding and tipping into lordosis, and then expanding in a parallel fashion. The angle tipping is driven by a difference in ramp angle x that is seen between the first end ramped portions 636a, 636b of the second endplate 630 and the upper nose ramps 684a, 684b of the nose 680. Similarly, the same difference in ramp angle x is also seen between the second end ramped portions 638a, 638b of the second endplate 630 and the rear upper ramps 618a, 618b of the body 610. In other words, at the contracted height, the difference in angle x between the different ramps causes a gap 702 between the ramps, with a first end gap 702a formed closer to the first end of the second endplate 630 and a second end gap 702b formed closer to the second end of the second endplate 630. The degree of the gap 702 will determine what lordosis the device will tip into upon expansion. For example, if the degree of the gap 702 is 4 degrees (e.g., x=4), the second endplate 630 will tip into 4 degrees of lordosis. As the same mechanism is provided for the first endplate 620, the first endplate 620 will also tip into 4 degrees of lordosis, thereby providing an overall lordosis of 8 degrees once both endplates 620, 630 have been tipped. In some embodiments, the endplates 620, 630 themselves can have built-in lordosis. For example, if the built in lordosis of both endplates 620, 630 was 7 degrees inclusive, then the overall lordosis following expansion wherein x=4 is 15 degrees of lordosis. While the present embodiment shows an angle x difference of 4 degrees, the angle can be less or more, thereby resulting in less or more lordosis.

Figure 71A:
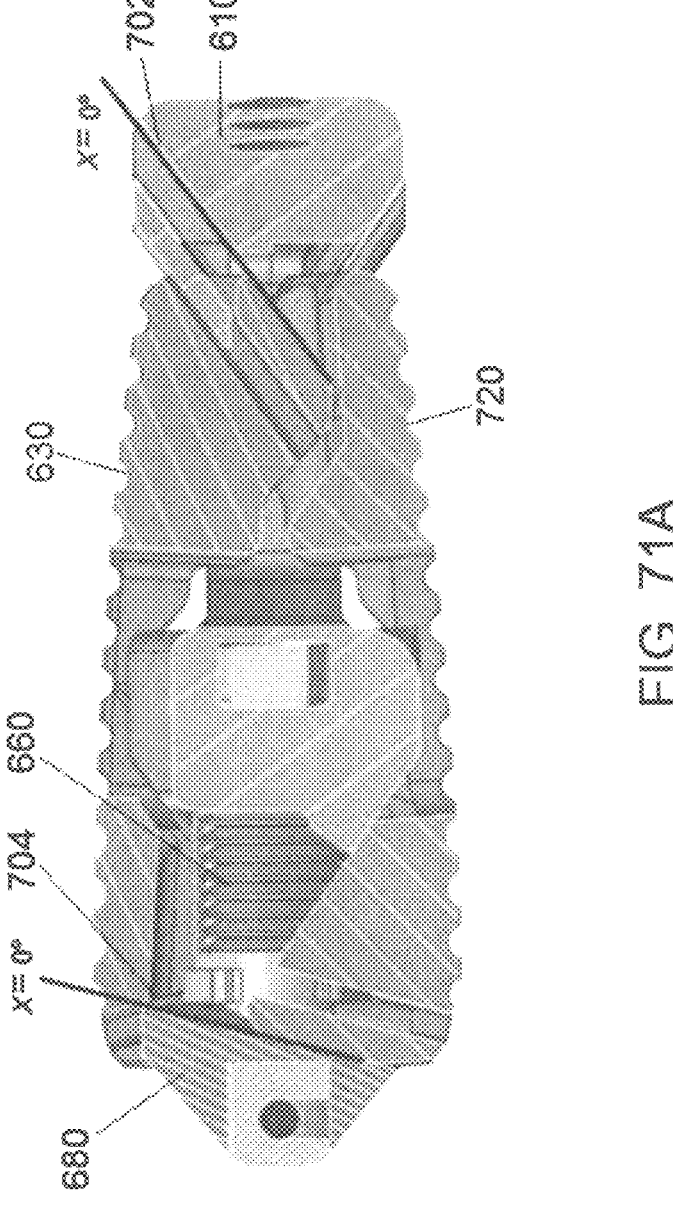
FIGS. 71A, 71B, and 71C are different views of the expandable fusion device of FIG. 68 in a tipped state without full expansion in accordance with some embodiments.
Figures 71B, 71C:
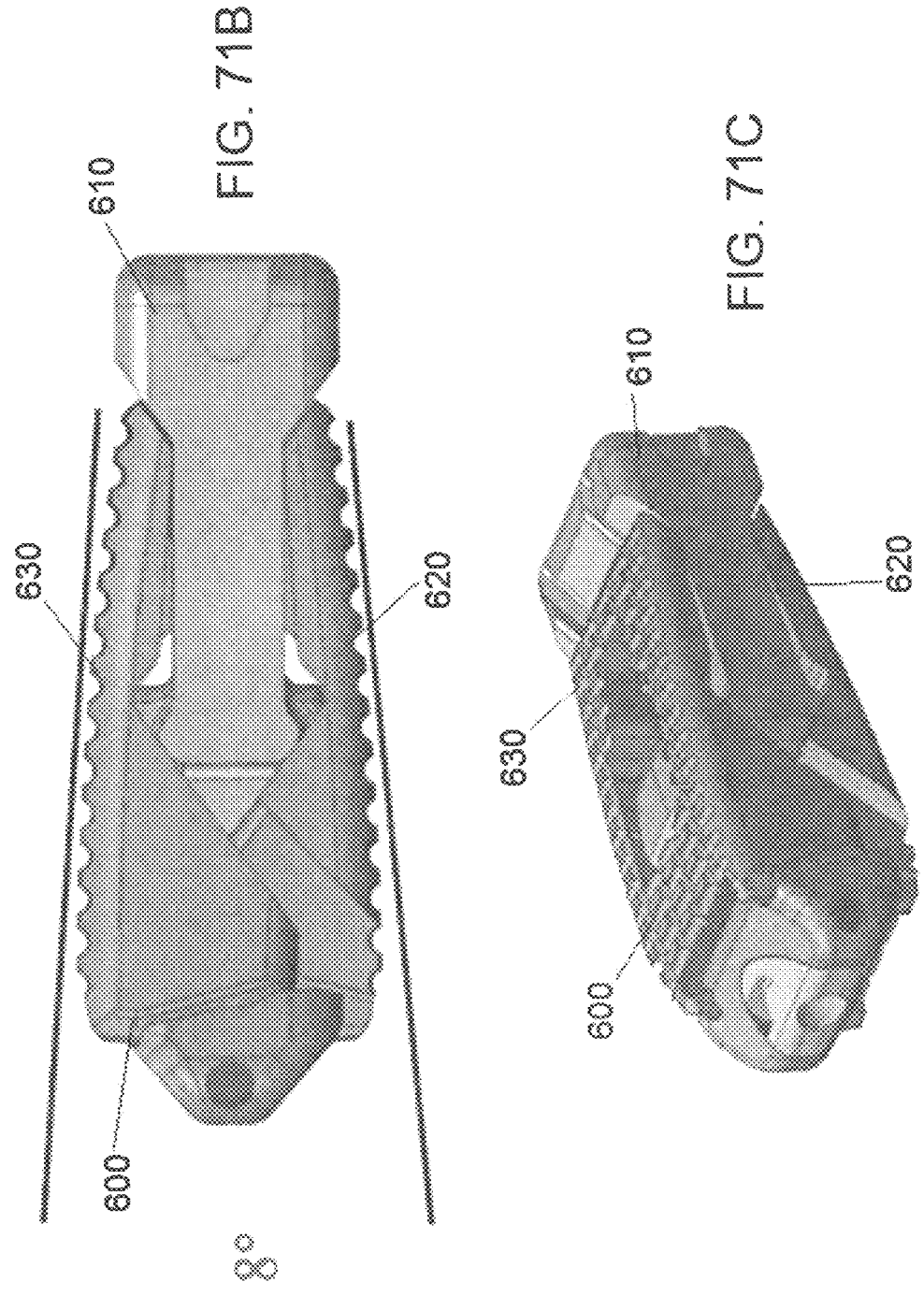

FIGS. 71A-71C are different views of the expandable fusion device of FIG. 68 in a tipped state without full expansion in accordance with some embodiments. To tip the expandable fusion device 600 into lordosis, the nose 680 is initially ratcheted or pulled back towards the body 610, thereby causing the gaps x to close and the corresponding ramps to mate. The amount of lordosis will be pre-determined based on the initial ramp gap x. In the present embodiment, the expandable fusion device 600 has been tipped into a lordotic angle of 4 degrees for the second endplate 630 and 4 degrees for the first endplate 620, thereby resulting in a total of 8 degrees of lordosis (as shown in FIG. 71B). One skilled in the art can appreciate that the total degree of lordosis can be less than or greater than 8 degrees, and that 8 degrees in just a representative example.

Figure 72A:
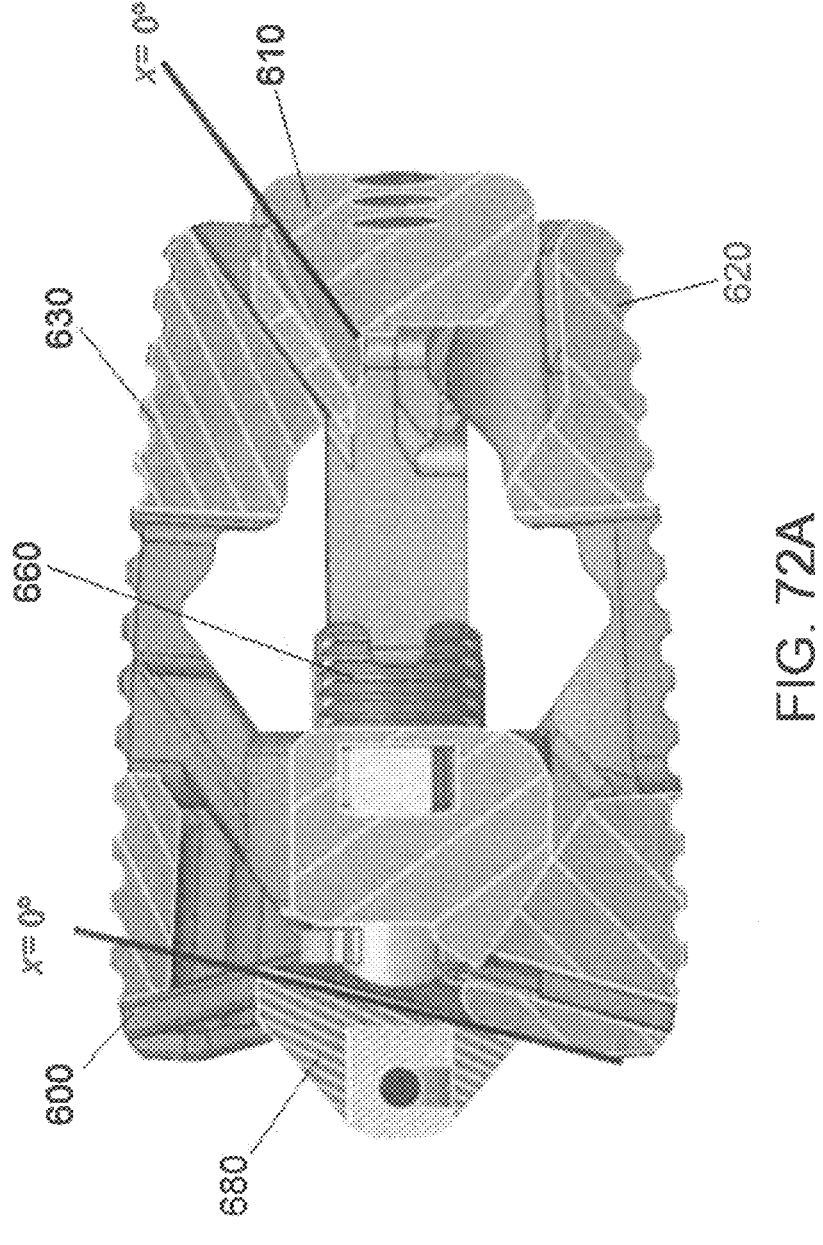
FIGS. 72A, 72B, and 72C are different views of the expandable fusion device of FIG. 68 in a fully expanded state in accordance with some embodiments.
Figures 72B, 72C:
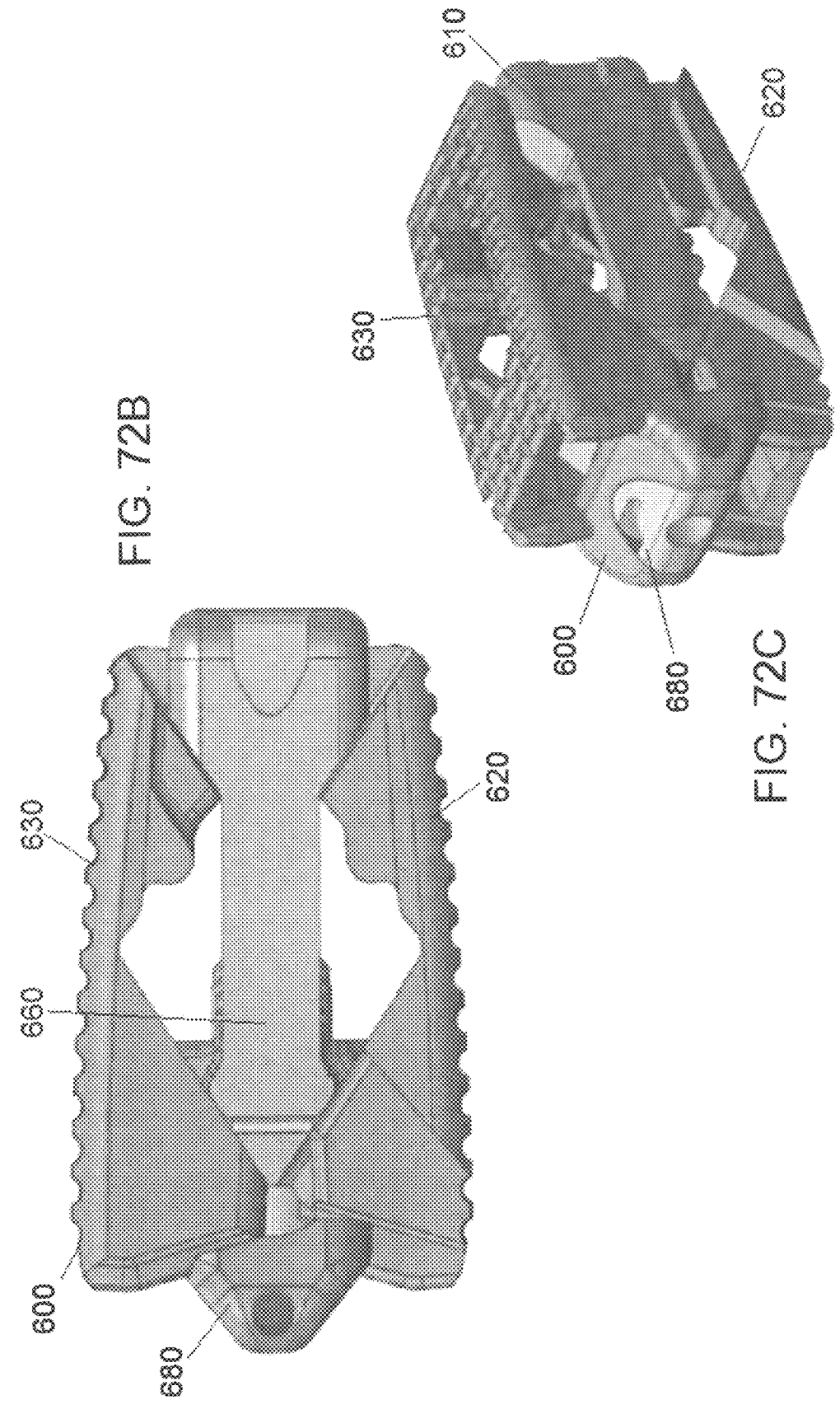

FIGS. 72A-72C are different views of the expandable fusion device of FIG. 68 in a fully expanded state in accordance with some embodiments. As the nose 680 is pulled back further the corresponding ramps of the device 600 are fully mated, the implant then begins to expand in overall height in a parallel fashion. In other words, the anterior and posterior aspects of the device 600 expand at the same rate. As this happens, the device maintains the same lordosis allowing the lordotic angle to be seen throughout the expansion range. For example, the degree of lordosis of the device 600 in the fully expanded state (as shown in FIG. 72B) is the same as the degree of lordosis of the device 600 after the endplates have been tipped (as shown in FIG. 71B). However, due to further parallel expansion, the height of the device 600 in the fully expanded state (as shown in FIG. 72B) is greater than the height of the device 600 after the endplates have been tipped (as shown in FIG. 71B).

The expandable fusion device 600 can advantageously be expanded via a ratcheting mechanism. More details regarding the ratcheting mechanism—in particular, the stem 660 and the collar 670—will be provided with respect to FIGS. 73-76.

Figure 73:
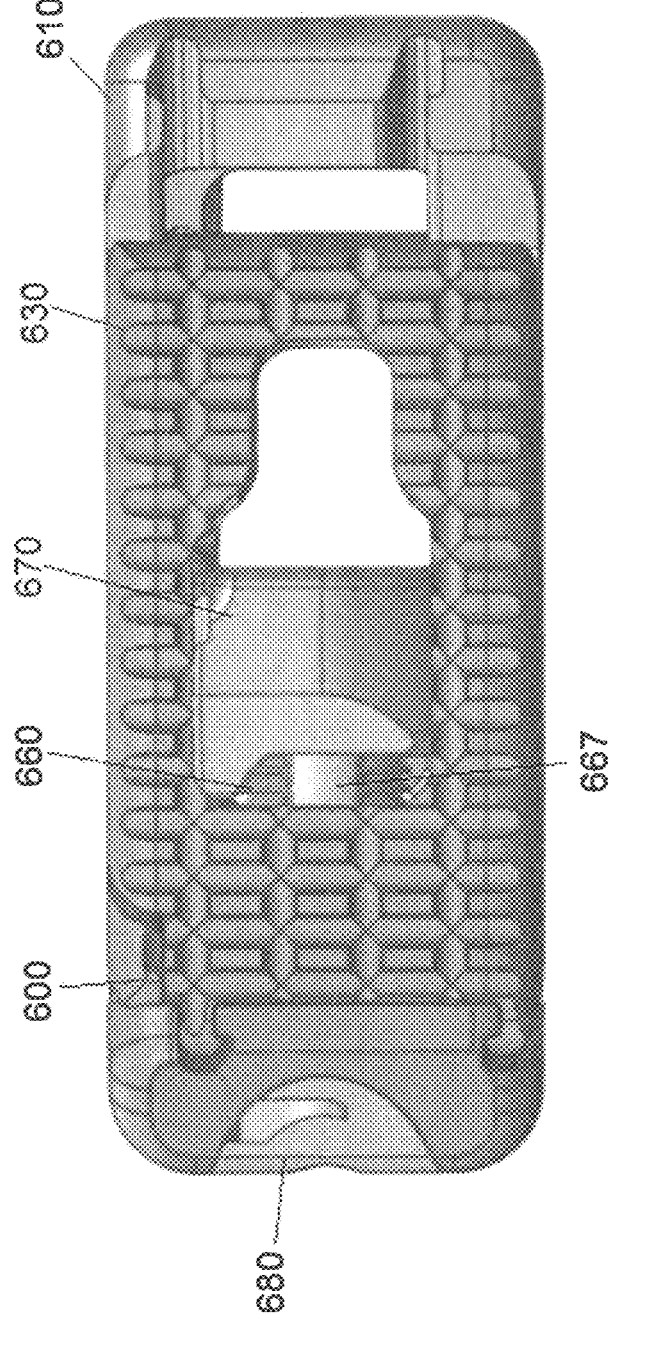
FIG. 73 is an upper view of the expandable fusion device of FIG. 68 in accordance with some embodiments.

FIG. 73 is an upper view of the expandable fusion device of FIG. 68 in accordance with some embodiments. From this view, one can see how collar 670 is housed in the body 610, and how the stem 660 is received in the collar 670. The stem 660 is further received in the nose 680, such that as the stem is pulled back, the nose 680 can also be pulled back thereby causing ratcheted expansion of the device 600.

Figure 74:
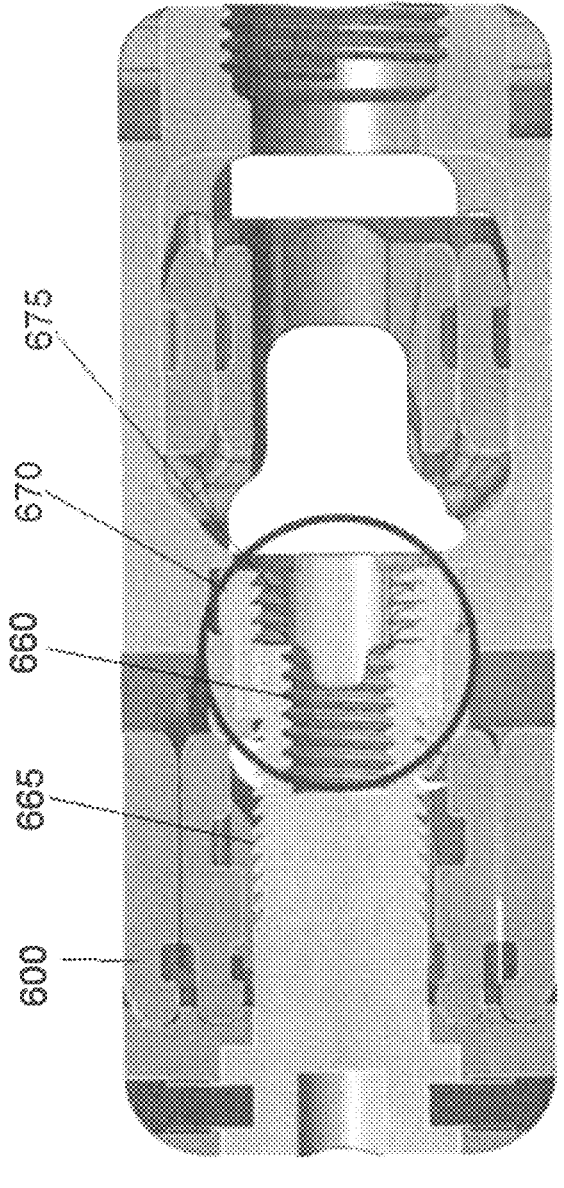
FIG. 74 is an upper cross-sectional view of the expandable fusion device of FIG. 68 in accordance with some embodiments.

FIG. 74 is an upper cross-sectional view of the expandable fusion device of FIG. 68 in accordance with some embodiments. In this view, one can see how the stem 660 having ratchet teeth 665 is engaged with the collar 670 to create an expandable ratcheting mechanism. In some embodiments, the stem 660 comprises the "male" ratcheting feature, while the collar 670 comprises the "female" ratcheting feature.

Figure 75:
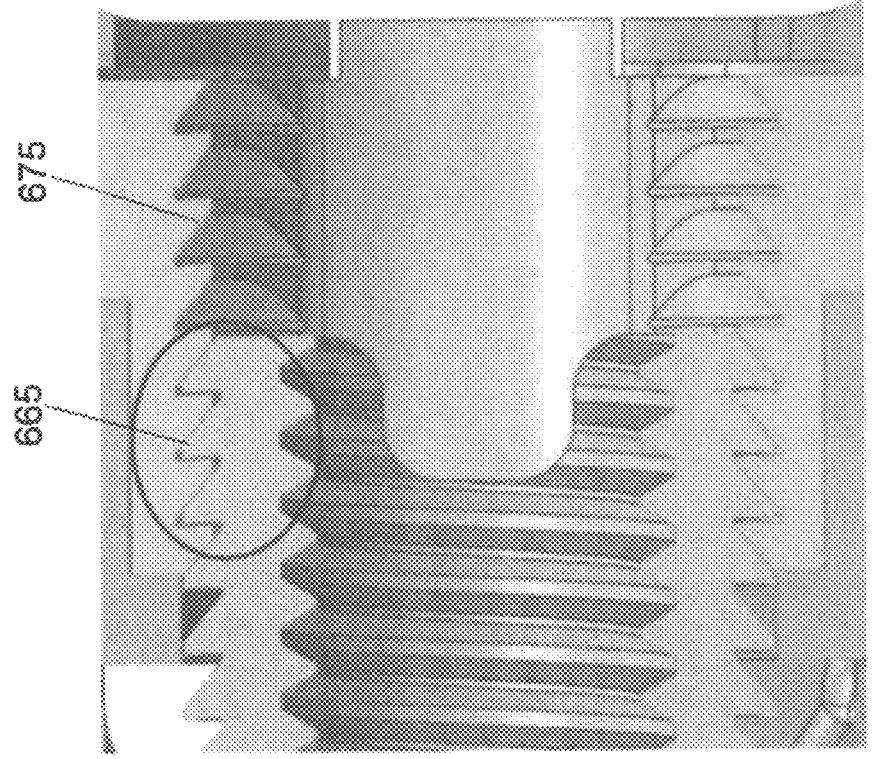
FIG. 75 is a close up view of the ratcheting mechanism of the expandable fusion device of FIG. 68 in accordance with some embodiments.

FIG. 75 is a close up view of the ratcheting mechanism of the expandable fusion device of FIG. 68 in accordance with some embodiments. This view shows the male ratchet of the stem 660 and the female ratchet of the collar 670 in more detail. As the stem 660 is pulled back, the collar 670 springs open like a C-ring and allows the ratchet teeth 665 of the stem 660 to advance to the next slot or recess 675 formed in the collar 670. The stem 660 advantageously moves in increments through the collar 670. These non-continuous increments drive height increases. In some embodiments, the height increases can increase in increments greater than 0.2 mm and 0.8 mm. In some embodiments, the height increases are in increments of approximately 0.5 mm.

Figure 76:
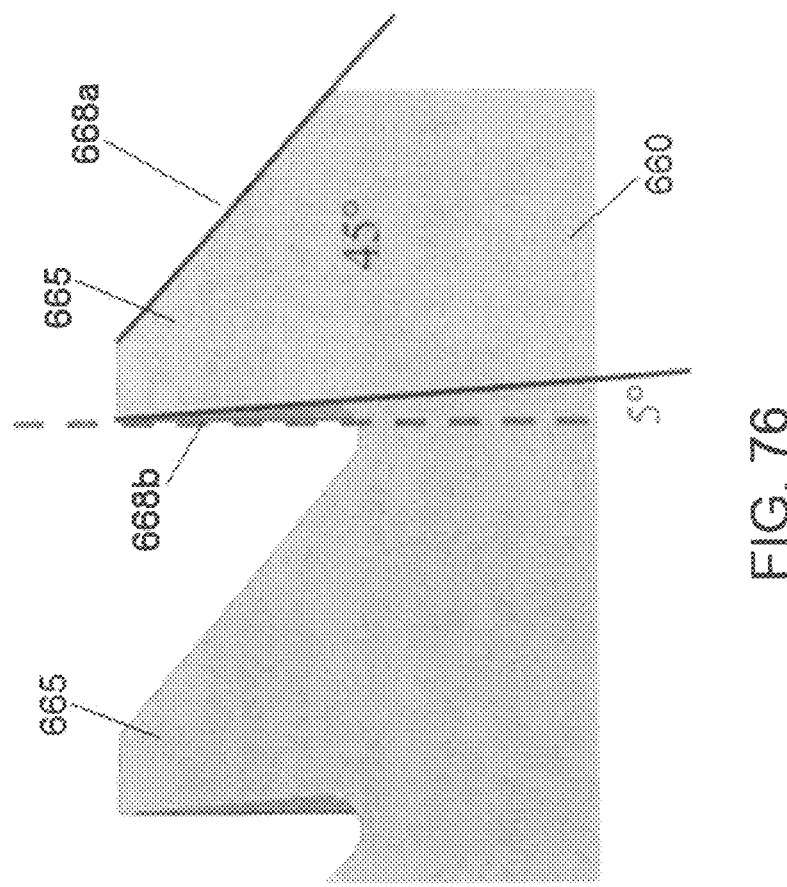
FIG. 76 is a close up view of the ratchet teeth of the expandable fusion device of FIG. 68 in accordance with some embodiments.

FIG. 76 is a close up view of the ratchet teeth of the expandable fusion device of FIG. 68 in accordance with some embodiments. Each of the ratchet teeth 665 comprises an inclusive angle 668a and a back angle 668b. In some embodiments, the ratchet teeth 665 comprise an inclusive angle 668a of between 30 and 60 degrees, and in particular about 45 degrees. In some embodiments, the back angle 668b comprises between 2 and 8 degrees, and in particular about 5 degrees. Under load, the ratchet connection is pulled in the direction of disengagement. Advantageously, the purpose of the back angle 668b is to keep the stem 660 more engaged, especially in the back area when the device 600 is under load by pulling the collar 670 closer to the ratchet teeth 665 when pulled in the direction of disengagement.

Figure 77:
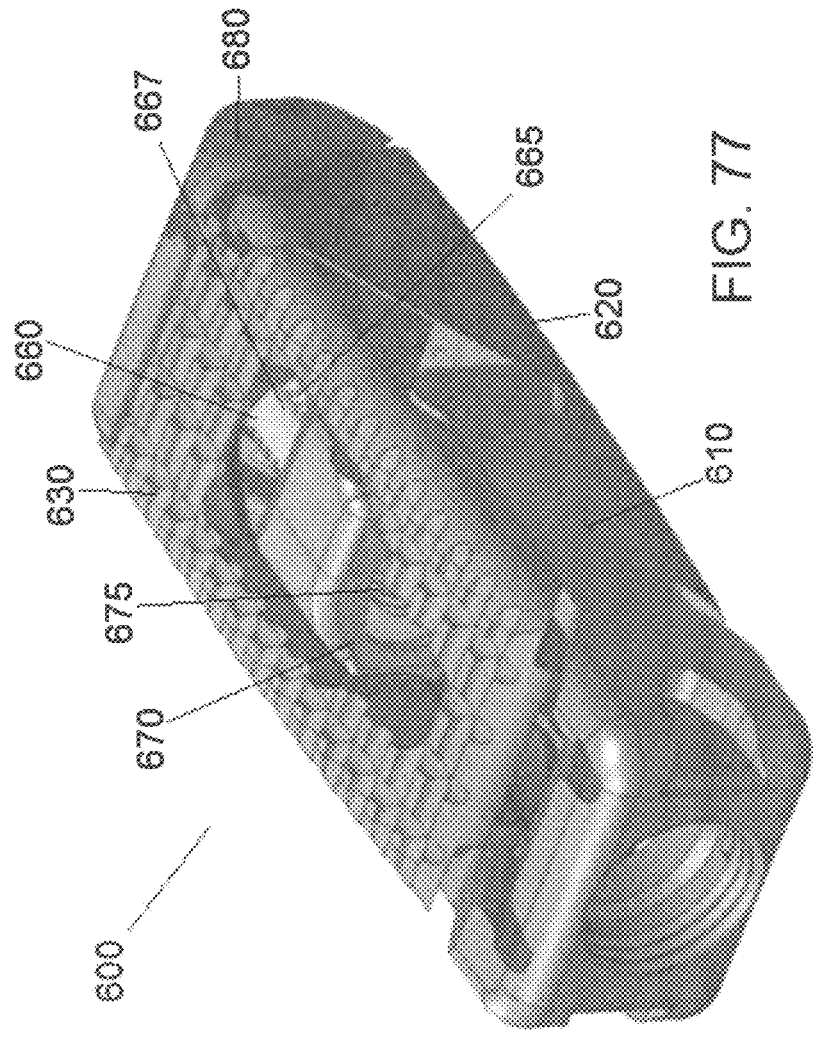
FIG. 77 is a top perspective view of the expandable fusion device of FIG. 68 in accordance with some embodiments.

FIG. 77 is a top perspective view of the expandable fusion device of FIG. 68 in accordance with some embodiments. In this configuration, the fusion device 600 is capable of ratcheted expansion. In addition to providing ratcheted expansion, the device is also capable of collapse and contraction. To accommodate contraction, the device 600 advantageously provides ratchet teeth 665 on only a portion of the stem 660, whereby the ratchet teeth 665 are separated by one or more flat areas 667. In the particular embodiment, the device 600 includes two sets of ratchet teeth 665 each of which is adjacent two sets of flat areas 667. These features allow a device to be converted between a "locked" configuration whereby ratcheting is enabled and a "disengaged" configuration whereby ratcheting is disabled. These features are discussed below with respect to FIGS. 78A-78G.

Figure 78A:
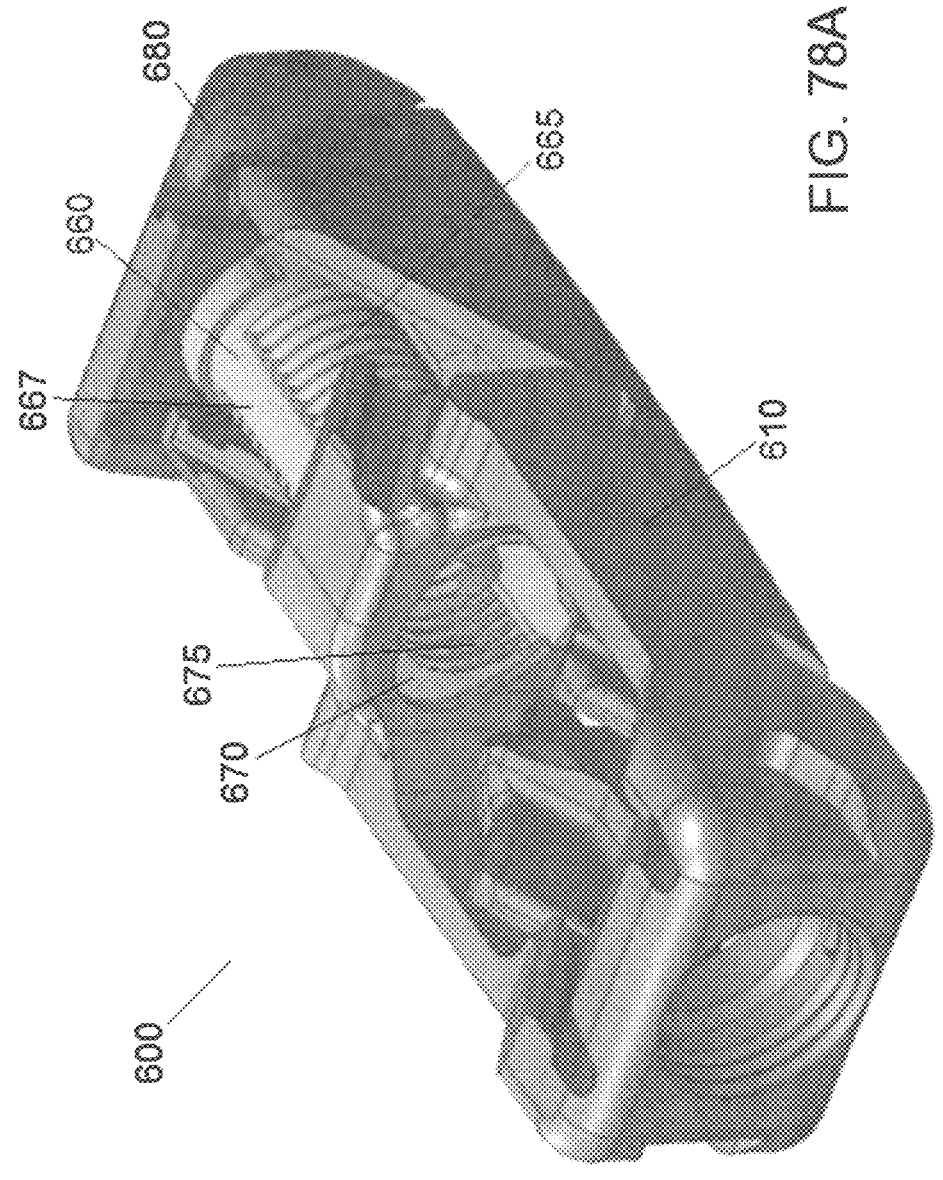
FIGS. 78A, 78B, 78C, 78D, 78E, 78F, and 78G are top perspective views of the expandable fusion device of FIG. 68 transitioning from a locked configuration to a disengaged configuration in accordance with some embodiments.
Figure 78B:
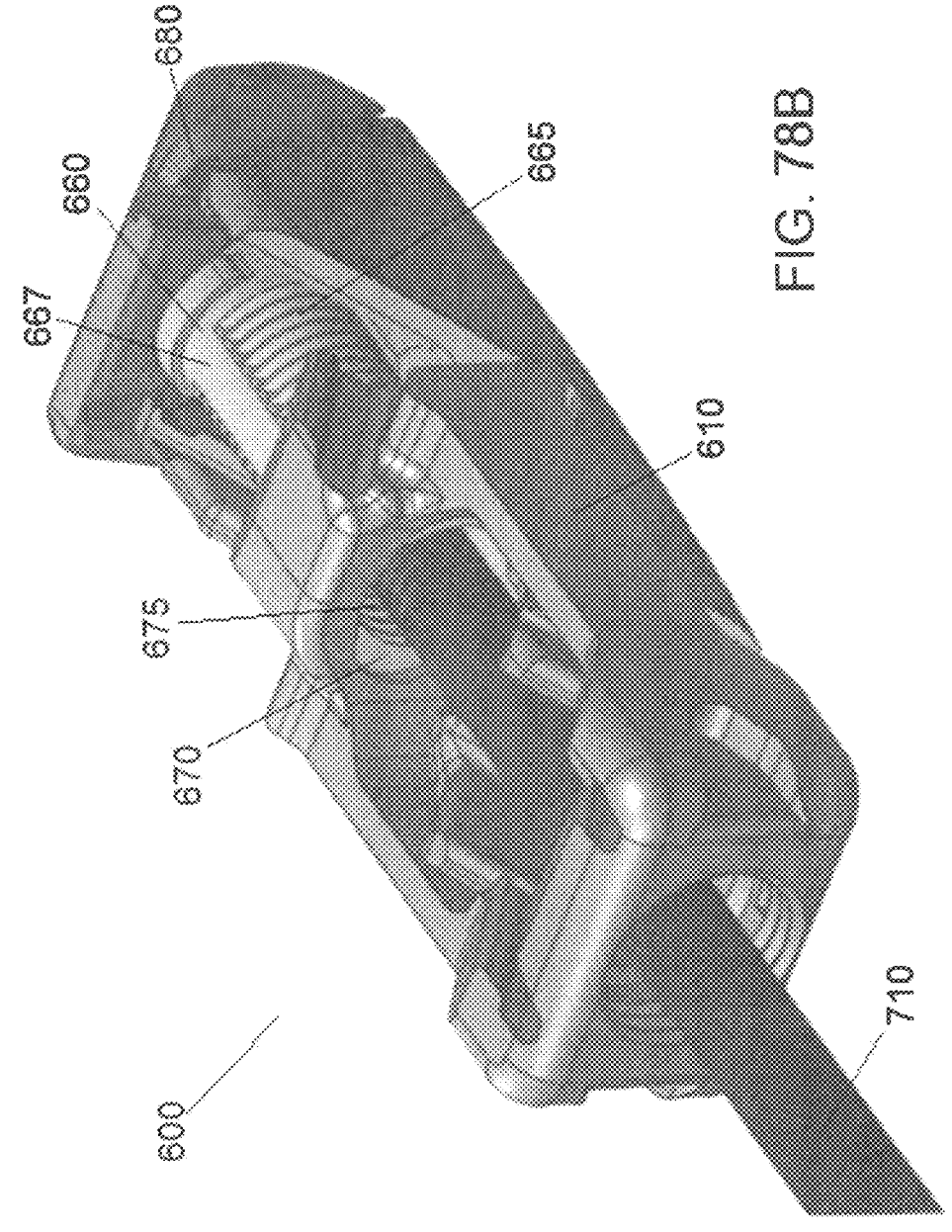
Figure 78C:
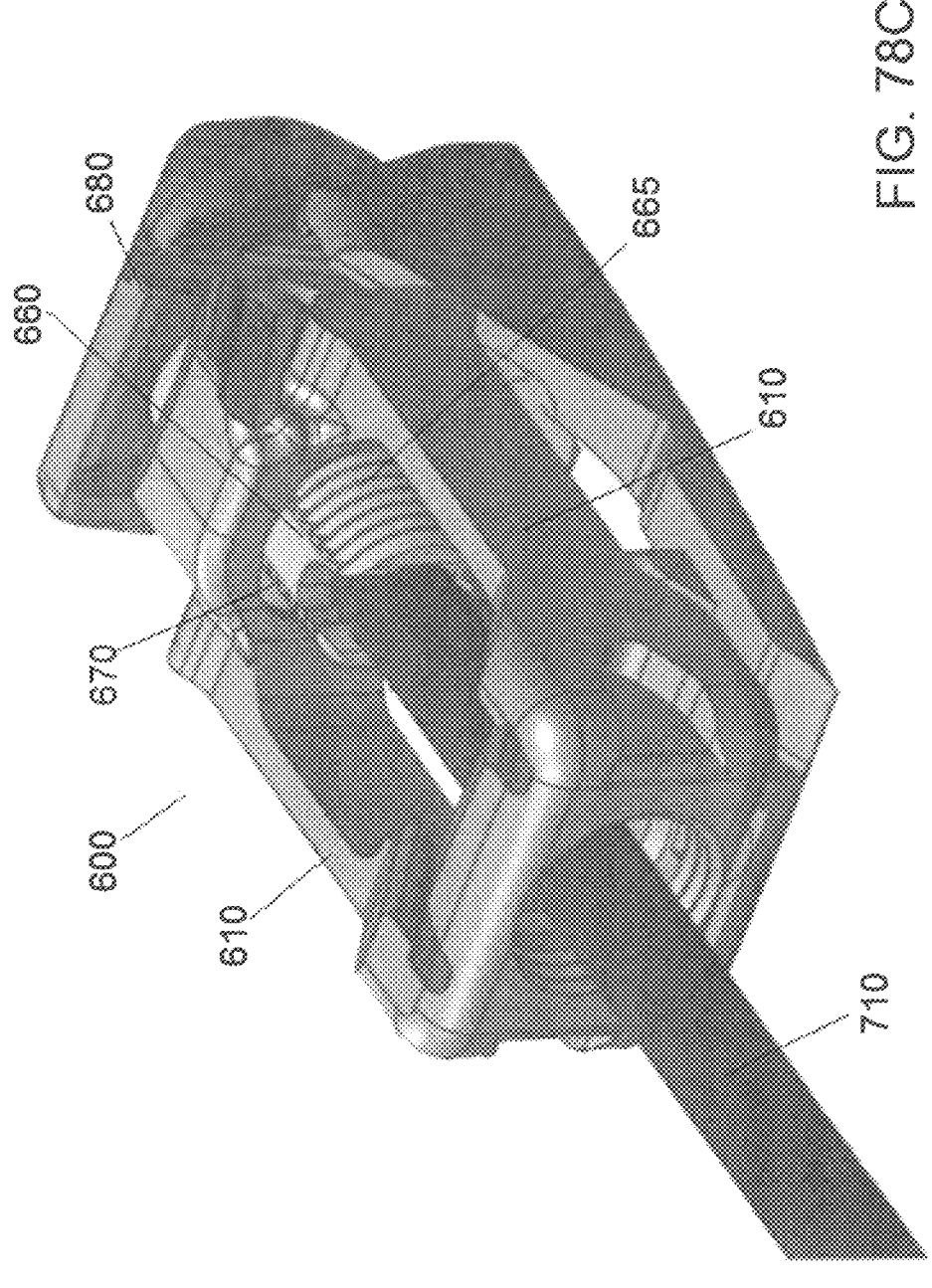
Figure 78D:
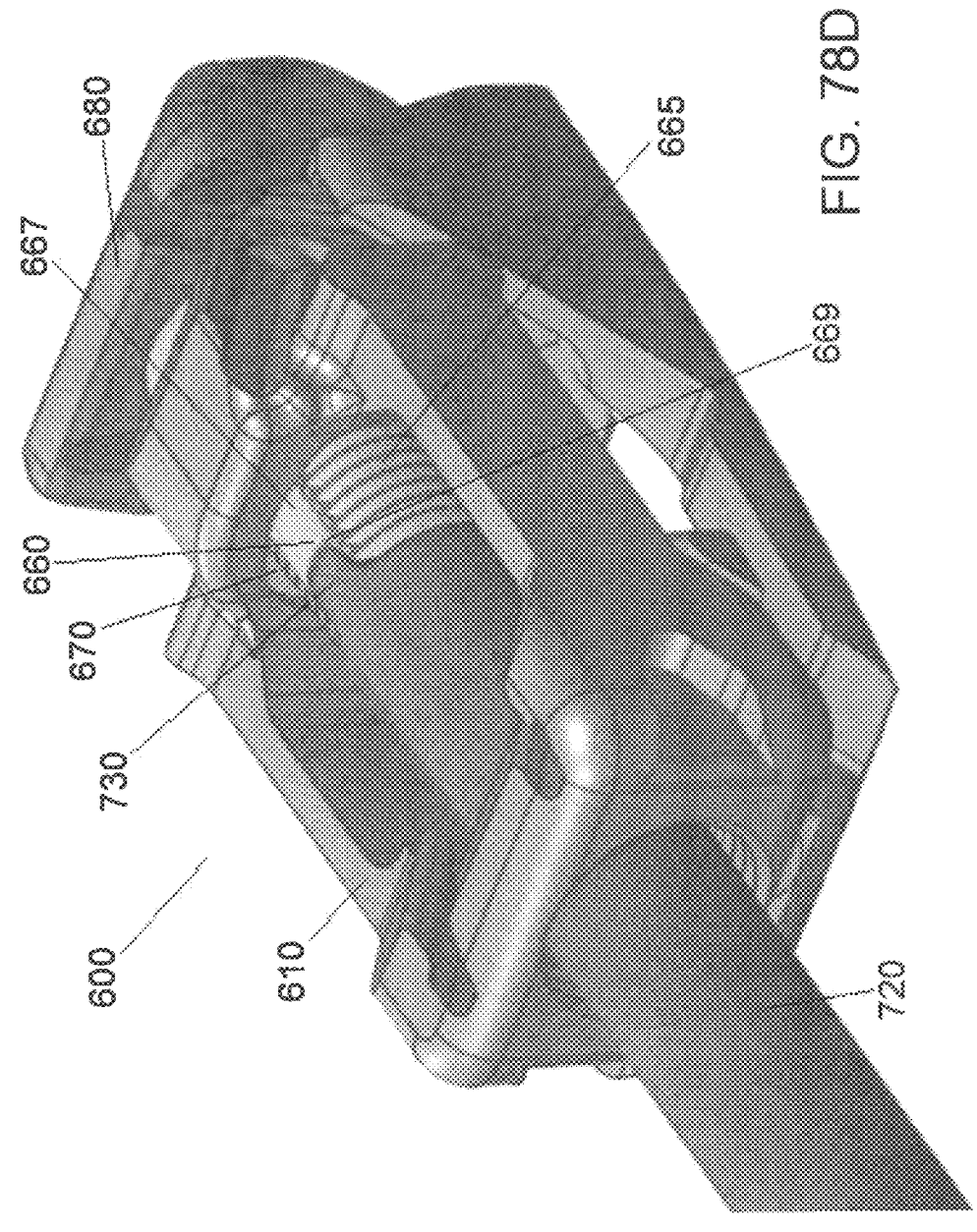

FIGS. 78A-78G are top perspective views of the expandable fusion device of FIG. 68 transitioning from a locked configuration to a disengaged configuration in accordance with some embodiments. FIG. 78A shows an expandable fusion device in a "locked" configuration whereby the device is capable of ratcheted expansion. As shown in FIG. 78A, the ratchet teeth 665 of the stem 660 are aligned and engaged with the ratchet recesses 675 of the collar 670, thereby enabling ratcheted expansion.

FIG. 78B shows the expandable fusion device with an expansion tool inserted therein. The expansion tool 710 is capable of engaging the stem 660 in the "locked" configuration, whereby the stem 660 (and hence the nose 680) is capable of being pulled back. As the stem 660 and nose 680 are drawn back, this causes incremental ratcheting expansion of the device 600 based on the design of the ratchet teeth.

FIG. 78C shows the expandable fusion device when fully expanded. As shown in the figure, the stem 660 has been pulled further into the body 610, thereby causing greater height expansion of the device. The fusion device 600 has a relatively higher height in FIG. 78C than in FIG. 78B. Advantageously, the fusion device 600 can also be contracted by a surgeon if desired.

FIG. 78D shows the expandable fusion device prior to contraction with the device still in a "locked" ratcheting configuration. To contract the device 600, a disengagement tool 720 (separate from the expansion tool 710) is provided. The disengagement tool 720 comprises a shaft having a distal nub 730. The disengagement tool 720 is advantageously designed to rotate the stem 660, such that the device is changed from a "locked" ratchetable configuration to a "disengaged" unratchetable configuration, as discussed above. To rotate the stem 660, the distal nub 730 of the disengagement tool 720 mates with a correspondingly shaped recess 669 in the stem 660. With the disengagement tool 720 engaged with the stem 660, the stem 660 can be rotated (e.g., 90 degrees), thereby converting the device into a disengaged configuration, as shown in FIG. 78E.

Figure 78E:
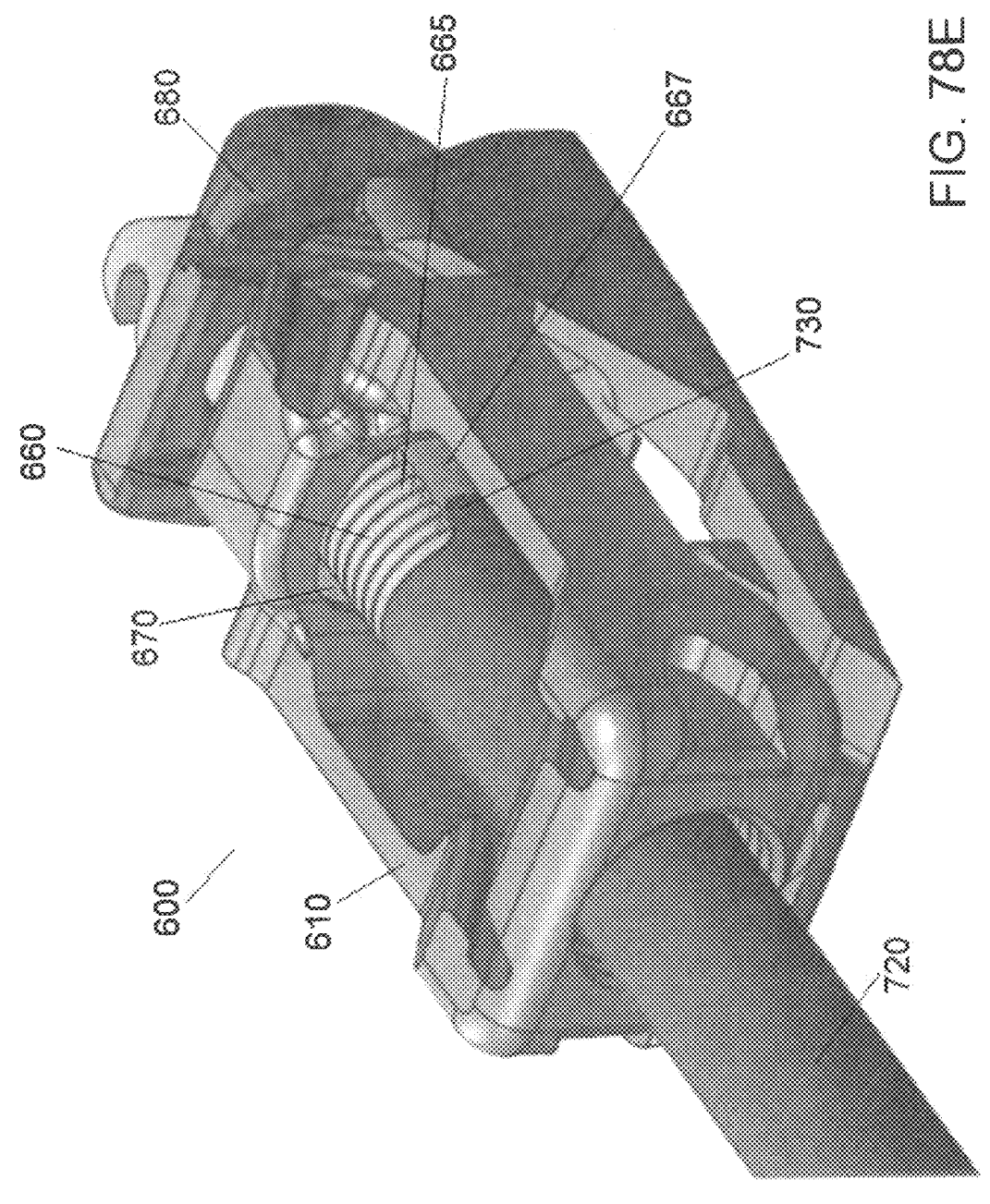

FIG. 78E shows the expandable fusion device in a "disengaged" non-ratchetable configuration. The stem 660 has been rotated such that its pair of flat areas 667 align and face the collar 670. As such, the ratchet teeth 665 of the stem are no longer engaged with ratchet slots of the collar 670, thereby allowing the stem 660 to be pushed forward to contract the device.

Figure 78F:
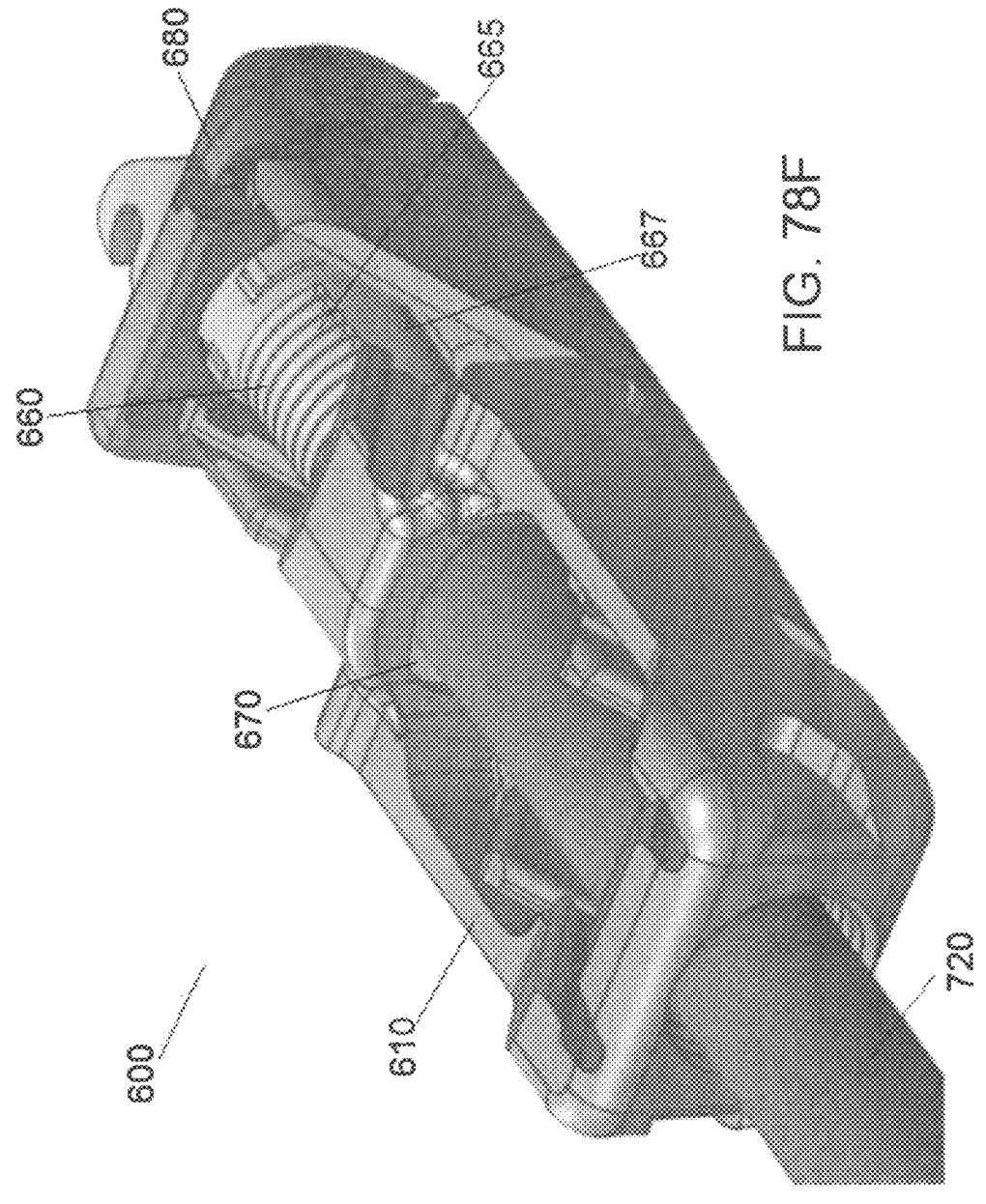

FIG. 78F shows the expandable fusion device in a "disengaged" configuration whereby the device has been fully contracted. At this stage, the device 600 is the same height as it was prior to expansion. The device 600 is fully capable of expansion again. A surgeon simply needs to rotate the stem 660 in an opposite direction 90 degrees, such that the device is brought back into a "locked" ratcheting configuration.

Figure 78G:
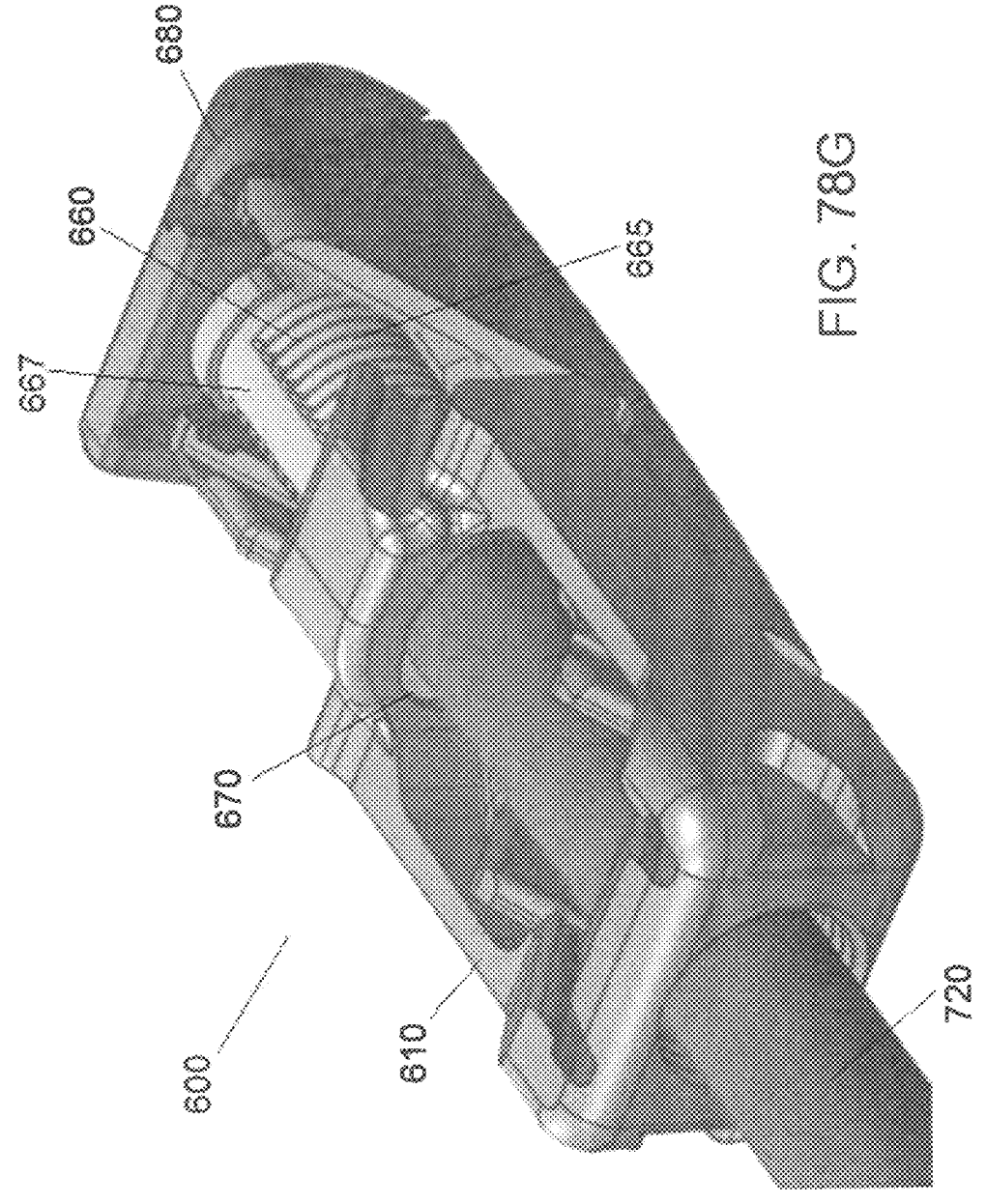

FIG. 78G shows the expandable fusion device whereby the device is brought back to a "locked" ratcheting configuration. By rotating the disengagement tool 720 in a reverse direction 90 degrees, this rotates the stem 660 whereby the ratchet teeth 665 are once again engaged with ratchet slots of the collar 670. The fusion device 600 can once again be expanded via a ratcheting mechanism if desired. Advantageously, the expandable fusion devices described above are each capable of being inserted through a minimal incision, as the devices can maintain a minimal profile prior to expansion.

In some embodiments, an expandable fusion device can be provided whereby expansion is performed via a threading mechanism. By providing a threading mechanism, this advantageously provides for controlled expansion and/or controlled of the fusion device.

Figure 79:
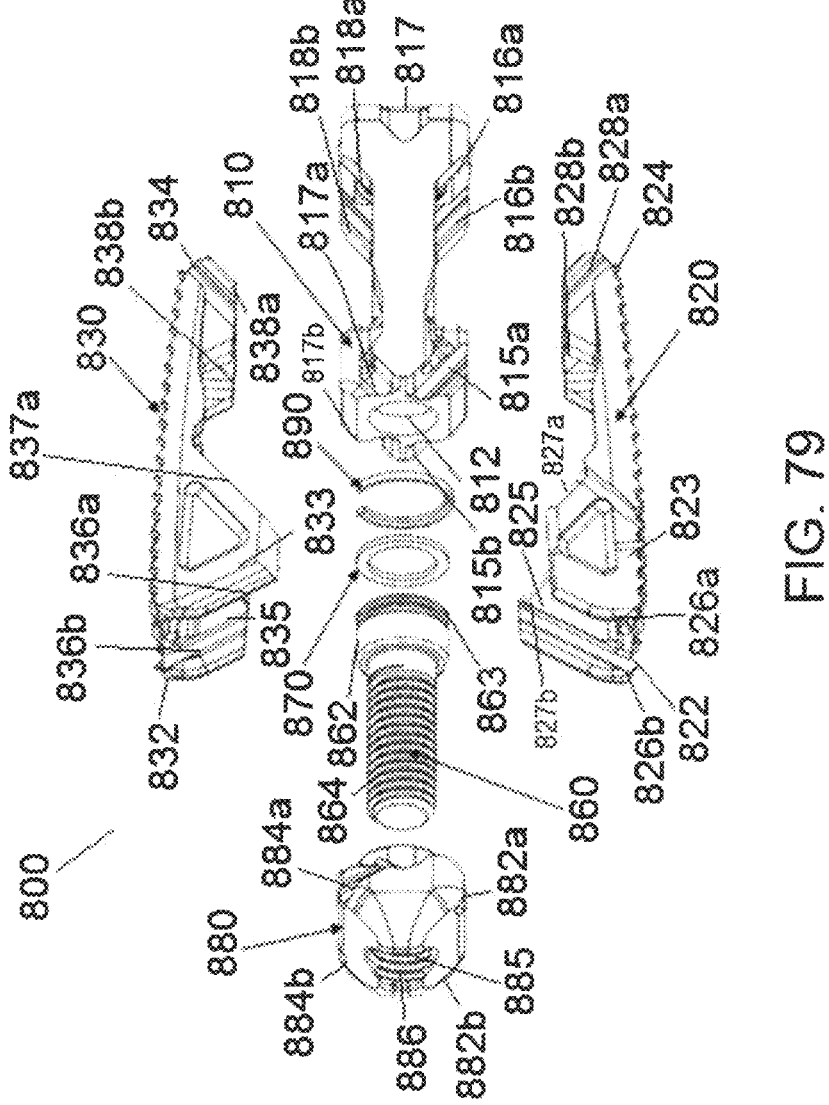
FIG. 79 is an exploded view of an expandable fusion device having a threading mechanism in accordance with some embodiments.

FIG. 79 is an exploded view of an expandable fusion device having a threaded mechanism in accordance with some embodiments. The expandable fusion device 800 comprises a first endplate 820, a second endplate 830, a body

810 positioned between the first endplate 820 and the second endplate 830, a drive screw 860, a washer 870, a retaining ring 890, and a nose 880. The drive screw 860 advantageously provides a threaded mechanism for expanding and contracting the expandable fusion device.

The first endplate 820 comprises a lower endplate having a first end 822 and a second end 824. The first end 822 comprises a pair of first end ramped portions 826a, 826b. Each of these ramped portions 826a, 826b is configured to engage corresponding lower nose ramps 882a, 882b on the nose 880 to aid with expansion of the expandable fusion device. The second end 824 comprises a pair of second end ramped portions 828a, 828b. Each of these ramped portions 828a, 828b is configured to engage corresponding rear lower ramps 816a, 816b on the body 810 to aid with expansion of the expandable fusion device. A first side portion 823 having a central ramp 827a and a second side portion 825 having a central ramp 827b are positioned between the first end 822 and the second end 824 of the first endplate 820. Each of the central ramps 827a, 827b is configured to engage corresponding front lower ramps 815a, 815b of the base 810 to aid with expansion of the expandable fusion device. The ramps of the first endplate 820 are formed along a perimeter that surrounds a central opening 829 (shown in FIG. 84A).

The second endplate 830 comprises an upper endplate having a first end 832 and a second end 834. The first end 832 comprises a pair of first end ramped portions 836a, 836b. Each of these ramped portions 836a, 836b is configured to engage corresponding upper nose ramps 884a, 884b on the nose 880 to aid with expansion of the expandable fusion device. The second end 834 comprises a pair of second end ramped portions 838a, 838b. Each of these ramped portions 838a, 838b is configured to engage corresponding rear upper ramps 818a, 818b on the body 810 to aid with expansion of the expandable fusion device. A first side portion 833 having a central ramp 837a and a second side portion 835 having a central ramp 837b are positioned between the first end 832 and the second end 834 of the second endplate 830. Each of the central ramps 837a, 837b (not visible) is configured to engage corresponding front upper ramps 817a, 817b of the base 810 to aid with expansion of the expandable fusion device. The ramps of the second endplate 830 are formed along a perimeter that surrounds a central opening 839 (shown overlapping with central opening 829 in FIG. 84A).

The body 810 comprises a front throughbore 812 and a rear throughbore 817. The front throughbore 812 comprises an opening through which the threaded shaft 864 of the drive screw 860 extends therethrough. The rear throughbore 817 comprises an opening through which the head 862 of the drive screw 860 extends therethrough. The rear throughbore 817 also receives the retaining ring 890 and washer 870 therethrough. The retaining ring 890 is received in a recess 863 of the head 862, which is then received in the rear throughbore 817. In some embodiments, the retaining ring 890 comprises a c-shaped ring.

The drive screw 860 comprises a head portion 862 and a shaft portion 864. The head portion 862 comprises a recess 863 for receiving a retaining ring 890 therethrough. The head portion 862 can be received in the rear throughbore 817 of the body 810. The shaft portion 864 comprises a threaded portion that extends through the nose 880. The threaded portion mates with threads 886 found within the nose 880. Rotation of the drive screw 860 thereby causes movement or translation of the nose 880.

In some embodiments, one or more tools (e.g., an expansion tool) can engage the head of the drive screw 860.

Rotation of the drive screw 860 in a first direction translates and draws the nose 880 inwardly, thereby causing expansion between the first endplate 820 and the second endplate 830. As the nose 880 is drawn inwardly, upper nose ramps 884a, 884b engage first end ramped portions 836a, 836b of the second endplate 830, while rear upper ramps 818a, 818b of the body 810 engage second end ramped portions 838a, 838b of the second endplate 830. Likewise, lower nose ramps 882a, 882b engage first end ramped portions 826a, 826b of the first endplate 820, while rear lower ramps 816a, 816b engage second end ramped portions 828a, 828b of the first endplate 820. The engagement of these ramps causes outward expansion between the first endplate 820 and the second endplate 830. Rotation of the drive screw 860 in a second direction opposite to the first direction translates the nose 880 outwardly, thereby causing contraction between the first endplate 820 and the second endplate 830.

The nose 880 comprises a throughhole 885 through which the shaft portion 864 of the drive screw 860 can extend. The throughhole 885 of the nose 880 comprises nose threads 886 that engage and mate with the threads of the shaft portion 864. As noted above, the nose 880 comprises one or more upper nose ramps 884a, 884b, which are configured to mate and engage corresponding ramps on the second endplate 830. In addition, the nose 880 comprises one or more lower nose ramps 882a, 882b, which are configured to mate and engage corresponding ramps on the first endplate 820.

Figures 80A, 80B, 80C:
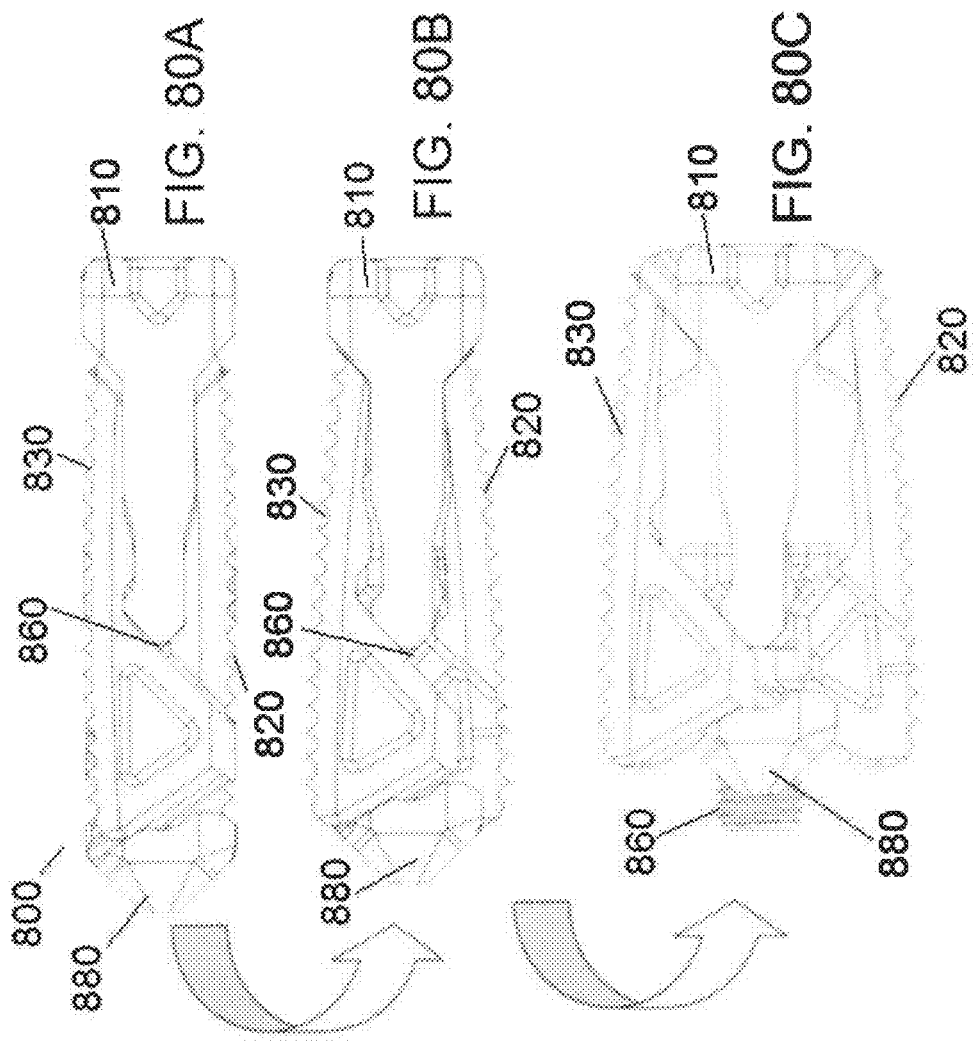
FIGS. 80A, 80B, and 80C are side views of the expandable fusion device of FIG. 79 in the process of expansion in accordance with some embodiments.

FIGS. 80A-80C are side views of the expandable fusion device of FIG. 79 in the process of expansion in accordance with some embodiments. In some embodiments, the expandable fusion device 800 is advantageously capable of expansion, and in particular, lordotic expansion. In some embodiments, the device 800 can begin in a contracted state, as shown in FIG. 80A. Afterwards, by pulling the nose 880 via rotation of the drive scre8 860, the device 800 can expand and tip into lordosis, as shown in FIG. 80B. Once the device 800 has achieved maximum lordosis, the device 800 can continue to expand in height in a parallel fashion, whereby both the anterior and posterior aspects expand at the same rate, until the implant 800 reaches a maximum expansion, as shown in FIG. 80C. In other words, once the device 800 reaches a particular lordotic angle (as shown in FIG. 80B), the device 800 will maintain the lordotic angle throughout the expansion range until maximum expansion has been achieved, as shown in FIG. 80C. More details on the expansion of the device 800 are provided with respect to FIGS. 81A-83B.

Figures 81A, 81B:
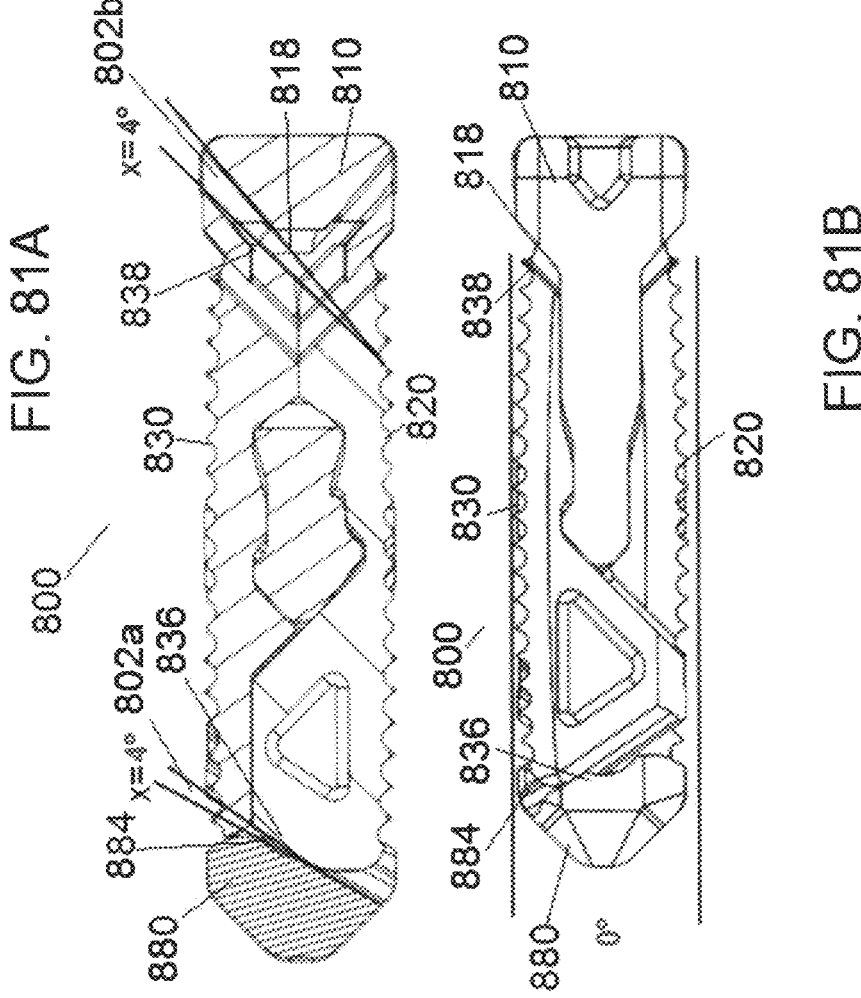
FIGS. 81A-81B are different views of the expandable fusion device of FIG. 79 in a contracted state in accordance with some embodiments.

FIGS. 81A-81B are different views of the expandable fusion device of FIG. 79 in a contracted state in accordance with some embodiments. From the contracted state, the device 800 is capable of first expanding and tipping into lordosis, and then expanding in a parallel fashion. The angle tipping is driven by a difference in ramp angle x that is seen between the first end ramped portions 836a, 836b of the second endplate 830 and the upper nose ramps 884a, 884b of the nose 880. Similarly, the same difference in ramp angle x is also seen between the second end ramped portions 838a, 838b of the second endplate 830 and the rear upper ramps 818a, 818b of the body 810. In other words, at the contracted height, the difference in angle x between the different ramps causes a gap 802 between the ramps, with a first end gap 802a formed closer to the first end of the second endplate 830 and a second end gap 802b formed closer to the second end of the second endplate 830. The degree of the gap 802 will determine what lordosis the device will tip into upon expansion. For example, if the degree of the gap 802 is 4 degrees (e.g., x=4), the second endplate 830 will tip into 4 degrees of lordosis. As the same mechanism is provided for the first endplate 820, the first endplate 820 will also tip into 4 degrees of lordosis, thereby providing an overall lordosis of 8 degrees once both endplates 820, 830 have been tipped. In some embodiments, the endplates 820, 830 themselves can have built-in lordosis. For example, if the built in lordosis of both endplates 820, 830 was 7 degrees inclusive, then the overall lordosis following expansion wherein x=4 is 15 degrees of lordosis. While the present embodiment shows an angle x difference of 4 degrees, the angle can be less or more, thereby resulting in less or more lordosis.

Figures 82A, 82B:
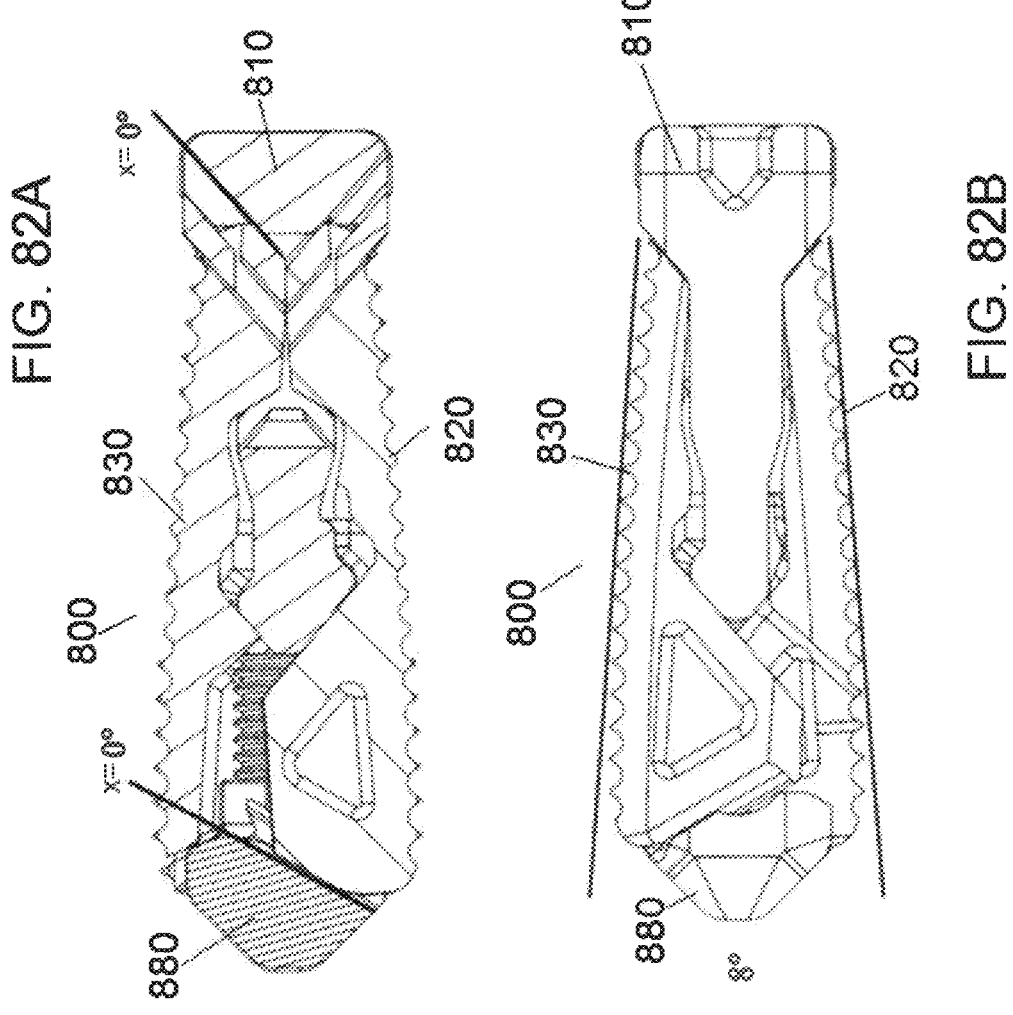
FIGS. 82A-82B are different views of the expandable fusion device of FIG. 79 in a tipped state without full expansion in accordance with some embodiments.

FIGS. 82A-82B are different views of the expandable fusion device of FIG. 79 in a tipped state without full expansion in accordance with some embodiments. To tip the expandable fusion device 800 into lordosis, the nose 880 is initially ratcheted or pulled back towards the body 810, thereby causing the gaps x to close and the corresponding ramps to mate. The amount of lordosis will be pre-determined based on the initial ramp gap x. In the present embodiment, the expandable fusion device 800 has been tipped into a lordotic angle of 8 degrees for the second endplate 830 and 8 degrees for the first endplate 820, thereby resulting in a total of 8 degrees of lordosis (as shown in FIG. 82B). One skilled in the art can appreciate that the total degree of lordosis can be less than or greater than 8 degrees, and that 8 degrees in just a representative example.

FIGS. 83A-83B are different views of the expandable fusion device of FIG. 79 in a fully expanded state in accordance with some embodiments. As the nose 880 is pulled back further the corresponding ramps of the device 800 are fully mated, the implant then begins to expand in overall height in a parallel fashion. In other words, the anterior and posterior aspects of the device 800 expand at the same rate. As this happens, the device maintains the same lordosis allowing the lordotic angle to be seen throughout the expansion range. For example, the degree of lordosis of the device 800 in the fully expanded state (as shown in FIG. 83B) is the same as the degree of lordosis of the device 800 after the endplates have been tipped (as shown in FIG. 82B). However, due to further parallel expansion, the height of the device 800 in the fully expanded state (as shown in FIG. 83B) is greater than the height of the device 800 after the endplates have been tipped (as shown in FIG. 82B).

In some embodiments, the device 800 can be used via different approaches. For example, in some embodiments, the device 800 can be a TLIF device that enters a disc space via a transforaminal approach, while in other embodiments, the device 800 can be a PLIF device that enters a disc space via a posterior approach. In other embodiments, the device 800 can be an ALIF device that enters via an anterior approach. One skilled in the art will appreciate that the device 800 is not limited to any particular approach. In some embodiments, depending on the approach, the device 800 can have distinct features, as will be discussed below.

Figures 84A, 84B, 84C, 84D:
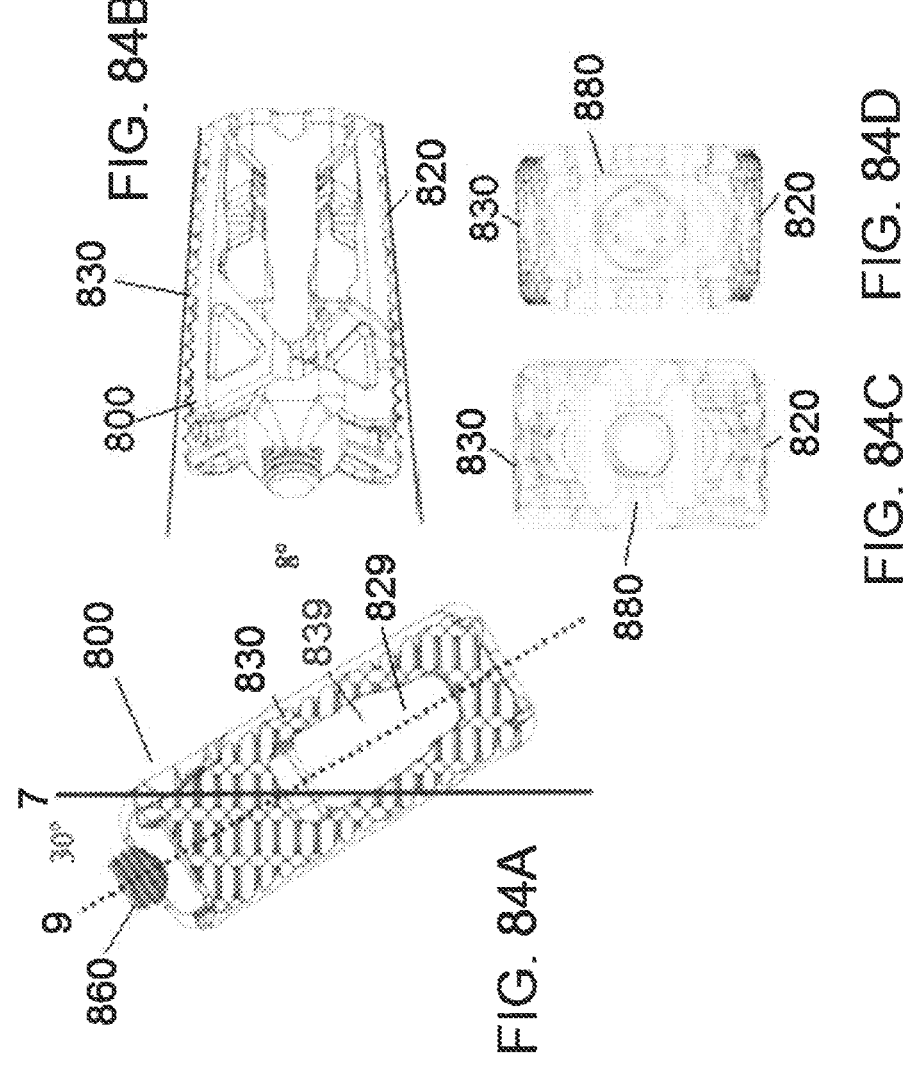
FIGS. 84A, 84B, 84C, and 84D are different views of a TLIF device having threaded expansion in accordance with embodiments of the present application.

FIGS. 84A-84D are different views of a TLIF device having threaded expansion in accordance with embodiments of the present application. FIG. 84A shows the device 800 from a top view. FIG. 84B shows the device 800 from a side perspective view. FIG. 84C shows the device 800 from an anterior view. FIG. 84D shows the device 800 from a posterior view. The TLIF device 800 has a specific curvature as shown in the figures. In particular, the TLIF device 800 has a curvature cut at a 30 degree angle from the sagittal plane of the device. This advantageously allows for the lordosis of the TLIF device to be in the same plane as the lordosis of the spine. In some embodiments, the curvature will provide a convex surface to the device. The curved surface can be particularly seen in FIGS. 84C and 84D.

FIG. 84A depicts a TLIF device. The dark line 7 represents the midline of the sagittal plane in a vertebral body, as well as the plane of the curvature of the device 800. The dotted line 9 represents the midline of the device itself. The angle between the midline of the sagittal plane and the midline of the device (e.g., 30 degrees) represents the orientation of the curvature cut in the device 800. While in some embodiments, the curvature cut is generally at a 30 degree angle from the sagittal plane of the device, in other embodiments, the curvature cut can be between 15 and 45 degrees, or 15 and 60 degrees.

Figures 85A, 85B, 85C, 85D:
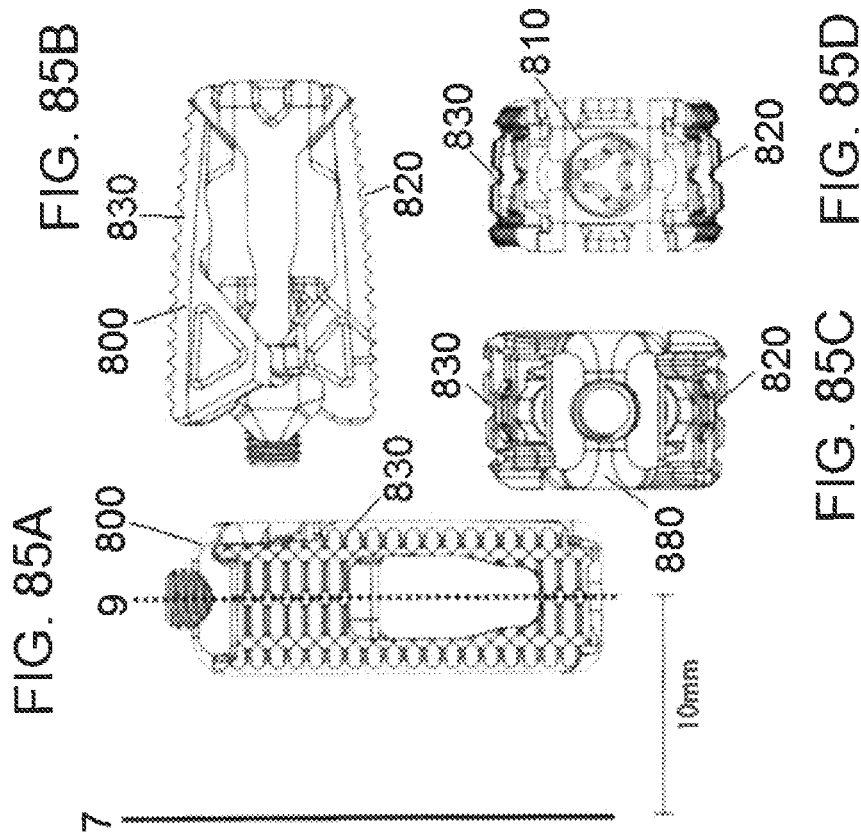
FIGS. 85A, 85B, 85C, and 85D are different views of a PLIF device having threaded expansion in accordance with embodiments of the present application.

FIGS. 85A-85D are different views of a PLIF device having threaded expansion in accordance with embodiments of the present application. FIG. 85A shows the device 800 from a top view. FIG. 85B shows the device 800 from a side perspective view. FIG. 85C shows the device 800 from an anterior view. FIG. 85D shows the device 800 from a posterior view. The PLIF device 800 has a specific curvature as shown in the figures. In particular, the PLIF device 800 has a curvature that is offset from its midline. This advantageously allows for the lordosis of the PLIF device to be in the same plane as the lordosis of the spine. In some embodiments, the curvature will provide a convex surface to the device. The curved surface can be particularly seen in FIGS. 85C and 85D.

FIG. 85A depicts a PLIF device. The dark line 7 represents the midline of the sagittal plane in a vertebral body, as well as the plane of the curvature of the device 800. The dotted line 9 represents the midline of the device itself. The curvature of the device 800 is offset from its midline to accommodate its offset placement relative to the midline of the sagittal plane. In some embodiments, the offset distance is 10 mm, while in other embodiments, the offset distance is between 8 and 12 mm, or between 5 and 15 mm.

Figure 86:
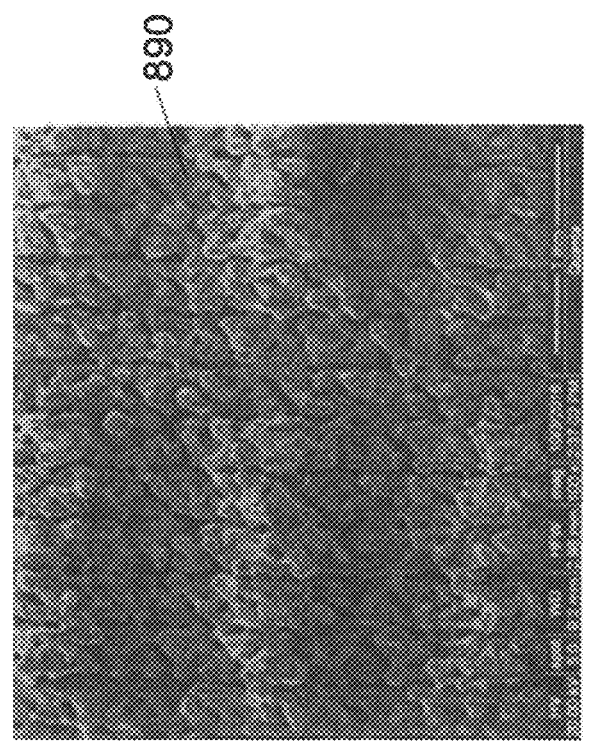
FIG. 86 is an exemplary surface of a device according to any of the embodiments of the present application.

In some embodiments, the devices above can have a novel surface treatment. In some embodiments, the treatment is a roughened and/or porous surface that can be achieved through several manufacturing processes. FIG. 86 is an exemplary surface 890 of a device having an exemplary roughened and/or porous surface. Various surface treatments can be provided to the devices above, including sinker EDM, chemical etching, laser etching, and blasting. A sinker EDM is used to burn a roughened profile into any surface of the implant. The roughness of a surface can be controlled by varying the power setting of the EDM machine. Sinker electrodes are customized for each surface profile for each part instance or family. In chemical etching, a surface of a device is introduced to a corrosive chemical which subtracts material, thereby leaving pores and pits. The etching chemical may be applied in a random or non-random arrangement. A mask may be used prior to the application of the etching chemical to better control the outcome of the texture. In laser etching, laser pulses are used to deform the surfaces of the devices. Multiple laser pulses create pores, pits, and peaks of varying dimensions based upon the laser raster rate, peak power, travel pattern and frequency. In blasting, treated surfaces are sprayed with an abrasive media, such as aluminum oxide, at high pressure to create a porous, pitted surface.

As discussed above, the actuator assembly 200 may comprise a fastening device, such as drive screw, in certain embodiments of the present invention. Various features of embodiments of an exemplary drive screw are discussed with reference to FIGS. 58 and 79 above. Those skilled in the art will understand that screws are used in multiple applications ranging from securing two items together to translating one item with respect to another. When enough torque is applied or the screw is continuously under a high amount of load, the screw is less likely to loosen over time to due to increased friction forces. However, if the screw is not held under sufficient load, known as low-load mode, it may loosen over time due to vibration or other outside forces.

To prevent loosening of a screw, one embodiment of the present invention may include a locking mechanism that substantially prevents rotation of the actuating device, such as the drive screw described with respect to FIGS. 58 and 79. Various embodiments of locking mechanisms are described individually below to facilitate their description. Those skilled in the art will understand that the different embodiments of locking mechanisms described below with respect to FIGS. 87-143 may be used separately, or in combination with one another. Certain embodiments, for example, may be combined with one another to ensure the locking mechanism can withstand vibration or other outside forces that are present in a particular application.

According to one embodiment of the present invention, the locking mechanism includes a screw ring that is operatively connected to a drive screw. When the screw ring is operatively connected to the drive screw, the two elements are rotationally engaged. A housing ring is also included that is operatively connected to the housing into which the drive screw is inserted. When the housing ring is operatively connected to the housing, these two elements are also rotationally engaged. The housing ring and screw ring include complementary mating surfaces that selectively engage with one another. When engaged, the housing ring (which is rotationally locked to the housing) prevents rotational movement of the screw ring, and therefore the drive screw, because the two are also rotationally engaged.

Figure 87:
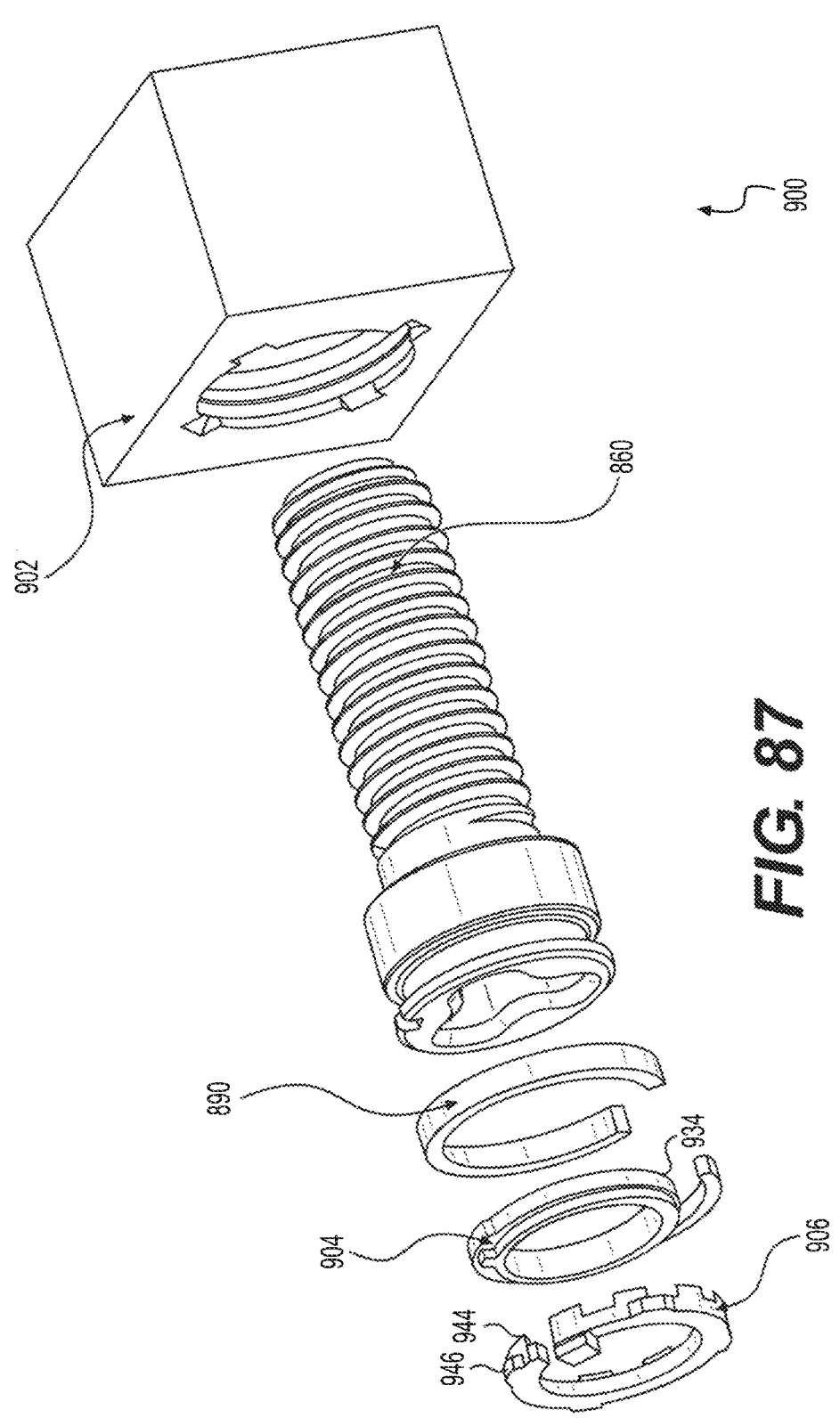
FIG. 87 is an exemplary locking mechanism according to any of the embodiments of the present application.

FIG. 87 illustrates one embodiment of a locking mechanism 900 that may be used in accordance with any of the embodiments described herein. In the illustrated embodiment, the locking mechanism 900 is described with respect to an actuator assembly 200 that comprises a drive screw 860 described with reference to FIGS. 58 and 79. This embodiment of the locking mechanism 900 includes a housing 902, a drive screw 860, a retaining ring 890, a screw lock ring 904, and a housing lock ring 906. As will be discussed in more detail below, the drive screw 860 sits inside of the housing 902 and is axially restrained by the retaining ring 890 but can rotate freely inside the housing 902. The screw lock ring 904 is then assembled inside the housing 902 and is radially keyed to the screw head 862 with the use of a tab or slot feature. The screw lock ring 904 is capable of flexing up and down but remains radially keyed to the drive screw 860 to rotate when the drive screw 860 rotates. The housing lock ring 906 is assembled next and is retained and radially keyed with a tab to the housing 902. The housing lock ring 906 cannot rotate once assembled.

Figure 88:
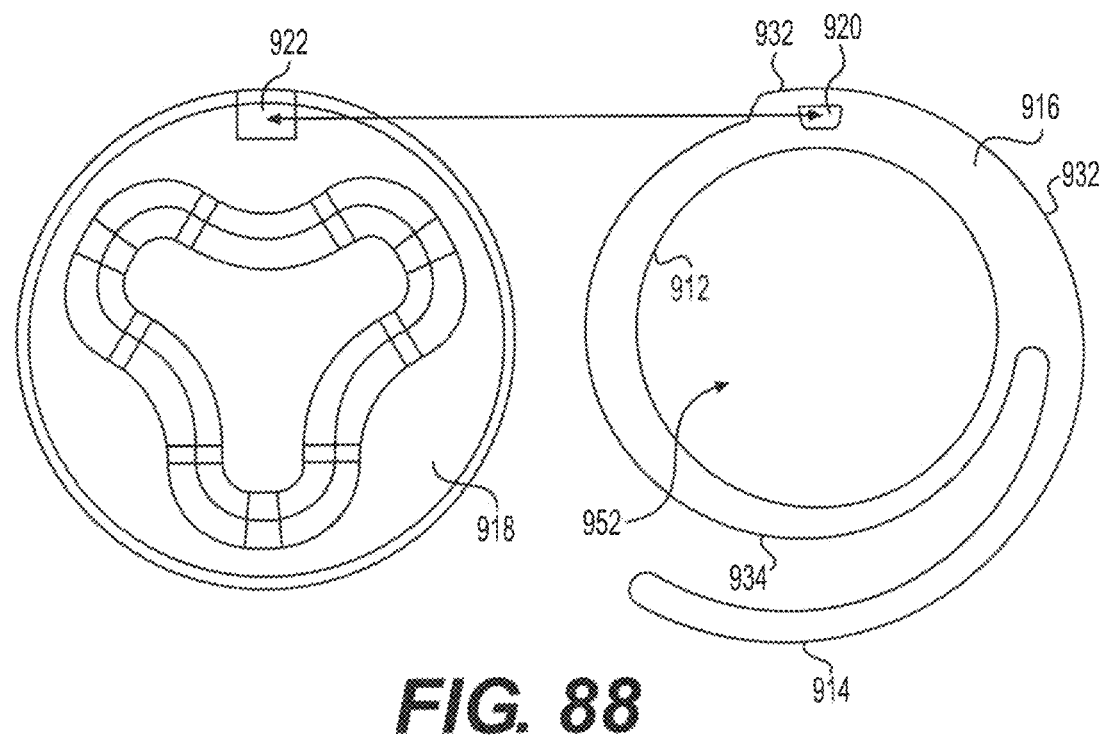
FIG. 88 is a diagram showing a close up view of one embodiment of the screw lock ring and the drive screw head.
Figure 89:
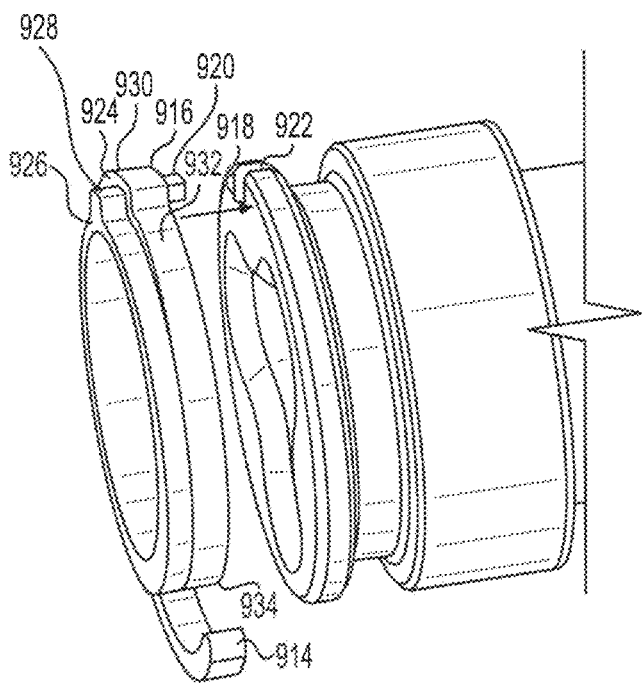
FIG. 89 is a diagram showing a side view of the embodiment of the screw lock ring and the drive screw head shown in FIG. 88.

With reference to FIGS. 87-89, one embodiment of the screw lock ring 904 is described in more detail. The screw lock ring 904 can be manufactured from a number of materials including titanium, stainless steel, titanium alloys, non-titanium metallic alloys, polymeric materials, plastics, plastic composites, PEEK, ceramic, and elastic materials. In an exemplary embodiment, the screw lock ring 904 comprises a substantially circular inner diameter 912. The screw lock ring 904 also includes a spring tail 914 that allows the lock ring 904 to flex when a force is applied, for example, to its inner surface 912 or its outer surface 932.

A first side 916 of the screw lock ring 904 includes a substantially flat surface that is operable to sit flush with a corresponding face 918 of the drive screw head 862. The screw lock ring 904 includes a first protuberance 920 that extends from at least a portion of the first side 916 that is operable to sit inside a corresponding recess 922 of the drive screw head 862. The first protuberance 920 can be selectively positioned such that it is located between the inner surface 912 and outer surface 932 of the screw lock ring 904. In alternate embodiments the protuberance 920 may extend to the inner surface 912, outer surface 932, or both surfaces. The protuberance 920 may comprise any shape and dimensions. In some embodiments, for example, the protuberance 920 may comprise a rectangular tab with flat surfaces, as shown in FIGS. 88-89. In other embodiments, however, the protuberance 920 may be configured and dimensioned to include at least one pointed surface, a ratcheted surface, or the like.

In one embodiment, the screw lock ring 904 also includes a second protuberance 926 that extends from at least a portion of the second side 924, as shown in FIGS. 87 and 89. The second protuberance 926 may extend from only a predetermined portion of the second side 924. For example, in one embodiment the second protuberance 926 extends from the second side 924 of the screw lock ring 904 and is configured and dimensioned to engage with the housing lock ring 906 described in more detail below. The second protuberance 926 is also configured and dimensioned such that the upper portion 928 does not extend to the top edge 930 of the outer surface 932 of the screw lock ring 904. In other words, the top edge 930 extends beyond the upper portion 928. Other portions of the second protuberance 926 may extend along the second side 924 from the inner surface 912 to the outer surface 932. For instance, as best illustrated in FIGS. 87 and 89, the second protuberance 926 may extend from the inner surface 912 to the outer surface 932 along a bottom portion 934 of the screw lock ring 904. As a result, at least a portion of the second side 924 may not include any protuberance 926.

When configured and dimensioned as described above, and operatively connected to one another, the screw lock ring 904 and the drive screw head 862 remain radially keyed to one another. The operative connection is accomplished when the first protuberance 920 sits inside the recess 922 on the drive screw head 862, as illustrated by the arrow in FIGS. 88 and 89. When assembled in this manner, the screw lock ring 904 and the drive screw head 862 are rotationally engaged.

Figure 90:
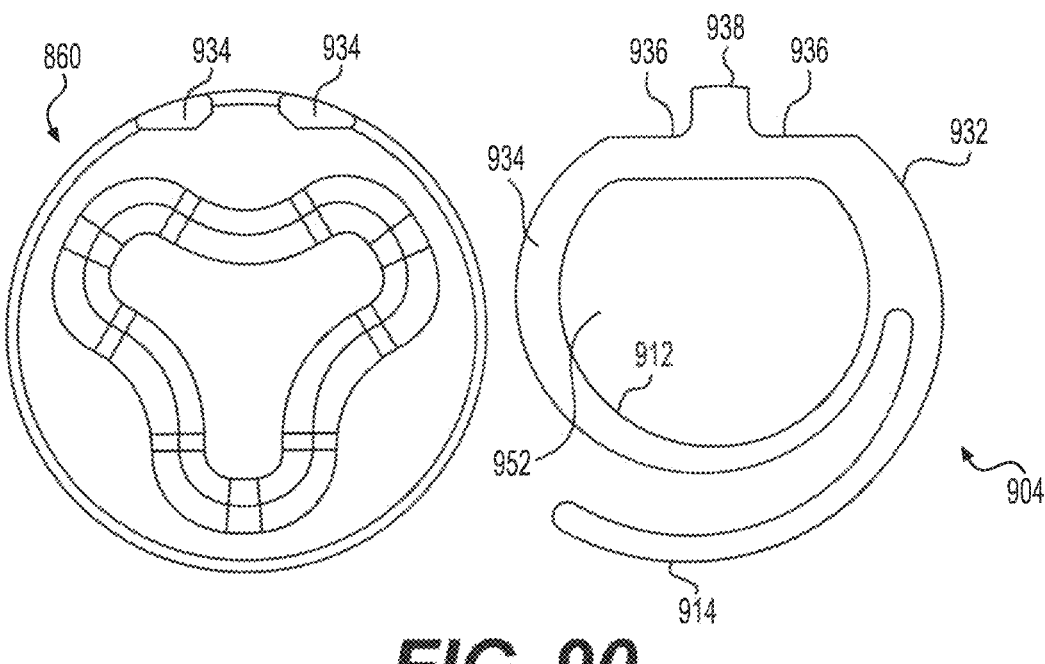
FIG. 90 is a diagram showing a close up view of another embodiment of the screw lock ring and the drive screw head.
Figure 91:
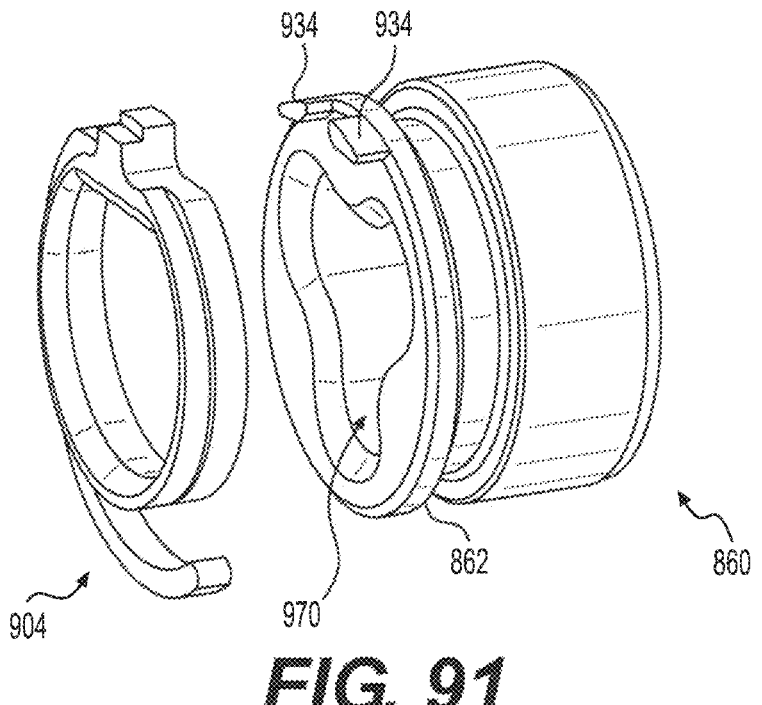
FIG. 91 is a diagram showing a side view of the screw lock ring and the drive screw head shown in FIG. 90.

With reference to FIGS. 90 and 91, in an exemplary embodiment, the screw locking ring 904 and the screw head 862 have been modified so that the drive screw head 862 includes at least one protuberance 934 and the screw lock ring 904 includes at least one recess 936. In other words, the recess 936 may be included on the screw lock ring 904 while the protuberance 934 may be included on the drive screw head 862, as shown in FIGS. 90-91. In the illustrated embodiment, the drive screw head 862 includes two protuberances 934. Those skilled in the art will understand that the number of protuberances and recesses can be modified as desired as long as they are able to operatively connect or otherwise engage to allow the drive screw head 862 and screw lock ring 904 to be radially keyed to one another.

In the embodiment illustrated in FIGS. 90-91, the outer surface 932 of the body 934 includes at least one recess 936 that is configured and dimensioned to matingly engage with the protuberances 934 on the screw head 862. The recesses 936 may be formed by configuring and dimensioning a protuberance 938 on the outer surface 932 of the screw lock ring 904. As shown best in FIG. 90, the protuberance 938 creates two recesses 936. The protuberances 934 on the screw head 862 are then able to engage with the recesses 936 to lock the screw head 862 to the screw lock ring 904. The screw lock ring 904 in the embodiment illustrated in FIGS. 90-91 also includes a second protuberance 926 that extends from at least a portion of the second side 924, in a manner similar to that described above with respect to the embodiment illustrated in FIGS. 87-89.

In any of the embodiments, for example as described with respect to FIG. 87-91 above, the screw lock ring 904 may be configured and dimensioned to include a body 934 and a spring tail 914. One advantage of the spring tail 914 is that it allows the screw lock ring 904 to translate, or flex, up and down inside the elongated groove in the housing 902. The spring tail 914 may be configured and dimensioned to allow the body 934 to flex when an external force is applied. When the screw lock ring 904 flexes, the protuberance 920, 944 can move up and down inside the mating recess 922, 936 of the screw head 862, while remaining engaged inside the recesses 922, 936.

The body 934 of the screw lock ring 904, according to one embodiment, includes a center opening 952, i.e., a center hole. The central opening 952 may be configured and dimensioned so that its center is offset from the center of the opening 970 in the drive screw head 862. One advantage of offsetting the center of the central opening with respect to the center of the opening 970 is that it allows the screw lock ring 904 to be displaced when a tool, such as a driver, is inserted into the screw lock ring 904 and the opening 970, as described in more detail below.

Figures 92, 93:
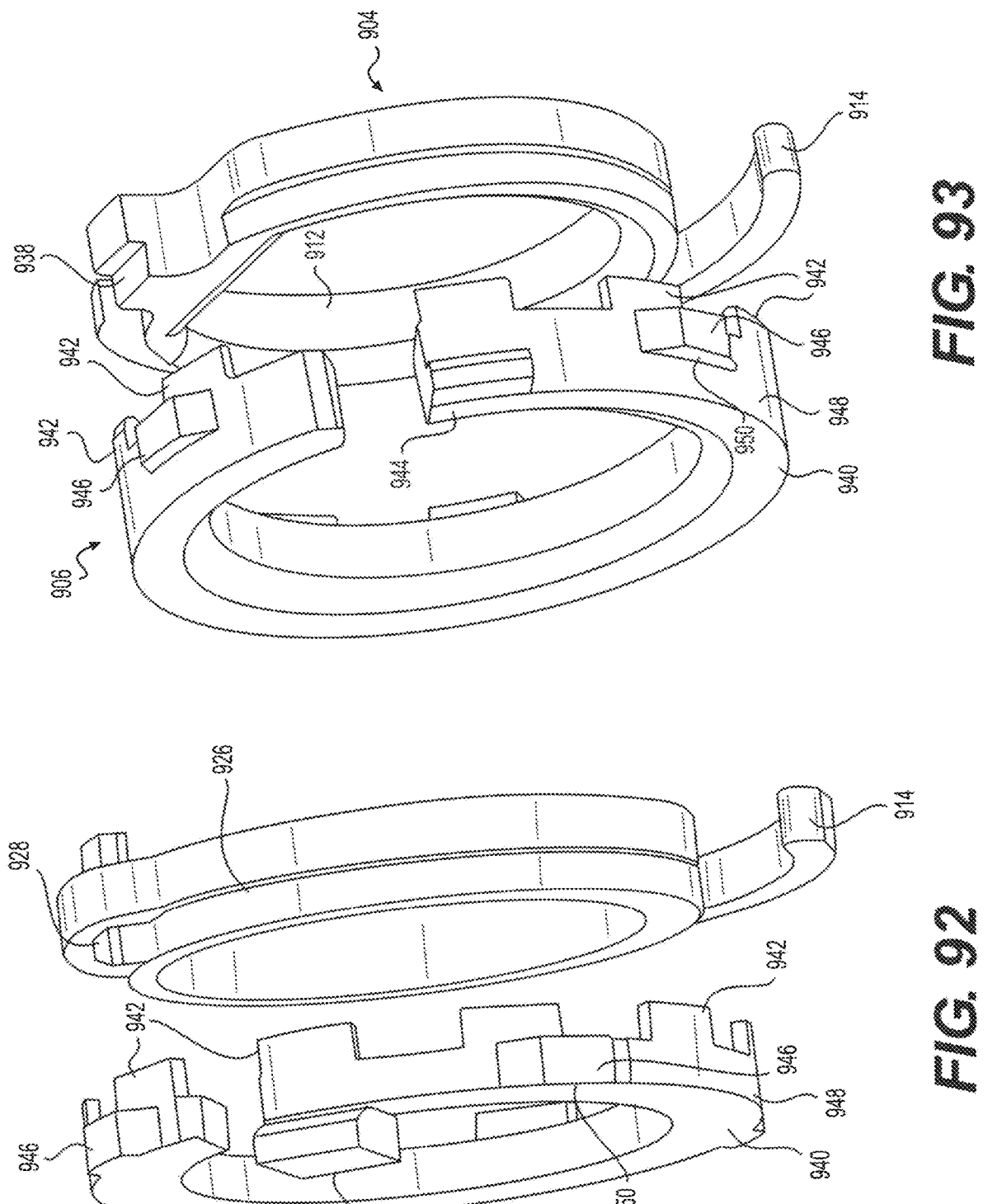
FIG. 92 is a diagram showing a side view of one embodiment of the housing lock ring and the screw lock ring.
FIG. 93 is a diagram showing a side view of another embodiment of the housing lock ring and the screw lock ring.

FIG. 92 illustrates one exemplary embodiment of a housing lock ring 906. The housing lock ring 906 includes a first side 940 that faces away from the screw head 862. The second side, opposite the first side 940 of the housing lock ring 906, comprises a castle feature that faces the second protuberance 926 of the screw lock ring 904. Those skilled in the art will understand that the castle feature 942 of the housing lock ring includes slots, also known as notches, cut into one end, similar to the castle feature of a castellated or slotted nut. The housing lock ring 906 also includes at least one protuberance 944 that is configured and dimensioned to extend from its first side 940, as shown in FIGS. 87 and 92. It may also be desirable for the protuberance 944 to be configured and dimensioned to extend outwardly from the center of the housing lock ring 906, as shown in FIG. 92. One or more additional protuberances 946 may be included that extend from the outer diameter 948 of the housing lock ring 906. One side 950 of one or more of the additional protuberances 946 may also sit substantially flush with the first side 940 of the housing lock ring 906 such that the side 950 of the additional protuberance 946 shares a common surface with the first side 940 of the housing lock ring 906. Each of the protuberances 944, 946 can selectively engage with corresponding recesses in the housing 902 in order to prevent rotational movement of the housing lock ring 906.

In the embodiments discussed here, the housing 902 may comprise any device that is operable to receive a drive screw 862. For example, the housing 902 may comprise at least a portion of the actuator assembly 200 described above, such as first endplate 14 and second endplate 16 described above. The housing 902 may have any shape or dimensions known to those skilled in the art. In certain embodiments described herein, the housing 902 may be configured and dimensioned to include recesses, notches, protuberances, or other features that allow for the elements described herein to engage one of its inner or outer surfaces, as described in more detail below.

Figure 94:
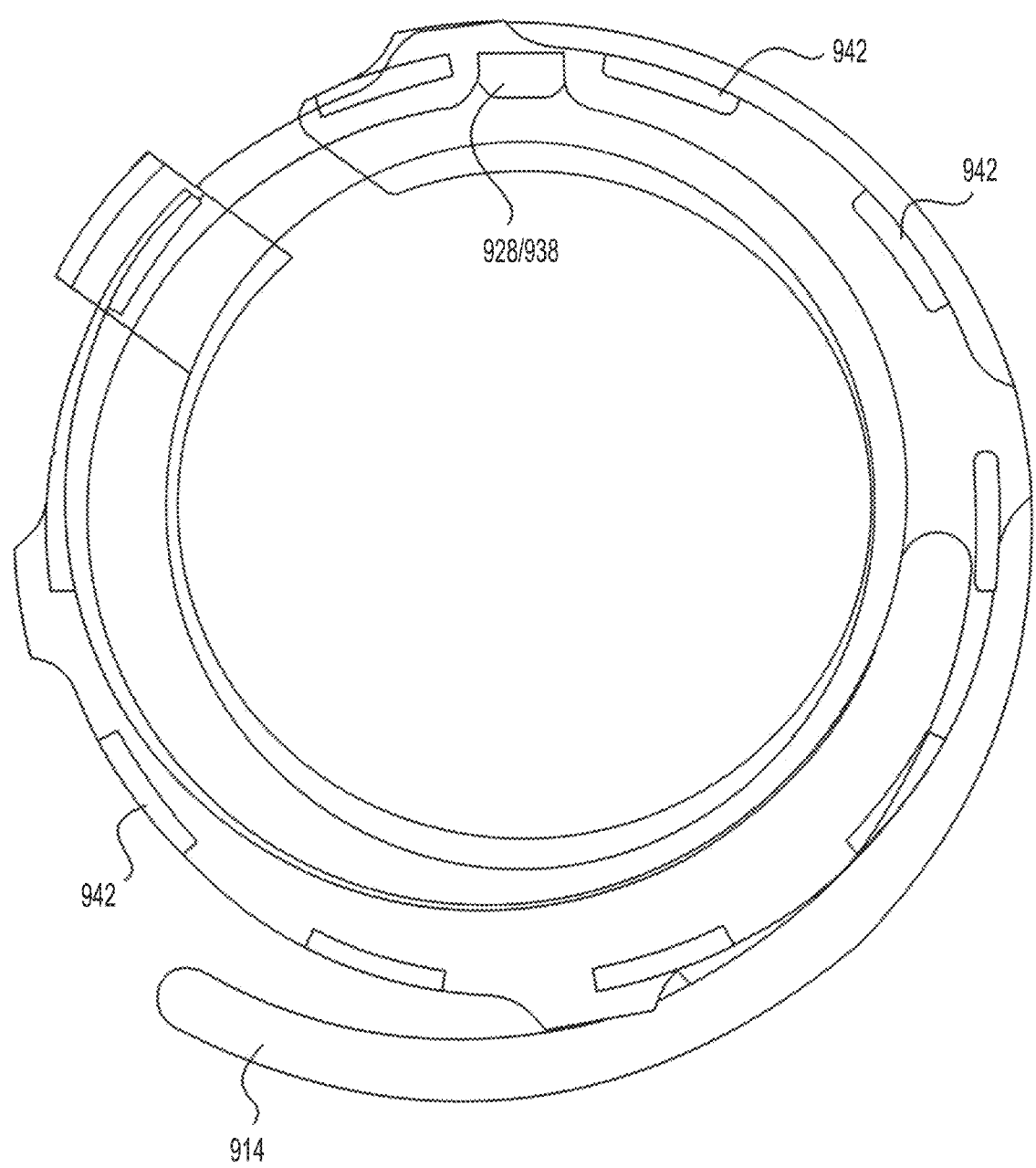
FIG. 94 is a diagram showing a close up view of one embodiment of the engagement between the housing lock ring and the screw lock ring.

When configured as discussed above with respect to exemplary embodiments illustrated in FIGS. 87 and 92, the housing lock ring 906 sits directly behind the screw lock ring 904, with the castle feature 942 facing, and operatively connecting to, the second protuberance 926 of the screw lock ring 904. When the screw lock ring 904 does not have external forces applied to its inner surface 912, at least the upper portion 928 of the second protuberance 926 (shown with an arrow in FIG. 92) will sit inside the grooves of the castle feature 942, as illustrated in FIG. 94 (circled in the figure). This prevents the screw lock ring 904, and subsequently the drive screw 860, from rotating because the housing lock ring 906 is keyed to the housing 902.

Referring to FIG. 93, an alternative embodiment of the housing lock ring 906 is shown in combination with the embodiment of the screw lock ring 904 described with respect to FIGS. 90-91. In the illustrated embodiment, the housing lock ring 906 includes a first side 940, castle feature 942, a first protuberance 944, and additional protuberances 946 along an outer diameter 948 of the housing lock ring 906. The housing lock ring 906 illustrated in FIG. 93 and its individual components are similar to the housing lock ring 906 described with respect to FIG. 92, with slight modifications. The modifications to the housing lock ring 906 will be described in turn below.

With reference to FIG. 93, the housing lock ring 906 has been modified to include a first protuberance 944 that extends from the outer diameter 948 of the housing lock ring 906. However, the first protuberance 944 in this embodiment is substantially flush with the first side 940 of the housing lock ring 906. In this embodiment, the additional protuberances 946 are selectively positioned between the first side 940 and the castle feature 942, as shown in FIG. 93. In this embodiment, the additional protuberances 946 extend from the outer diameter 948, and a first side 950 of the additional protuberance 946 does not share a common surface with the first side 940 of the housing lock ring 906.

When configured and dimensioned as discussed above with respect to FIG. 93, the housing lock ring 906 sits directly behind the screw lock ring 904, with the castle feature 942 facing the protuberance 938 of the screw lock ring 904. When the screw lock ring 904 does not have external forces applied to its inner surface 912, at least a portion of the protuberance 938 (shown with an arrow in FIG. 93) will sit inside the grooves of the castle feature 942, as illustrated in FIG. 94 (circled in the figure). This prevents the screw lock ring 904, and subsequently the drive screw 860, from rotating because the housing lock ring 906 is keyed to the housing 902.

According to one embodiment, when the housing 902, drive screw 860, retaining ring 890, screw lock ring 904, and housing lock ring 906, the drive screw 860 is prevented from rotating on its own. To rotate the drive screw 860, the screw lock ring 904 must be flexed such that the protuberance 920, 938 disengages from the housing lock ring 906. In one embodiment, this may be accomplished by inserting one or more tools, such as a driver, into an opening 970 in the drive screw head 862. The center hole 952 of the screw lock ring 904 is offset such that when a tool, e.g., a driver is inserted into the drive screw head 862, it displaces that center hole 952 and aligns it with the drive screw 860 and driver.

The displacement of the center hole 952 is sufficient to flex the screw lock ring 904 and disengage it from the castle feature 942 of the housing lock ring 906, as shown in FIG.

Figure 95:
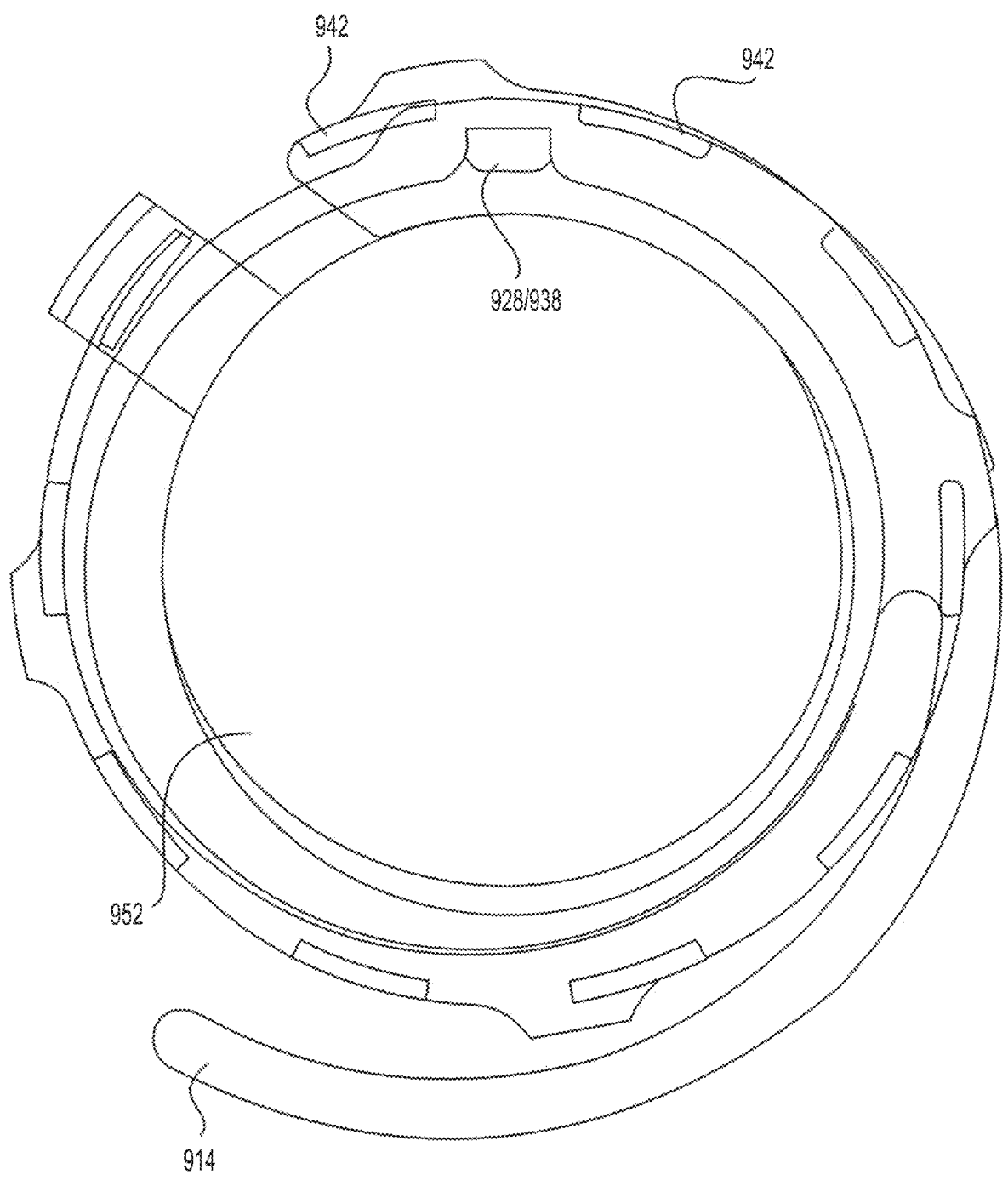
FIG. 95 is a diagram showing a close up view of one embodiment of the housing lock ring and the screw lock ring in a disengaged position.

95 (the circled portion). In this manner, the drive screw 860 and the screw lock ring 904 can rotate freely using a driver. In the disengaged state, the screw lock ring 904 and the housing lock ring 906 are oriented as shown in FIG. 95 and indicated by the arrow. The protuberance 928, 938 is no longer engaged with the castle feature 942 and can freely rotate underneath, allowing the drive screw 860 to rotate as well.

Once the driver is removed from the center hole 952 of the screw lock ring 904, the tail spring 914 of the screw lock ring 904 flexes the protuberance 928, 938 back into engagement with the castle feature 942 of the housing lock ring 906, once again preventing the drive screw 860 from rotating. Thus, the screw lock ring 904 is always rotationally engaged with the drive screw 860, and the housing lock ring 906 is rotationally engaged with the housing 902. When a driver is not engaged with the drive screw 860, the screw lock ring 904 engages with the housing lock ring 906 preventing the drive screw 860 from rotating. Conversely, when a driver is engaged with the center hole 952 and the opening 970 in the drive screw head 862, the screw lock ring 904 translates as the driver pushes it down and disengages from the housing lock ring 906, allowing the drive screw 860 to be rotated by the driver. Once the driver is removed, the screw lock ring 904 is reengaged inside the castle feature 942 of the housing lock ring 906, thereby locking the rotation of the drive screw 860 again.

Figure 96:
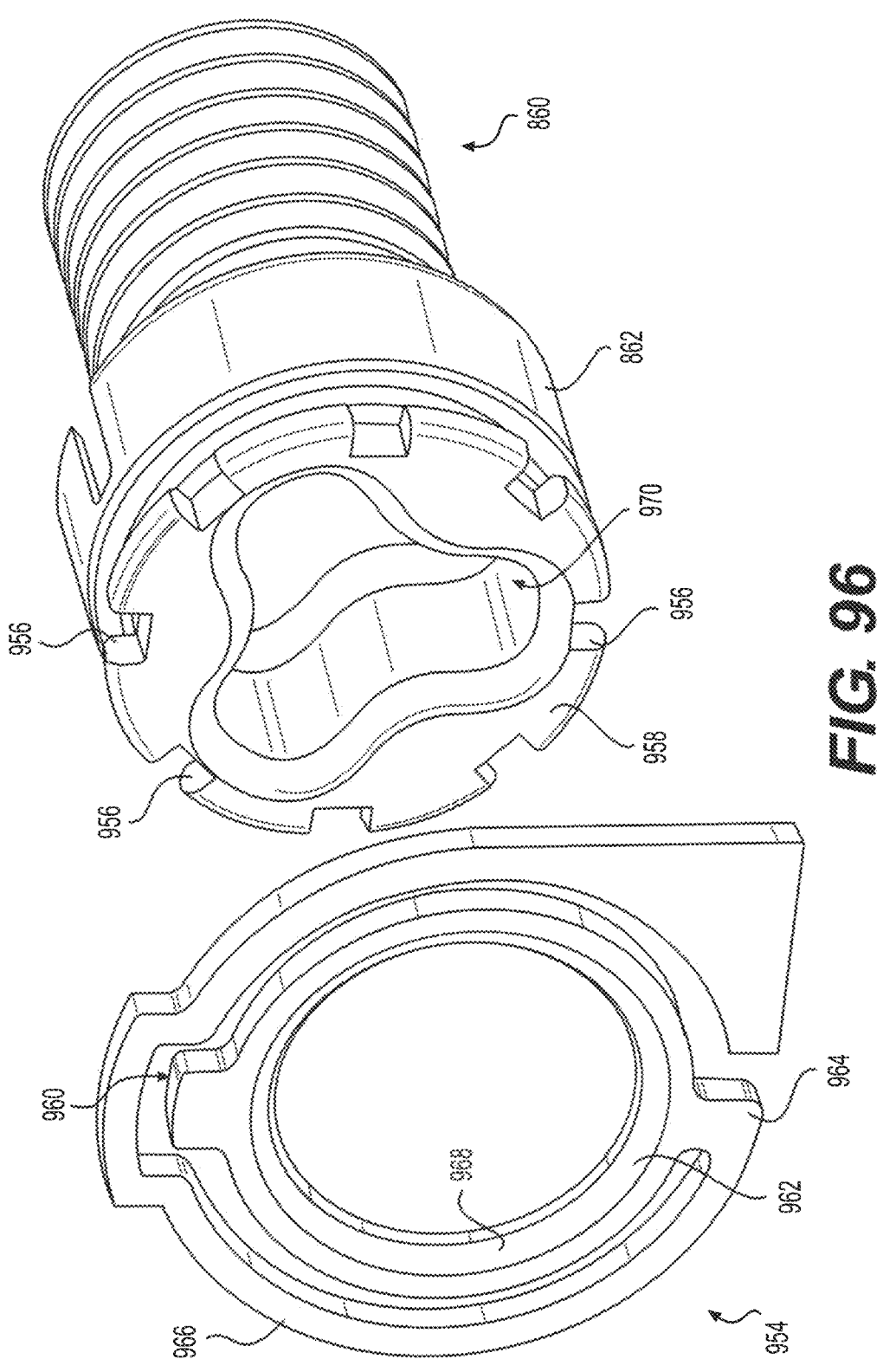
FIG. 96 is a diagram showing one embodiment of a spring component and drive screw head.
Figure 97:
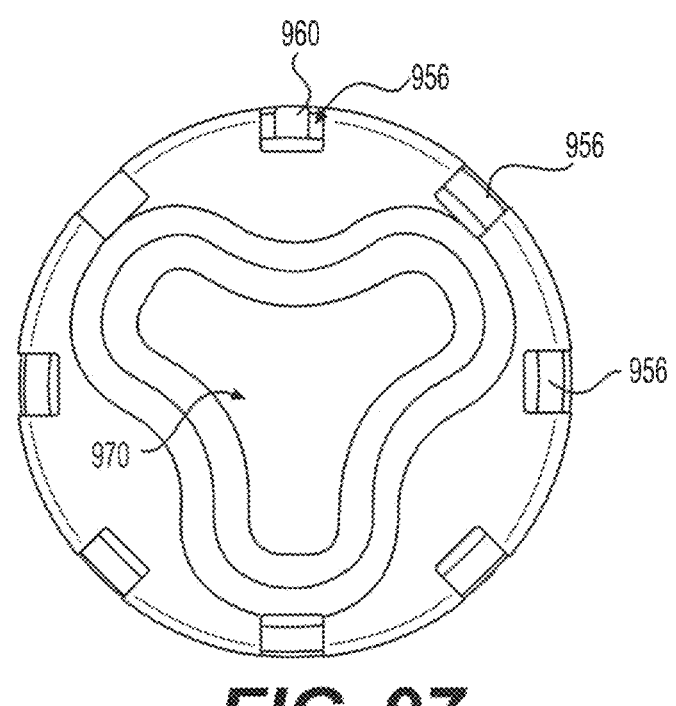
FIG. 97 is a diagram showing one embodiment of the spring component and drive screw head of FIG. 96 in the engaged position.
Figure 98:
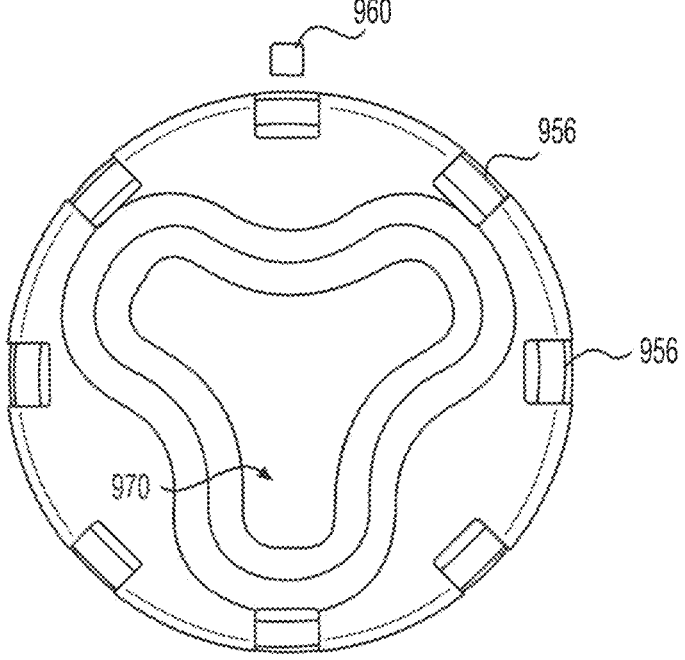
FIG. 98 is a diagram showing one embodiment of the spring component and drive screw head in the disengaged position.

Referring now to FIGS. 96-98, an alternate embodiment of a locking mechanism is shown. In this embodiment, the locking mechanism comprises a drive screw 860, a spring component 954, and a housing 902. The housing 902 and drive screw 860 of FIGS. 96-98 and their individual components are similar to the those described with respect to FIGS. 87-95, with several modifications. The modifications and components that differ from the locking mechanism illustrated in FIGS. 87-95 will be described in turn below.

As shown in FIG. 96, the drive screw head 862 includes at least one recess 956 selectively positioned around the outer diameter of the drive screw head 862. Each recess 956 may be configured and dimensioned to extend to the front face 958 of the drive screw head 862. The recesses 956 may comprise any shape or dimensions known to those skilled in the art.

In one embodiment, the spring component 954 includes a protuberance 960 that is configured and dimensioned to be operable to engage with at least one recess 956. The spring component 954 may comprise a flat disc having an extruded geometry that allows a central portion 962 to move, e.g., translate or flex. The protuberance 960 may extend away from a back side (not shown) of the central portion 962 of the spring component 954, as shown in FIG. 96. The central portion 962 may be supported by an arm 964 that maintains a spacing, or gap, between the central portion 962 and the outer frame 966 of the spring component 954. One advantage of including a spacing between the central portion 962 and the outer frame 966 is that the central portion 962 is operable to translate when a force is applied to its inner surface 968.

One embodiment of the protuberance 960 extends from the back side (not shown) of the central portion 962 and sits flush on the face 958 of the screw, with the protuberance 960 engaged with a recess 956, as shown in FIG. 97. The spring component 954 may then be installed into a housing 902 and fixed thereto to prevent rotational motion of the spring component 954. Those skilled in the art will understand that the spring component 954 may be fixed to the housing 902 in any manner known to those skilled in the art including, but not limited to, geometry, weld, or a pin. When the spring component 954 is rotationally locked to the housing 902, and the protuberance 960 is engaged with the recess 956 of the drive screw head 862, the drive screw 860 is rotationally locked with respect to the housing 902.

An opening in the central portion 962 of the spring component 954 may be offset from the center of the opening 970 in the drive screw head 862, as described with respect to the screw lock ring 904 described with respect to FIGS. 87-95. When a tool, such as driver, is inserted into this opening 970, the central portion 962 moves, e.g., translates or flexes, to be in line with the driver. When this occurs, the protuberance 960 disengages from the recess 956 on the screw head 862, as shown in FIG. 98. When the protuberance 960 is disengaged, the drive screw 860 can rotate with respect to the housing 902. By removing the driver, the central portion 962 moves back into position and reengages the protuberance 960 with one of the recesses 956, once again preventing rotational movement of the drive screw 860.

Referring now to FIGS. 99-103, an alternative embodiment of the locking mechanism is shown. In the illustrated embodiment, the locking mechanism comprises a housing 902, a drive screw 860, a collar 972, a spring 974, and a lock tab 976. The housing 902 and drive screw 860 of FIGS. 99-103 and their individual components are similar to the locking mechanism 900 illustrated in FIGS. 87-95 with several modifications. The modifications and components that differ from the locking mechanism 900 illustrated in FIGS. 87-95 will be described in turn below.

Figure 99:
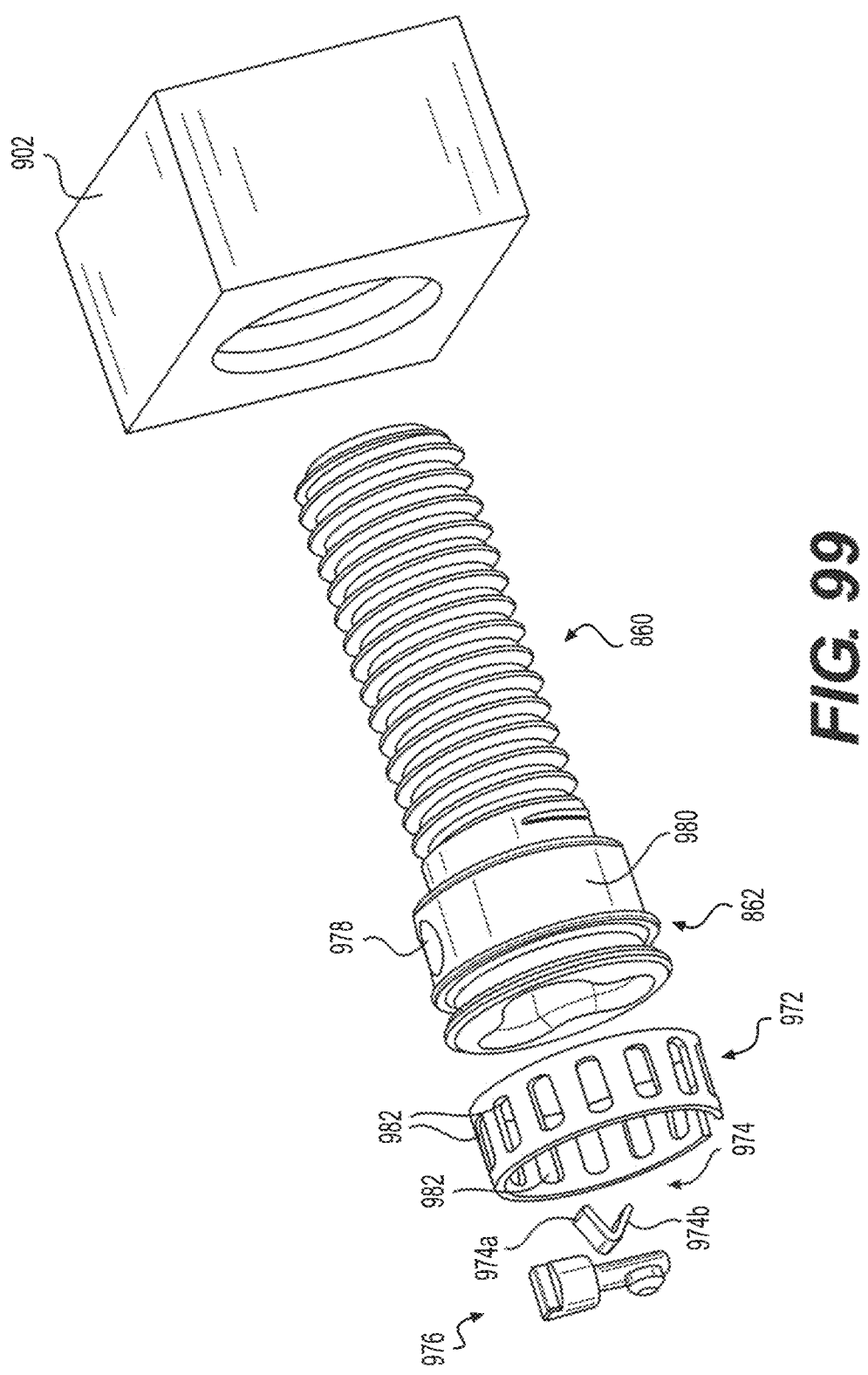
FIG. 99 is a diagram showing one embodiment of a locking mechanism according to the present invention.

According to one embodiment shown in FIG. 99, the drive screw 860 includes a bore 978 configured and dimensioned into the side 980 of the drive screw head 862. The bore 978 may include any dimensions, such as depth, shape, width, that is desirable according to a particular application. In some applications, the dimensions of the bore 978 may be selected based on the dimensions of at least one of the drive screw 860, drive screw head 862, or both. Alternately, the dimensions of the bore 978 may also be determined based on the dimensions of at least one of the spring 974 and/or lock tab 976. If desired, more than one bore 978 may be selectively positioned along the side 980 of the drive screw head 862.

Figure 100:
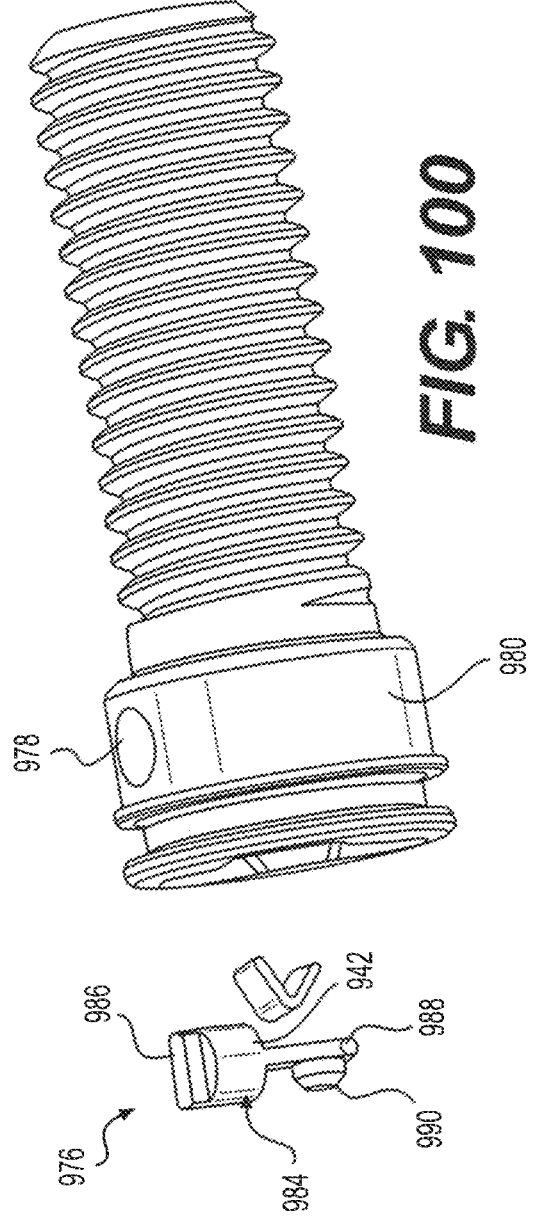
FIG. 100 is a diagram showing a side view of one embodiment of the locking mechanism.

The lock tab 976 and spring 974 are configured and dimensioned to sit inside the drive screw head 862 through the bore 978, according to one embodiment of the present invention. Thus, the dimensions of the lock tab 976 and the spring 974 may be selected such that they are operable to fit inside the bore 978. As shown in FIGS. 99-100, one embodiment of the spring 974 may comprise a v-spring. The v-spring may include two longitudinal walls 974a and 974b provided with an angle therebetween. The angle between the two longitudinal walls 974a, 974b of the v-spring may vary, and can be selected based on a number of factors including, but not limited to, the dimensions of the bore 978.

Although a v-shaped spring is exemplified in this embodiment, the spring 974 may be formed in any suitable shape or configuration not limited to the v-shape, and may include, for example, U-shape, S-shape, coiled, square, rectangular, sinusoidal, corrugated, and accordion pleated. In addition, the shape of the spring features 974 may be symmetrical or non-symmetrical. For example, the longitudinal walls 974a, 974b may be symmetrical or non-symmetrical with respect to one another.

Figure 101:
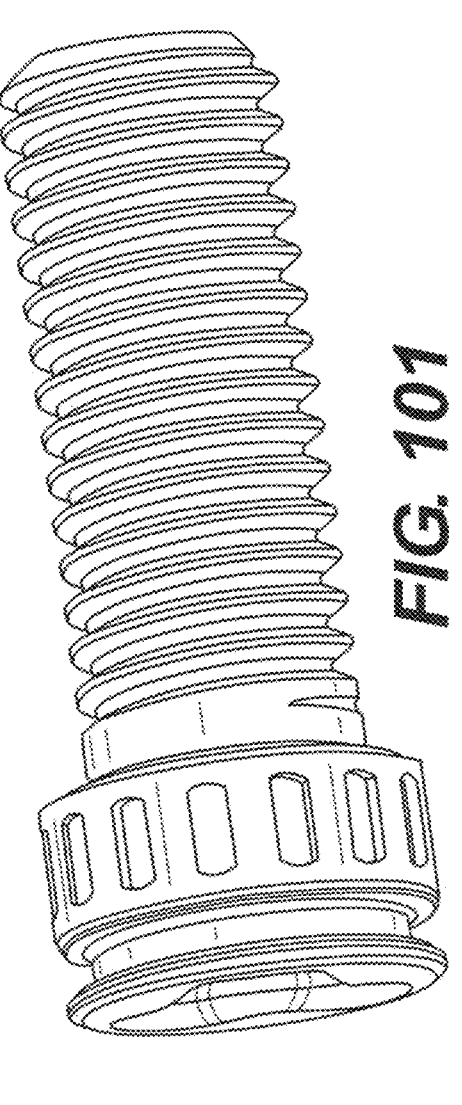
FIG. 101 is a diagram showing a side view of one embodiment of the collar and the drive screw head.

One embodiment of the collar 972 may include an opening, resulting in a C-shaped ring, as shown in FIG. 99, or it may comprise a closed ring (not shown). The collar 972 may be configured and dimensioned such that it can slide axially over the drive screw head 862. One advantage of using a C-shaped collar 972 is that it includes an opening that can facilitate insertion over the drive screw head 862. As shown in FIGS. 99 and 101, the collar 972 includes at least one opening 982. The at least one opening 982 is configured and dimensioned to receive a top protrusion 986 of the lock tab 976, discussed below. As such, it may be desirable for the dimensions of the lock tab to be configured to allow the top protrusion 986 to engage with the opening 982 while preventing the lock tab 976 from exiting through the opening 982. In embodiments where more than one opening 982 is included, the openings 982 may be selectively positioned to have spaces between the openings 982, as shown in FIGS. 99 and 101.

In an exemplary embodiment, the lock tab 976 includes a body 984 and an upper protuberance 986 that extends from the upper surface of the body 984. The lock tab 976 may also include a lower protuberance 988 that extends from a lower surface of the body 984 that is opposite the upper surface of the body 984 from which the upper protuberance 986 extends. As shown in FIG. 100, the lower protuberance 988 may extend away further from the body 984 than the upper protuberance 986.

The protuberances 986, 988 may comprise any suitable configuration and dimensions known to those skilled in the art. In embodiments where the protuberances 986, 988 comprise a substantially rectangular shape, it may be desirable for the upper protuberance 986 to be formed such that it is substantially perpendicular to the lower protuberance 988. One advantage of forming the protuberances 986 and 988 at a substantially perpendicular angle is to promote stability of the lock tab 976 when it sits inside the bore 978. The lower protuberance 988 can also include a stabilizing projection 990. One advantage of the stabilizing projection 990 is that it minimizes movement of the lower protuberance 988, and therefore the lock tab 976, within the bore 978.

In this embodiment, the lock tab 976 and the spring 974 may be installed within the bore 978 in the drive screw head 862. The spring 974, e.g., the v-spring, pushes up against a shoulder 992 of the body 984 of the lock tab 976. At the same time, the spring 974 pushes down against the bottom surface of the bore 978, which allows the lock tab 976 to flex up and down within the bore 978. The collar 972 may then be positioned over the side 980 of the drive screw head 862 in any suitable manner known to those skilled in the art. This may include, for example, flexing the collar to expand it such that it can fit over the drive screw head 862, or by sliding it over the threads of the drive screw 860.

When the lock tab 976 is in its natural position, the upper protuberance 986 sits inside one of the openings 982 of the collar 972, preventing the drive screw 860 from rotating relative to the collar 972. The drive screw 860, collar 972, spring 974, and lock tab 976 may then sit inside the housing 902, according to one embodiment. A retaining ring 890 may also be fit over the drive screw head 862 to retain the drive screw 860 within the housing 902. The collar 972 may be fastened to the inside of the housing 902 in any manner known to those skilled in the art including, but not limited to, press fit, pin, or welding to prevent the collar 972 from moving, e.g., rotating.

Figure 102:
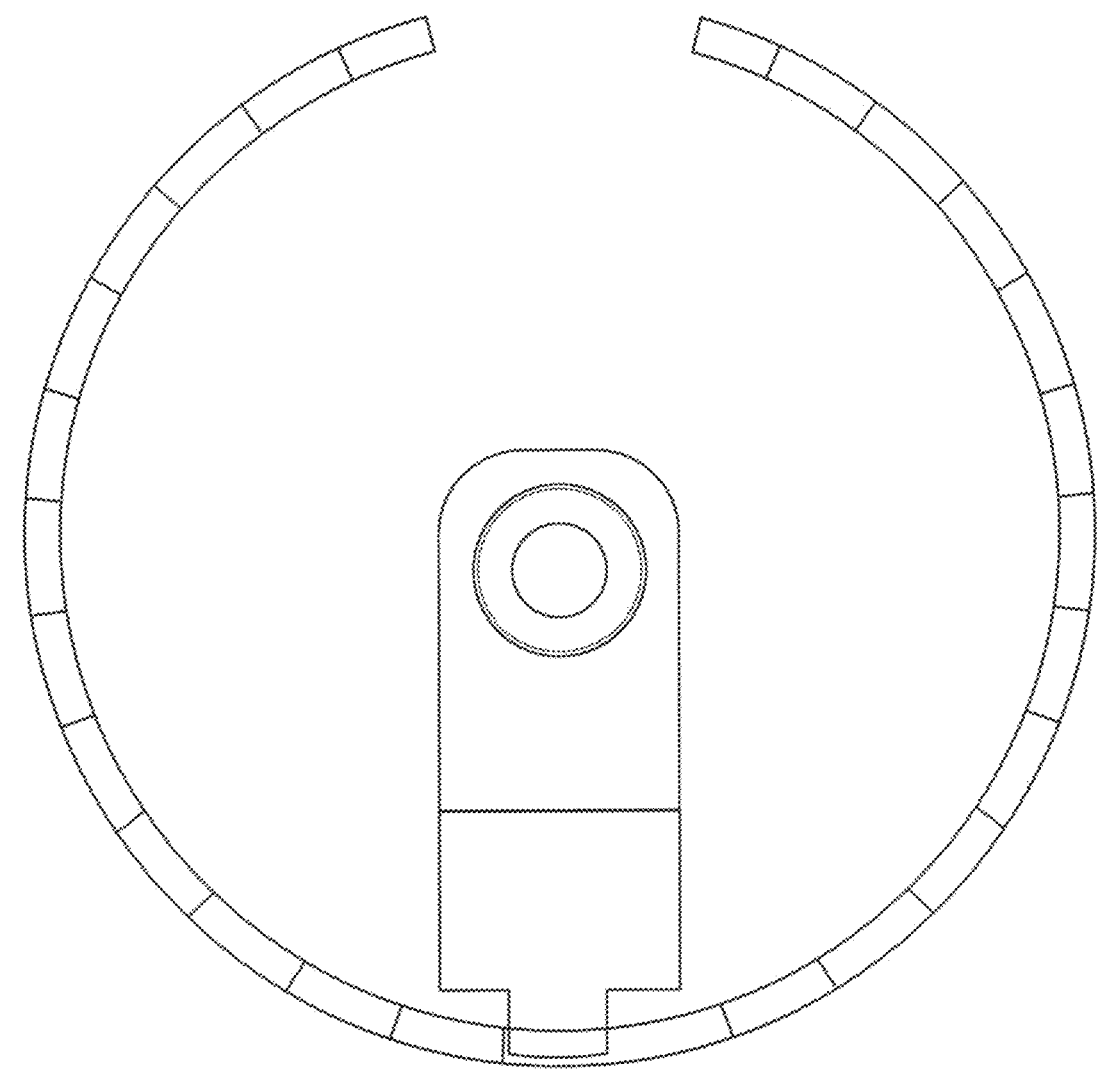
FIG. 102 is a diagram showing one embodiment of the lock tab and the collar in the engaged position.

When the elements described with respect to FIGS. 99-101 are assembled and in their natural position, the lock tab 976 is selectively positioned inside the bore 978 and engaged with the collar 972, as illustrated in FIG. 102. Since the collar 972 is rotationally locked to the housing 902, the lock tab 976 and therefore the drive screw 860 is prevented from rotating within the housing 902 due to the lock tab 976 and collar 972 being engaged.

Figure 103:
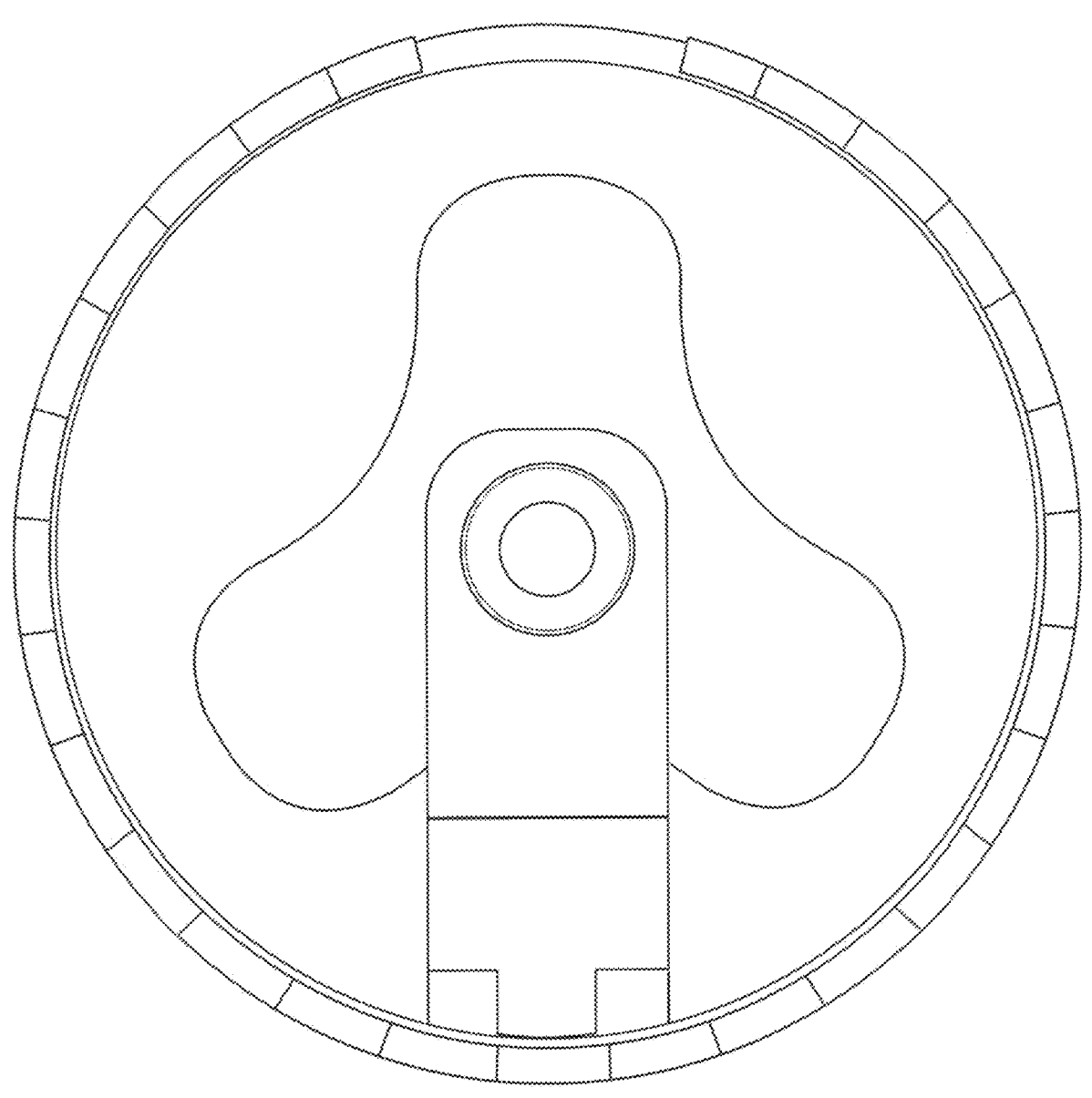
FIG. 103 is a diagram showing one embodiment of the lock tab, collar, and drive screw in the disengaged position.
Figure 104:
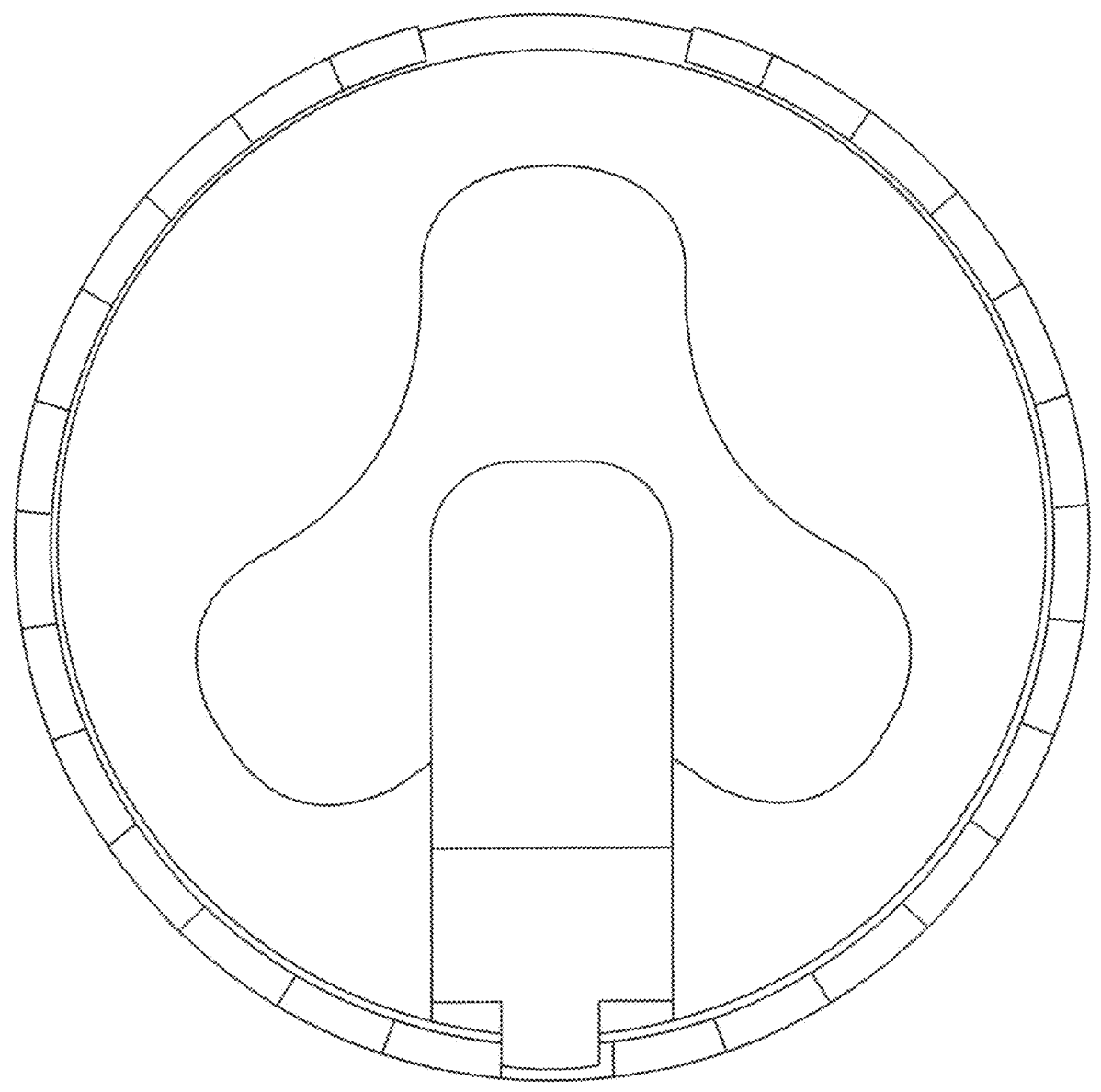
FIG. 104 is a diagram showing one embodiment of the lock tab, collar, and drive screw in the engaged position.

According to one embodiment, an instrument is required to allow rotation of the drive screw 860. The instrument can be any device known to those skilled in the art, such as a driver or the like. When the driver is engaged with the drive screw 860, it grabs the lock tab 976 and flexes it downwards into the bore 978, disengaging it from the collar 972, as illustrated in FIG. 103. When the diver is removed from the drive screw 860, the spring 974 pushes the lock tab back into its steady state position, illustrated in FIG. 104, locking the rotation of the drive screw 860.

With reference to FIGS. 105-109, an alternative embodiment of the locking mechanism is described. In the illustrated embodiment, the locking mechanism comprises a housing 902, a drive screw 860, a spring 994, a retaining ring 890, and a housing lock ring 906. The housing 902, drive screw 860, retaining ring 890, and drive screw 860 of FIGS. 105-109 and their individual components are similar to the components described with respect to the embodiments illustrated in FIGS. 87-95, with several modifications. The modifications and components that differ from the locking mechanism 900 illustrated in FIGS. 87-95 will be described in turn below.

According to one aspect of this embodiment, the drive screw 860 includes a drive screw head 862 that includes a first, back portion 862a and a second, front portion 862b. The back portion 862a comprises an outer diameter that is greater than the outer diameter of the front portion 862b. In one embodiment, the front portion 862b extends beyond the back portion 862a in a direction away from the threads of the drive screw 860, as shown in FIGS. 105-107. The front portion 862b may include an opening 970 through which an instrument such as a driver may be inserted. As shown in the FIG. 105, part of the front portion 862b may include a second opening 996 selectively positioned along its outer diameter, such that the circumference of the front portion 862b is non-contiguous. In other words, the second opening 996 extends to a side of the front portion 862b. The second opening 996 may pass completely through to the opening 970, as shown in FIG. 105. In one embodiment, the second opening 996 is positioned at one of the trilobe nodules shown in FIG. 106, for example. In other embodiments, however, the second opening may be separate, and non-contiguous with, the first opening 970.

It may be desirable for the outer diameter of the front portion substantially near the face of the front portion 862b to include a flanged opening, such as a ledge 998. One advantage of including a ledge 998 is that it requires the spring 994 to be splayed open to get past it. Once the spring 994 returns to its natural, steady state behind the ledge 998, it is prevented from disassembling from the front portion 862b, and thus also the drive screw head 862.

The spring 994, according to one embodiment, comprises a C-shaped ring that includes a protuberance 1000. The protuberance 1000 may be selectively positioned substantially opposite the opening in the C-shaped ring, and may comprise a first portion 1000a and a second portion 1000b. The first portion 1000b may extend from a surface of the C-shaped ring, and the second portion 1000b may extend from a surface of the first portion 1000b. In the illustrated embodiment, the first portion 1000a may be operatively connected to the drive screw head 862 by slidingly engaging with flats on the interior of the second opening 996. When the spring 994 is splayed open, i.e., expanded, to get past the ledge 998, the first portion 1000a can be aligned with the flats and engaged to fit within the second opening 996.

Figure 108:
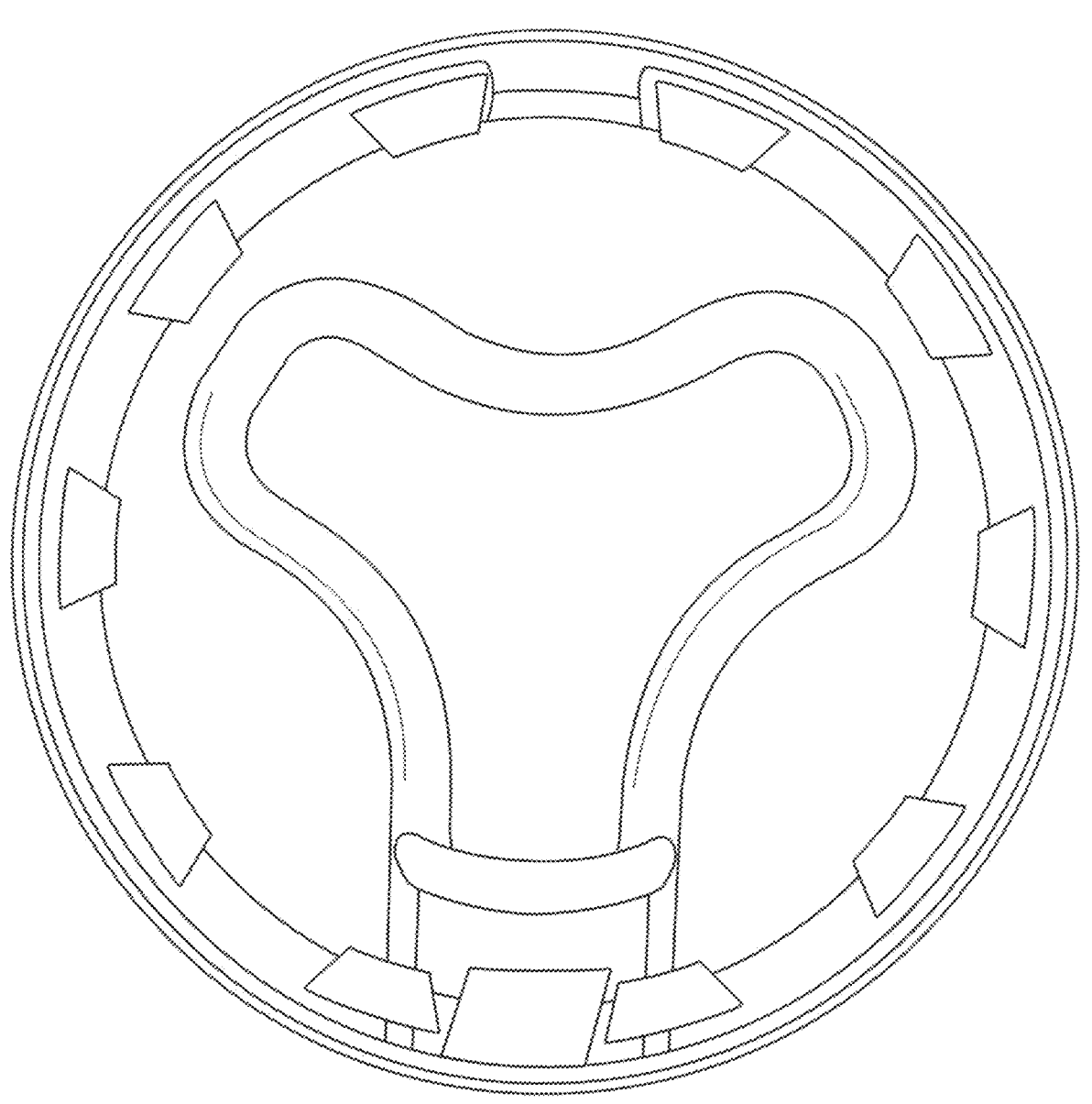
FIG. 108 is a diagram showing a close up view of one embodiment of the spring and housing lock ring in the engaged position.
Figure 109:
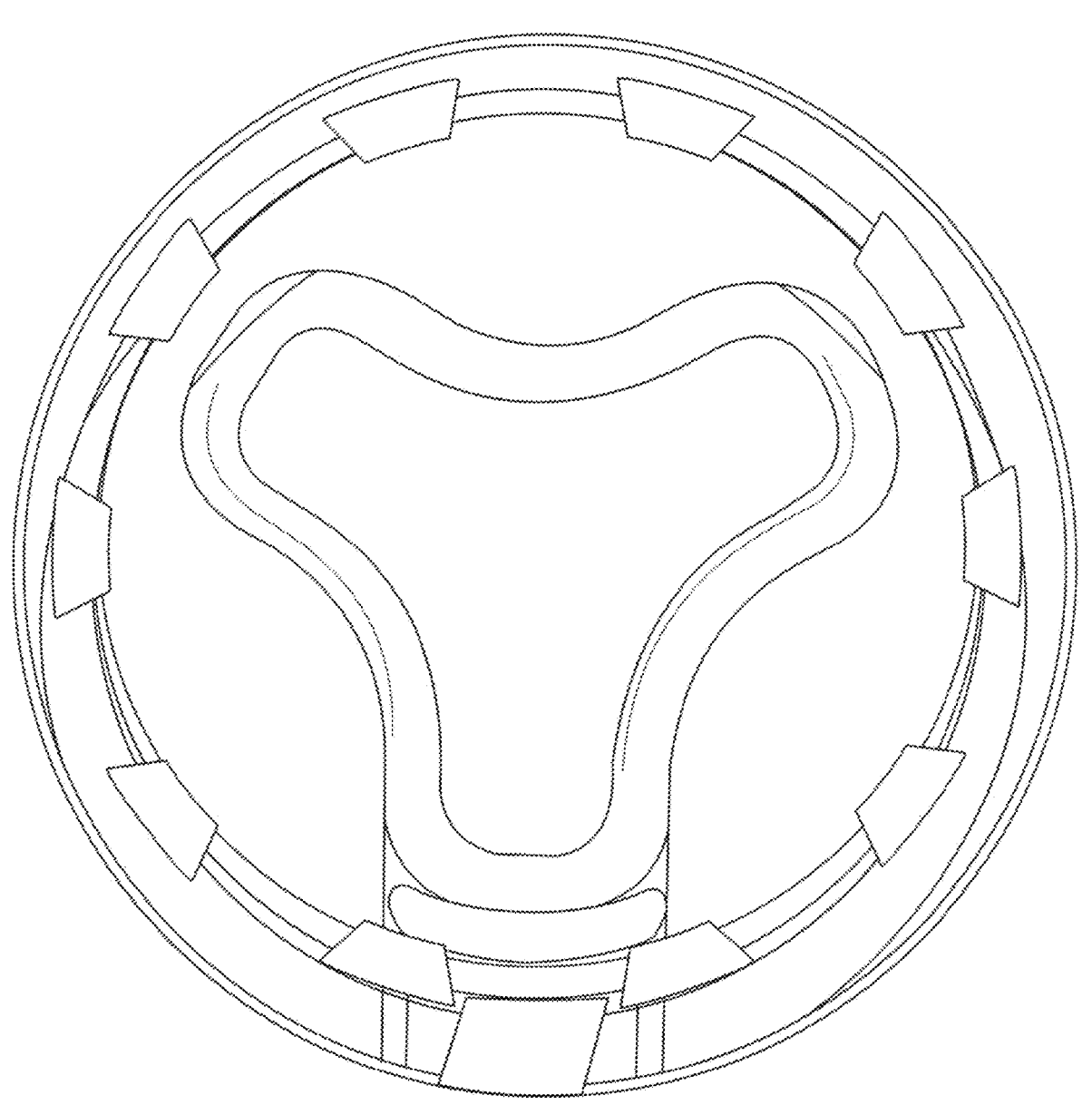
FIG. 109 is a diagram showing a close up view of one embodiment of the spring and housing lock ring in the disengaged position.

It is desirable for the first portion 1000a to be configured and dimensioned such that it substantially fills the opening 996 without extending substantially beyond the ledge 998 of the front portion 862b. The second portion 1000b may be configured and dimensioned to extend beyond the front portion 862b, and may have smaller dimensions than the first portion 1000a. The second portion 1000b may comprise at least one tab that may be straight sided, as shown in FIGS. 105-107, or angled, as shown in FIG. 108. Alternately, the second portion 1000b may comprise at least one straight tab and one angled tab. One advantage of including an angled tab is that it prevents the tab from springing into an unlocked position when rotational forces are present, as discussed in more detail below.

One embodiment of the housing lock ring 906 is substantially similar to the housing lock ring 906 described with reference to FIGS. 92-95 above. For instance, the housing lock ring 906 of this embodiment includes a castle feature 942 that includes slots into which the second portion 1000b, e.g., the tab, can align. This embodiment of the housing lock ring 906 also includes at least one protuberance 1002 that is configured and dimensioned to align with slots included in the housing 902 to prevent rotation.

As described above, the protuberance 1000 on the spring 994 may be aligned with the second opening 996 of the drive screw head 862. When the spring 994 is splayed open and positioned over the front portion 862b, according to this embodiment, the C-shaped ring may sit substantially flush with the back portion 862a, as shown in FIG. 107. The ledge 998 prevents the spring 994 from disengaging with the drive screw head 862. When configured and installed in the manner shown in FIG. 107, the spring 994 is rotationally locked to the drive screw 860. The drive screw 860 and spring 994 may then be inserted into the housing 902 and are free to rotate.

The retaining ring 890 may be placed on the housing lock ring 906, which can then be inserted into the housing 902. The at least one protuberance 1002 of the housing lock ring 906 may be aligned with the slots on the housing 902 to prevent rotation. The slots in the castle feature 942 of the housing lock ring 906 may be aligned with the second portion 1000b of the protuberance 1000 on the spring 994.

In the steady state position, the second portion 1000b of the protuberance 1000 aligns with a slot in the castle feature 942 on the housing lock ring 906. Since the housing lock ring 906 is rotationally aligned with the housing 902, and the second portion 1000b of the protuberance 1000 is rotationally aligned with the drive screw 860, the drive screw 860 is now rotationally locked relative to the housing 902, as shown in FIG. 108.

To unlock the second portion 1000b of the protuberance 1000 from the housing lock ring 906 to allow the drive screw 860 to rotate, a tool, e.g. a driver may be inserted into the opening 970 of the drive screw head 862. An interference between the second portion 1000b of the protuberance 1000 and the driver will translate the second portion 1000b down when the driver is present, disengaging the second portion 1000b from the slots in the castle feature 942 on the housing lock ring 906, as shown FIG. 109, and allowing the drive screw 860 to rotate. Once the driver is removed, the two arms of the C-shaped spring 994 act as springs, pulling the tab back into its steady state position and reengaging the second portion 1000b with the slots on the castle feature 942 of the housing lock ring 906. This, once again, prevents rotation of the drive screw 860.

With reference to FIGS. 110-116, an alternative embodiment of the locking mechanism is described. In the illustrated embodiment, the locking mechanism comprises a housing 902, a drive screw 860, an actuating tab 1004, and a retaining ring 890. The housing 902, drive screw 860, and retaining ring 890 of FIGS. 110-116 and their individual components are similar to the elements described with respect to the locking mechanism 900 illustrated in FIGS. 87-95, with several modifications. The modifications and components that differ from the locking mechanism 900 illustrated in FIGS. 87-95 will be described in turn below.

Figure 110:
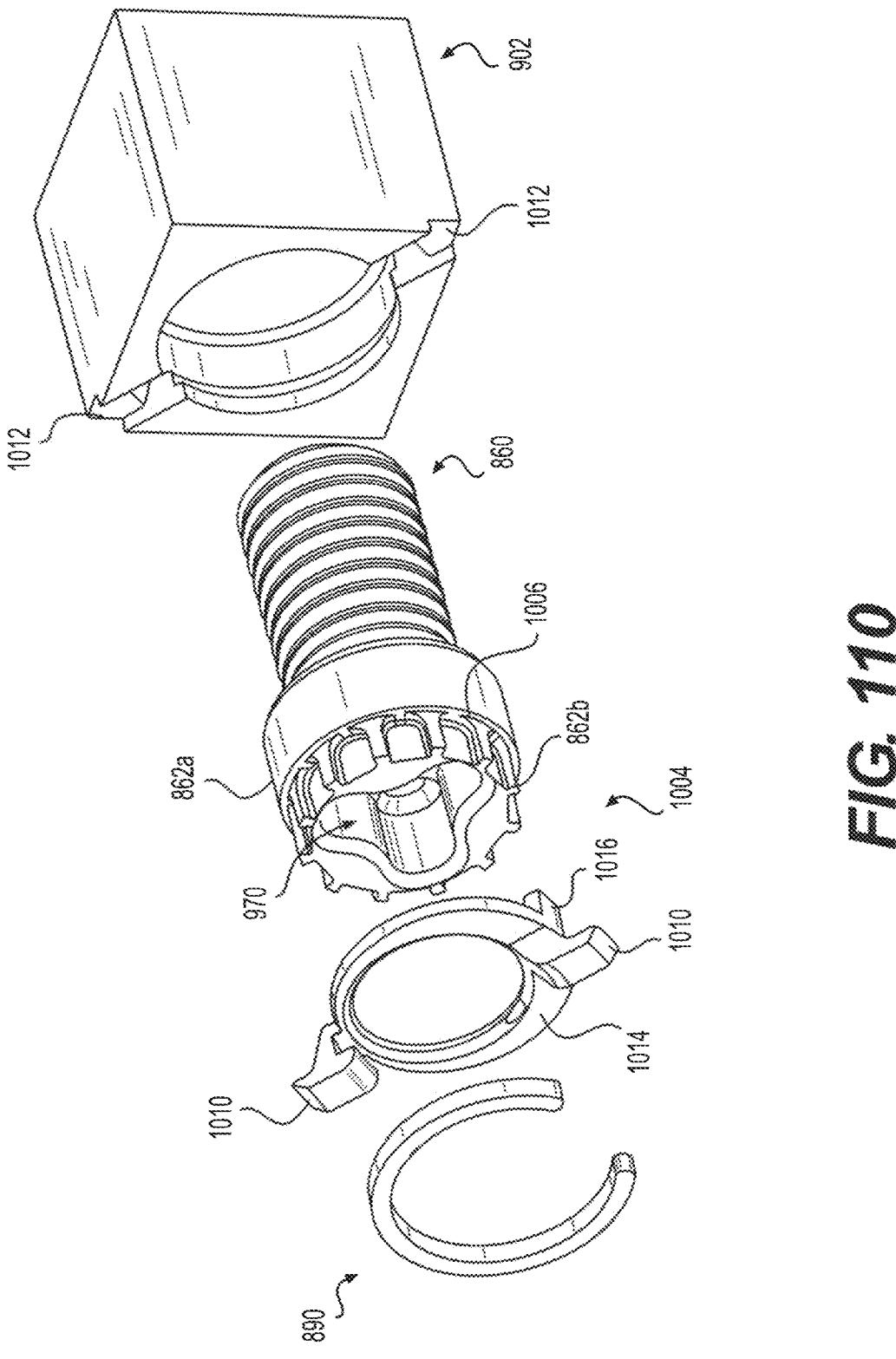
FIG. 110 is a diagram showing one embodiment of a locking mechanism according to the present invention.
Figure 111:
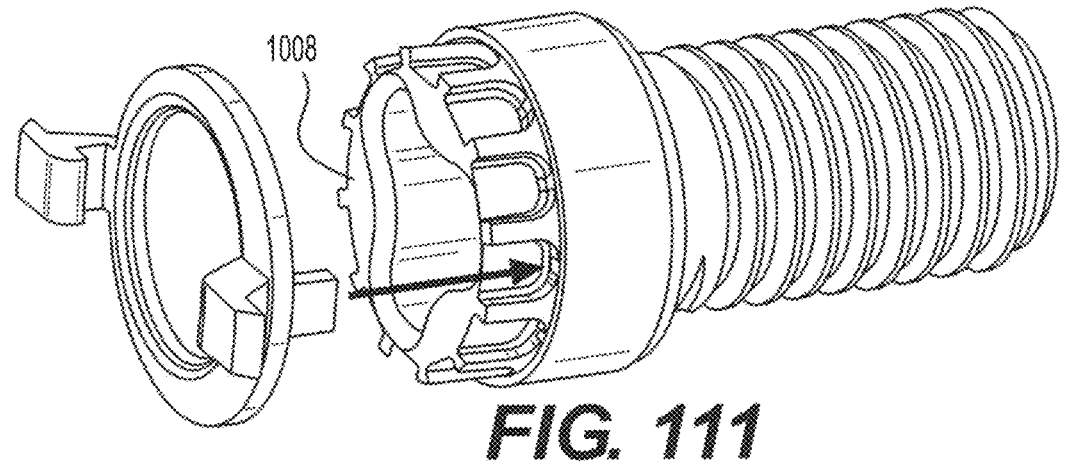
FIG. 111 is a diagram showing a close up view of components of one embodiment of the present invention.

Similar to the embodiment described with respect to FIGS. 105-109, the drive screw 860 includes a drive screw head 862 that includes a first, back portion 862*a*, and a second, front portion 862*b*. In the embodiment illustrated in FIG. 110, the front portion 862*b* includes notches 1006 that are selectively positioned around its outer diameter. The notches 1006 are configured and dimensioned to extend to the back portion 862*a* as well as the front face 1008 of the front portion 862*b*, as shown in FIG. 111. The notches 1006 may have any shape and dimensions known to those skilled in the art. In some embodiments, the shape and dimensions of the notches 1006 may be selected such that they are operable to receive and engage with correspondingly shaped protrusions included on the actuating tab 1004, as described in more detail below.

The actuating tab 1004, according to one embodiment, comprises a ring that includes at least one protuberance. In the embodiment illustrated in FIG. 110, for example, two protuberances 1010 may be included. The protuberances 1010 may be located on a first side 1014 of the ring and can operatively connect with the housing 902 to prevent rotational movement. In order to maximize stability and prevent rotation, the protuberances may be selectively positioned opposite one another, at about a 180° angle, as shown in FIG. 110. In other embodiments, four protuberances 1010 may be included that are selectively spaced apart from one another by about 90°. The number of protuberances 1010 may be selected, for example, depending on the structural integrity required to prevent rotation of the actuating tab 1004. In applications where the rotational forces are greater, a larger number of protuberances 1010 may be desirable. Conversely, when the rotational forces are smaller, fewer protuberances 1010 may be used.

The shape and dimensions of the protuberances 1010 may also be varied as desired. In one embodiment, the shape and dimensions of the protuberances 1010 may be selected so that they are operable to engage with recesses 1012 in the housing 902. The shape and dimensions of the protuberances 1010 may also be selected based on the rotational forces that are present in a particular application. For instance, when the rotational forces are greater, the protuberances 1010 may be configured and dimensioned to be larger to maintain their structural integrity. If, however, the rotational forces are not as large, the protuberances 1010 may be configured and dimensioned to minimize dimensions in order to reduce the size and shape of the overall locking mechanism.

The back side (not shown) of the actuating tab 1004 opposite the first side 1014, includes at least one protuberance 1016, e.g., a tab, that faces towards and is operatively connectable to the front portion 862*b* of the drive screw head 862, as shown in FIG. 110. The protuberance 1016 may be configured and dimensioned to comprise any desirable shape and dimensions, as described with respect to the embodiments shown in FIGS. 87-95, 96-98, and 105-109, for example. The actuating tab 1004 may be positioned opposite at least one of the protuberances 1010

In one embodiment, the actuating tab 1004 is positioned between about 175° and about 185° from at least one of the protuberances 1010. In another embodiment, the actuating tab is positioned about 180° degrees from at least one of the protuberances 1010. One advantage of positioning the actuating tab 1004 in this manner is that it allows the actuating tab 1004 to be forced into one of the notches 1006 when pressure is applied to a recess formed by the protuberance 1010. The pressure may be applied to the recess using a spring component, such as the retaining ring 890, as described in more detail below.

Figure 112:
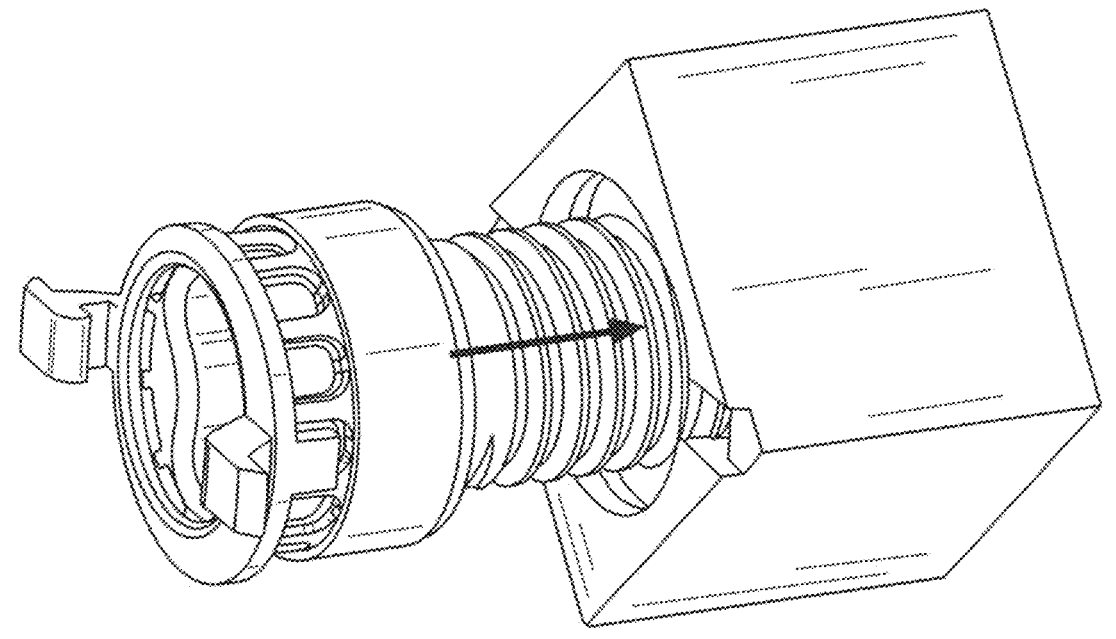
FIG. 112 is a diagram showing a close up view of components of one embodiment of the present invention.

The protuberance 1016, e.g., the tab, is configured and dimensioned to engage with the notches 1006 in the front portion 862*b*, shown in FIGS. 110-112, so that the drive screw 860 and the actuating tab 1004 are rotationally constrained to one another. The retaining ring 890 may comprise any ring shaped component that substantially prevents the actuating tab 1004 and the drive screw 860 from moving axially out of the housing 902, as described with respect to the embodiments illustrated in FIGS. 87-95, 96-96, and 105-109, for instance. The retaining ring 890 may also act as a spring to translate the actuating tab 1004 from the unlocked to the locked position, as described in more detail below. In some embodiments, a secondary retaining ring (not shown) may also be used directly between the drive screw head 862 and the housing 902 for increased drive screw retention.

With respect to FIGS. 111-116, the exemplary operation of the locking mechanism illustrated in FIG. 110 is described. In one embodiment, the actuating tab 1004 is operatively connected, i.e., engaged, with one of the notches 1006, as indicated by the arrow in FIG. 111. The drive screw 860 and the actuating tab 1004 may then be positioned inside the housing 902 so that the protuberances 1010 engage with the recesses 1012. In this manner, the actuating tab 1004 may be secured to the housing 902 to substantially prevent rotation of the actuating tab 1004, as illustrated in FIG. 112.

Figures 113, 114:
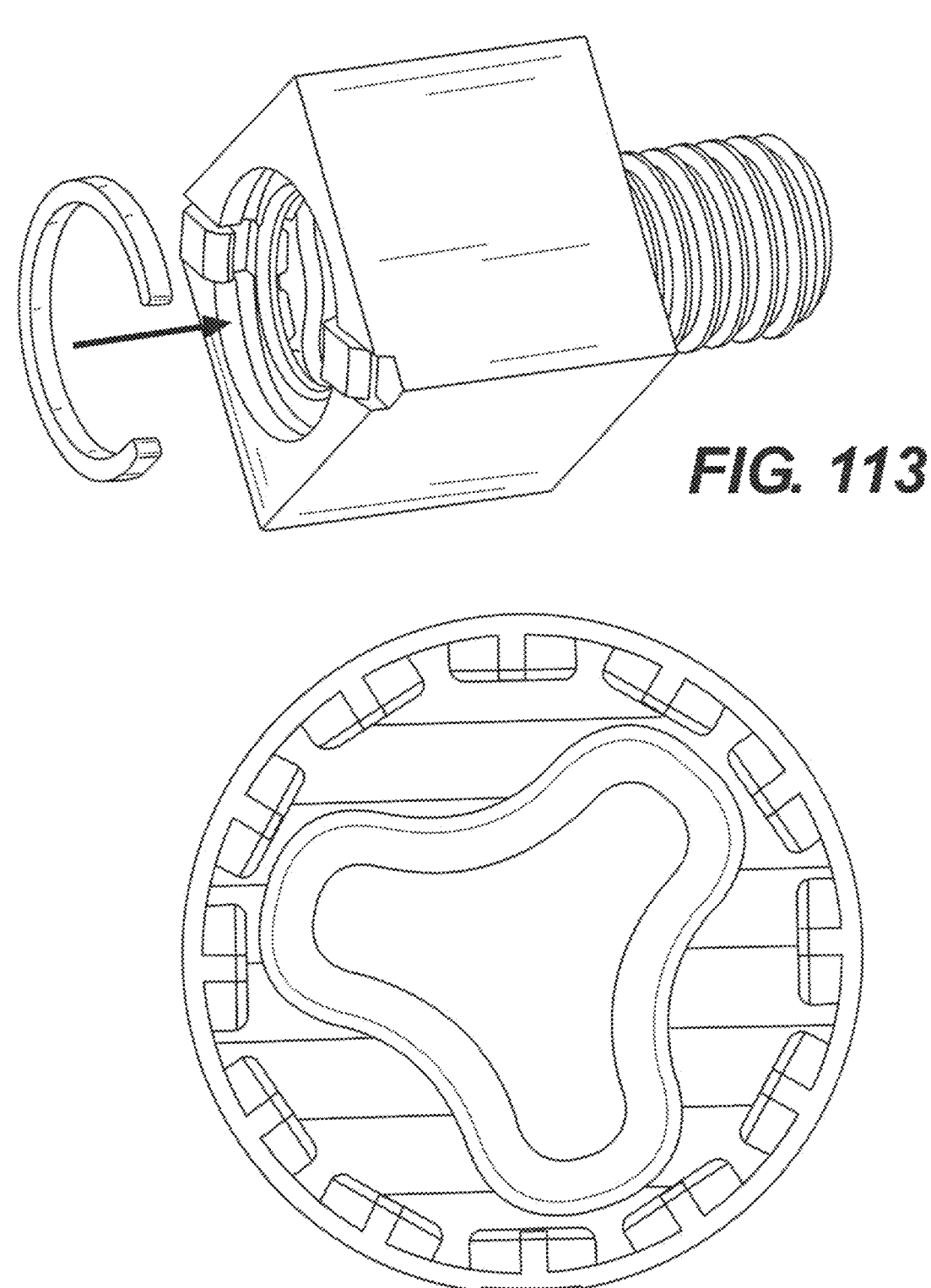
FIG. 113 is a diagram showing a close up view of components of one embodiment of the present invention.
FIG. 114 is a diagram showing components of one embodiment of the present invention in the disengaged position.

The retaining ring 890 may then be collapsed and inserted into the housing 902, as shown in FIG. 113. The housing 902 includes a groove to capture the retaining ring 890 once it springs back out to its natural shape. In one embodiment, the retaining ring 890 is selectively positioned so that its opening is in the same location as the protuberance 1016, e.g., tab on the actuating tab 1004. The actuating ring 1004 may be configured and dimensioned so that its inner diameter contacts the outer diameter of the retaining ring 890 on the side of the retaining ring 890 that is opposite its opening. When the retaining ring 890 is in its natural state, the actuating tab 1004 may be forced into a locked position because the protuberance 1016, e.g., tab, engages with one of the notches 1006. In this manner, the actuating tab 1004 may be rotationally locked to the housing 902 based on the two protuberances 1010, and the drive screw 860 is rotationally locked to the actuating tab 1004 with the engaged protuberance 1016. In this exemplary configuration, therefore, the drive screw 860 is also rotationally locked with respect to the housing 902.

According to one embodiment, a central opening in the actuating tab 1004 is configured and dimensioned such that it is offset from the opening 970 in the drive screw head 862, as described with respect to the screw lock ring 904 illustrated in FIGS. 87-95. When a tool, e.g., a driver is introduced and engaged with the opening 970, the actuating tab 1004 is pulled into alignment with the opening 970. The retaining ring 890 may act as a spring, so that when the driver displaces the actuating tab 1004, its contact with the retaining ring 890 pushes it against the outer wall of the housing 902, collapsing the retaining ring 890.

Figure 115:
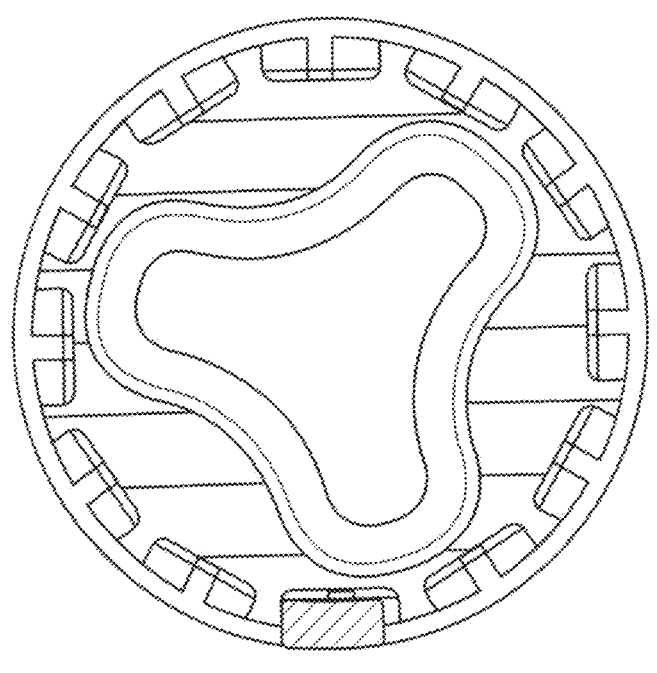
FIG. 115 is a diagram showing components of one embodiment of the present invention in the engaged position.

As shown in FIG. 114, with the translation of the actuating tab 1004, the protuberance 1016 moves as well and disengages from the notches 1006. The drive screw 860 is then free to rotationally move independent of the actuating tab 1004 and housing 902. As shown in FIG. 115, when the tool, e.g., the driver is removed from the opening 970, the retaining ring 890 pushes back to its natural, open position, contacting the actuating tab 1004 and returning the protuberance 1016 to one of the notches 1006 in the drive screw head 862. The drive screw 860 is then rotationally locked with respect to the actuating tab 1004 and the housing 902.

Figure 116:
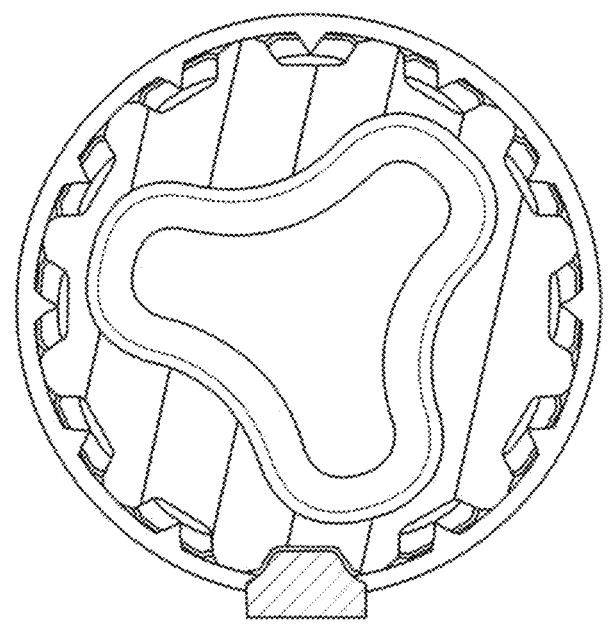
FIG. 116 is a diagram showing another embodiment of teeth that may be used in combination with embodiments of the present invention.
Figure 117:
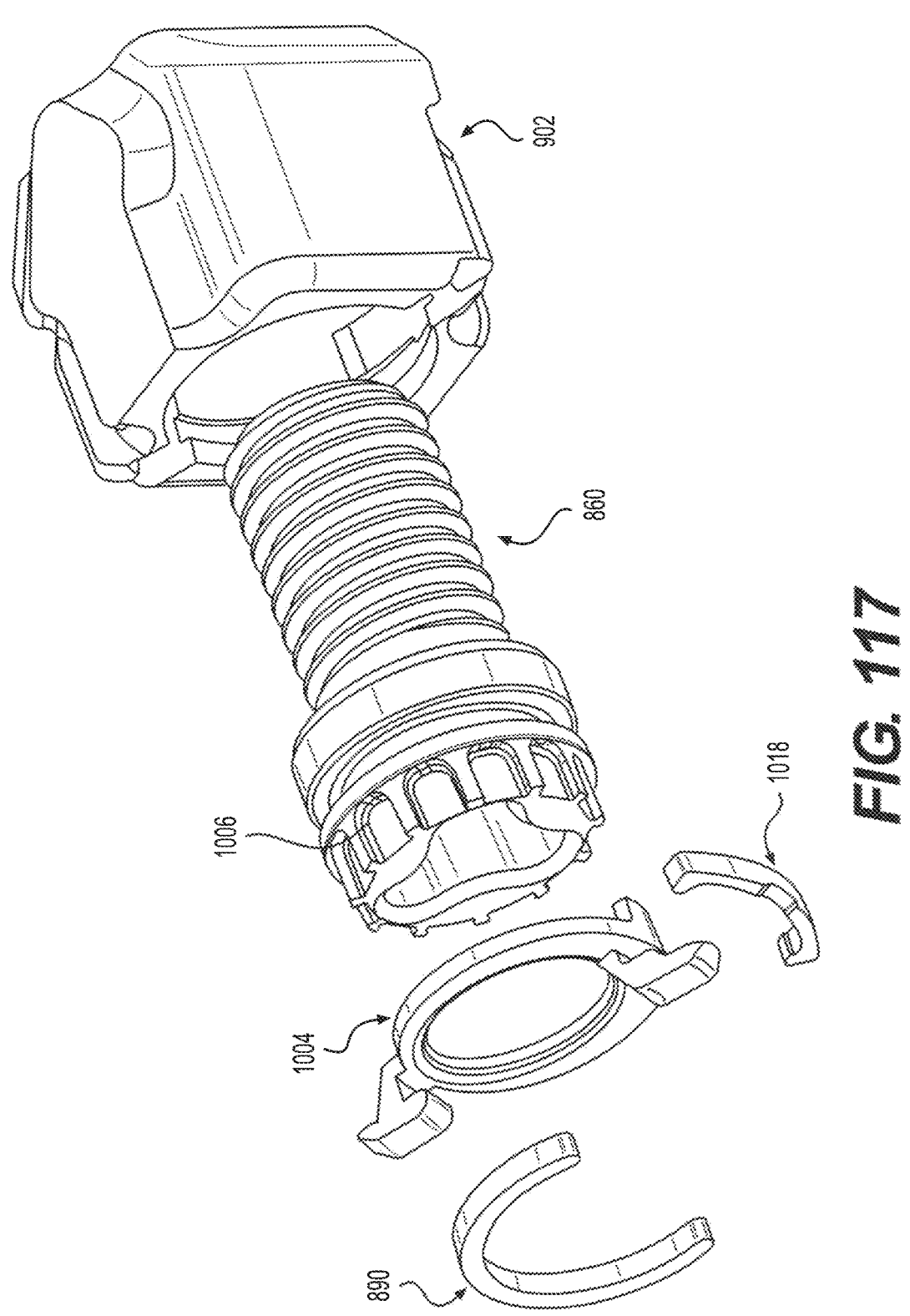
FIG. 117 is a diagram showing one embodiment of a locking mechanism according to the present invention.

As described above, the at least one protuberance 1016 may be configured and dimensioned as desired. For instance, in some embodiments the at least one protuberance 1016 may be tapered to provide a ratcheting design that substantially resists fracturing under excessive loads. One advantage of this design is that the at least one protuberance 1016 may ratchet into the next notch 1006 under excessive loads, as shown in FIG. 116.

With reference to FIGS. 117-121, an alternative embodiment of the locking mechanism is described. In the illustrated embodiment, the locking mechanism comprises a housing 902, a drive screw 860, an actuating tab 1004, retaining ring 890, and spring bar 1018. The housing 902, drive screw 860, actuating tab 1004, and retaining ring 890 of FIGS. 117-121 and their individual components are similar to the locking mechanism described with respect to FIGS. 110-116, with several modifications. The modifications and components that differ from the locking mechanism illustrated in FIGS. 110-116 will be described in turn below.

The embodiment illustrated in FIGS. 117-121 is substantially similar to the embodiment described with respect to FIGS. 110-116, except that the spring mechanism comprises a separate element. In this embodiment, the spring mechanism comprises a spring bar 1018. The spring bar 1018 may be preassembled to the actuating tab 1004 prior to installation into the housing 902 using any means known to those skilled in the art. The spring bar 1018 may be configured and dimensioned so that it may be keyed to the actuating tab 1004 to maintain rotational position, and then operatively connected together.

In this embodiment, the retaining ring 890 may configured and dimensioned such that it is spaced from the spring bar 1018 when positioned within the housing, as described in more detail below. The retaining ring 890, for example, may comprise a C-shaped ring that extends around about 180° or less of the outer diameter of the drive screw head 862. Alternately, the retaining ring 890 may comprise a C-shaped ring that extends around about 200° or less of the outer diameter of the drive screw head 862. In still another embodiment, the retaining ring 890 may comprise a C-shaped ring that extends around about 250° or less of the outer diameter of the drive screw head 862.

The spring bar 1018, according to one embodiment, may be configured and dimensioned according to any method known to those skilled in the art. In one embodiment illustrated in FIG. 117, the spring bar 1018 comprises two arms that flex around a central point. One advantage of configuring the spring bar 1018 in this manner is that it allows a load to be created when the arms of the spring bar 1018 push against the inner diameter of the housing 902 and the actuating tab 1004. The two arms may be configured and dimensioned to engage with at least one of the actuating tab 1004, the housing 902, and/or the drive screw 860. In the FIG. 117 embodiment, the spring bar 1018 may also include a groove, notch, recess, depression, or the like that may be selectively positioned, for example, substantially near a central point between the two arms of the spring bar 1018. One advantage of including a groove, notch, recess, or depression is that it allows the spring bar 1018 to operatively connect with the protuberance 1010 on the front face 1008 of the actuating tab 1004, as shown in FIG. 118.

Figures 118, 119:
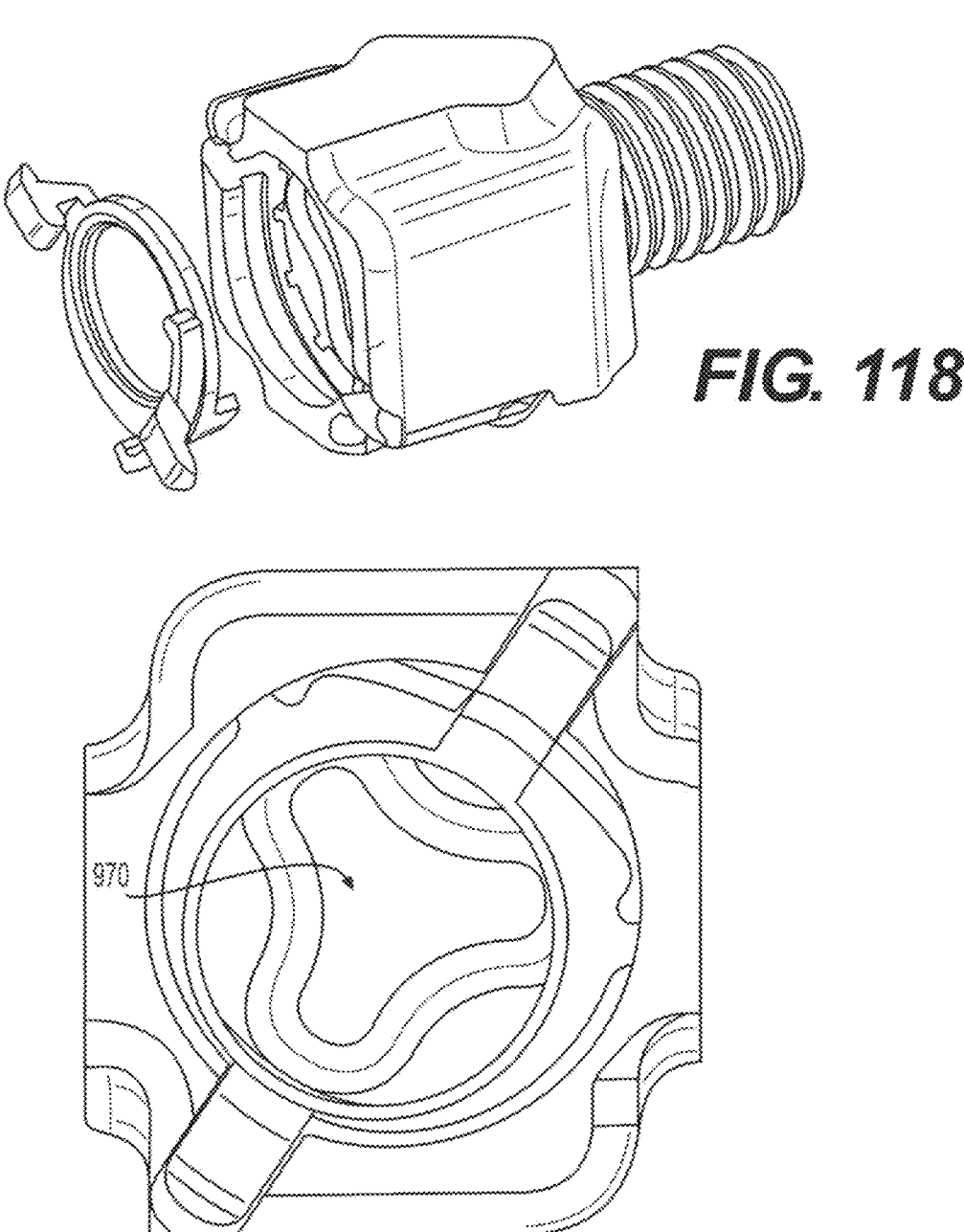
FIG. 118 is a diagram showing a close up view of one embodiment of components shown in FIG. 117.
FIG. 119 is a diagram showing a top view of one embodiment of components shown in FIG. 117.

After the drive screw 860 is inserted into the housing 902, the spring bar 1018 is deflected inward and it, along with the actuating tab 1004 is selectively positioned within the housing 902, as shown in FIG. 118. Once inserted into the housing 902, the spring bar 1018 may return to its natural, expanded position and engage with a groove of the housing 902 that is configured and dimensioned to receive the spring bar 1018, as shown in FIG. 119. The spring bar 1018 operatively connects or otherwise engages with a portion of the actuating tab 1004 that is substantially near the protuberance 1016, along with the inner diameter of the housing 902, creating a load that pushes the actuating tab 1004 into a locked position with the notches 1006. In an exemplary embodiment, the spring bar 1018 acts as a partial retaining ring to hold its side of the actuating tab 1004 and drive screw 860 in the housing 902. The retaining ring 890 may be inserted to provide additional retaining strength on the substantially opposite side of the spring bar 1018.

Figure 120:
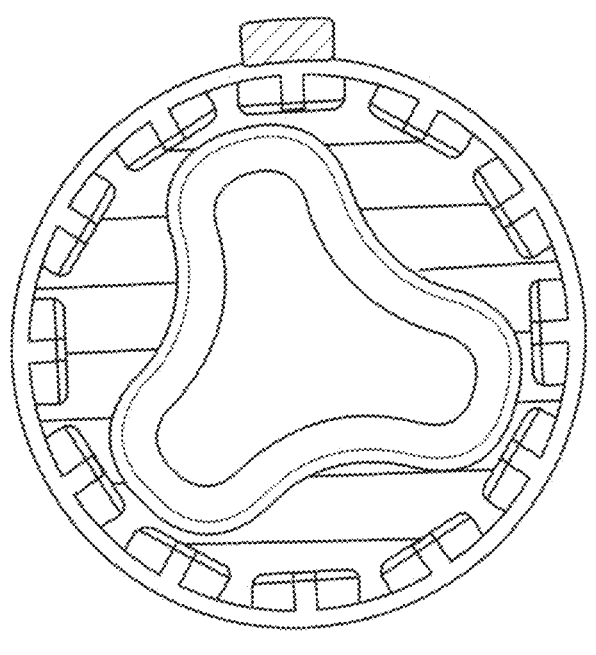
FIG. 120 is a diagram showing exemplary components shown in FIG. 117 in the disengaged position.
Figure 121:
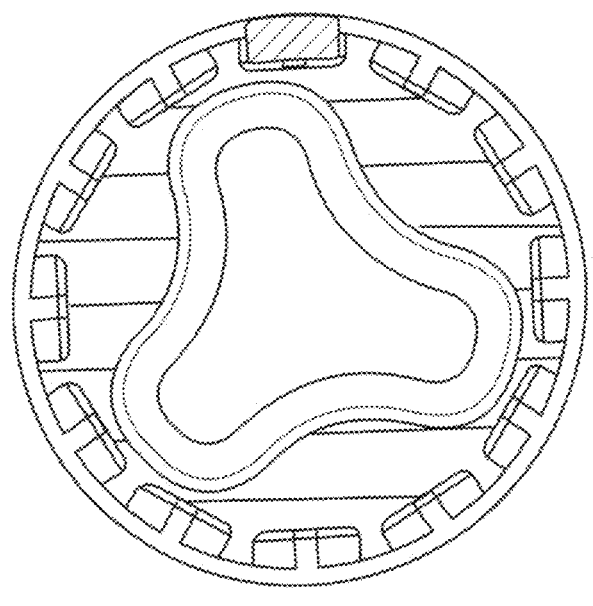
FIG. 121 is a diagram showing exemplary components shown in FIG. 117 in the engaged position.

As shown in FIG. 120, when a tool, e.g., a driver or the like, is inserted into the opening 970 in the drive screw head 860, the actuating tab 1004 translates against the spring bar 1018, disengaging the protuberance 1016 from the notches 1006 and allowing it to rotate independently. When the driver is removed from the opening 970, as illustrated in FIG. 121, the spring bar 1018 pushes against the actuating tab 1004, reengaging the protuberance 1016 with one of the notches 1006 of the drive screw head 862, substantially preventing rotation of the drive screw 860.

Figure 122:
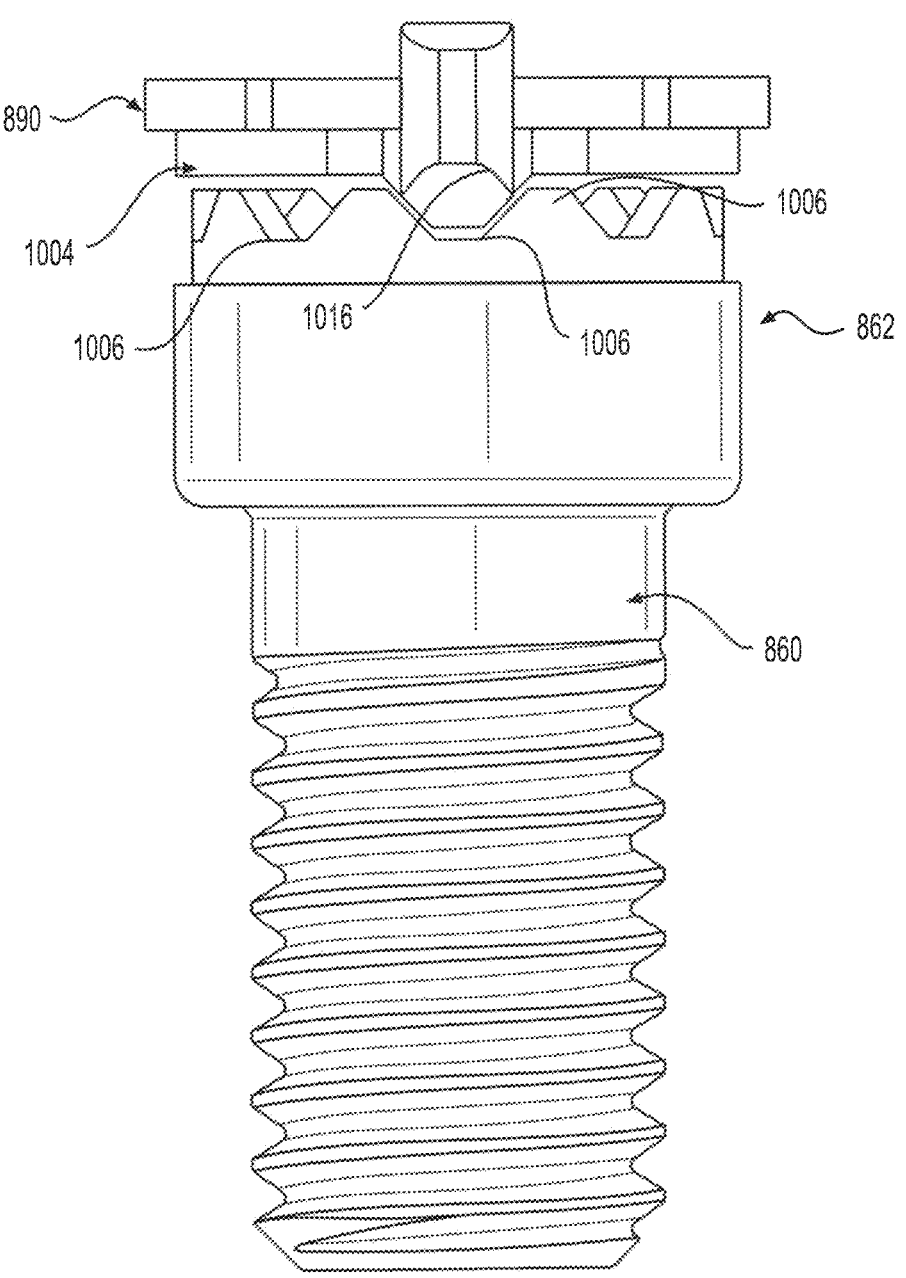

As described above, the notches 1006 in the front portion 862b of the drive screw head 862 described with respect to FIGS. 110-121 may comprise varied dimensions. For instance, in an embodiment shown in FIG. 122, the notches 1006 may be configured and dimensioned to comprise tapered sides in the vertical direction. Although the tapered notches 1006 are illustrated as external protuberances on the drive screw head 862 (indicated by the arrow in the diagram), they may also be removed material around the outer diameter of the front portion 862b of the drive screw head 862. In this embodiment, the actuating tab 1004 similarly includes at least one tapered protuberance 1016. The tapered protuberance 1016 includes two edges that are configured and dimensioned to operatively connect to, or engage with, the tapered edges of the tapered notches 1006.

In this embodiment, a central opening in the actuating tab 1004 is configured and dimensioned such that its center is offset from the center of the opening 970 in the drive screw head 862, as described with respect to the screw lock ring 904 illustrated in FIGS. 87-95. When a tool, such a driver or the like, is introduced and engaged with the opening 970, the actuating tab 1004 is pulled into alignment with the opening 970. The retaining ring 890, or spring bar 1018, may act as a spring so that when the driver displaces the actuating tab 1004, its contact with the retaining ring 890 or spring bar 1018 pushes it against the far wall of the housing 902, collapsing the retaining ring 890 or spring bar 1018. With the translation of the actuating tab 1004, the protuberance 1016 moves as well and disengages from the tapered notches 1006. The drive screw 860 is then free to rotationally move independently of the actuating tab 1004 and the housing 902.

When the tool, such as a driver or the like, is removed from the opening 970, the retaining ring 890 or spring bar 1018 pushes back to its natural, open, position, contacting the actuating tab 1004 and returning the protuberance 1016 to one of the tapered notches 1006 in the drive screw head 862. In this position, the drive screw 860 is rotationally locked with respect to the actuating tab 1004 and the housing 902. When an external force attempts to rotate the drive screw 860, the tapers on the notches 1006 will ramp the drive screw 860 and actuator tab 1004 apart from one another. Since the drive screw 860 is axially contained within the housing 902, and the actuating tab 1004 is axially retained by the retaining ring 890 and/or the spring bar 1018, the tapered notches 1006 and tapered protuberance 1016 will engage and prevent rotation of the drive screw 860.

With reference to FIGS. 123-125, an alternative embodiment of the locking mechanism is described. In the illustrated embodiment, the locking mechanism comprises a housing 902, a drive screw 860, a screw lock ring 904, a pivot pin 1020, and a snap ring 1022. The housing 902, drive screw 860, and screw lock ring 904 of FIGS. 123-125 and their individual components are similar to the elements described with respect to locking mechanism illustrated in FIGS. 87-95, with several modifications. The modifications and components that differ from the locking mechanism illustrated in FIGS. 87-95 will be described in turn below.

In the embodiment illustrated in FIGS. 123-125, the screw lock ring 904 comprises an e-shape including a spring tail 914. The screw lock ring 904 of this embodiment includes at least one locking tooth 1024 (or teeth), as shown in FIG. 123. The locking tooth 1024 may be selectively positioned around the central hole 952. The positioning of the locking tooth 1024 may be selected such that it can be disengaged from corresponding mating teeth on the snap ring 1022, discussed in more detail below, when the spring tail 914 is compressed.

In one embodiment, the screw lock ring 904 also includes a pivot pin 1020. The pivot pin 1020 may be machined as part of the screw lock ring 904, may be a separate element, or it may be part of the screw head 862. In embodiments where the pivot pin 1020 is a separate element from the screw lock ring 904, the screw lock ring 904 may include an opening that is configured and dimensioned to receive the pivot pin 1020. The pivot pin 1020 (or opening to receive the pivot pin 1020) may be selectively positioned around the center hole 952 as part of the "e" piece of the screw lock ring 904, away from the spring tail 914.

The screw lock ring 904 may be rotationally restricted using a snap ring 1022, according to one embodiment illustrated in FIG. 124. The snap ring 1022 may comprise a variety of shapes including, but not limited to, a circular ring shape or a C-shaped ring. The snap ring 1022 may include mating teeth 1028 machined on one side with which the at least one tooth 1024 of the screw lock ring 904 is operable to engage. It may desirable for the mating teeth 1028 teeth on the snap ring 1022 to be manufactured along its inner diameter, for instance, as shown in FIG. 124. The snap ring 1022 may also include a wavy outer diameter. The advantage of including a wavy outer diameter is that relief can be provided for larger interference fits.

The snap ring 1022 may be prevented from rotating within the housing 902 by including a pin 1026 that occupies the space between its opening, in embodiments where it comprises a C-shaped ring. The pin 1026 and the pivot pin 1020 may comprise a single element in some embodiments or, alternately, they may comprise separate elements that are operatively connected to one another. In other embodiments, however, the pin 1026 and the pivot pin 1020 may comprise separate elements in substantially different locations within the housing 902. In other embodiments, the snap ring 1022 may be welded into place within the housing 902.

Similar to the embodiments described with respect to FIGS. 87-95, the center of center hole 952 of the screw lock ring 904 is offset from the center of the opening 970 in the drive screw head 862. When a tool, such a driver or the like, is engaged with the opening 970, the center hole 952 (and thus the e-shaped piece) will be pushed into alignment with the driver and will pivot on the pivot pin 1020, compressing the spring tail 914. When the spring tail 914 is compressed, the lock tooth 1024 (or teeth) disengage from the mating teeth 1028 on the snap ring 1022. One advantage of the pivot pin 1020 is that the relative motion unlocking the lock tooth 1024 can be controlled to a greater degree when the driver causes the spring tail 914 to compress.

Those skilled in the art will understand that the magnitude of the unlocking motion or translation of the screw lock ring 904 may be obtained with different geometries separating the pivot pin 1020 and the lock tooth 1024. Additional manipulation of the translation of the screw lock ring 904 may also be generated based on geometries separating the pivot pin 1020, locking tooth 1024, and spring tail 914. Another advantage of the screw lock ring 904 of this embodiment is that the geometry between the pivot pin 1020, lock tooth 1024, and spring tail 914 enables a strong locking motion to be created when the drive screw 860 is rotated in the unlocking, or collapsing, direction. The tendency of the spring tail 914 to compress when a counterclockwise motion is applied may be reduced by the positioning of the pivot pin 1020, lock tooth 1024, and spring tail 914 when compared to a conventional up/down spring action of a screw lock ring 904 without a pivot pin 1020

As discussed above, the screw lock ring 904 is rotationally restricted based on the snap ring 1022. The locking tooth 1024 of the screw lock ring 904 operatively connects, or otherwise engages with the mating teeth 1028 of the snap ring 1022 to prevent rotation of the drive screw 860. Because the screw lock ring 904 is rotationally locked to the drive screw 860, and the snap ring 1022 is rotationally locked to the housing 902, the drive screw 860 is also rotationally locked until a driver is inserted into the opening 970.

Figure 126:
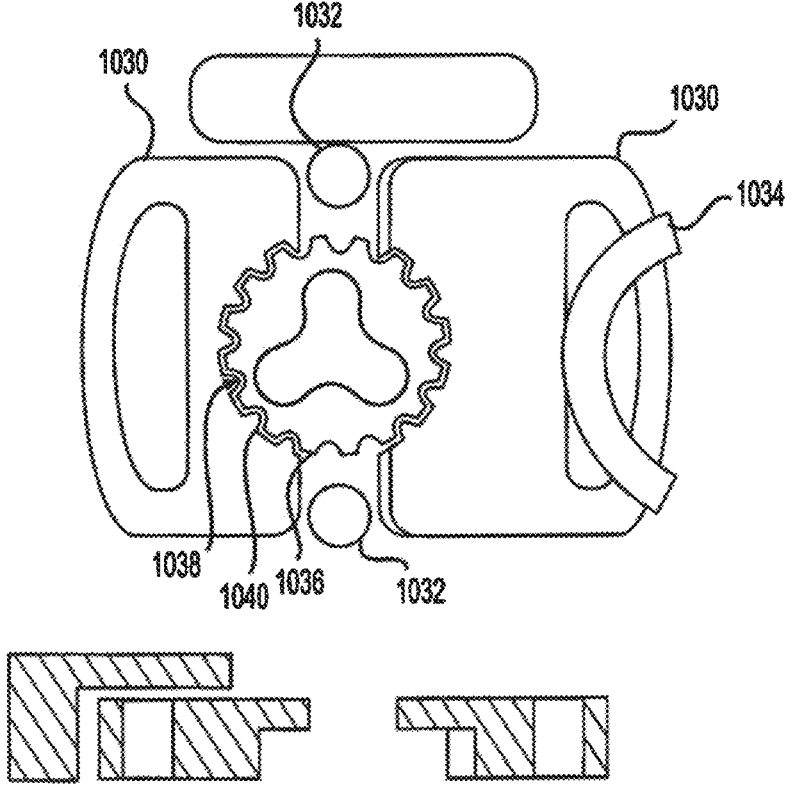

With respect to FIG. 126, another embodiment of the present invention is described. In this embodiment, the locking mechanism comprises at least two locking elements 1030, at least two pins 1032, at least one spring 1034, and a drive screw 860. The drive screw 860 is similar to the drive screw 860 described with respect to FIGS. 87-125 with slight modifications, which will be described below.

In this embodiment, the drive screw 860 includes at least one tooth 1036 cut around the drive screw head 862. It certain embodiments, however, it may be desirable for the drive screw head 862 to include a plurality of teeth 1036. According to one embodiment, the drive screw head 862 may be rotationally restricted based on at least two locking elements 1030. Each of the locking elements 1030 includes a recess 1038, facing the drive screw head 862, that is configured and dimensioned to engage with the shape of the drive screw head 862. In the embodiment shown in FIG. 126, for example, each recess 1038 is semi-circular so that locking elements 1030 together form a recess that is operable to engage with the circular drive screw head 862. Those skilled in the art will understand that the shape of the recesses 1038 can be varied as desired based on the shape of the drive screw head 862.

At least one opening may be included to allow a pin 1032 to pass through the body of the locking elements 1030. In the embodiment illustrated in FIG. 126, each of the locking elements 1030 include at least two openings. When the recesses 1038 of each of the locking elements 1030 are facing one another, the openings on each side can overlap one another, allowing a pin 1032 to pass through each set of openings. In this embodiment, the pins 1032 placed between pairs of locking elements 1030 prevents them from coming too close together and disassembling within the housing 902. The openings may be configured and dimensioned such that they are larger than the pins 1032. One advantage of including openings that are larger than the pins 1032 is that it allows for motion of the locking elements 1030 while also preventing disassembly. The recesses 1038 may also include teeth 1040 that are operable to engage with the one or more teeth 1036 included in the drive screw head 862. The teeth 1036 and teeth 1040 may be configured and dimensioned such that they are operable to matingly engage with one another.

Each of the locking elements 1030, according to one embodiment, may be further held in place by at least one spring element 1034. One advantage of including at least one spring element 1034 is that it forces the locking elements 1030 to be held close to the center of the drive screw head 862. In combination with the pins 1032, which prevents the locking elements 1030 from getting too close to one another and disassembling, the spring element 1034 maintains the engagement of the teeth 1040 of the locking element 1030 and the teeth 1036 of the drive screw head 862.

In some embodiments, one of the locking elements 1030 may be locked in place within the housing 902, while the other may be operable to move when impacted by an outside force, such as driver the like. In other embodiments where the locking elements 1030 are both configured and dimensioned to be selectively movable, a spring element 1034 may be used with each of the locking elements 1030. In the FIG. 126 embodiment, for instance, a spring element 1034 may be included on the side of the locking element 1030 opposite the recesses 1038 to provide a load that forces each of the locking elements 1030 towards the drive screw head 862. Those skilled in the art will understand that, although a curved leaf spring is shown in the FIG. 126 embodiment, any spring known to those skilled in the art (including those discussed above with respect to FIGS. 87-125) may be used as desired for a particular application. In addition, skilled artisans will understand that more than two locking elements 1030 may be used to engage the drive screw head 862 as long as the locking elements 1030 are operable to engage the drive screw head 862 with their teeth 1040.

In this embodiment, the locking elements 1030 are fastened to the housing 902 (not shown) such that they are rotationally restricted with respect to the housing 902. The locking elements 1030 may be fasted to the housing using, for example, pins 1032. Each of the locking elements 1030 are then are pushed towards the drive screw head 862 by the at least one spring 1034. The teeth from the locking elements 1030 engage the teeth 1036 on the drive screw head to prevent motion. Because the locking elements 1030 are rotationally locked with respect to the housing, and the teeth 1040 and teeth 1036 on the drive screw head 862 are engaged, rotation of the drive screw 860 is prevented. In one embodiment, a tool, such as a driver or the like, is inserted and overlaps the drive screw head 862, disengaging the teeth 1036 from teeth 1040 and allowing the drive screw 860 to rotate.

Figure 127A:
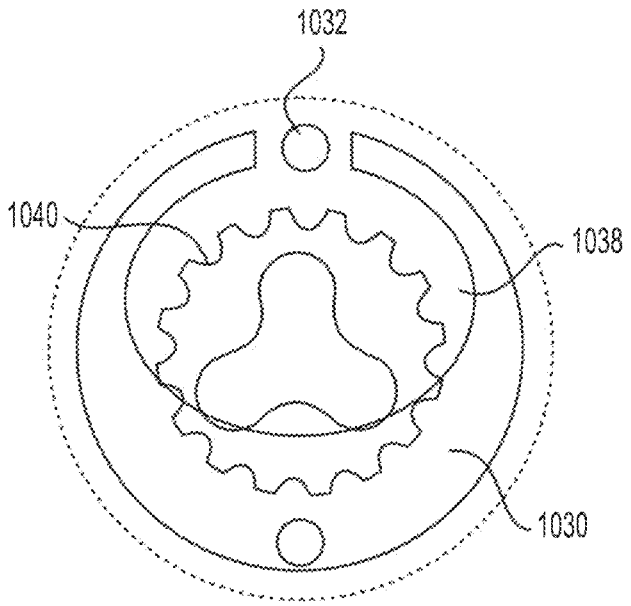
Figure 127B:
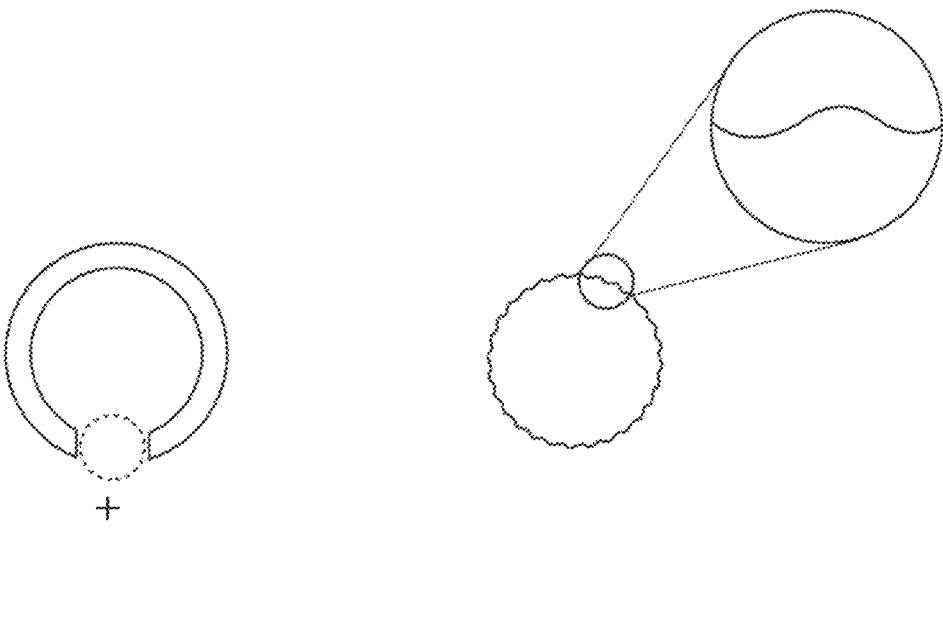
Figure 127C:
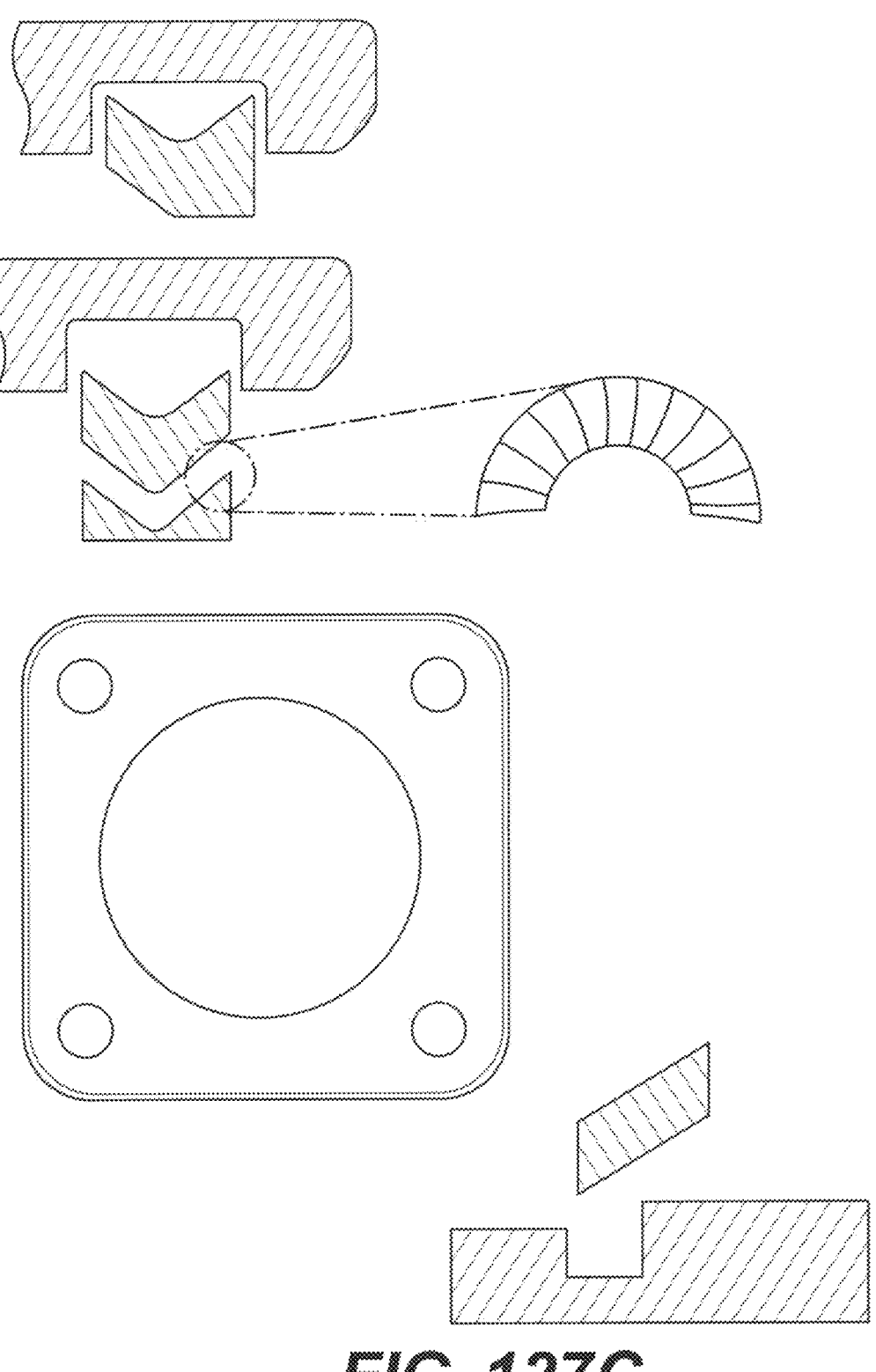
Figure 128:
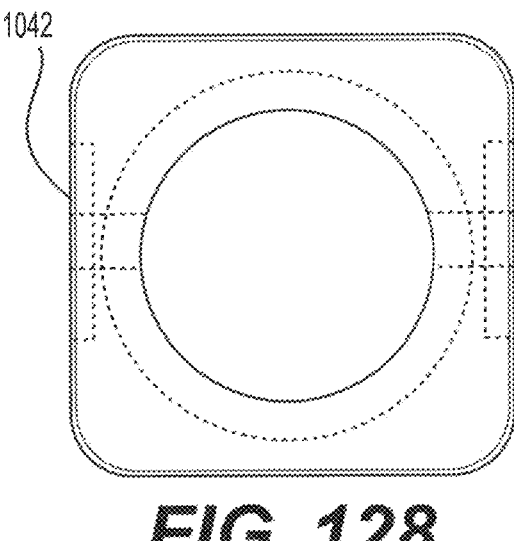

In an alternate embodiment, a single locking element 1030 may be used instead of the two or more locking elements 1030 described with respect to FIG. 126. As shown in FIG. 127, another embodiment comprises a drive screw 860 that includes one or more teeth, as described with respect to FIG. 126. However, in this embodiment, the locking element 1030 comprises a single locking element 1030 that comprises a ring shape with an opening, e.g., a c-shaped ring. The locking element 1030 may comprise a snap ring that is spring loaded to force its recess 1038 into engagement with the drive screw head 862. Alternately, a spring 1034 may be included to force the locking element 1030 into engagement with the drive screw head 862, as described with respect to FIG. 126. In other embodiments, a retaining ring 890 that is spring loaded may be selectively positioned around the c-shaped locking element 1030 to force the locking element 1030 into contact with the drive screw 860.

Similar to the embodiment of FIG. 126, the locking element 1030 includes a plurality of teeth 1040 along a surface of the recess 1038. The teeth 1040 engage the teeth 1036 around the drive screw head 862 to prevent rotational motion. In this embodiment, a pin 1032 may be selectively positioned within the opening of the c-shaped locking element 1030 to prevent it from rotating when installed in the housing 902. When a driver is inserted into the opening 970 of the drive screw head 862, it displaces the locking element 1030 which disengages the teeth 1040 and 1036, allowing the drive screw 860 to rotate.

With reference to FIGS. 128-131, an alternative embodiment of the locking mechanism is described. In the illustrated embodiment, the locking mechanism comprises a housing 902, a drive screw 860, and a screw lock ring 904. The housing 902, drive screw 860, and screw lock ring 904 of FIGS. 128-131 and their individual components are similar to the elements described with respect to the locking mechanism illustrated in FIGS. 87-95, with several modifications. The modifications and components that differ from the locking mechanism illustrated in FIGS. 87-95 will be described in turn below.

In this embodiment, the housing 902 includes a groove with lateral access openings 1042. The groove may be configured and dimensioned to receive at least a portion of the screw lock ring 904, a portion of which is similarly configured and dimensioned to fit within the groove. In this embodiment, the groove houses the screw lock ring 904 which includes an interference fit with a corresponding groove in the drive screw 860. The interference fit or engagement may be via fit or via discrete features, as will be appreciate by those skilled in the art. One advantage of the interference is that it serves to prevent free rotation of the drive screw 860.

Figure 129A:
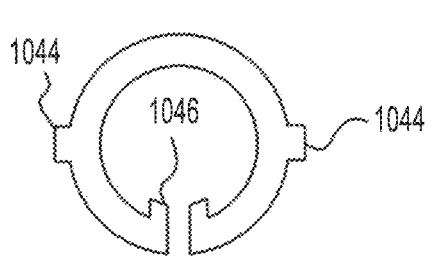
Figure 130:
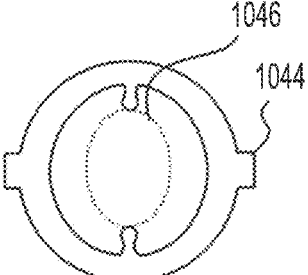
Figure 129B:
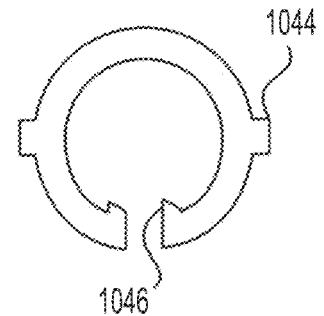
Figure 131:
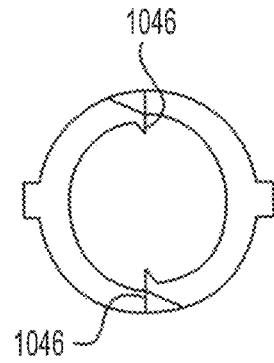

In this embodiment, the screw lock ring 904 may comprise one or more elements. For example, the screw lock ring 904 may comprise either a solid or split configuration, as illustrated in FIGS. 129-131. The embodiment shown in FIGS. 129*a-b*, for instance, illustrates a screw lock ring 904 that comprises a single solid element with an opening at one end. The portion of the screw lock ring 904 near the opening may include protuberances 1046 along its inner diameter. In the closed configuration shown in FIG. 129*a*, the two protuberances 1046 join together to create an interference that operatively connects with a groove in the drive screw 860 to prevents rotation of the drive screw 860.

Other aspects of the screw lock ring 904 may also be varied. The thickness of the screw lock ring 904 may be configured and dimensioned as desired. Varying the thickness of the screw lock ring 904 and/or and the shape of the opening in the screw lock ring 904, as shown in FIG. 130, allows the amount of friction exerted on the drive screw 860 to be selected as desired. For instance, the screw lock ring 904 may be configured and dimensioned to comprise an oval opening. If the protuberances 1046 are selectively positioned along a portion of the oval opening that is in closer contact with the drive screw 860, the amount of friction exerted on the drive screw 860 may be increased, which also increases the ability of the locking mechanism to resist rotational movement of the drive screw 860. In some embodiments, the screw lock ring 904 may also comprise a uniform thickness. Alternately, other embodiments may include a tapered thickness to coerce deflection only in certain regions.

In embodiments where the screw lock ring 904 comprises a split configuration, as shown in FIG. 131, the thicker portions may be positioned towards the protuberances 1044 that engage with the lateral access openings 1042 and the thinner portions may be positioned towards the interference area that engages with the groove in the drive screw 860. For instance, each part of the split configuration may have one end that is thick and one that is thinner, as shown in FIG. 131. The thicker portion may be configured substantially near the protuberances 1046, for example, while the thinner portions may be configured and dimensioned to join together, or overlap, to form one or more protuberances 1046, as shown in FIG. 131. Configuring each of part of the split configuration of the screw lock ring 904 in this manner creates at least one ratcheted protuberance 1046 that can then engage with a groove in the drive screw 860. Of course, the thickness may be varied in different configurations in other embodiments.

To configure the screw lock ring 904 to prevent rotation of the drive screw 860, it can be compressed from its open form, e.g. as shown in FIG. 129*b*, to its compressed form, e.g., as shown in FIG. 129*a*, and inserted into the housing 902. In this embodiment, the protuberances 1044 on the outer diameter can be operatively connected with the lateral access openings 1042. The protuberances 1046 on the inner diameter may selectively engage with the one or more grooves on the drive screw head 862 to prevent rotational movement. The protuberances 1046 can be contacted and deflected by using a tool that attaches to the housing 902. This action causes elastic deformation of the screw lock ring 904 such that the interference is removed, i.e., the protuberances 1046 are disengaged from the one or more grooves in the drive screw head 862, permitting the drive screw 860 to rotate. Removing the tool, e.g., driver or lateral jaw style holder, permits the screw lock ring 904 to relax back to its original shape, reengaging the interference and preventing free rotation of the drive screw 860.

With reference to FIGS. 132-134, an alternative embodiment of the locking mechanism is described. In the illustrated embodiment, the locking mechanism comprises a housing 902, a drive screw 860, and a screw lock ring 904. The housing 902, drive screw 860, and screw lock ring 904 of FIGS. 132-134 and their individual components are similar to the elements described with respect to the locking mechanism illustrated in FIGS. 105-109, with several modifications. The modifications and components that differ from the locking mechanism illustrated in FIGS. 105-109 will be described in turn below.

The screw lock ring 904 according to this embodiment includes at least one protuberance 1048, or tab, on the inner diameter of the ring 904, as shown in FIGS. 132-133. The protuberance 1048 may be configured and dimensioned such that it can be inserted into the side of the opening 970 in the drive screw head 862 to prevent it from rotating. In this embodiment, the opening 970 is configured and dimensioned to extend to the outer diameter of at least one portion of the drive screw head 862. The screw lock ring 904 may also include vertical protrusions 1052 that are configured and dimensioned to operatively connect with at least a portion of the housing 902.

The housing 902, according to one embodiment, includes openings 1050, e.g., blind pockets, that are configured and dimensioned to receive the vertical protrusions 1052 from the screw lock ring 904, as shown in FIG. 134. Additionally, the housing 902 includes an expansion space 1054 that allows the screw lock ring 904 to expand when impacted by a tool, such as a driver. The openings 1050 in the housing 902 operatively connect with the vertical protrusions 1052 to rotationally constrain the screw lock ring 904 within the housing 902. In this embodiment, the insertion of a driver into the opening 970 translates the protuberance 1048 outside of the outer diameter of the drive screw 860, allowing rotation within the housing 902.

An alternative embodiment of the locking mechanism is described with reference to FIGS. 135-136. In the illustrated embodiment, the locking mechanism comprises a housing 902 and a drive screw 860. The illustrated embodiment may optionally include one or more washers 1056-1060. The housing 902 and the drive screw 860 of FIGS. 135-136 and their individual components are similar to the elements described with respect to the locking mechanism illustrated in FIGS. 87-95, with several modifications. The modifications and components that differ from the locking mechanism illustrated in FIGS. 87-95 will be described in turn below.

According to this embodiment, the drive screw head 862 includes one or more protuberances, such as teeth or the like, on either the top face 1062 or bottom face 1064 of the drive screw head 862, or both. In the embodiment shown in FIG. 135, for example, teeth are included on the bottom face 1064 of the drive screw head 862. Alternately, the protuberances, e.g., teeth, can be included on the top face 1062 of the drive screw head 862.

The housing 902 in this embodiment also includes one or more recesses that are operable to receive the protuberances on the top face 1062 or bottom face 1064 of the drive screw head 862. In the embodiment shown in FIG. 135, a locking washer 1056 may be included in combination with the housing 902 and drive screw head 862. The locking washer 1056 also includes protuberances, such as teeth or the like, that are configured and dimensioned to engage with the protuberances on the bottom face 1064 of the drive screw head 862. The locking washer 1056 may comprise any washer known to those skilled in the art, such as a Belleville washer, and may optionally be spring loaded such that it is operable to operatively connect, or otherwise engage with, the bottom face 1064 of the drive screw head 862.

The teeth on the bottom face 1064 of the drive screw head 862, according to the embodiment shown in FIG. 135, engage with teeth that are configured and dimensioned to be included on a locking washer 1056 that sits between the housing 902 and the drive screw head 862. When a tool, such as a driver or the like, applies a force on the locking washer 1056 axially away from the protuberances on the bottom face 1064, the drive screw head 862 is free to rotate. When the driver is removed, the spring load of the locking washer 1056 pushes it against the bottom face 1064, reengaging the protrusions and rotationally locking the drive screw head 862.

In an alternate embodiment, drive screw head 862 may include protuberances on both the top face 1062 and the bottom face 1064. In this embodiment, the housing 902 also includes protuberances, such as teeth or the like, that are operable to engage with the protuberances on the top face 1062 of the drive screw head 862. The combination of the locking washer 1056, teeth on the bottom face 1064 and top face 1062, and teeth included in the housing 902 may prevent undesirable rotational movement of the drive screw head 862.

In other embodiments, other washers may be included to further prevent rotation of the drive screw 860 when it is engaged within the housing 902. For instance, as shown in FIG. 136, at least one of a thrust washer 1058 and bent washer 1060 may be included either alone or in combination with the locking washer 1056 described above. In an exemplary embodiment, the thrust washer 1058 is positioned between the drive screw 860 and the bent washer 1060. The bent washer 1060, in turn, is positioned between the housing 902 and the thrust washer 1058, as shown in FIG. 136. One advantage of the bent washer 1060 is that it provides a force on the thrust washer 1058, and thereby the bottom face 1064 of the drive screw head 862, when the drive screw 860 is not being driven into the housing 902. In such an embodiment, the drive screw head 862 may include protuberances on the top face 1062 that are then forced into engagement with protuberances, e.g., teeth included in the housing 902, as described above.

Those skilled in the art will appreciate that the thrust washer 1058 may include protuberances in some embodiments that are operable to engage with corresponding protuberances on the bottom face 1064 of the drive screw head 862. Alternately, the bent washer 1060 may be used in combination with the locking washer 1056 to provide additional force that drives the protuberances on the locking washer 1056 into engagement with protuberances on the bottom face 1064. The locking washer 1056, thrust washer 1058, and bent washer 1060 may optionally be rotationally locked with respect to the housing 902 using pins, welding, or any other method known to those skilled in the art. Rotationally locking these elements may assist with preventing the rotation of the drive screw 860 when the protuberances included on the surface of these elements and the drive screw head 862 are forced into engagement. Any combination of elements described with respect to FIGS. 135-136 may be used to prevent rotational movement of the drive screw 860, as will be appreciated by those skilled in the art.

In embodiments described above with respect to FIGS. 87-136, it may be desirable to include a set screw to provide an additional mechanism to prevent rotation of the drive screw 860. However, in other embodiments, a set screw alone may provide sufficient force to prevent rotation of the drive screw 860. As described above with respect to FIGS. 50-52 and 70, for example, a set screw 438 may be inserted through the hole 436 to secure the driving ramp 300 to the actuator assembly 200. In an exemplary embodiment, a spring element 1066 may be selectively positioned within the housing 902 to interfaces, engage, and/or operatively connect to the set screw 438.

For example, in one embodiment the spring element 1066 may be selectively positioned within the housing 902 that interfaces with the set screw 438, as illustrated in FIG. 137. In such an embodiment, the set screw 438 may be inserted into the hole 436 configured and dimensioned in a portion of the housing 902 and operatively connected to the drive screw head 862. The set screw 438 may include a tip point 1068 that that is configured and dimensioned to engage with protuberances, e.g., teeth, included on a portion of the drive screw head 862. The set screw 438 may comprise any tip point 1068 known to those skilled in the art, such as conical tip point, as shown in FIG. 138a. The tip point 1068 can be configured and dimensioned so that it may engage with the protuberances on the drive screw head 862 to prevent rotational movement within the housing 902.

The top end 1070 of the set screw 438, opposite the tip point 1068, may be configured and dimensioned to include an interface that can selectively engage with the spring element 1066. For instance, the top end 1070 may include protuberances, such as teeth, that include angles that prevent the set screw 438 from turning counterclockwise, as shown in FIG. 138b. Alternately, the top end 1070 may comprise a recess 1072, such as a groove or a notch, that relies on friction to resist rotational movement, e.g. counterclockwise or loosening movement.

The spring element 1066, according to an exemplary embodiment, is configured and dimensioned to fit within the hole 436. One end of the spring element 1066 may include one or more protuberances that are configured and dimensioned to engage with the corresponding protuberances on the top end 1070 of the set screw 438. The protuberances may include, for example, teeth that are operable to engage with teeth on the top end 1070 of the set screw 438. Alternately, the protuberance may include a tab that is operable to engage with the recess 1072 in the top end 1070 of the set screw 438. When the spring element 1066 is inserted into the hole 436 after the set screw 438 is in place, the protuberances on the spring element 1066 engage with the protuberances or recess 1072 on the top end 1070 of the set screw 438. Because the spring element 1066 applies a constant force on the set screw 438, the engagement of the protuberances and/or recess 1072 prevents rotation of the set screw 438. In turn, the tip point 1068 of the set screw 438 engages with protuberances on the drive screw head 862, thereby preventing rotational movement of the drive screw 860.

An alternative embodiment of the locking mechanism is described with reference to FIG. 139. In the illustrated embodiment, the locking mechanism comprises a housing 902, drive screw 860, retaining ring 890, ring 514, deflectable arm 1074, spring 1076, and spring retention device 1078. The housing 902, drive screw 860, retaining ring 890, and ring 514 of FIG. 139 and their individual components are similar to the those described with respect to FIGS. 58 and 87-136, with several modifications. The modifications and components that differ from the locking mechanism illustrated in FIGS. 58 and 87-136 will be described in turn below.

The spring 1076 may include any spring known to those skilled in the art. It is desirable for the spring 1076 to be configured and dimensioned so that it can fit within a recess 1080 within the drive screw head 862. The recess 1080 may be configured and dimensioned as part of opening 970 in the drive screw head 862. While it may comprise any shape and/or dimensions, the recess 1080 may be large enough to receive the spring 1076 and/or spring retention device 1078 while also not compromising the structural integrity of the drive screw head 862.

The drive screw head 862 in this embodiment includes a deflectable arm 1074, and a recess through which the deflectable arm 1074 can pass through the side of the drive screw head 862. The recess may extend through the side of the drive screw head 862 in at least one portion, or alternately, it may extend through the side of the drive screw head 862 in at least two places. The deflectable arm 1074 may comprise a separate element that is installed within the drive screw head 862 prior to installation in the housing 902. Alternately, at least a portion of the deflectable arm 1074 may be formed as part of the drive screw head 862. The deflectable arm 1074 may comprise a single arm as shown in FIG. 139, or it may extend from at least two sides of the drive screw head 862 (not shown) in order to increase the ability to resist rotational movement. The end of the deflectable arm 1074 that protrudes from the drive screw head 862 may comprise a ratcheting interface in order to prevent rotational movement, and may face upwards towards the face of the drive screw head 862 or downwards, away from the face of the drive screw head. In alternate embodiments, one end of the deflectable arm 1074 may face towards the face of the drive screw head 862 while the other may be face towards the body of the drive screw 860. One advantage of configuring the deflectable arm 1074 in this manner is that at least one side of the deflectable arm 1074 may be engaged with the housing 902 regardless of the direction the drive screw 860 rotates.

The spring retention device 1078 illustrated in FIG. 139 may comprise a button or other type of retention device known to those skilled in the art. The spring retention device 1078 may be a separate element, may comprise a part of the spring 1076, or it may comprise a separate element that is operatively connected to the spring 1076. Alternately, the spring retention device 1078 may comprise a part of the deflectable arm 1074 or be operatively connected to the deflectable arm 1074. The spring retention device 1078 may be configured and dimensioned to fit within the recess 1080 in the drive screw head 862.

The housing 902 of this embodiment includes protuberances, such as teeth, that can engage with the deflectable arm 1074. In order to assemble this embodiment, the spring 1076 is inserted into the recess 1080. If the deflectable arm 1074 is a separate element, it may be inserted into the side recess of the drive screw head 862 before or after the spring 1076 is inserted. The spring retention device 1078 may then be inserted into the recess 1080. When installed, the spring retention device 1078 forces the spring 1076 to be compressed and also exerts a downward (towards the spring 1076) force on at least a portion of the deflectable arm 1074 that is within the recess 1080, forcing the end of the deflectable arm into engagement with the protuberances included in the housing 902. The spring retention device 1078 may be secured in place using any method or device known to those skilled in the art. In this manner, rotation of the drive screw head 862 may be rotationally limited. When a tool, such as a driver, is inserted into the opening 970 of the drive screw head 862, the spring 1076 pushes the spring retention device 1078 out of the recess 1080, which also pushes the deflectable arm 1074 downwards (away from the face of the drive screw head 862) so that it disengages from the protuberances included in the housing 902, permitting rotational movement of the drive screw 860.

An alternative embodiment of the locking mechanism is described with reference to FIGS. 140-141. In the illustrated embodiment, the locking mechanism comprises a housing 902, drive screw 860, retaining ring 890, ball bearing 1082, spring 1076, and shuttle ramp 1084. The housing 902, drive screw 860, and retaining ring 890 of FIGS. 140-141 and their individual components are similar to the those described with respect to FIGS. 87-136, with several modifications. The modifications and components that differ from the locking mechanism illustrated in FIGS. 87-136 will be described in turn below.

In one embodiment, one or more ball bearings 1082 are included. The ball bearings 1082 may comprise any dimensions known to those skilled in the art. It is desirable, however, for the ball bearings 1082 to be configured and dimensioned such that they can fit into a space between the drive screw head 862 and the housing 902, as described below. This embodiment also includes a spring 1076, which is operatively connected to a shuttle ramp 1084. The shuttle ramp 1084 and the spring 1076 may fit into a recess that is included in the housing 902, as shown in FIGS. 140-141. It is desirable for the recess to be selectively positioned such that it is substantially near the drive screw head 862. The recess may be configured and dimensioned to allow the spring 1076, shuttle ramp 1084, and ball bearing 1082 to fit within and be retained when the drive screw 860 is positioned within the housing 902, as shown in FIG. 141.

As shown in FIGS. 140-141, when the drive screw 860 is inserted into the housing 902, the one or more ball bearings 1082 push against the wall of the drive screw head 862. The ball bearings 1082 are pushed against the drive screw head 862 by the force of the spring 1076 pushing against the shuttle ramp 1084, which is operatively connected to the ball bearing 1082. When a tool, such as a driver or the like, is inserted into the space between the drive screw head 862 and the housing 902, the ball bearing 1082 may be displaced, allowing the drive screw 860 to turn. Those skilled in the art will appreciate that the locking mechanism described with respect to FIGS. 140-141 may be used in combination with any of the locking mechanisms described with respect to FIGS. 87-139.

An alternative embodiment of the locking mechanism is described with reference to FIGS. 142-143. In the illustrated embodiment, the locking mechanism comprises a housing 902, drive screw 860, retaining ring 890, secondary set screw 1086, and deflectable arm 1074. The housing 902, drive screw 860, retaining ring 890, and deflectable arm 1074 of FIGS. 142-143 and their individual components are similar to the those described with respect to FIGS. 87-136, with several modifications. The modifications and components that differ from the locking mechanism illustrated in FIGS. 87-136 will be described in turn below.

In this embodiment, the deflectable arm 1074 faces downwards, towards the body of the drive screw 860. The deflectable arm 1074 passes through the side of the drive screw head 862 in two places, 180° apart, as shown in FIG. 143. A secondary set screw 1086 can be configured and dimensioned to lock the deflectable arm 1074 in place with respect to the drive screw head 862. The drive screw head 862 may include a recess that is configured and dimensioned to engage with the secondary set screw 1086. The recess may be a part of the opening 970 in the drive screw head 862. The housing 902 may include a friction surface, such as protuberances or teeth, that operatively engage with the ends of the deflectable arms 1074 that protrude from the side of the drive screw head 862. In this manner, the drive screw head 862 is rotationally locked to the housing 902. When a device, such as a driver or the like, is inserted into the opening 972, it forces the ends of the deflectable arm 1074 away from the friction surface included in the housing 902, allowing rotation of the drive screw 860.

Particular embodiments of the present disclosure may be directed to an anti-rotation locking mechanism for use in spinal implants.

Typically, screws are used in multiple applications, from securing two items together to translating one item with respect to another. When enough torque is applied or the screw is continuously under a high amount of load, the screw is less likely to loosen over time due to increased friction forces. However, if the screw is not held under a sufficient load, a low-load mode, it may loosen over time from vibration. Embodiments of the present disclosure may prevent a screw from rotating, regardless of loading and friction forces.

FIG. 144 illustrates an anti-rotation locking mechanism ("ARLM") 1450 in accordance with particular embodiments of the present disclosure. The ARLM 1450 may include a screw 1452. The screw 1452 may include a threaded portion 1454 and a screw head 1456. The screw head 1456 may include notches 1458 extending along a circumference of the screw head 1456, as shown. The screw head 1456 may include a recess 1460. In certain embodiments, the recess 1460 may include lobes 1462, as shown. The lobes 1462 may correspond with a shape of an insertion tool (not shown) utilized to attach or remove the screw 1452 from a housing 1464.

The screw 1452 may also include a flange 1466 positioned adjacent to the screw head 1456 extending along the circumference of the screw 1452 and also extending radially outward as shown. The flange 1466 may also be positioned adjacent to a band 1468. The band 1468 may be a smooth surface extending along the circumference of the screw 1452, as shown.

FIG. 145 is a lengthwise cross-section of the receptacle 1464a taken along the longitudinal axis L of the ARLM 1450, as shown in FIG. 144. In certain embodiments, the passage 1472 may be tapered in a direction of the tapering of the tapered portion 1464b. That is, an inner diameter ("ID") of the passage 1472 may decrease in a direction extending toward the tip 1464d (e.g., shown on FIG. 144). The friction ring 1470 may be secured between the inner surface 1472a and the threaded portion 1454. The friction ring 1470 may be made of any suitable material, for example, PEEK or other suitable materials, such as titanium, stainless steel, titanium alloys, non-titanium metallic alloys, polymeric materials, plastics, plastic composites, ceramic, and elastic materials. The tapering of the passage 1472 should radially compress the friction ring 1470 inward against the band portion 1468 as the screw 1452 is tightened. The tapering should allow a gradual compression of the friction ring 1470 thereby preventing damage thereof, such as peeling of the friction ring 1470, for example. The friction ring 1470 may be secured between the inner surface 1472a and the band portion 1468. With additional reference to FIG. 145, the friction ring 1470 should prevent rotation of the screw 1452 due to a compressed fit, as can be seen on FIG. 145. Therefore, depending on an extent of compression, different amounts of torque may be required to overcome the static friction.

With reference to FIGS. 144 and 145, during insertion of the screw 1452 into the passage 1472, the band 1468 may receive the friction ring 1470 thereby securing the friction ring 1470 between the flange 1466, the inner surface 1472a, and the band 1468. In certain embodiments, the flange 1466 may have an outer diameter ("OD") and/or a thickness that is equal to an OD of the friction ring 1470. An OD of the screw 1452 may be less than an ID of the friction ring 1470. The position of the friction ring 1470 on the band 1468 and against the flange 1466 allows the friction ring 1470 to act as a thrust washer and reduce the likelihood of galling between metal of the screw 1452 and metal of the housing 1464 when high torques are reached during installation or removal of the screw 1452.

FIG. 146 illustrates the ARLM 1450 further including a locking member 1474 and a retaining member 1476 in accordance with particular embodiments of the present disclosure. In certain embodiments, the friction ring 1470 is not included in the ARLM 1450.

FIG. 147 is a close-up view of the locking member 1474 and the screw head 1456 in accordance with particular embodiments of the present disclosure. The locking ring 1474 may include a partial ring 1480 (e.g., a c-ring) coupled to a ring 1482 via a strut 1484. The notches 1458 may be positioned between projections 1490. The projections 1490 may extend outward from a surface 1456a of the screw head 1456 between the notches 1458. The projections 1490 may be smooth and tapered surfaces allowing pushing or sliding of the locking member 1474 onto the screw head 1456.

FIG. 148 illustrates the locking member 1474 removably attached to the screw head 1456 to form a screw assembly 1457, in accordance with particular embodiments of the present disclosure. As shown, the notches 1458 may be positioned between the ring 1482 and the partial ring 1480. The strut 1484 may be disposed within one of the notches 1458 and may extend further outward than the flange 1466, as shown. The partial ring 1480 may be positioned between the flange 1466 and the notches 1458. That is, the partial ring 1480 may be secured between the projections 1490 and the flange 1466. The ring 1482 may be positioned adjacent to the notches 1458, as shown.

FIG. 149A is a cross-section of the screw assembly 1457 inserted into the housing 1464. This cross-section is taken along $L_2$ of FIG. 148A. It should be noted that FIG. 149B also illustrates a cross-section of the housing 1464 taken along L3. As shown on FIG. 148A, the strut 1484 may be aligned with a recess 1500 extending radially outward from an opening 1472a of the passage 1472 of the housing 1464.

The ring 1482 may include a portion 1482a that has a tapered thickness, as shown. That is, a center $C_1$ of a through-hole 1504 of the ring 1482 is off-center relative to a center $C_2$ of the ring 1482. The tapered thickness creates spaces 1502 in the opening 1472a of the passage 1472 between an inner surface 1472b of the opening 1472a and an outer surface 1473 of the ring 1482.

FIG. 149B is a cross-section of the screw head 1456 positioned in the housing 1464. This cross-section is taken along $L_3$ of FIG. 147. It should be noted that FIG. 149B also illustrates a cross-section of the housing 1464 taken along L. As shown on FIG. 149B, the strut 1484 may be partially positioned within a notch 1458, thereby preventing rotation of the screw 1452 relative to the housing 1464.

FIG. 150A is a cross-section similar to FIG. 149A. The screw 1452 is positioned into place within the housing 1464. The strut 1484 is completely positioned within the recess 1500.

FIG. 150B is a cross-section similar to FIG. 150A in accordance with particular embodiments of the present disclosure. As shown, the strut 1484 may be completely positioned and secured within the recess 1500, thereby allows rotation of the screw head 1456 relative to the housing 1464.

FIG. 151 illustrates the retaining member 1476 in accordance with particular embodiments of the present disclosure. The retaining member 1476 may be a partial ring that includes radial notches 1478 to secure or retain the screw assembly 1457 within the housing 1464 (shown on FIG. 149A for example). The retaining member 1476 may also include a tab 1530 utilized for grasping and moving the retaining member 1476 as well as securing the retaining member 1476 within the housing 1464. The retaining member 1476 may be positioned adjacent to the ring 1482 within the housing 1464 (as shown on FIG. 149A, for example). The tab 1530 may be positioned within the recess 1500.

While the invention is described herein according to the above embodiments, it will be obvious that the same may be varied in many ways. Such variations are not to be regarded as a departure from the spirit and scope of the invention, and all such modifications as would be obvious to one skilled in the art are intended to be included within the scope of the following claims.

While the invention is described herein according to the above embodiments, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. An expandable spacer with an anti-rotation lock, comprising:
   a pair of endplates;
   a body having a through hole and disposed between the pair of endplates;
   a screw received in the through hole of the body and having a screw head, the screw head including a plurality of circumferentially disposed notches, wherein rotation of the screw causes the pair of endplates to move apart relative to each other;
   a retainer ring disposed in the body to retain the screw in the body;
   an anti-rotation lock disposed around the screw head and including:
   a ring;
   a partial ring; and
   a strut directly attached between the ring and the partial ring, and configured to rest in one of the notches.

2. The expandable spacer of claim 1, wherein an opening of the ring is off-center relative to a center of the screw head.

3. The expandable spacer of claim 1, wherein:
   the strut includes a radially extending portion;
   the through hole of the body has a recess for receiving the radially extending portion.

4. The expandable spacer of claim 3, wherein an opening of the ring is off-center relative to a center of the screw head and when a driver of the screw is inserted through the ring, the radially extending portion is pushed into the recess which disengages the strut from the notch to allow rotation of the screw relative to the body.

5. The expandable spacer of claim 1, wherein:
   an opening of the ring is off-center relative to a center of the screw head;
   the strut includes a radially extending portion;
   the through hole of the body has a recess for receiving the radially extending portion to prevent the screw head from rotating relative to the body.

6. The expandable spacer of claim 1, further comprising a driving ramp having an internal threading configured to threadably receive a shaft of the screw.

7. The expandable spacer of claim 1, wherein a thickness of the ring tapers circumferentially.

8. The expandable spacer of claim 1, wherein a thickness of the ring tapers circumferentially such that an opening of the ring is off-center relative to an outer perimeter of the ring.

9. The expandable spacer of claim 1, wherein the screw head includes a flange.

10. The expandable spacer of claim 9, wherein the screw head includes a circumferential recess between the notches and the flange for receiving the partial ring.

11. An expandable spacer with an anti-rotation lock, comprising:
   a pair of endplates;
   a body having a through hole and disposed between the pair of endplates, the body further having a recess extending radially outwardly from the through hole;
   a screw received in the through hole of the body and having a screw head, the screw head including a plurality of circumferentially disposed notches, wherein rotation of the screw causes the pair of endplates to move apart relative to each other;
   an anti-rotation lock disposed around the screw head and including:
   a ring defining an opening;
   a partial ring; and
   a strut directly attached between the ring and the partial ring, and configured to rest in one of the notches, the strut having a radially extending portion received in the recess to prevent the screw from rotation relative to the body.

12. The expandable spacer of claim 11, wherein the ring opening is off-center relative to a center of the screw head.

13. The expandable spacer of claim 12, wherein when a driver of the screw is inserted through the ring, the radially extending portion is pushed further into the recess which disengages the strut from the notch to allow rotation of the screw relative to the body.

14. The expandable spacer of claim 11, further comprising a driving ramp having an internal threading configured to threadably receive a shaft of the screw.

15. The expandable spacer of claim 11, wherein a thickness of the ring tapers circumferentially.

16. The expandable spacer of claim 11, wherein a thickness of the ring tapers circumferentially such that the opening of the ring is off-center relative to an outer perimeter of the ring.

17. The expandable spacer of claim 11, wherein the screw head includes a flange.

18. The expandable spacer of claim 17, wherein the screw head includes a circumferential recess between the notches and the flange for receiving the partial ring.

19. The expandable spacer of claim 11, further comprising a retainer ring disposed proximally of the screw head and secured to the body to retain the screw in the body.

* * * * *